(12) United States Patent
Imoto et al.

(10) Patent No.: US 7,430,475 B2
(45) Date of Patent: Sep. 30, 2008

(54) BIOLOGICAL DISCOVERY USING GENE REGULATORY NETWORKS GENERATED FROM MULTIPLE-DISRUPTION EXPRESSION LIBRARIES

(75) Inventors: Seiyo Imoto, Tokyo (JP); Takao Goto, Tokyo (JP); Satoru Miyano, Tokyo (JP); Kosuke Tashiro, Fukuoka (JP); Michiel de Hoon, Tokyo (JP); Christopher J. Savoie, Shinhoka-machi (JP); Saturo Kuhara, Fukuoka (JP)

(73) Assignee: GNI KK, Tokyo (JP)

( * ) Notice: Subject to any disclaimer, the term of this patent is extended or adjusted under 35 U.S.C. 154(b) by 0 days.

(21) Appl. No.: 10/259,723

(22) Filed: Sep. 26, 2002

(65) Prior Publication Data

US 2003/0219764 A1 Nov. 27, 2003

Related U.S. Application Data

(60) Provisional application No. 60/325,016, filed on Sep. 26, 2001, provisional application No. 60/334,372, filed on Nov. 29, 2001, provisional application No. 60/334,255, filed on Nov. 29, 2001, provisional application No. 60/334,230, filed on Nov. 29, 2001, provisional application No. 60/370,824, filed on Apr. 8, 2002, provisional application No. 60/397,458, filed on Jul. 19, 2002.

(51) Int. Cl.
*G06F 19/00* (2006.01)
*C12Q 1/68* (2006.01)

(52) U.S. Cl. .................. 702/19; 702/20; 435/6
(58) Field of Classification Search .................... 702/19, 702/20; 435/6; 422/68.1
See application file for complete search history.

(56) References Cited

OTHER PUBLICATIONS

Pe'er et al. (Bioinfomatics (2001) vol. 17, Suppl. 1, pp. S215-S224).*

Ideker, et al., Integrated Genomic and Proteoic Analyses of a Systematically Perturbed Metabolic Newtork. Science. May 4, 2001, vol. 292, pp. 929-934.
Friedman, et al.., Using Bayesian Networks to Analyze Expression Data. J. Computational Biology. 2000, vol. 7, Nos. 3/4, pp. 601-620.
Pe'er, et al., "Inferring subnetworks from perturbed expression profiles", In: School of Computer Science and Engineering (Hegrew University, Jerusalm). Oxford University Press. Jun. 2001, vol. 17, Suppl. 1, pp. S214-S224.
Imoto, et al. Bayesian network and nonparametric heteroscedastic regression for nonlinear modeling of genetic network. Proc IEEE Comput Soc Bioinform Conf. 2002; 1:219-27.
Imoto, et al. Estimation of genetic networks and functional structures between genes by using Bayesian networks and nonparametric regression. Pac Symp Biocomput. 2002; 175-86.

* cited by examiner

*Primary Examiner*—Lori A Clow
(74) *Attorney, Agent, or Firm*—Wilson Sonsini Goodrich & Rosati

(57) ABSTRACT

Embodiments of this invention include application of new inferential methods to analysis of complex biological information, including gene networks. In some embodiments, disruptant data and/or drug induction/inhibition data are obtained simultaneously for a number of genes in an organism. New methods include modifications of Boolean inferential methods and application of those methods to determining relationships between expressed genes in organisms. Additional new methods include modifications of Bayesian inferential methods and application of those methods to determining cause and effect relationships between expressed genes, and in some embodiments, for determining upstream effectors of regulated genes. Additional modifications of Bayesian methods include use of heterogeneous variance and different curve fitting methods, including spline functions, to improve estimation of graphs of networks of expressed genes. Other embodiments include the use of bootstrapping methods and determination of edge effects to more accurately provide network information between expressed genes. Methods of this invention were validated using information obtained from prior studies, as well as from newly carried out studies of gene expression.

13 Claims, 38 Drawing Sheets

Fig. 7a

AAH1,AAT1,ADE13,ADE3,AGA2,ALD4,ALPHA2,APC1,APG13,APM3,APT2,ARO3,ARO9,ASK10,ATP7,ATP8,ATP9,BCS1,CBF5,CDC15,CDC37,CDC50,CEM1,CHD1,CIT1,CLN2,CMK2,CNB1,COS6,COX17,CPA1,CPR7,CTT1,CWP2,CYP2,DAL3,DBF2,DBP2,DBP3,DLD1,DNA2,DPH2,ECM29,ECM4,ENP1,FAS1,FIG2,FOL1,FRE1,GAL2,GAL7,GAT1,GBP2,GCD10,GCY1,GIC1,GLK1,GTT1,GTT2,GUA1,HAS1,HEM12,HGH1,HIS4,HKR1,HMG1,HMS2,HSP12,HXK1,HXT17,HXT6,HYM1,IMG1,JA2,JEN1,KEL3,KIN28,LCB1,LYS2,LYS4,MAL13,MAL23,MBP1,MIS1,MLP1,MRP4,MRPL36,MRT4,MSS4,NGG1,NHP2,NOG1,NOP1,NOP2,NOP5,NSR1,NTG2,NUP116,OM45,ORF_Q0144,OSH1,OST3,PGM2,PHB2,POM152,PPT1,PTC4,PUS2,PUT2,PXA2,PYC1,PYK2,RGA2,RPA135,RPA14,RPA49,RPC40,RPL15B,RPL16B,RPL19B,RPL3,RPL31B,RRN3,RTT103,SAC2,SAM1,SAM3,SCC2,SCW4,SDS23,SDS24,SEC11,SEC63,SEN1,SKO1,SMM1,SNF5,SOL1,SOL4,SPI1,SRP40,STE5,SWI5,SXM1,TAF61,TBS1,TFS1,THI12,TID3,TIF3,TOM7,TPS2,TRM1,UBP11,UGA1,URA7,VAR1,XBP1,YAL028W,YAL036C,YAL060W,YAP6,YAR009C,YBR204C,YBR238C,YBR271W,YCL036W,YCL042W,YCL056C,YCR044C,YCR062W,YCR086W,YCR087W,YDL034W,YDL063C,YDL085W,YDL139C,YDL204W,YDL214C,YDL222C,YDL223C,YDL239C,YDR026C,YDR070C,YDR091C,YDR101C,YDR134C,YDR153C,YDR186C,YDR233C,YDR326C,YDR332W,YDR361C,YDR366C,YDR380W,YDR384C,YDR387C,YDR479C,YDR493W,YDR504C,YDR516C,YER049W,YER067W,YER084W,YER175C,YER182W,YFR012W,YGL037W,YGR001C,YGR064W,YGR086C,YGR101W,YGR160W,YGR196C,YGR200C,YGR228W,YGR235C,YGR245C,YGR271W,YHB1,YHL021C,YHL026C,YHL037C,YHM2,YHR020W,YHR059W,YHR087W,YHR097C,YHR155W,YHR186C,YIL044C,YIL124W,YIL149C,YIL169C,YIR036C,YJL021C,YJL066C,YJL068C,YJL086C,YJL161W,YJL200C,YJL211C,YJR041C,YJR070C,YJR071W,YJR120W,YJR157W,YKL014C,YKL026C,YKL036C,YKL111C,YKL179C,YKR088C,YKR096W,YLA1,YLL064C,YLR002C,YLR033W,YLR073C,YLR177W,YLR270W,YLR327C,YMC2,YML047C,YML128C,YMR090W,YMR131C,YMR250W,YNL058C,YNL095C,YNL114C,YNL132W,YNL156C,YNL170W,YNL175C,YNL195C,YNL203C,YNL305C,YNR037C,YNR059W,YOL027C,YOL071W,YOL082W,YOL084W,YOL106W,YOL155C,YOR004W,YOR093C,YOR121C,YOR145C,YOR146W,YOR154W,YOR155C,YOR173W,YOR289W,YOR309C,YOR325W,YPL134C,YPR118W,YTM1,YTP1,ZPR1

Fig. 7b

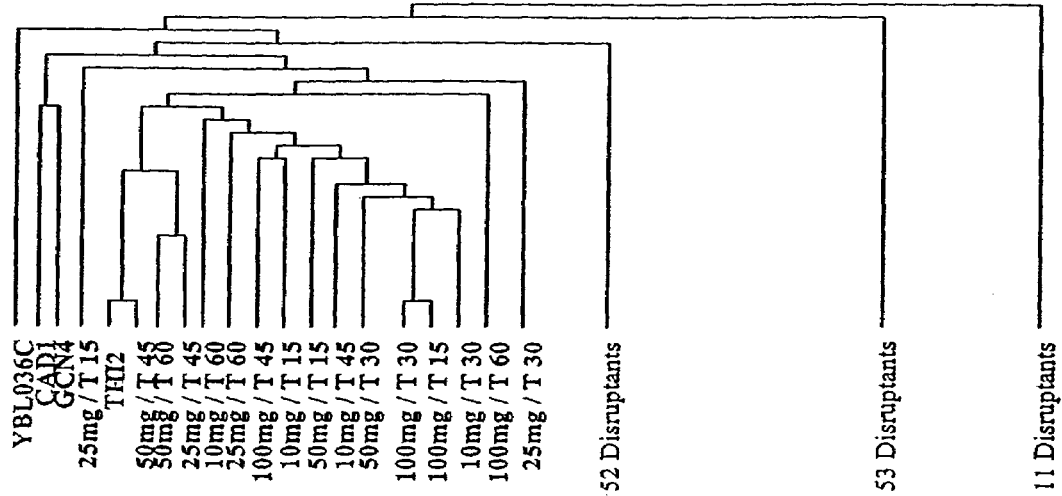

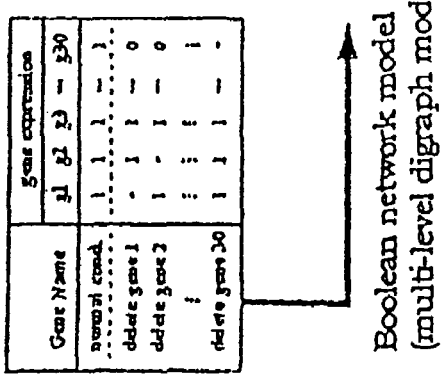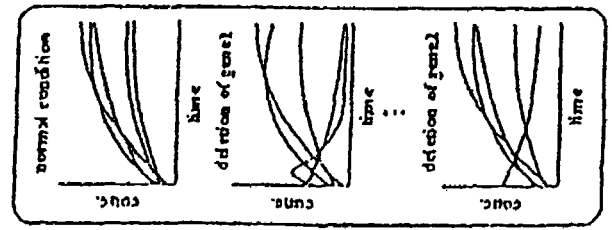
Figure 32

Multi-level digraph approach

Presumption of expression control network from expression profile

① Gene expression matrix $G_E$

| Gene | G1 | G2 | G3 | G4 |
|---|---|---|---|---|
| Wild type | 1 | 1 | 1 | 1 |
| G4 disruptant | 2.3 | 3.5 | 0.1 | - |
| G3 disruptant | 4.1 | 2.8 | - | 0.2 |
| G2 disruptant | 3.0 | - | 0.3 | 0.3 |
| G1 disruptant | - | 0.4 | 0.3 | 0.2 |

② Binomial relation $A_B$

G4 affects G3
G3 affects G4
G2 affects G3
G2 affects G4
G1 affects G2
G1 affects G3
G1 affects G4

③ Binary adjoining matrix $A$

| From \ To | G1 | G2 | G3 | G4 |
|---|---|---|---|---|
| G1 | 0 | 1 | 1 | 1 |
| G2 | 0 | 0 | 1 | 1 |
| G3 | 0 | 0 | 0 | 1 |
| G4 | 0 | 0 | 1 | 0 |

④ Gene group having a loop structure is treated as an equivalence group

| From \ To | G1 | G2 | G3' |
|---|---|---|---|
| G1 | 0 | 1 | 1 |
| G2 | 0 | 0 | 1 |
| G3' | 0 | 0 | 0 |

G3' = {G3, G4}

Induction of control relation among genes from the gene expression matrix

⑤ Skeleton matrix $R$

| From \ To | G1 | G2 | G3' |
|---|---|---|---|
| G1 | 0 | 1 | 0 |
| G2 | 0 | 0 | 1 |
| G3' | 0 | 0 | 0 |

⑥ Multi-level digraph

Table 13. Connection analysis of each "Cellular Roles"

| | Amino acid metabolism | Carbohydrate metabolism | Cell cycle | Cell stress | Chromatin /chromosome structure | Differentiation | DNA repair | Energy generation | Lipid fatty-acid metabolism | Meiosis, Mating response | Other metabolism | SUM |
|---|---|---|---|---|---|---|---|---|---|---|---|---|
| Amino acid metabolism | 1 | 0 | 0 | 3 | 1 | 1 | 2 | 1 | 0 | 2 | 2 | 13 |
| Carbohydrate metabolism | 3 | 5 | 0 | 7 | 4 | 1 | 4 | 6 | 2 | 10 | 2 | 44 |
| Cell cycle | 0 | 0 | 0 | 2 | 0 | 1 | 0 | 1 | 0 | 1 | 1 | 6 |
| Cell stress | 0 | 4 | 1 | 1 | 4 | 2 | 1 | 0 | 0 | 5 | 0 | 18 |
| Chromatin /chromosome structure | 0 | 1 | 0 | 3 | 0 | 1 | 0 | 1 | 0 | 1 | 1 | 7 |
| Differentiation | 0 | 0 | 0 | 0 | 1 | 0 | 0 | 1 | 0 | 1 | 1 | 4 |
| DNA repair | 0 | 0 | 0 | 0 | 0 | 0 | 0 | 0 | 0 | 0 | 0 | 0 |
| Energy generation | 0 | 0 | 0 | 0 | 0 | 0 | 0 | 0 | 0 | 0 | 0 | 0 |
| Lipid fatty-acid metabolism | 0 | 4 | 0 | 2 | 0 | 1 | 1 | 0 | 0 | 2 | 0 | 8 |
| Meiosis, Mating response | 4 | 3 | 2 | 2 | 1 | 0 | 2 | 2 | 0 | 2 | 1 | 20 |
| Other metabolism | 0 | 1 | 0 | 0 | 2 | 0 | 1 | 0 | 0 | 3 | 0 | 7 |
| SUM | 8 | 18 | 3 | 18 | 13 | 8 | 11 | 11 | 2 | 27 | 8 | |

Figure 36

BIOLOGICAL DISCOVERY USING GENE REGULATORY NETWORKS GENERATED FROM MULTIPLE-DISRUPTION EXPRESSION LIBRARIES

RELATED APPLICATIONS

This application claims priority under 35 U.S.C. Section 119(e) to U.S. provisional application Ser. Nos. 60/325,016, filed Sep. 26, 2001; 60/334,372, filed Nov. 29, 2001; 60/334,255, filed Nov. 29, 2001; 60/334,230, filed Nov. 29, 2001; 60/370,824, filed Apr. 8, 2002; and 60/397,458 filed Jul. 19, 2002. Each of the above provisional patent applications is herein incorporated fully by reference.

FIELD OF THE INVENTION

Embodiments of this invention relate to methods for elucidating network relationships between genes. Methods include Boolean logic, Bayesian estimation, maximum likelihood analysis, spline functions and other curve-fitting methods, and methods to determine edge relationships between groups of genes that are functionally related to each other.

BACKGROUND

Gene regulatory networks elucidated from strategic, genome-wide experimental data can aid in the discovery of novel gene function information and expression regulation events from observation of transcriptional regulation events among genes of known and unknown biological function.

Methods designed to elucidate gene regulation pathways have been reported previously (Y. Pilpel et al., *Nature Genetics*, 29, 153-159, 2001; Friedman et al., *J. Comp. Biol.*, 7, 601, 2000; R. Somogyi et al., *Complexity*, 1, 45-63, 1996). The inferred networks reported in these studies were derived from gene expression data sets derived from time course, cell cycle and environmental perturbation (P. Spellman et al., *Mol. Biol Cell*, 9, 3273-3297, 1998; A. P. Gasch, et al., *Mol. Cell Biol.* 17, 2099-2106, 1997). However, control relationships inferred from such data sets are suspect since they are not based on comprehensive experimental data designed to elucidate transcription-related regulatory control functions. To rigorously and precisely identify novel and complex gene regulatory networks from de novo expression data sets, a systematic and integrated strategy of expression experiments on genomic deletion mutants combined with suitable computational methods is necessary (T. Akutsu et al., *J. Comp. Biol.*, 7, 331, 2000; T. Akutsu et al., *Bioinformatics*, 16, 727, 2000; M. P. Brown et al., *Proc. Natl. Acad. Sci.*, 97, 262-267, 2000; T. Ideker et al., *Science*, 292, 929-934, 2001).

Of particular importance in the creation of inferred regulatory networks is the biological relevance of the expression experiments from which the putative control relationships are derived. Genome-wide expression data generated from competitive hybridization disruption experiments offer the advantages of internal control and quantitative measurement of the direct effects of a gene's presence or absence on the expression of other genes. Selection of disruptant experiments to maximize the elucidation of control relationships is valuable for generating useful gene regulatory information.

SUMMARY

The present invention provides methods useful for establishing interrelationships among genes or groups of genes in a system, e.g., establishing gene pathways or gene networks in a system. In one embodiment, gene networks or gene pathways can be constructed based on analyzing gene disruption expression profiles using improved Boolean methods, improved Bayesian methods, or a combination of Boolean and Bayesian methods, as provided by the present invention. In another embodiment, gene networks or gene pathways can be constructed based on analyzing expression profiles of genes affected by an agent, e.g., a drug. In yet another embodiment, gene networks or gene pathways affected by an agent can be constructed by analyzing the gene networks or pathways obtained from the gene disruption expression profiles and the agent affected expression profiles.

In general, gene disruption expression profiles can be obtained based on expression profiles of a library of genes, each of which disrupted individually or in combination with others, e.g., other genes in a related function to provide an expression profile. For example, a library of genes can be selected (e.g., an entire genome or a series of genes selected based on other criteria, including polymerase chain reaction (PCR) primers). Regardless of how the library of genes is selected, once selected, each gene of the library can be disrupted individually and/or in combination with others resulting in a collection of libraries, each of which containing at least one disrupted gene along with other non-disrupted genes. Thus, if one selects 100 genes, the resulting library will consist of at least 101 different sub-libraries e.g., one sub-library of non-disrupted genes or wild-type and at least one disruptant sub-library for each of the 100 genes. Thus, libraries of disrupted genes can be created and expression profiles for each sub-library and the entire library can be obtained.

Agent affected expression profiles can be obtained by administering one or more desired agents to a system containing selected genes and collecting expression profiles of the genes at different dosage or time point of agent administration. In some cases the agent has no effect on gene expression, in other cases the agent is inhibitory (e.g., decreases gene expression) and in other cases the agent increases gene expression (e.g., is an inducer).

Gene expression profiles can be obtained in a quantified form using any suitable means, e.g., using microarray. In one embodiment, a gene expression profile can be organized into gene expression matrix, e.g., a binary matrix categorizing the genes into affected and not affected. In another embodiment, one can introduce an "equivalence set" in which data is normalized, thereby revealing the quantitative relationships in gene expression. From an equivalence set, network information relating the genes with each other can be created. Then, one can use networks to determine functional relationships between genes. One can then use the deduced functional relationships between genes to predict drug and or biological effects. Then, those predictions can be experimentally tested using, for example, microarray experiments. This process can result in what we call a "final common pathway" of gene expression, that is, alteration in the function of one gene results in effects on genes "downstream" from the altered gene.

According to one embodiment of the present invention, one can analyze "downstream" effect from a directly affected gene by using the improved Boolean methods of the present invention. According to another embodiment of the present invention, one can go "upstream" from an affected gene by applying an improved Bayesian method of the present invention. The present invention provides a new approach to Bayesian gene network analysis, in which non-linear, and/or non-parametric regression models are used. Using this approach means that one need not make any a priori assumptions about causal relationships, but rather can infer causal relationships, thereby providing "upstream" or "initial pathways" by which a gene observed to be affected by a drug or treatment is induced to alter its expression by other genes in an upstream relationship to the affected, observed gene. The present invention provides an improved criterion, herein termed "BNRC" for estimating a Bayesian graph of gene networks. Thus, the gene relationships are selected that minimize the BNRC criterion.

In other embodiments, other new methods are provided that not dependent upon Gaussian or other assumed variance in the data. Rather, in certain embodiments, we can measure the variance of the data and use the observed variance to affect the BNRC criterion. Using such non-parametric regression with heterogeneous error variances and interactions, one can optimize the curve fitting of data obtained, and predict how many experiments are needed to obtain data having a desired variance. Using methods such as these, one can obtain gene network information that has a desired degree of accuracy and reliability, and provides both upstream and downstream effects. In some embodiments, the new Bayesian model and penalized maximum likelihood estimation (PMLE) yield similar results.

In still other embodiments, relationships between two genes can be elucidated by analysis of a graph of expression of one gene compared to the expression of another gene. Such graphs may be linear or non-linear. To characterize the relationships, in some embodiments, linear splines, B-splines, Fourier transforms, wavelet transforms, or other basis functions can be used. In some cases, B-splines are conveniently employed.

Determining whether a particular gene or series of genes is important in regulating other genes can be very useful. However, in certain cases, outliers in the data can complicate interpretation of results. This problem can be especially troubling where outliers are near boundaries of gene groups in the overall network. Thus, in certain embodiments, boundary effects can be elucidated, in which the edge intensity and the degree of confidence of the direction of Bayes causality can be determined.

In other embodiments, time-course of gene expression can be determined using linear splines. Using splines, time-ordered data can be more reliably analyzed that prior art, "fold-change" methods, which can be relatively insensitive.

Using one or more of the above-described general methods, the present invention provides gene network information that is useful and validated by certain results already known for the yeast genome. However, the methods are widely applicable to any genetic network (e.g., "transcriptome"), and to interactions at the level of proteins ("proteome"). Additionally, using one or more of the new methods, we have determined novel relationships between functional genes relating to antifungal therapies. Thus, using methods of this invention, one can predict putative therapeutic targets based on an understanding of the initial and final common pathways of gene expression.

BRIEF DESCRIPTION OF THE DRAWINGS

This invention is described with respect to specific embodiments thereof, in which:

FIG. 2A depicts a Gene Expression Matrix, in which numerous profiles are integrated. Each element of the matrix represents a ratio of gene expression between a gene in a column and a gene in a row. FIG. 2B depicts binary relationships between genes to produce a Binary Matrix. If gene 'G1' is deleted and the intensity of gene 'G2' is significantly altered as a result, then gene 'G1' affects gene 'G2'. FIG. 2C depicts an adjacency matrix of identified looped regulation genes. If gene 'G3' and gene 'G4' affect each other mutually, they form a loop (strongly connected component) regulation. FIG. 2D depicts a step in which genes are partitioned into an Equivalence Set, which treats a loop logically as a "virtual gene". An equivalence set is a group of genes that affect each other or as a group affect one discrete gene. FIG. 2E depicts a skeleton relation between virtual genes. The shortest path relationships should be selected to build hierarchical connections. FIG. 2F depicts a regulation pathway formed from the skeleton matrix.

FIGS. 7a and 7b depict conventional methods for analyzing drug response expression data. FIG. 7a includes list of Yeast genes whose expression levels are significantly affected by Griseofulvin exposure at 100 mg at 1 minute (one of 20 experiments). FIG. 7b depicts hierarchical clustering of expression data from drug response and gene disruption experiments.

FIG. 32 conceptual diagram of identification of gene network.

FIG. 33 outline of multi-level digraph method.

FIG. 36 Table 13 connection analysis of each "cellular roles."

DETAILED DESCRIPTION

The descriptions that follow include specific examples drawn from studies in the yeast, *Saccharomyces*. The methods for analyzing relationships between yeast genes are equally applicable to analysis of relationships among genes of different species, including eukaryotes, prokaryotes, and viruses. Thus, the descriptions and examples that follow are illustrative and are not intended to limit the scope of the invention.

I. Biological Discovery with Gene Regulatory Networks in Yeast Generated from Multiple-Disruption Full Genome Expression Libraries Gene regulatory networks elucidated from strategic, genome-wide experimental data can aid in the discovery of novel gene function information and expression regulation events form observation of transcriptional regulation events among genes of known and unknown biological function. Of particular importance in the creation of inferred regulatory networks is the biological relevance of the expression experiments from which the putative control relationships are derived. Genome-wide expression data generated from competitive hybridization disruption experiments offer the advantages of internal control and quantitative measurement of the direct effects of a gene's presence or absence on the expression of other genes. Selection of disruptant experiments to maximize the elucidation of control relationships is important for generating useful gene regulatory information. To create a reliable and comprehensive data set for the elucidation of transcription regulation on 120 genes with known involvement in transcription regulation. We report several novel regulatory relationships between known transcription factors and other genes with previously unknown biological function discovered with this expression library.

Figure 1:
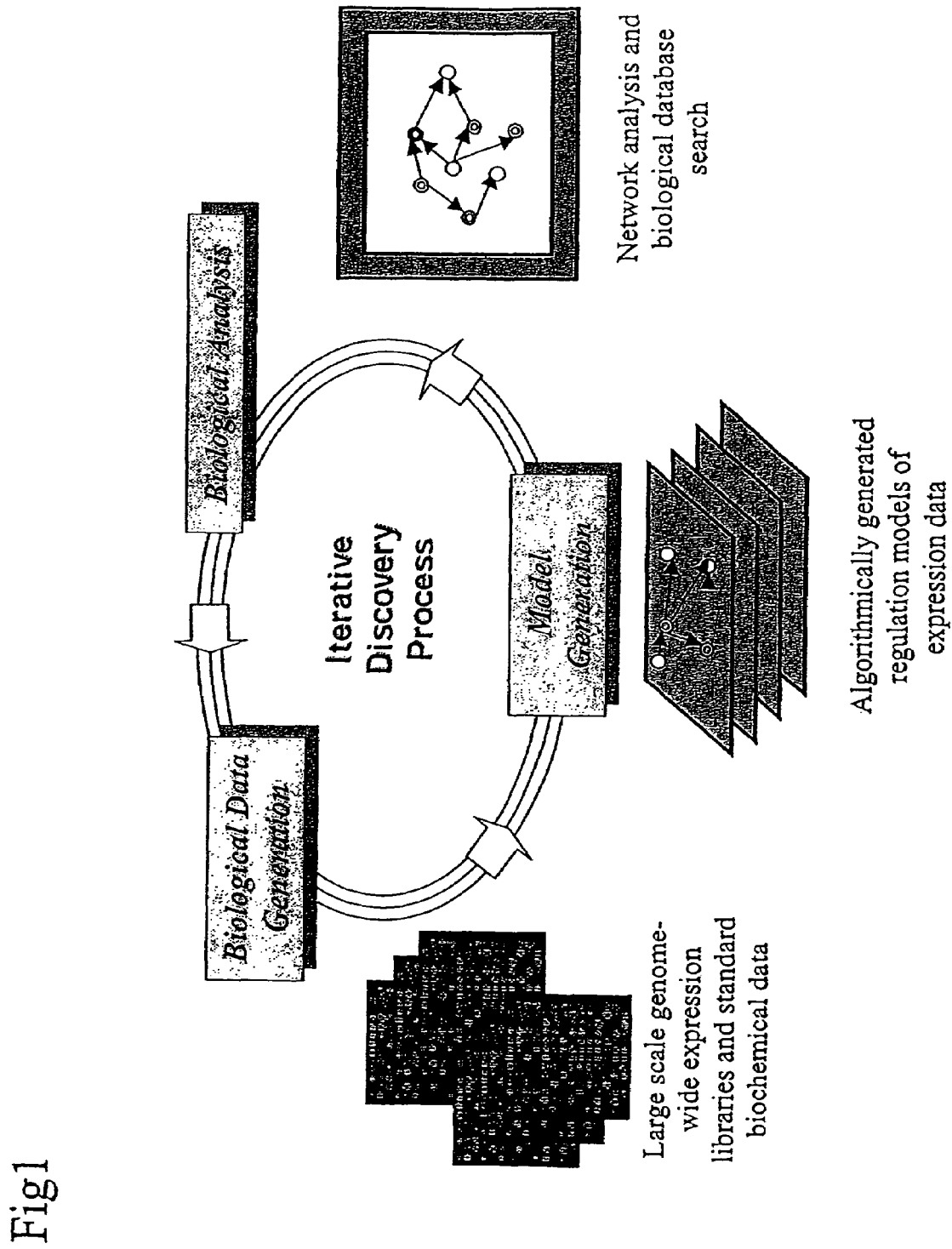
FIG. 1 depicts a schematic diagram of model-based interactive biological discovery of this invention.

We have implemented, for the yeast genome, a systematic, iterative approach that combines full-genome biological expression experiments with gene regulatory inference, as shown in FIG. 1. In certain embodiments, we start with the creation of a library of hundreds of full genome expression experiments, with one gene's expression disrupted per experiment. From this data we used computational techniques to infer approximations of gene expression regulatory relationships. We then examined the biological relevance of regulatory relationships with computerized visualization and simulation software and validated our findings on novel or biologically interesting sub-networks through other databases as well as through further experimentation, including combinatorial disruption experiments.

Figure 2:
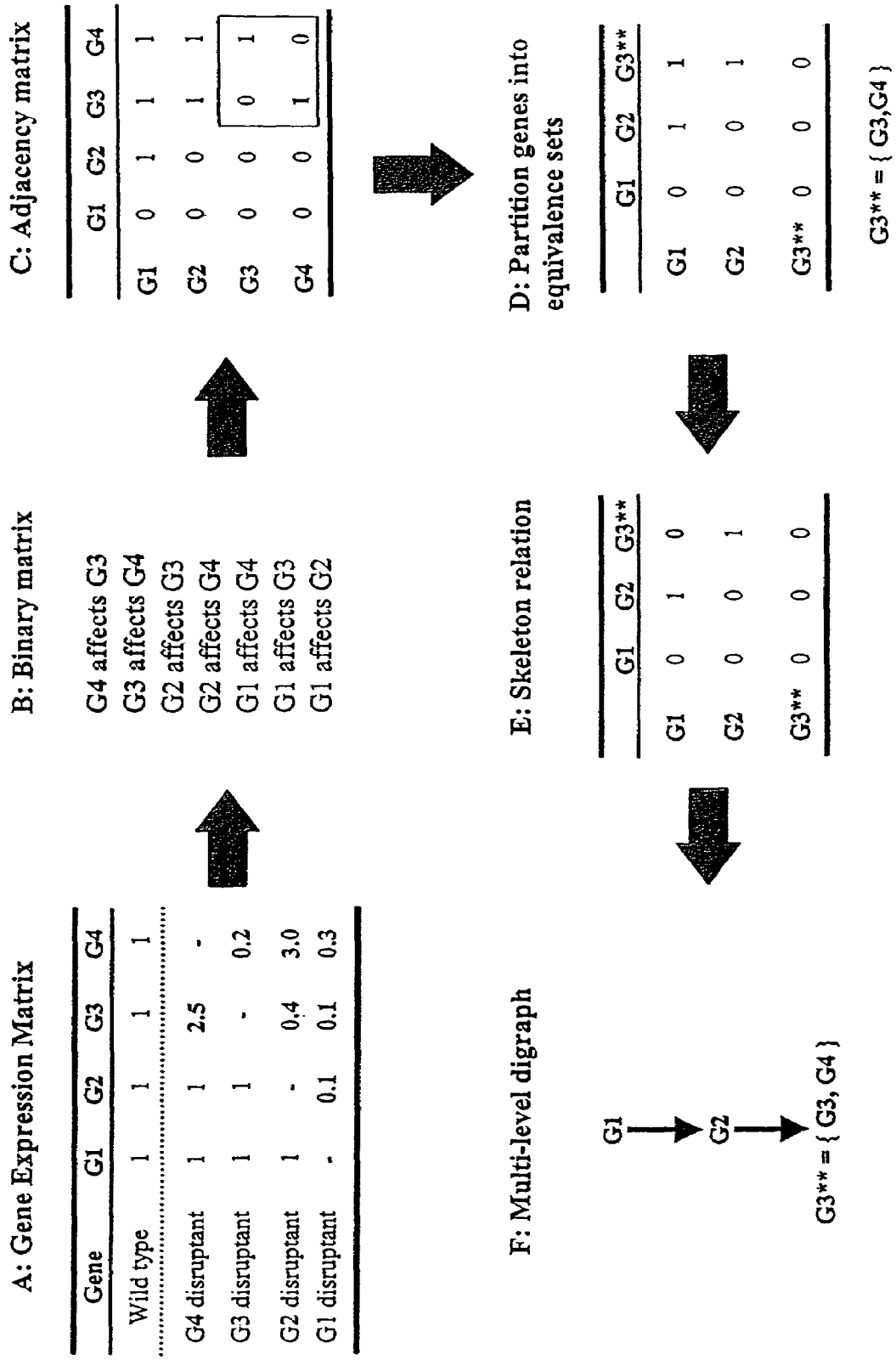
FIG. 2 depicts construction of a gene regulatory sub-network model, using a Boolean method of this invention.
Figure 3:
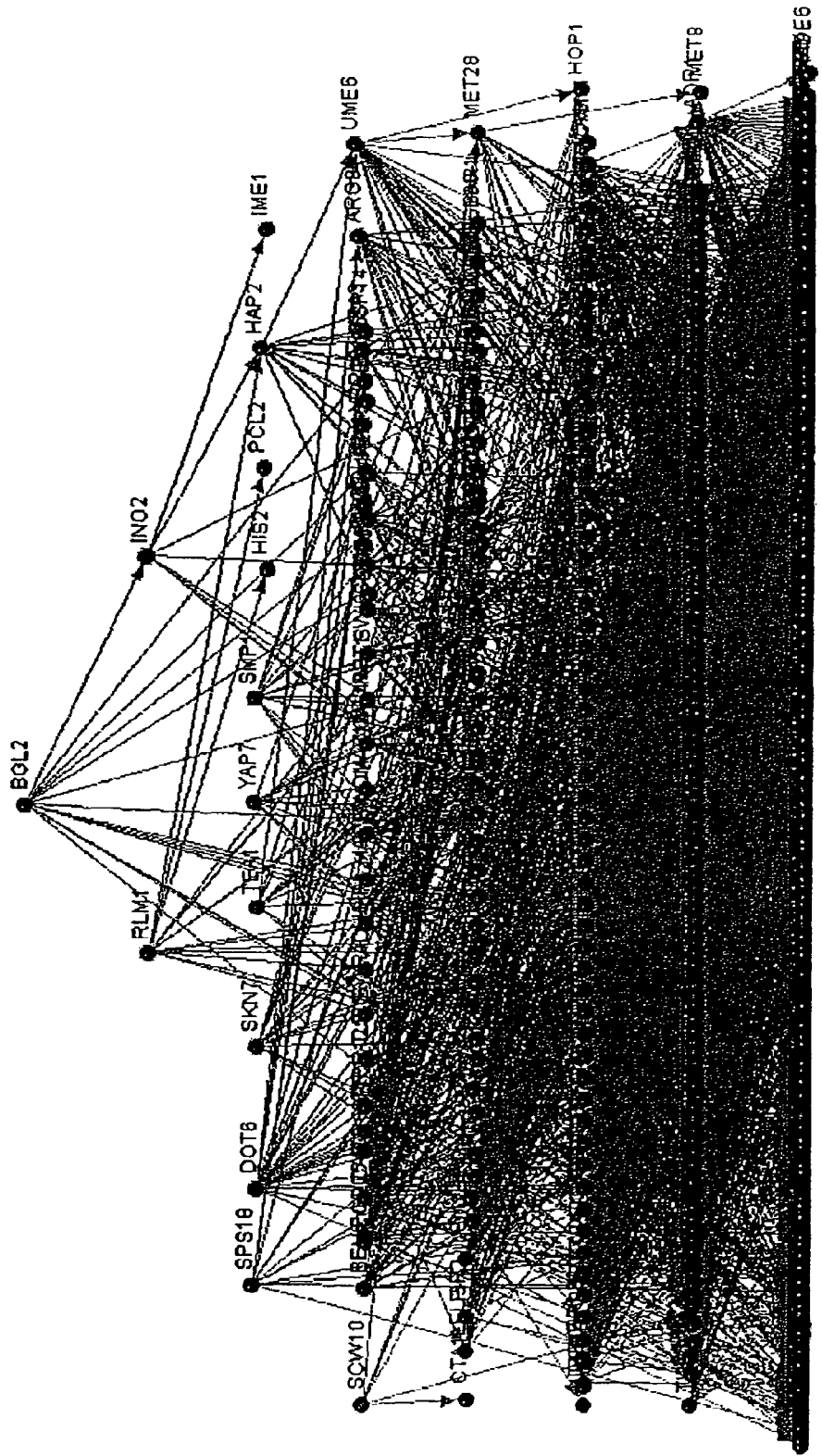
FIG. 3 depicts results of a disruptant-based study and analysis of this invention in yeast in which 552 nodes representing the included genes and 2953 putative regulatory links among these genes.

We constructed a gene expression data library using full-genome yeast c-DNA microarrays. The library was comprised of expression experiments on 120 yeast strains, each with one gene disrupted by homologous recombination. Each of the genes in this library was selected for experimentation because it was reported in the Yeast Proteome Database (YPD) to be a factor involved in transcription regulation. Previously reported gene regulatory networks show that genes can interact with themselves and with other regulatory genes (L. Shoudan, *Pac. Sym. Bio.*, 3, 18-29, 1998). To reconstruct hierarchical regulatory relationships from the expression library, in certain embodiments, we developed a novel Boolean algorithm that accommodates common looped regulatory relationships. As shown in FIG. 2, gene regulatory relationships modeled by this method can be represented as a directed graph of up-regulation or down-regulation of gene expression between 2 given genes of the 5871 genes measured in the each expression experiments. We constructed a 552 genes member model of regulatory control relationships and then further constrained a sub-network model composed of 98 well known transcription factors. The resultant model, shown in FIG. 3, contains a total of 552 nodes representing the included genes and 2953 putative regulatory links among these genes.

Figure 4:
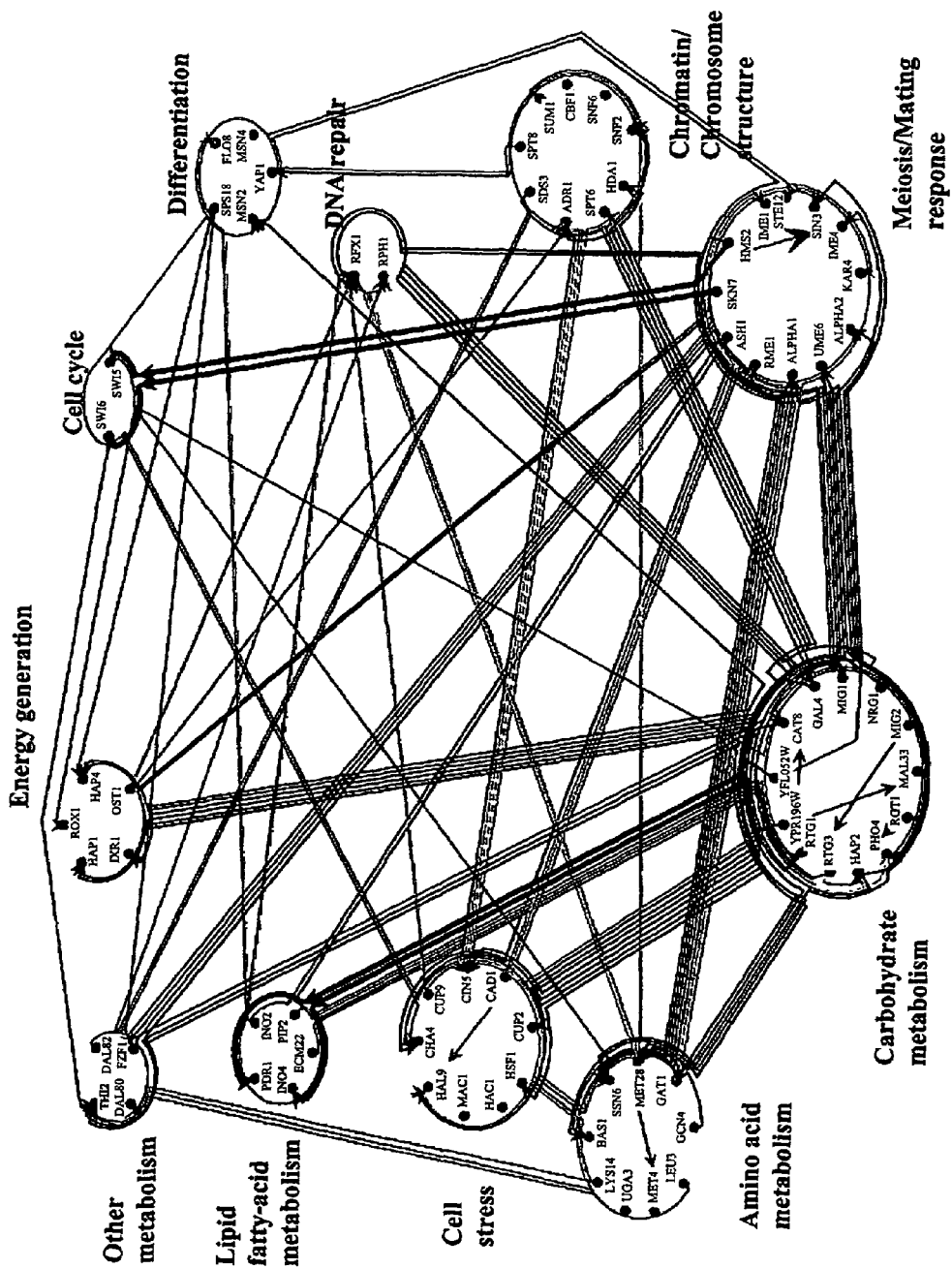
FIG. 4 depicts a transcription factor regulatory network model of this invention classified by cellular functional roles (CFR) in yeast. In this model, there were 98 transcription factors grouped by cellular functional roles according to information provided in the Yeast Proteome Database. Genes inside the circles are grouped into a given cellular functional category. Regulatory control relationships are depicted with colored lines. Colors indicate the category of genes from which the control relationships emanate. Blue: Carbohydrate metabolism, Bluish purple: Chromatin/Chromosome structure, Brown: Energy generation, Dark Green: Other metabolism, Gray: DNA repair, Green: Lipid, fatty acid metabolism, Light Green: Amino acid metabolism, Orange: Cell stress, Red: Meiosis/Mating response, Pink: Differentiation, Purple: Cell cycle. The bold red lines indicate regulatory control of transcription factors related to cell cycle originating from genes in the meiosis/mating response group. The bold blue lines indicate control relationships emanating from the carbohydrate metabolism group exerting influence over genes in the lipid fatty-acid metabolism group. Several control lines emanating from "carbohydrate metabolism" are depicted. In sharp contrast, only 2 individual genes, SKN7 and HMS2 independently influence cell cycle related gene expression.

In certain embodiments, we classified transcription factors in the network model according to cellular functional roles (CFR) as defined in YPD. FIG. 4 shows the control relationships among classified transcription factors in the network. Only SKN7 and HMS2 directly influenced expression of cell cycle related genes. We identified several control lines emanating from "carbohydrate metabolism" genes to all other functional gene groups. This finding is consistent with the energy dependent nature of many cellular processes and metabolic pathways.

As shown in FIG. 4, a distinct feature is that expression levels of lipid fatty-acid metabolism transcription factors were exclusively under control of carbohydrate metabolism transcription factors. This relation was given an account of interactions among proteins involved in phospholipid synthesis pathway with the glucose response pathway, the lipid signaling pathway and other lipid synthesis pathways have been reported (M. Hiesinger et al., *Curr. Genet.*, 39, 68-76, 2001).

Figure 5:
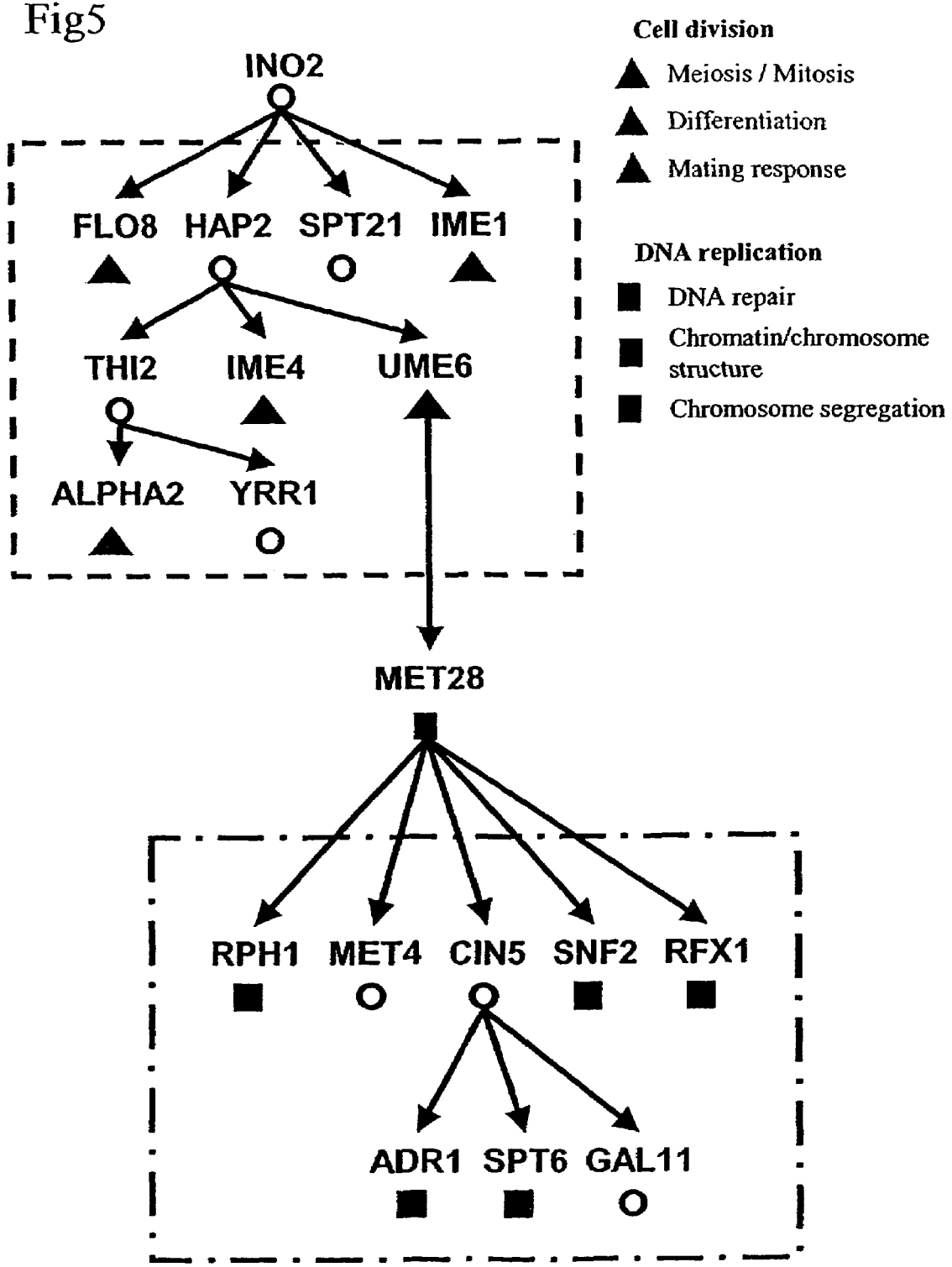
FIG. 5 depicts a detailed view of a gene regulatory sub-network of transcription factors reconstructed from Boolean analysis of gene expression experiments on disruptant mutant yeast strains. Black lines indicate a regulatory relationship, with the arrows showing the direction of expression influence. The colors and shapes of the nodes denote the general categories of cellular function of the gene product according to their descriptions in the YPD. Genes related to cell division mechanisms are indicated with triangular nodes and genes related to DNA repair and chromosome structure are depicted with squares. The elucidated network shows novel topological control relationships among genes related to meiosis, the mating response and DNA structure and repair mechanisms via UME6 and MET28. Genes related to meiosis and mating response genes are downstream of a cascade regulated by INO2 and a further sub-grouping of genes related to DNA repair and structure appears hierarchically downstream of MET28.

Our new methods were employed to further explore detailed relationships between expression regulatory genes, such as transcription factors with regulatory and non-regulatory genes, from all of gene expression experimental data. One can characterize regulatory roles of genes with unreported biological function by virtue of their expression control by and/or over genes with known function. FIG. 5 shows an example of newly elucidated control relationships among transcription factors involved in cell division regulation and DNA replication/repair regulation. We found two discrete functional branches in the sub-network that correspond to cell division regulation and DNA replication/repair are linked by UME6 and MET28, indicating the important role of these two transcription factors in coordinating expression regulation of these interdependent regulatory pathways. MET28, as its name suggests, was previously characterized as a transcription factor related to methionine metabolism (L. Kuras et al., *Embo Journal*, 15, 2519-2529, 1996). The novel putative role for Met28p in regulation of chromosome segregation is supported by its reported interaction with known chromosomal segregation component Smc1p, as part of a larger nexus of chromosomal segregation proteins, in mating-type two-hybrid assays (J. R. S. Newman et al., *Proc. Natl. Acad. Sci.*, 97, 13203, 2000).

Through sequence analysis of coding sequences and upstream regions of genes in the above-mentioned sub network, we validated the sequence level control mechanisms between transcription factors and their target genes and DNA binding sequences. In the case of UME6, which is known as a global transcriptional regulation of many meiotic genes (K. S. Bowdish et al., *Mol. Cell. Biol.*, 15, 2955, 1995; I. Rubin-Bejerano et al., *Mol. Cell. Biol.*, 16, 2518, 1996) and its control system, we performed Multiple Expectation-Maximization for motif Elicitation (MEME) analysis of regions upstream of the 34 genes controlled by UME6 in our model (T. L. Baifley et al., *Proceedings of the Second International Conference on Intelligent Systems for Molecular Biology*, 28-36, AAAI Press, Menlo Park, Calif., 1994). We found two consensus sequences, TAGCCGCCGA (SEQ ID NO: 1) and TGGGCGGCTA (SEQ ID NO: 2) that were present in 14.7% and 32.4% of the 34 genes respectively, and that had significant P values according to the MEME search. According to the TRANSFAC database, TAGCCGCCGA (SEQ ID NO: 1) is defined as the binding site of Ume6p (K. S. Bowdish et al., *Mol. Cell. Biol.*, 15, 2955, 1995) and TGGGCGGCTA (SEQ ID NO: 2) is reported to be the binding site of a repressor of CAR1 (R. M. Luche et al., *Mol. Cell. Biol.*, 10, 3884, 1990) which were repressed by a three components complex containing Ume6p (Ume6p, Sin3p and Rpd3p) (F. Messenguy et al., *J. Bacteriol.*, 182, 3158, 2000). Aside from the Ume6p related binding motifs, no other MEME consensus sequence was present upstream of the 11 meiosis related genes, a finding which suggests that these 11 genes are regulated exclusively by UME6 and that Ume6p directly influences their expression. Only two other genes possessed the putative binding sequence but did not show expression influence on the count of UME6 in our experiments.

Experimentally driven discovery of network models of expression control allows for specific biological insights relevant to gene regulatory pathways that are not readily reconstructed from the available biological literature or present in pre-compiled pathway databases. We have shown here that such a system is useful in discovering novel gene function information as well as novel regulatory mechanisms. Use of this and similar strategies to elucidate hierarchical regulatory pathways from full genome expression libraries will allow for rapid insight into transcription regulation that can be applied to rational drug discovery and agrochemical targeting.

Methods

Boolean Network Inference Algorithms

A gene expression matrix E is created from a set of gene disruption experiments. The value of matrix element E(a,b) indicates the expression ratio of gene 'b' to the normal condition in the disruptant in which gene 'a' which is caused by the deletion of gene 'a'.

(1) Using the gene expression matrix E, if the intensity of gene 'b' is changed higher than a given threshold value $\theta$, or is changed lower than a given threshold $1/\theta$ resulting from the disruption of gene 'a', it is defined that gene 'a' affects gene 'b' in directly or indirectly and the value of element (a,b) in the binary matrix R is set to 1; R(a,b)=1. Thus the binary matrix R is created by cutting the value of each element in the gene expression matrix E at the threshold ($\theta$ or $1/\theta$).

(2) In the binary matrix R, if there is the relation that gene 'a' and 'b' affect each other, that is R(a,b)=R(b,a)=1, we cannot decide which gene is located at the upper stream. This is the limitation or disadvantage of this method, however, we introduce an equivalence set, which makes a set of the group consisting of genes affecting each other and the group is assumed to be one gene.

(3) Ordering genes (topological sort) Equivalence sets have the semi-order relation and we can be drawn up equivalence set in semi-order (topological sort) to infer the network (4) Skeleton matrix; semi-ordered accessibility matrix between equivalence sets includes indirect affections. In order to remove them and to make a skeleton matrix, we set the rank to each equivalence set defined as follows: Equivalence set belonging to rank 1 gives no indirect affection to another equivalence sets. Equivalence set belonging to rank 3 gives direct affection to the sets with rank 2 and does indirect affection to ones with rank 1. After setting the rank to each equivalence set, remove all indirect affection from the semi-ordered accessibility matrix.

(5) Draw multi-level digraph; draw the lines between nodes based on the value of each element in the skeleton matrix.

Microarray Experiments

Information on gene expression can be obtained using any conventional methods known in the art. For example, microarrays can be used in which complementary DNAs (cDNA) unique to each gene whose expression is to be measured are placed on a substrate. RNA obtained from samples can be analyzed by hybridization to corresponding cDNA, and can be detected using a variety of methods. In some embodiments, it can be desirable to use a microarray detectors and/or methods as described in U.S. Provisional Patent Application Ser. No. 60/382,669, filed May 23, 2002, herein incorporated fully by reference.

We collected gene expression data using full-genome yeast c-DNA microarrays (J. R. S. Newman et al., *Proc. Natl. Acad. Sci.*, 97, 13203, 2000). BY4741 (MATa, HIS3D1, LEU2D0, MET15D0, URA3D0) served as the wild type strain. Gene disruptions for strain BY4741 were purchased from Research Genetics, Inc. Cells were inoculated and grown in YPD (1% yeast extract, 1% bacto-peptone, 2% glucose) at 30° C. until $OD_{600}$ reached 1.0 in the logarithmic growth phase and harvested to isolate mRNA for assay of gene expression. The parental strain was the control used for each disruptant strain.

Data Normalization

We measured the quantities of 5871 mRNA species from 155 disruptants by cDNA microarray assay. A difference in fluorescent strength between Cy3, Cy5 causes bias of the expression quantity ratio. We normalized the expression quantity ratios of each expression profile. The ratio bias had a fixed trend in each spotted block, thus we calculated a linear regression to normalize the mean value ratio of each block to 1.0. The logarithm value of the ratio was used to indicate the standard expression level, therefore we found the logarithm value of ratio and calculated the average and standard deviation of these log values (see table 1). The Standard Deviation (SD) of expression levels of all spotted genes from the UME6 (YDR207C) disruptant expression array for which UME6 is defined as a "Global Regulator" in YPD[33] disruptant was 0.4931, therefore we recognize that there may be an unacceptable number of errors in array data whose overall SD was larger than 0.5. Thus, in certain embodiments, one can eliminate such experiments from analysis. It can be appreciated that one can select the SD of the data in different ways. By selecting a SD of less than 0.5, one can take a relatively conservative approach, in that errors of the above type are relatively unlikely to affect the overall gene network inference. However, one can appreciate that SD of less than 0.4, less than 0.3, less than 0.2, less than 0.1, less than about 0.05, less than about 0.01, less than about 0.005, or less than about 0.001 can be selected.

Selection of Genes

In YPD, 314 genes were defined as "Transcription Factors", and 98 of these have previously been studied for control mechanism. The expression profile data of 552 genes including the genes that controlled by this 98 "Transcription factors" were selected from 5871 profiles. Thus we constructed the gene regulatory network from the expression profile data set based on the values of these 552 genes in 120 gene disruption experiments.

II. Estimation of Genetic Networks and Functional Structures Between Genes Using Bayesian Networks and Nonparametric Regression 1. Introduction Improvement of the genetic engineering provides us enormous amount of valuable data such as microarray gene expression data. The analysis of the relationship among genes has drawn remarkable attention in the field of molecular biology and Bioinformatics. However, due to the cause of dimensionality and complexity of the data, it will be no easy task to find structures, which are buried in noise. To extract the effective information from biological data, thus, theory and methodology are expected to be developed from a statistical point of view. Our purpose is to establish a new method for understanding the relationships among genes clearer. Example 1 below provides the mathematical basis for these methods.

In certain embodiments of this invention, Bayesian networks are adopted for constructing genetic networks using microarray gene expression data from a graph-theoretic approach. Friedman and Goldszmidt (N. Friedman et al., in M. I. Jordan, ed., *Learning in Graphical Models*, Kluwer Academic Publisher 421 (1998)) proposed an interesting method for constructing genetic links by using Bayesian networks. They discretized the expression value of genes and considered to fit the models based on multinomial distributions. However, a problem still remains in choosing the threshold value for discretizing (by not only the experiments). The threshold value assuredly gives essential changes of affects of the results and unsuitable threshold value leads to incorrect results. On the other hand, recently, Friedman et al. (N. Friedman et al., *J. Comput Biol.*, 7, 601-620, 2000) pointed out that discretizing could result in losses of information. To use the expression data as continuous values, they used Gaussian models based on linear regression. However this model can only detect linear dependencies and cannot produce a complete picture of relationships. We developed a new method for constructing genetic networks using Bayesian networks. To capture not only linear dependencies but also nonlinear structures between genes we use nonparametric regression models with Gaussian noise. Nonparametric regression has been developed in order to explore the complex nonlinear form of the expected responses without the knowledge about the functional relationship in advance. Due to the new structure of the Bayesian networks, a suitable criterion was needed for evaluating models. Thus, this invention includes a new criterion from Bayesian statistics. By using these methods we overcame defects of previous methods and attained more information. In addition, our methods include previous methods as special cases. We validated our methods through the analysis of the *S. cerevisiae* cell cycle data.

We found that using Bayesian analysis according to these methods, we could identify upstream causative relationships between genes, thereby identifying potential therapeutic targets.

2. Bayesian Networks and Nonparametric Regression

Using a Bayesian network framework, we consider a gene as a random variable and decompose the joint probability into the product of conditional probabilities. For example, if we have a series of observations of the random vector, we can denote the probability of obtaining a given observation can depend upon the conditional probability densities. In certain embodiments, one can use nonparametric regression models for capturing the relationships between the variables. A variety of graphic tools can be used to elucidate the relationships. For example, polynomials, Fourier series, regression spline gases, B-spline bases, wavelet bases and the like can be used for defining a graph of gene relationships. One difficulty in selecting a proper graph is to properly evaluate variance and noise in the system.

3. Criterion for Choosing a Proper Graph

In certain embodiments, we can let $\pi(\theta_G|\lambda)$ be the prior distribution on the unknown parameter $\theta_G$ with hyper parameter vector $\lambda$ and let $\log \pi(\theta_G|\lambda) = 0(n)$. The marginal probability of the data $X_n$ is obtained by integrating over the parameter space, and we choose a graph G with the largest posterior probability. Friedman and Goldszmidt (N. Friedman et al., in M. I. Jordan, ed., *Learning in Graphical Models*, Kluwer Academic Publisher 421 (1998)) considered the multinomial distribution as the Bayesian network model and also supposed the Dirichlet prior on the parameter $\theta_G$. In this case, the Dirichlet prior is the conjugate prior and the posterior distribution belongs to the same class of distribution. Then a closed form solution of the integration in (4) is obtained, and they called it BDe score for choosing graph. A BDe score is confined to the multinomial model, and we propose a criterion for choosing graph in more general and various situations.

A problem of constructing criteria based on the above model is how to compute the integration. Some methods that can be used include Markov chain, and Monte Carlo methods. In certain embodiments of this invention, we use the Laplace approximation for integrals. Thus, the optimal graph is chosen such that the criterion BNRC in equation (5) is minimized.

This criterion is derived under $\log(\theta_G|\lambda)=0(n)$. If $\log(\theta_G|\lambda)=0(1)$, the mode $\theta_G$ is equivalent to the maximum likelihood estimate, MLE, and the criterion resulted in a Bayesian information criterion, known as BIC by removing the higher order terms $0(n^{-j})(j \geq 0)$. Konishi (S. Konishi (in Japanese), *Sugaku*, 52, 128, 2000) provided a general framework for constructing model selection criteria based on the Kullback-Leibler information and Bayes approach. As can be seen from Example 1 below, the final graph can be selected as a minimizer of the BNRC and does not have to minimize each local score, $BNRC_j$, because the graph is constructed as acyclic.

4. Estimating Graphs and Related Structures Using a BNRC Criterion

Figure 8:
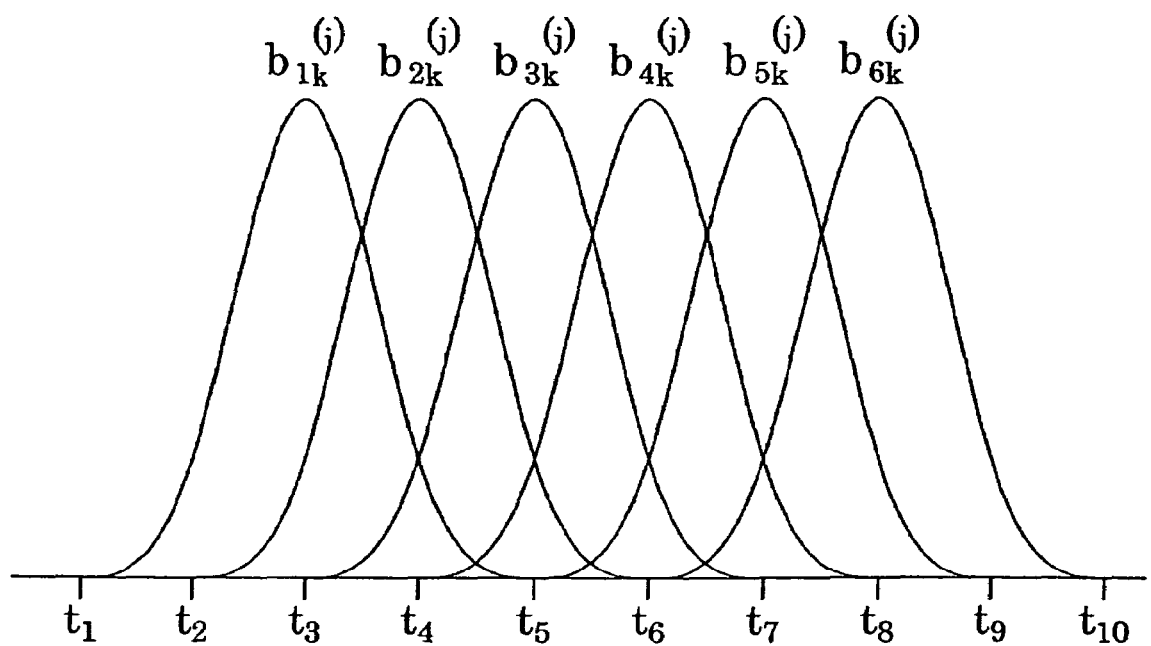
FIG. 8 example of 6 B-splines of degree 3. $t_1, \ldots, t_{10}$ are called knots. These knots are equally spaced.

For example, one can express our method in an illustration. Essential points of our method are the use of the nonparametric regression and the new criterion for choosing graph from Bayesian statistics. As for nonparametric regression in Section 2 of Example 1, we use B-splines as the basis functions. FIG. 8 is an example of B-splines of degree 3 with equidistance knots $t_1 \ldots, t_{10}$. By using a backfitting algorithm, the modes can be obtained when the values of $\beta_{jk}$ are given. The backfitting algorithm is shown in Example 1 below.

The modes depend on the hyper parameters $\beta_{jk}$, and we have to choose the optimal value of $\beta_{jk}$. In the context of our method the optimal values of $\beta_{jk}$ are chosen as the minimizers of $BNRC_j$.

The B-splines coefficient vectors can be estimated by maximizing equation (6) of Example 1. The modes of equation (6) are the same as the penalized likelihood estimates and we can look upon the hyper parameters $\lambda_{jk}$ or $\beta_{jk}$ as the smoothing parameters in penalized likelihood. Hence, the hyper parameters play an important role for fitting the curve to the data.

5. Computation Experiments

We used Monte Carlo simulations to examine the properties of our method. Data were generated from an artificial graph and structures between variables (FIG. 9) and then the results summarized as follows: The criterion BNRC can detect linear and nonlinear structure of the data. A BNRC score may have a tendency toward over growth of the graph. Therefore, we use Akaike's information criterion, known as AIC and use both methods. AIC was originally introduced as a criterion for evaluating models estimated by maximum likelihood methods. But estimates by this method are the same as the maximum penalized likelihood estimate and is not MLE. The trace of $S_{jk}$ shows the degree of freedom of the fitted curve and is a great help. That is to say, if $trS_{jk}$ is nearly 2, the dependency can be considered linear. We use both BNRC and AIC for deciding whether to add a parent variable.

To validate these methods, we analyzed the *S. cerevisiae* cell cycle data discussed by Spellman et al. (P. Spellman, et al., *Mol. Biol. Cell*, 9, 3273, 1998) and Friedman et al. (N. Friedman et al., *J Comput Biol.*, 7, 601-620, 2000). The data were collected from 800 genes and 77 experiments. We set the prior probability $\pi_G$ as constant, because we have no information about the size of the true graph. The nonparametric regressors are constructed of 20 B-splines. The number of B-splines can be varied as desired. The hyperparameters control the smoothness of fitted curve and it can be desirable to select hyper parameters and the number of B-splines to provide a good fit to the data with a minimum of B-splines.

Figure 10:
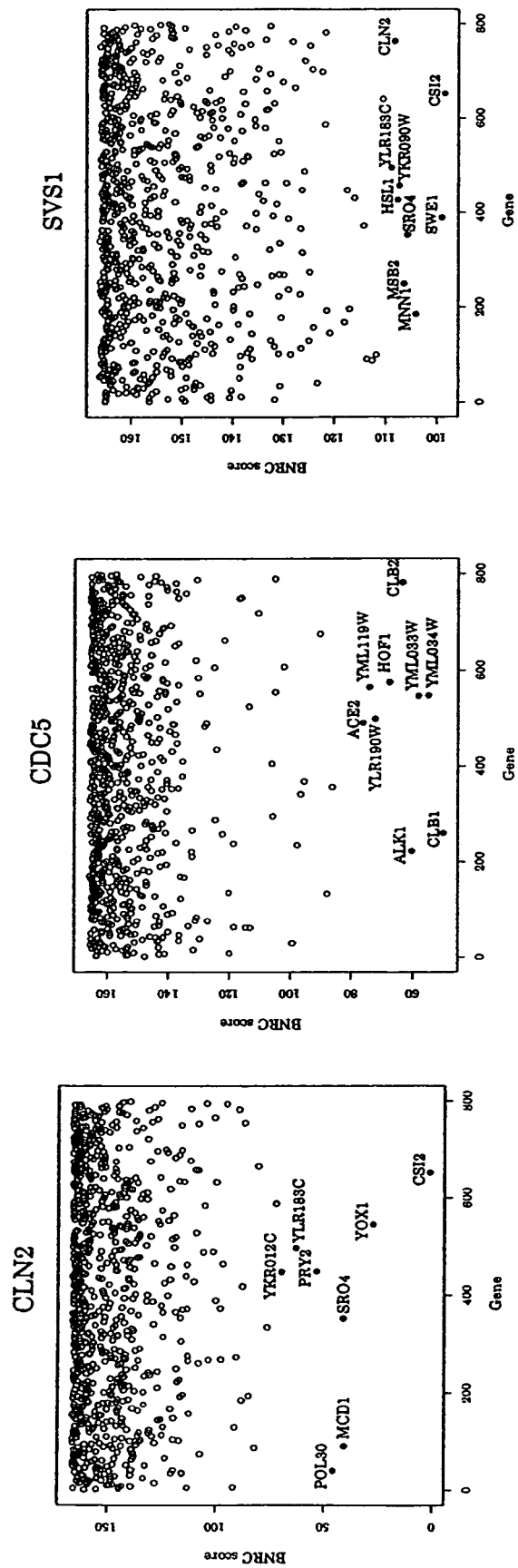
FIGS. 10 a, 10b and 10c BNRC scores for CNL2, CDC5 and SVS1.

The results of the analysis can be summarized as follows: FIG. 10 shows BNRC scores when we predicted CLN2, CDC5 and SVS1 by one gene. The genes which give smaller BRNC scores produce a more reliable effect on the target gene. We can observe that which gene is associated with the target gene and we find the gene set which strongly depend on the expression of the target gene. In fact, we can construct a brief network by using these information. We can look upon the optimal graph as a revised version of the brief network by taking account of the effect of interactions. If there is a linear dependency between genes, the score BNRC is good when the parent-child relationship is reversed. Therefore, the directions of the causal associations in the graph are not strict, especially when the dependencies are almost linear. There are some genes that mediate Friedman et al.'s (N. Friedman et al., *J Comput Biol.*, 7, 601-620, 2000) result, such as MCD1, CSI2, YOX1 and so on. Most of these genes have been reported to play an important role. A large number of the relationships between genes are nearly linear. But we could find some nonlinear dependencies which linear models can rarely find.

Figure 11:
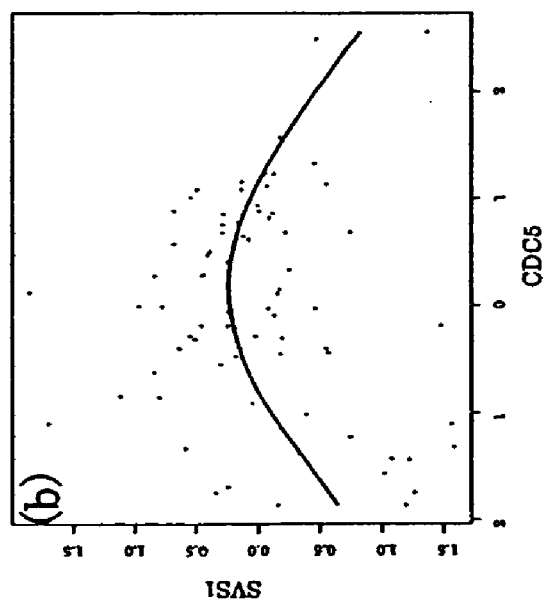
FIGS. 11a-11d cell cycle data and smoothed estimates. (a) (b) Friedman et al. (2000), BNRC=57.71, AIC=167.96; (c) and (d) proposed method, BNRC=32.53, AIC=140.16
Figure 11:
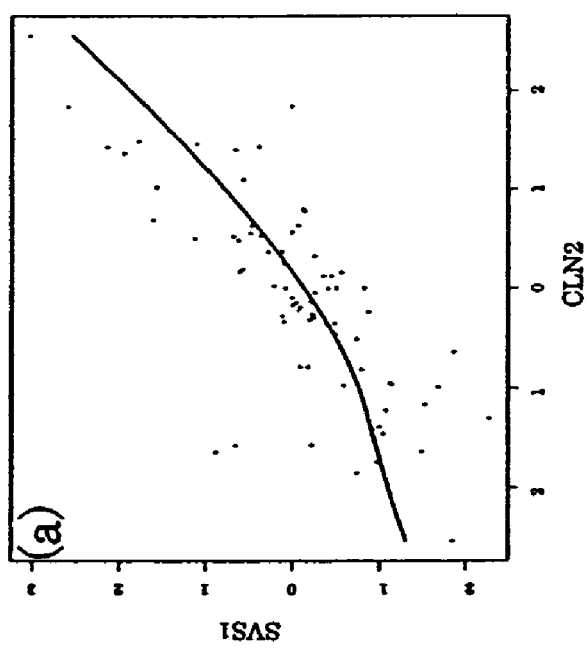
Figure 11:
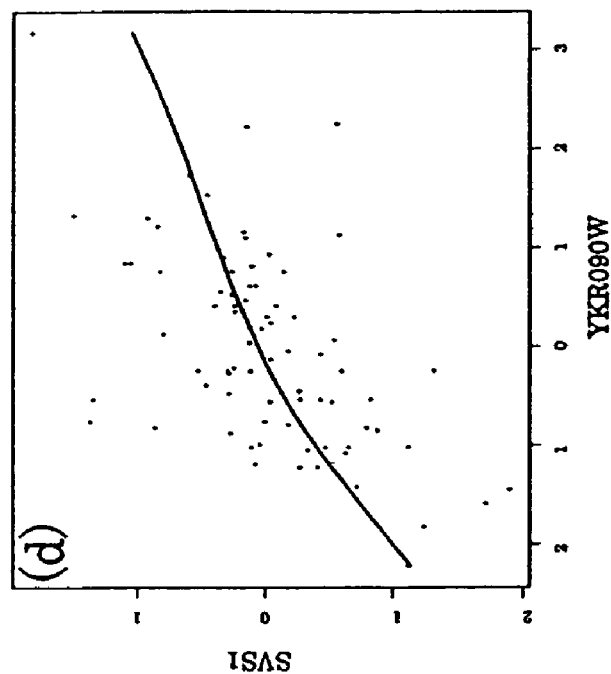
Figure 11:
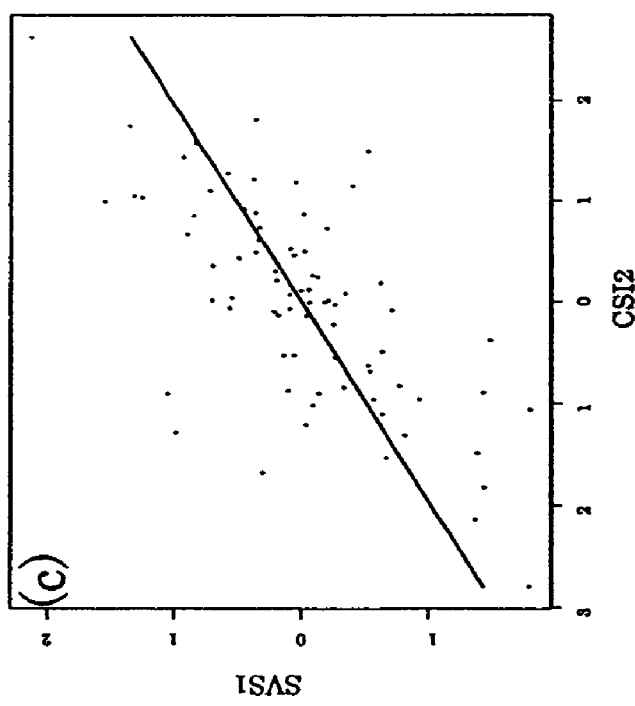
Figure 12:
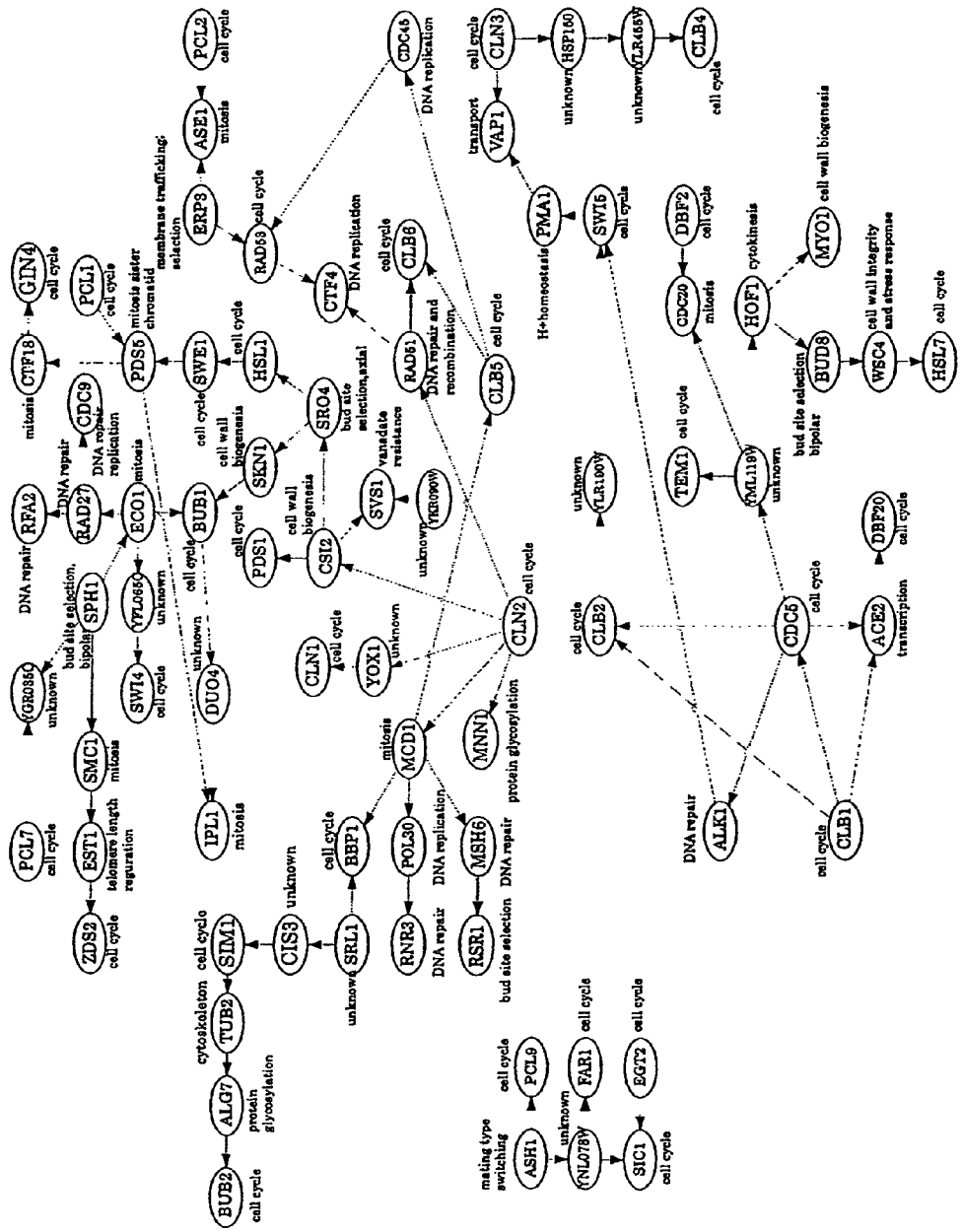
FIG. 12 cell cycle data result.

FIG. 12 shows the estimated graph associated with genes which were classified by their processes into cell cycle and their neighborhood. We omitted some branches in FIG. 12, but important information is shown. As for the networks given by us and Friedman et al. (N. Friedman et al., *J Comput Biol.*, 7, 601-620, 2000), we confirmed parent-children relationships and observed that both two networks are similar to each other. Especially, our network includes typical relationships which were reported by Friedman et al. As for the differences between both networks, we attention the parents of SVS1. Friedman et al. employed CLN2 and CDC5 as the parent genes of SVS1. On one hand, our result gives CSI2 and YKR090W for SVS1. Our candidate parent genes were found to be more appropriate than those of Friedman et al. Our model suitably fits to both cases in FIG. 11. Especially, we conclude that CDC5 has weak effects on SVS1 compared with other genes in Spellman's (P. Spellman, et al., *Mol. Biol. Cell*, 9, 3273, 1998) data (see also FIG. 10). In fact, as the parent gene of SVS1, the order of BNRC score of CDC5 is $247^{th}$. Considering the circumstances mentioned above, our method can provide us valuable information in understandable and useful form.

Figure 6:
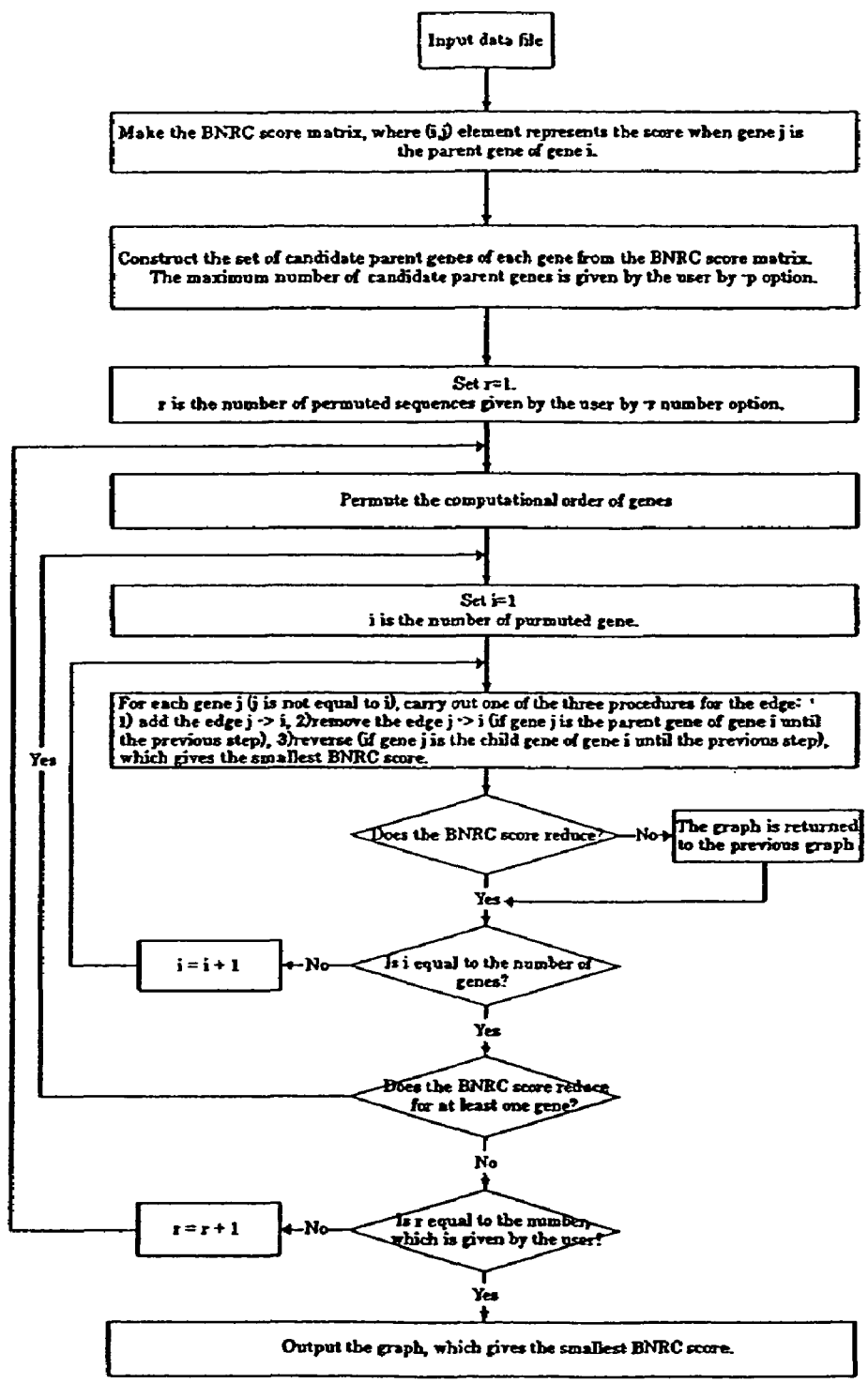
FIG. 6 depicts a flow chart showing methods of this invention for the estimation of network relationships between genes using Bayesian inference and minimization of a BNRC criterion.

FIG. 6 schematically depicts a method of this invention for determining gene network relationships.

6. Discussion

The new methods for estimating genetic networks from microarray gene expression data by using Bayesian network and nonparametric regression provide improved accuracy. We derived a new criterion for choosing graph theoretically, and represented its effectiveness through the analysis of the cell cycle data. The advantages of our methods include (1) we can use the expression data as continuous values; (2) we can also detect nonlinear structures and can visualize their functional structures being easily understandable; and (3) automatic search can accomplish the creation of an optimal graph.

Friedman et al's (N. Friedman et al., *J Comput Biol.*, 7, 601-620, 2000) method retains known parameters such as threshold value for discretizing and hyper parameters in the Dirichlet priors selected by trial and error and were not optimized in a narrow sense. On the other hand, our method can automatically and appropriately estimate any parameter based on criterion which has sound theoretical basis.

In other embodiments we can derive criterion BNRC in more general situations. By way of example, we can construct graph selection criterion based on other statistical models.

III. Nonlinear Modeling of Genetic Network by Bayesian Network and Nonparametric Regression with Heterogeneous Error Variances and Interactions In other embodiments, one can use different statistical methods for constructing genetic networks from microarray gene expression data based on Bayesian networks. In these embodiments, we estimate the conditional distribution of each random variable. We consider fitting the nonparametric regression models with heterogeneous error variances and interactions for capturing the nonlinear structures between genes. Once we set a graph using Bayesian network and nonparametric regression, a problem still remain to be solved in selecting an optimal graph, which gives a best representation of the system among genes. A new criterion for choosing graph from Bayes approach contains the previous methods for estimating networks using Bayesian methods. We demonstrated the effectiveness of proposed method through the analysis of *Saccharomyces cerevisiae* gene expression data newly obtained by disrupting 100 genes.

1. Introduction

Use of Bayesian networks can be effective methods in modeling the phenomena through the joint distribution of a large number of variables. Friedman and Goldszmidt (N. Friedman et al., in M. I. Jordan, ed., *Learning in Graphical Models*, Kluwer Academic Publisher 421 (1998)) discretized the expression values and assumed the multinomial distributions as candidate statistical models. Pe'er et al. (D. Pe'er, et al., *Bioinformatics*, 17, Suppl.1, 215 (ISMB 2001)) investigated the threshold value for discretizing. Friedman et al. (N. Friedman et al., *J Comput Biol.*, 7, 601-620, 2000) pointed out that discretizing can lose some information considered to fit the linear regression models, which analyze the data as continuous. However, the assumption that the parent genes depend linearly on the objective gene is not always warranted. Imoto et al described the use of nonparametric additive regression models for capturing not only linear dependencies but also nonlinear relationships between genes.

In certain embodiments, we use Bayesian networks and the nonparametric heteroscedastic regression which can be more resistant to effect of outliers and can also capture effects of the interactions of parent genes.

After setting the graph, we evaluate its goodness or closeness to the true graph, which is completely unknown. The construction of a suitable criterion becomes important. Friedman and Goldszmidt (N. Friedman et al., in M. I. Jordan, ed., *Learning in Graphical Models*, Kluwer Academic Publisher 421 (1998)) derived the criterion, BDe, for choosing a graph based on multinomial models and Dirichlet priors. However, unknown hyper parameters in Dirichlet priors remain and one can only set the values experientially. We derived a new criterion for choosing a graph from Bayes approach. The criterion automatically optimizes the all parameters model and gives the optimal graph. In addition, our method includes the previous methods for constructing genetic network by Bayesian network. To show the effectiveness of the new method we analyze gene expression data of *Saccharomyces cerevisiae* by disrupting 100 genes.

2. Bayesian Network and Nonparametric Heteroscedastic Regression Model with Interactions Suppose that we have n sets of data $\{x_1, \ldots, x_n\}$ of the p-dimensional random variable vector $X=(X_1 \ldots, X_p)^T$ where $x_i = x_{i1}, \ldots x_{ip})^T$ and $x^T$ denotes the transpose of x. In microarray gene expression data, n and p correspond to the numbers of arrays and genes. Under Bayesian network framework, we considered a directed acyclic graph G and Markov assumption between nodes. The joint density function is then decomposed into the conditional density. Assuming that the conditional densities are parameterized by the parameter vectors $\theta_j$ and the effective information is extracted from these probabilistic models.

We then used nonparametric regression strategy for capturing the nonlinear relationships between $x_{ij}$ and $p_{ij}$. In many cases, this method can capture the objective relationships very well. When the data, however, contain outliers especially near the boundary on the domain $\{p_{ij}\}$, nonparametric regression models sometimes can lead to unsuitable smoothed estimates, i.e., the estimated curve exhibits some spurious waviness due to the effects of outliers. To avoid this problem, the nonparametric regression model with heterogeneous error variances as described below in Example 2.

Criterion For Choosing a Graph

Once we set a graph, a statistical model (equation 8 of Example 2) based on the Bayesian network and nonparametric regression can be constructed and can be estimated by a suitable method. However, to choose the optimal graph, which gives a best approximation of the system underlying the data, it is undesirable to use the likelihood function as a model selection criterion, because the value of likelihood becomes larger in a more complicated model. Hence, a statistical approach based on the generalized or predictive error, Kullback-Leibler information, Bayes approach and so on (20) can be desirable. We therefore constructed a criterion for evaluating a graph based on our model (equation 8 of Example 2) from Bayes approach.

A criterion for evaluating the goodness of the graph can be constructed from Bayesian theoretic approach as follows:

(1) Obtain the posterior probability of the graph by the product of the prior probability of the graph $\pi_G$ and the marginal probability of the data;
(2) Remove the standardized constant, the posterior probability of the graph is proportional to equation 9 of Example 2.
(3) Using Bayes approach, choose a graph such that $\pi(G|X_n)$ is maximum.
(4) Determine if the computation involves a high dimensional integral (equation 9 of Example 2).
(5) If Yes to (4), use equation 11 of Example 2. (See D. Heckerman, A tutorial on learning with Bayesian networks, in M. I. Jordan ed., *Learning in Graphical Models* 301, Kluwer Academic Publisher (1998); L. Tinerey et al., *J. Amer. Statist. Assoc.*, 81, 82 (1986)) for integrals.

Thus, a graph is chosen such that the criterion BNRC is minimal. An advantage of using the Laplace method is that it is not necessary to consider the use of the conjugate prior distribution. Hence modeling in larger classes of distributions of the model and prior is attained.

3. Estimating Genetic Network

Nonparametric Regression

We present methods for constructing a genetic network based on the method described in Section 2 above. The nonparametric regressor (equation 5 of Example 2) has the two components: the main effects component represented by the additive model of each parent gene, and the interactions component. In the additive model, we construct each smooth function $m_{jk}(\cdot)$ by B-splines (equation 9 of Example 2) (see Imoto et al., *Estimation of genetic networks and functional structures between genes by using Bayesian networks and nonparametric regression*, Proc. Pacific Symposium on Biocomputing 2002, In Press; see Example 1 herein).

In the interaction terms, we use a Gaussian radial basis function. In the context of the regression modeling based on the radial basis functions, we used two methods for estimating the centers $z_{jl}$ and the widths. This method can be termed "fully supervised learning." An alternative method determines the values by using only the parent observation data in advance. The latter method can be employed, and a k-means clustering algorithm for constructing the basis functions can be used. Details of the radial basis functions are described further in (T. Andou et al., *Nonlinear regression modeling using radial basis function networks*. Submitted, J. Moody et al., *Neur. Comp.* 1, 281, 1989; and B. D. Ripley, *Pattern recognition and neural networks*, Cambridge University Press (1996)). Hyper parameters control the amount of overlapping among basis functions.

In error variances, we consider a heteroscedastic regression model and assume the structure shown in equation 6 of Example 2. The design of the constants can affect the accuracy of capturing the heteroscedasticity of the data. We set the weights according to equation 12 of Example 2. If the hyper parameter p is set to 0, then the variances are homogeneous. If we use a large value of p, then the error variances of the data, which exist near the boundary on the domain of the parent variables, are large. Hence, if there are outliers near the boundary, this method can reduce their effects and thereby gain suitably smoothed estimates using appropriate values of p.

4. Real Data Analysis

We demonstrated the effectiveness of the above methods through analysis of *S. cerevisiae* gene expression data. We observed the changes of expression level of genes on a microarray by gene disruption. By using this method we revealed gene regulatory networks between genes of *Saccharomyces cerevisiae*. We collected a large number of expression profiles from gene disruption experiments to evaluate genetic regulatory networks. Over 400 mutants are stocked and gene expression profiles are accumulated.

We monitored the transcriptional level of 5871 genes spotted on a microarray by a scanner. The expression profiles of over 400 disruptants were piled up in our database. The standard deviation (SD) of all genes on a microarray was evaluated and the value of SD represented roughly the error of a experiment. We needed the value of 0.5 as the critical point of the standard deviation of the expression ratio of all genes. 107 disruptants including 68 mutants where the transcription factors were disrupted were selected from 400 profiles.

We used 100 microarrays and constructed the genetic network of 521 genes from the above data. 94 transcription factors whose regulating genes are identified were found, and the profiles of 421 genes controlled by 94 factors were selected from 5871 profiles. We constructed the nonparametric regression model using 20 B-splines and 20 radial basis functions. We confirmed that the differences of the smoothed estimates against the various number of the basis functions can not visually be found, because when we use the somewhat large number of the basis functions, the hyper parameters control the smoothness of the fitted curves. We applied the two-genes effect to the interaction components. Hence, the effects of the interactions were obtained as the fitted surfaces and can be visually understandable.

We showed the roles of the hyper parameters in the prior distributions and weight constants. FIG. 13a shows the scatter plot of YGL237C and YEL071W with smoothed estimates by 3 difference values of the hyper parameters. The smoothed estimate depends on the values of the hyper parameters. FIG. 13b depicts the behavior of the BNRC criterion of the two genes in FIG. 13a. We can choose the optimal value of the hyper parameter as the minimizers of the BNRC, and the optimal smoothed estimates (solid curve) can capture structure between these genes well. The dashed and dotted curves are near the maximum likelihood estimate and the parametric linear fit, respectively. The effect of the weight constants w1j, . . . , wnj is shown in FIG. 14a. If we use a homoscedastic regression model, we obtain the dashed curve, which exhibits some spurious waviness due to the effect of the data in the upper-left corner. By adjusting the hyper parameter p in equation 12 of Example 2, the estimated curve resulted in the solid curve. The optimal value of p chosen by minimizing the BNRC criterion (see FIG. 14b). When the smoothed estimate is properly obtained, the optimal value of p tends to zero.

Figure 15:
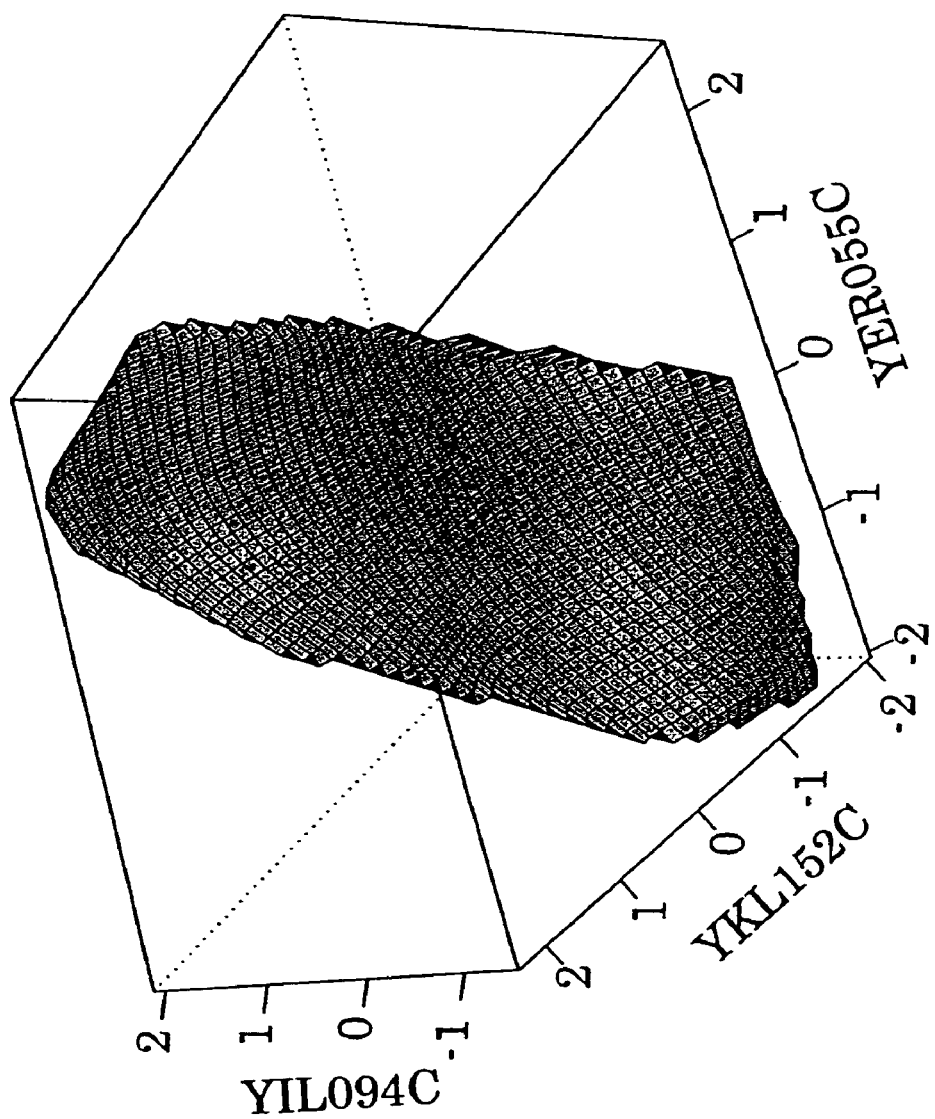
FIG. 15 the estimated surface by nonparametric regression with interaction.

We employed a two-step strategy for fitting the non-parametric regression model with interactions. First, we estimated the main effects represented by the additive B-spline regressors. Next, we fit the interactions components to the residuals. FIG. 15 depicts an example of the fitted surface to the relationship between YIL094C and its parent genes, YKL152C and YER055C. The interaction of the two parent genes leads to over expression when both parent genes increased.

In *Saccharomyces cerevisiae*, the GCN4 gene encodes the transcriptional activator of the "general control" system of amino acid biosynthesis, a network of at least 12 different biosynthetic pathways (G. Albrecht et al., *J. Biol. Chem.*, 273, 12696, 1998). Experiments showed that the consequences of the general control response upon the signal "amino acid starvation" induced by the histidine analogue 3-aminotriazole with respect to GCN4p levels. GCN4 activates transcription of more than 30 genes involved in the biosynthesis of 11 amino acids in response to amino acid starvation or impaired activity of tRNA synthetases (see R. J. Rolfes and A. G. Hinnebusch, *Mol. Cell Biol,* 13, 5099, 1993). Purine biosynthetic genes ADE1, ADE4, ADE5,7 and ADE8 display GCN4-dependent expression in response to amino acid starvation R. J. Rolfes, Id. GCN4 activates transcription of biosynthetic genes for amino acids and purines in response to either amino acid or purine starvation R. J. Rolfes, Id. Those results of experiments show that there are strong relationships between purine metabolism and amino acid metabolism through GCN4. Our map of relationships fit well known relationships between purine and amino acid metabolism.

IV. Bootstrap Nonlinear Modeling of Genetic Network by Using Bayesian Network and Nonparametric Heteroscedastic Regression In other embodiments, we modified the above approaches. A relevant feature of Bayesian network construction is in the estimation of conditional distribution of each random variable. We fit non-parametric regression models with heterogeneous error variances to the microarray gene expression data to capture nonlinear structures between genes. A problem still remained to be solved in selecting an optimal graph, which gives the best representation of the system among genes. We derived a new graph selection criterion from Bayes approach in general situation. The proposed method includes previous methods based on Bayesian networks. We also used a method for measuring the edge intensity and the degree of confidence of the direction of Bayes causality in an estimated genetic network. We demonstrated the effectiveness of the proposed method through the analysis of *Saccharomyces cerevisiae* gene expression data newly obtained by disrupting 100 genes.

Once we set the graph, it is desirable to evaluate its goodness or closeness to the true graph, which is unknown. For our method we needed to establish the method for measuring the edge intensity. We used a "bootstrap" method (B. Efron, *Ann. Stat.,* 7, 1, 1979; B. Efron and R. J. Tibshirani, *An Introduction to the Bootstrap*, Chapman and Hall (1993)) to solve this problem. By using this method, one can measure not only the intensity of edge, but also the degree of confidence of Bayes causality. To show the effectiveness of the proposed method, we analyzed gene expression data of *Saccharomyces cerevisiae* newly obtained by disrupting 100 genes.

1. Bayesian Network and Nonparametric Heteroscedastic Regression for Non-Linear Modeling of a Genetic Network 1.1 Nonlinear Bayesian Network Model As described elsewhere in this application, in the Bayesian network framework, one can consider a directed acyclic graph G and Markov assumption between nodes. The joint density function is then decomposed into the conditional density of each variable. Through formula 1 of Example 3 below, the focus of interest in statistical modeling by Bayesian networks is how one can construct the conditional densities, $f_j$. One can assume that the conditional densities, $f_j$, are parameterized by the parameter vectors, and information is extracted from these probabilistic models as described further in Example 3.

In certain embodiments, one can use nonparametric regression strategies for capturing nonlinear relationships between xij and Pij and suggested that there are many nonlinear relationships between genes and the linear model hardly achieves a sufficient result. In many cases, these methods can capture the objective relationships well. When the data, however, contain outliers, especially near the boundary of the domain, standard nonparametric regression models sometimes lead to unsuitable smoothed estimates, i.e., the estimated curve exhibits some spurious waviness due to the effects of the outliers. To avoid this problem, we fit a nonparametric regression model with heterogeneous error variances. If the number of the parameters in the model is much larger than the number of observations, it has a tendency toward unstable parameter estimates.

In certain cases it can be desirable to use nonparametric regression instead of linear regression, because linear regression cannot evaluate the direction of the Bayes causality or can lead to the wrong direction in many cases. We show an advantage of the new model compared with linear regression through a simple example. Suppose that we have data of $gene_1$ and $gene_2$ in FIG. 17a. We consider the two models $gene_1 \rightarrow gene_2$ and $gene_2 \rightarrow gene_1$, and obtain the smoothed estimates shown in FIGS. 17b and 17c, respectively. We then can decide that the model (b: $gene_1 \rightarrow gene_2$) is better than (c: $gene_2 \rightarrow gene_1$) by our criterion, which is derived in a later section (the scores of the models are (b) 120.6 (c) 134.8). Since we generated this data from the true graph $gene \rightarrow gene_2$, our method yields the correct result. However, if we fit the linear regression model to this data, the mode (c) is chosen (the scores of the linear models are (b) 156.0 (c) 135.8). The method based on linear regression yields an incorrect result in this case, whereas non-linear regression analysis yields a correct result.

Even in the case where the relationship between genes is almost linear. Our method and linear regression can fit the data appropriately. However, using the linear model it is difficult to decide the direction of Bayes causality.

We have previously described the criterion BNRC. We derived the criterion, $BNRC_{hetero}$, for choosing the graph in a general framework. By using the equation (8), the BNRC$_{hetero}$ score of the graph can be obtained by the sum of the local scores, $BNRC_{hetero}$. The optimal graph is chosen such that the criterion $BNRC_{hetero}$ (equation 7 of Example 3) is minimal. An advantage of the Laplace method is that it is not necessary to consider the use of the conjugate prior distribution. Hence the modeling in the larger classes of distributions of the model and prior is attained. Genetic networks are estimated as described further in Example 3. However, regarding error variances, we consider a heteroscedastic regression model and assume the structure shown in equation 3 of Example 3.

Learning Network

In Bayesian network literature, determining the optimal network is an NP-hard problem. To resolve the networks, one can use a "greedy hill-climbing" algorithm as follows:

(1) Step 1: Make the score matrix whose (i, j)-th elements is the $BNRC_{hetero}$ score of the graph $gene_i \rightarrow gene_j$;

(2) Step 2: For each gene, implement one of three procedures for an edge: add, remove, reverse, which gives the smallest $BNRC_{hetero}$;

(3) Step 3: Repeat Step 2 until the $BNRC_{hetero}$ does not reduce further; and (4) Permute the computational order of genes and make many candidate learning orders in Step 3.

Step 4 can be desirable in situations in which a greedy hill-climbing algorithm produces many local minima and the result depends on the computational order of variables. Another problem of the learning network is that the search space of the parent genes is wide when the number of genes is large. In such circumstances, one can restrict the set of candidate parent genes based on the score matrix, which is given by Step 1.

One also can use this learning strategy for learning genetic network and showed the effectiveness of their method by the Monte Carlo simulation method. We also checked the efficiencies of our new model through the same Monte Carlo simulations and found improvements due to the nonparametric heteroscedastic regression model. We illustrate the effectiveness of the heteroscedastic regression model in the next subsection.

Hyperparameters

Figure 17:
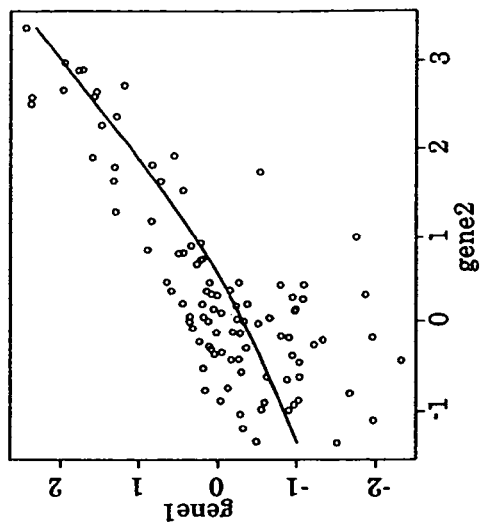
FIGS. 17a-17c simulated data: The true causality is gene$_1 \rightarrow$ gene$_2$. (a) scatter plot of the simulated data. (b) smoothed curve of the graph gene$_1 \rightarrow$ gene$_2$. (c) smoothed curve of the graph gene$_2 \rightarrow$ gene$_1$. These curves are obtained by the proposed method.
Figure 17:
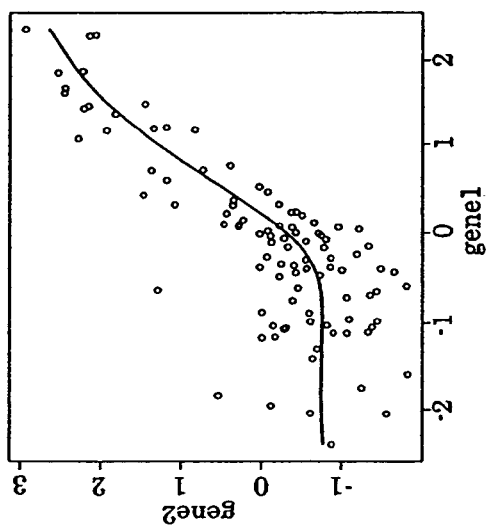
Figure 17:
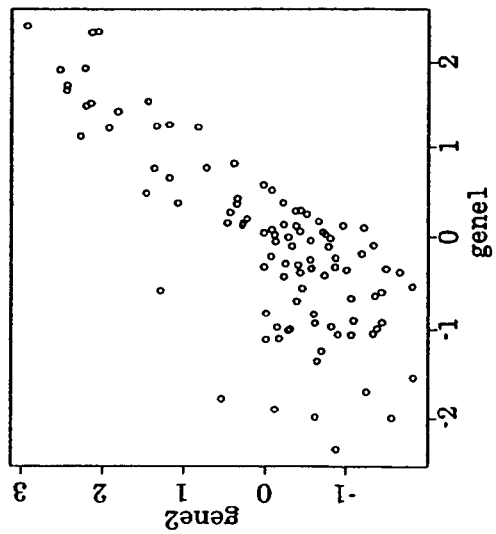

Consider the nonparametric regression model defined in equation 4 of Example 3. The estimate $\theta_j$ is a mode of log $\pi(\theta_j|X_n)$ and can depend on the hyper parameters used. We constructed the nonparametric regression model using 20 B-splines. We confirmed that the differences of the smoothed estimates against the various number of the basis functions cannot be visually detected. When we used a somewhat large number of basis functions, the hyper parameters control the smoothness of the fitted curves. FIG. 17a shows the scatter plot of YGL237C and YEL071W with smoothed estimates for 3 different values of the hyper parameters. The details of the data are shown in later section. The smoothed estimate strongly depended on the values of the parameters. FIG. 17b depicts the behavior of the $BNRC_{hetero}$ criterion of the two genes in FIG. 17a. One can choose the optimal value of the hyper parameter as the minimizer of the $BNRC_{hetero}$ and the optimal smoothed estimate (solid curve in FIG. 17a can capture the structure between these genes well. The dashed and dotted curves are near the maximum likelihood estimate and the parametric linear fit, respectively.

Figure 20C:
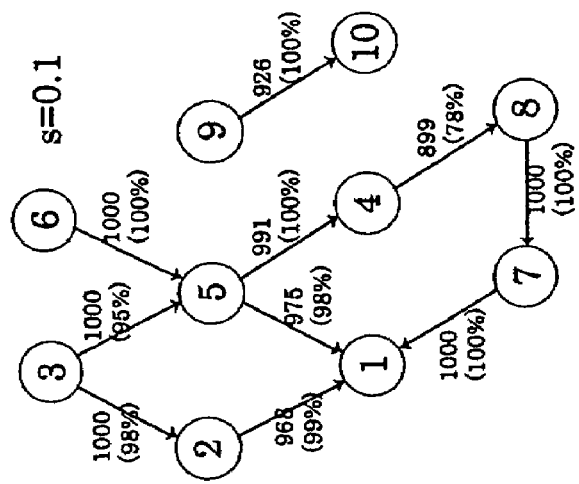
FIGS. 20a-20c the results of the Monte Carlo simulations. (a): True network. (b): Result for s=0.2. (c): Result for s=0.1. The number next to edge represents the number of estimated connections from 1000 Monte Carlo experiments. The percentage includes the information of the edge direction. For example, in s=0.2, the connection between X5 and X1 appeared 958 times from 1000 Monte Carlo experiments and those 97% is the correct direction from (X5 to X1).
Figure 20B:
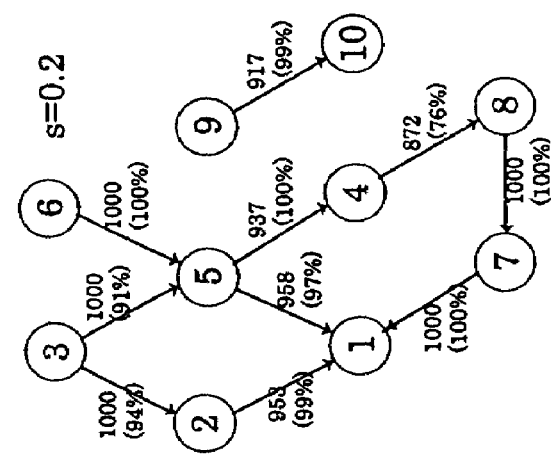
Figure 20A:
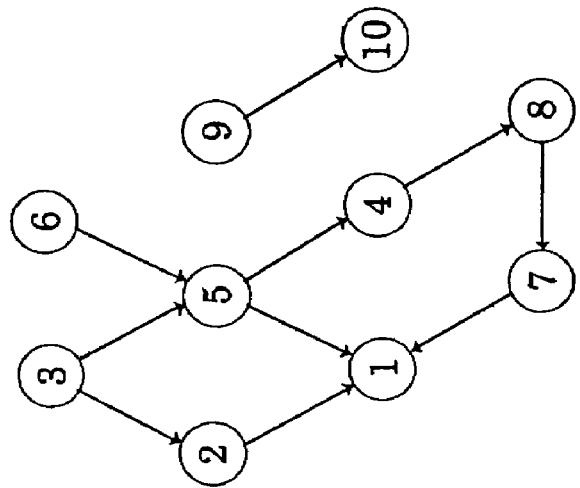

Effects of the weight constants wij, ... wnj is shown in FIG. 20a. If one uses the homoscedastic regression model, we obtain the dashed curve, which exhibits some spurious waviness due to the effect of data in the upper-left corner. By adjusting the hyper parameter pj in equation 9 of Example 3, the estimated curve resulted in the solid curve. The optimal value of pj can be also chosen by minimizing the $BNRC_{hetero}$ criterion see FIG. 20b. When the smoothed estimate is properly obtained, the optimal value of pj tends to zero.

Finally, in Section 3 of Example 3, we provide an algorithm for estimating the smoothed curve and optimizing the hyper parameters.

Step 1: Fix the hyper parameter $p_j$;

Step 2: Initialize: $\gamma_{jk}=0, k-1, \ldots, q_j$;

Step 3: Find the optimal $\beta_{jk}$ by repeating Steps 3-1 and 3-2;

Step 3-1: Compute: $\gamma jk = (B_{jk}^T W_{jk} B_{jk} + n\beta_{jk} K_{jk})^{-1} B_{jk}^T W_{jk} \times \left( x_{(j)} - \sum_{k' \neq k} \beta_{jk'} \gamma_{jk'} \right)$, for fixed $\beta_{jk}$.

Step 3-2: Evaluate: Repeat Step 3-1 against the candidate value of $\beta_{jk}$ and choose the optimal value of $\beta_{jk}$, which minimizes the $BNRC_{hetero}$.

Step 4: Convergence: repeat Step 3 for k=1, ..., qj, 1, ..., qj, 1, ... until a suitable convergence criterion is satisfied.

Step 5: Repeat Step 1 to Step 4 against the candidate value of pj, and choose the optimal value of pj, which minimizes the $BNRC_{hetero}$.

Bootstrap Edge Intensity and Degree of Confidence of Bayes Causality

We measured the intensity of the edge and the degree of confidence of the direction of the Bayes causality in the estimated genetic network by the bootstrap method. The algorithm can be expressed as follows:

(1) Make a bootstrap gene expression matrix $X^*_n = \{x^*_1, \ldots x^*_n\}^T$. by randomly sampling n times, with replacement, from the original gene expression data $\{x_1, \ldots, x_n\}$;

(2): Estimate the genetic network from $X^*_n$ based on the proposed method; and (3): Repeat Step 1 and Step 2 T times.

From this algorithm, we obtain T genetic networks. We define the bootstrap intensity of edge and direction of Bayes causality as follows.

Edge intensity

If the edges $gene_i \rightarrow gene_j$ and $gene_j \rightarrow gene_i$ exist $t_1$ and $t_2$ times in the T networks, respectively, we define the bootstrap edge intensity between $gene_i$ and $gene_j$ as $(t_1+t_2)/T$.

Degree of Confidence of the Bayes Causality

If $t_1 > t_2$, we adopt the direction $gene_i \rightarrow gene_j$ and define that the degree of confidence of causality is $t_1/(t_1+t_2)$. However, we can use a certain threshold. For example, we set a real number $\delta$ and decide $gene_1 \rightarrow gene_2$ if $t_1/t_1+t_2) > \delta$.

At least two ways can be used to show the resulting network. First, it can be desirable to determine the edge intensity and the degree of confidence of direction of Bayes causality in the original genetic network. One can add the intensity to each edge in the original network. From this network, one can find the reliability of the original network. Second, one can superpose the bootstrap networks and original network. However, the superposed network contains edges that have small intensities. Therefore, we can set a certain threshold value and remove the edges whose intensities are under the threshold. While setting the threshold remains a problem, it is just a visualization problem. We note that the superposed network may not hold the acyclic assumption, but much effective information are in this network.

Real Data Analysis

We illustrate the effectiveness of our methods through the analysis of *Saccharomyces cerevisiae* gene expression data. We monitored the transcriptional level of 5871 genes spotted on a microarray by a scanner. The expression profiles of over 400 disruntants were stored in our database. The standard deviation (SD) of the levels of all genes on a microarray was evaluated. The value of SD represents roughly the experimental error. In our data, we considered the value of 0.5 as the critical point of the accuracy of experiments. We evaluated the accuracy of those profiles based on the standard deviation of the expression ratio of all genes. 107 disruptants including 68 mutants where the transcription factors were disrupted could be selected from 400 profiles.

It can be appreciated that other values of SD can be considered critical for accuracy. For example, SD values can be 0.4, 0.3, 0.2, 0.1, about 0.05, about 0.01, about 0.005, about 0.001, or any other value considered to produce information having a desired reliability.

We used 100 microarrays and constructed a genetic network of 521 genes from the above data. The 94 transcription factors whose regulating genes have been clearly identified were found. The profiles of the 521 genes controlled by those 94 factors were selected from 5871 profiles.

Figure 16:
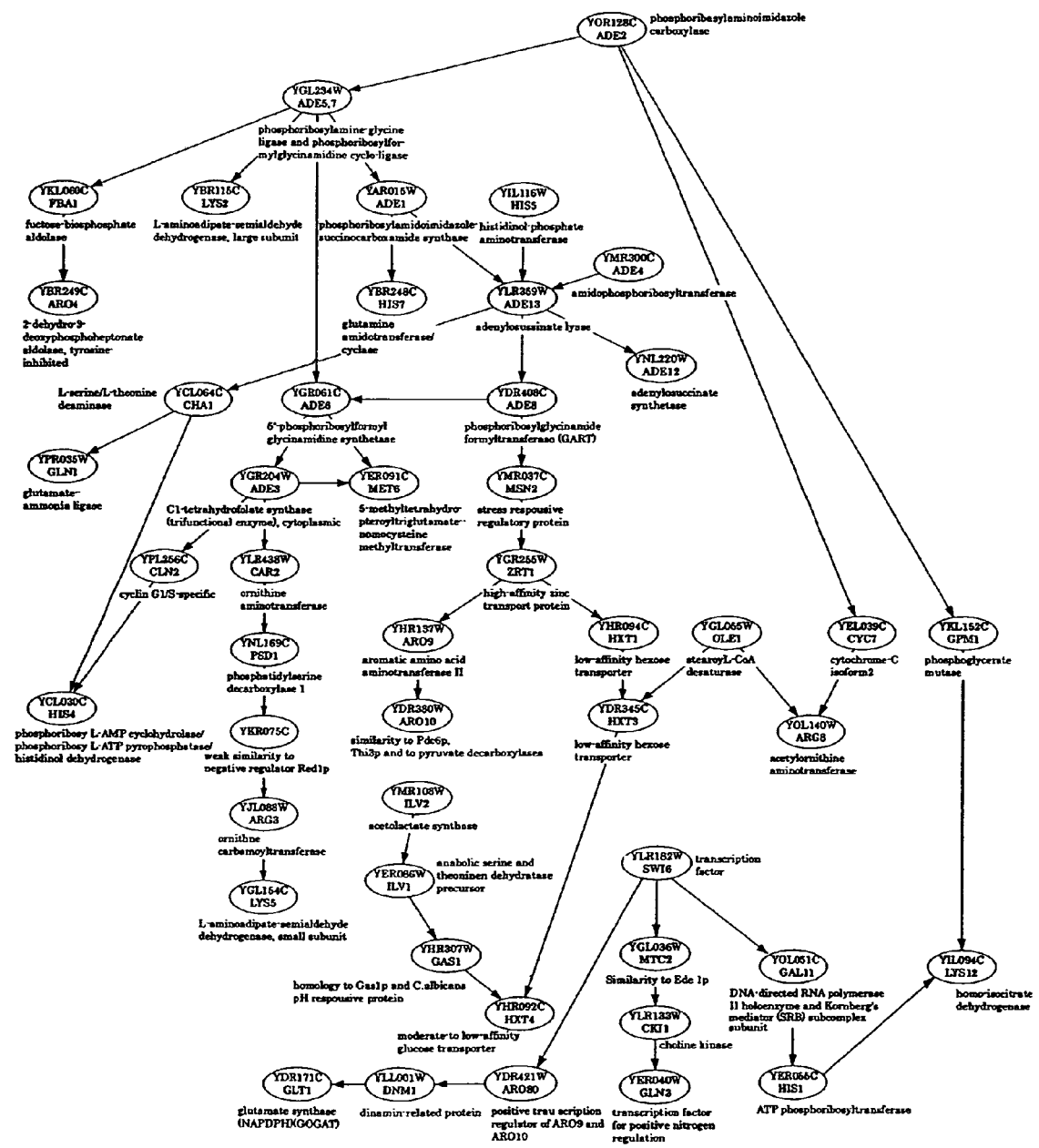
FIG. 16 the resulted partial network of the analysis of 521 Saccharomyces cerevisiae genes.

Table 1 shows the gene pairs with high bootstrap edge intensities. "Inte." and "Dire. "mean the bootstrap edge intensity and the degree of confidence of direction of Bayes causality, respectively. "F. "is the function of parent gene, i.e. "+" and "−" are respectively, induce and repress. If we cannot decide whether the function is to induce or repress, we enter "0" in "F." FIG. 16 shows the resulting partial network by superposing 100 bootstrap networks. We denote the edge intensity by the line width, and the number next to the line is the degree of confidence of the direction of Bayes causality. From Table 1, we conclude the following: Over 60% gene pairs in the Table 1 agree with the biological knowledge. Most of the genetic sets, whose value of edge intensity equals 1, have the relation of "Related protein" in the YPD data base. Some other genetic sets, like ARO genes and PDR genes, have the same regulatory systems. These results indicated that there were some relations between genes which were previously unknown and revealed for the first time using the methods of this invention. We also notice that the other 9 genetic sets have the relation "Functional genomics". The relation of "Functional genomics" indicated that some relations were revealed by previous information derived from large-scale, high-throughput experiments such as microarray analysis, designed to uncover properties of large groups of proteins.

Studies on the regulation of the purine biosynthesis pathway in Saccharomyces cerevisiae revealed that all the genes encoding enzyme required for AMP de novo biosynthesis are repressed at the transcriptional level by the presence of extracellular purines. Two transcriptional factors, named Bas1p and Bas2p, are required for regulated activation of the ADE genes (B. Daignan-Fornier and Fink, *Proc. Natl. Acad. Sci. USA*, 89, 6746-6750, 1992) as well as some histidine biosynthesis genes (V. Denis et al., *Mol. Microbiol.*, 30, 556-566, 1998). Those purine biosynthetic genes, like ADE1, ADE4, ADE5,7 and ADE8, display GCN4-dependent expression in response to amino acid starvation (R. J. Rolfes and A. G. Hinnebusch, *Mol. Cell Biol*, 13, 5099, 1993). The starvation for purines stimulates GCN4 translation by the same mechanism that operates in amino acid-starved cells leads to a substantial increase in HIS4 expression, one of the targets of GCN4 transcriptional activation. FIG. 16 indicates that those ADE genes and histidine biosynthesis genes are related with both BAS1 and GCN4.

A desirable feature of the methods of this invention involve the use of non-parametric heteroscedastic regression for capturing nonlinear relationships between genes and heteroscedasticity of the expression data. Therefore, our methods can be useful in the analysis of an unknown system, such as human genome, genomes from other eukaryotic organisms, prokaryotic organisms and viruses.

V. Statistical Analysis of a Small Set of Time-Ordered Gene Expression Data Using Linear Splines Recently, the temporal responses of genes to changes in their environment has been investigated using cDNA microarray technology by measuring the gene expression levels at a small number of time points. Conventional techniques for time series analysis are not suitable for such a short series of time-ordered data. The analysis of gene expression data has therefore usually been limited to a fold-change analysis, instead of a systematic statistical approach.

We use the maximum likelihood method together with Akaike's Information Criterion to fit linear splines to a small set of time-ordered gene expression data in order to infer statistically meaningful information from the measurements. The significance of measured gene expression data is assessed using Student's t-test.

Previous gene expression measurements of the cyanobacterium *Synechocystis* sp. PCC6803 were reanalyzed using linear splines. The temporal response was identified of many genes that had been missed by a fold-change analysis. Based on our statistical analysis, we found that about four gene expression measurements or more are needed at each time point. These conclusions and further description can be found in Example 4 herein below.

1. Introduction

In recent years, many cDNA microarray experiments have been performed measuring gene expression levels under different conditions. Measured gene expression data have become widely available in publicly accessible databases, such as the KEGG database (M. Nakao et al. *Genome Informatics*, 10, 94-103, 1999).

In some of these experiments, the steady-state gene express levels are measured under several environmental conditions. For instance, the expression levels of the cyanobacterium *Synechocystis* sp. PCC6803 and a mutant have been measured at different temperatures, leading to the identification of the gene Hik33 as a potential cold sensor in this cyanobacterium (I. Suzuki et al., *Synechocystis. Mol. Microbiol.*, 40, 235-244, 2001).

In other experiments, the temporal pattern of gene expression is considered by measuring gene expression levels at a number of points in time. Gene expression levels that vary periodically have for instance been measured during the cell cycle of the yeast *Saccharomyces cerevisiae* (P. Spellman et al., *Mol. Biol. Cell*, 9, 3273, 1998). The gene expression levels of the same yeast species were measured during the metabolic shift from fermentation to respiration (J. L. DeRisi et al., *Science*, 278, 680-686, 1997). In those experiments, environmental conditions were changing slowly over time. Conversely, gene responses to an abruptly changing environment can be measured. As an example, the gene expression levels of the cyanobacterium *Synechocystis sp. PCC 6803* were measured at several points in time after a sudden shift from low light to high light (Y. Hihara et al., *The Plant Cell*, 13, 793-806, 2001).

In cDNA microarray experiments, gene expression levels are typically measured at a small number of time points. Conventional techniques of time series analysis, such as Fourier analysis or autoregressive or moving-average modeling, are not suitable for such a small number of data points. Instead, the gene expression data are often analyzed by clustering techniques or by considering the relative change in the gene expression level only. Such a "fold-change" analysis may miss significant changes in gene expression levels, while it may inadvertently attribute significance to measurements dominated by noise. In addition, a fold-change analysis may not be able to identify important features in the temporal gene expression response.

Several techniques to analyze gene expression data, such as deriving Boolean or Bayesian networks, have been used in the past (S. Liang et al., *Proc. Pac. Symp. on Biocomputing*, 3, 18-29, 1998; T. Akutsu et al. *Bioinformatics*, 16, 727-734, 2001; N. Friedman et al., *J. Comp. Biol.*, 7, 601-620, 2000; and S. Imoto et al. *Proc. Pac. Symp. On Biocomputing*, 2002, In Press). Describing gene interactions in terms of a regulatory network is can be desirable, and developing a network model may benefit from gene expression data obtained for a large number of time points. However, data for large numbers of time points for a large number of genes is currently not available. Although the number of genes in a given organism may be on the order of several thousands, gene expression levels are often measured at only five or ten points in time.

So far, a systematic method has been lacking to statistically analyze gene expression measurements from a small number of time-ordered data. We developed a strategy based on fitting linear spline functions to time-ordered data using the maximum likelihood method and Akaike's Information Criterion (H. Akaike, Information theory and an extension of the maximum likelihood principle, Research Memorandum No. 46, Institute of Statistical Mathematics, Tokyo, In Petrov, B. N., Csaki, F. (eds.), *2nd Int. Symp. on Inf. Theory*, Akadémiai Kiadó, Budapest (1973), pp. 267-281, 1971). The significance of the gene expression measurements is assessed by applying Student's t-test. This allows us to infer information from gene expression measurements while taking the statistical significance of the data into consideration. This kind of analysis can be viewed as an additional step toward building gene regulatory networks. As an example, we reanalyzed the gene expression measurements of the cyanobacterium *Synechocystis* sp. PCC 6803 (Y. Hihara et al., *The Plant Cell*, 13, 793-806, 2001). Using linear splines, information can be deduced and measured data that is missed by methods using the fold-change only. By repeating our analysis with a subset of the available data, we determined how many measurements are needed at each time point in order to reliably estimate the linear spline function.

2. Methods

Student's t-Test

We assessed whether the measured gene expression rations are significantly different from unity. If for a specific gene, we can conclude that for all time points the measured expression rations are not significantly different from unity, we can eliminate that gene from further analysis. The significance level can be established by applying Student's t-test for each time point separately. Since multiple comparisons are being made for each gene, the value of the significance level a should be chosen carefully.

We define $H_0^{(i)}$ as the hypothesis that for a given gene the expression ratio is equal to unity at a given time point $t_i$, and $H_0$ as the hypothesis that for a given gene the expression rations at all time points are equal to unity. If we denote $\alpha$ as the significance level for rejection of hypothesis $H_0$, and $\alpha'$ as the significance level for rejection of hypothesis $H_0^{(i)}$, then $\alpha'$ and $\alpha$ are related via $1-\alpha=(1-\alpha')^a$, in which a is the number of time points at which the gene expression ratio was measured. Note that by expanding the right hand side in a first order Taylor series, this equation reduces to Bonferoni's method for adjusting the significance levels (see also T. W. Anderson and J. D. Finn, *The New Statistical Analysis of Data*, Springer-Verlag, New York, 1996).

By performing Student's t-test at every time point for each gene using $\alpha'$ as the significance level, we will find whether $H_0^{(i)}$ and therefore $H_0$ should be rejected. If $H_0$ is not rejected, we can conclude that that gene is not significantly affected by the experimental manipulation, and should therefore not be included in further analyses. If for a given gene the null hypothesis $H_0$ is rejected, we conclude that that gene was significantly affected by the experimental manipulation.

Analyzing Time-Ordered Data Using Lenear Splines

Figure 22:
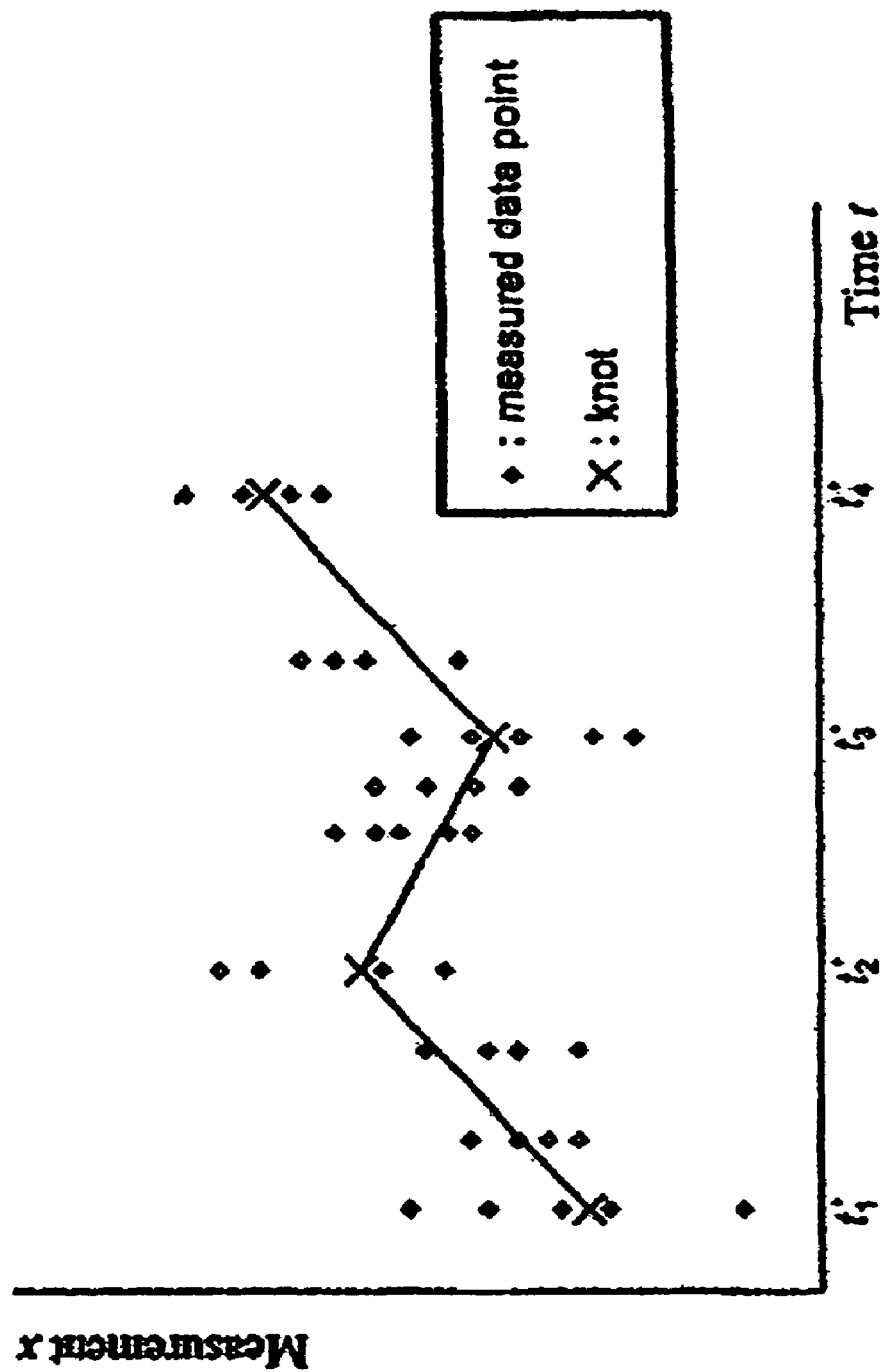
FIG. 22 a conceptual diagram of a linear spline function fitted to measured data.

Next, we analyzed temporal gene expression response for genes that were found to be significantly affected. The measured gene expression ratios formed a small set of time-ordered data, to which we fit a linear spline function. A linear spline function is a continuous function consisting of piecewise linear functions, which are connected to each other at knots (J. H. Friedman et al, *Technometrics*, 31, 3-39, 1989; T. Higuchi. Whereas cubic splines are used more commonly, for the small number of data pints we can use linear spline functions more suitably. A conceptual example of a linear spline function with knots $t^*_1, t^*_2, t^*_3, t^*_4$, is shown in FIG. 22. We wish to fit a nonparametric regression model of the form $x_j=g(t_j)+\epsilon_j$ to these data, in which g is a linear spline function and $\epsilon_j$ is an independent random variable with a normal distribution with zero mean and variance $\sigma^2$.

We estimated the linear spline function g using the maximum likelihood method. The probability distribution of one data point xj given t j, is shown in equation 3 of Example 4. The log-likelihood function for the n data points is then given by equation 4 of Example 4. The maximum likelihood estimate of the variance $\sigma^2$ can be found by maximizing the log-likelihood function with respect to $\sigma^2$. This yields equation 5 of Example 4. In *Saccharomyces cerevisiae*, the GCN4 gene encodes the transcriptional activator of the "general control" system of amino acid biosynthesis, a network of at least 12 different biosynthetic pathways (G. Albrecht et al., *J. Biol. Chem.*, 273, 12696, 1998). Experiments showed that the consequences of the general control response upon the signal "amino acid starvation" induced by the histidine analogue 3-aminotriazole with respect to GCN4p levels. GCN4 activates transcription of more than 30 genes involved in the biosynthesis of 11 amino acids in response to amino acid starvation or impaired activity of tRNA synthetases (see (R. J. Rolfes and A. G. Hinnebusch, *Mol. Cell Biol*, 13, 5099, 1993). Purine biosynthetic genes ADE1, ADE4, ADE5,7 and ADE8 display GCN4-dependent expression in response to amino acid starvation R. J. Rolfes, Id. GCN4 activates transcription of biosynthetic genes for amino acids and purines in response to either amino acid or purine starvation R. J. Rolfes, Id. Those results of experiments show that there are strong relationships between purine metabolism and amino acid metabolism through GCN4. Our map of relationships fit well known relationships between purine and amino acid metabolism.

The fitted model depends on the number of knots q. The number of knots can be chosen using Akaike's Information Criterion, known as the AIC (Akaike, H. *Information Theory and an extension of the maximum likelihood principle*. Research Memorandum No. 46, Institute of Statistical Mathematics, Tokyo (1971) in Petrov, B. N., Csaki, F. (eds.), $2^{nd}$ Int. Symp. On Inf. Theory, Akademiai Kaido, Budapest (1973), pp. 267-281; see also Priestly, M. B. Spectral Analysis and Time Series. Academic Press, London 1974)). For each value of q, we calculated the value of the AIC after fitting the linear spline function as described in Example 4, and selected the value of q that yields the minimum value of the AIC. The case q=2 corresponds to linear regression. For the special case q=1, we effectively fit a flat line to the data. If we find that for a particular gene, the minimum AIC is achieved for the constant function (q=1), then we can conclude that the expression level of that gene was unaffected by the experimental manipulations. Gene expression data are typically given in terms of expression rations. At time zero, the expression ration is equal to unity by definition. This fixed point can be incorporated easily in our methodology by modifying equation 7 of Example 4. The minimum value of $\hat{c}^2$ can be achieved by choosing the linear spline function shown in equation 17 of Example 4.

3. Results

Student's t-Test

We herein illustrate using Student's t-test and fitting linear spline functions, by reanalyzing measured gene expression profile of the *cyanobacterium* sp. PCC 6803 after a sudden exposure to high light (HL) (Y. Hihara et al., *The Plant Cell*, 13, 793-806, 2001). The expression levels of 3079 ORFs were measured at zero, fifteen minutes, hone hour, six hours, and fifteen hours both for cyanobacteria exposed to HL and cyanobacteria that remained in the low light (LL) condition. Table 2 shows the number of measurements at each time point. Data from the cDNA expression measurements were obtained from the KEGG database (M. Nakao et al. *Genome Informatics*, 10, 94-103, 1999).

The data used for the original analysis (Y. Hihara et al., *The Plant Cell*, 13, 793-806, 2001) may not be identical to the raw data submitted to KEGG (Y. Hihara, personal communication). In addition, two measurement sets out of six at the t=15 minutes time point are missing in the KEGG database. Recalculating the gene expression rations from the raw data gives numbers close to the previously published results.

After subtracting the background signal intensities from the HL and LL raw data, global normalization was applied and the ration of the HL to the LL signal intensities was calculated to find the relative change in gene expression level with respect to the control (LL) condition. In the fold-change analysis, a gene was regarded as being affected by HL if its expression level changed by a factor of two or more. The statistical significance of such changes was assessed heuristically by considering the size of the standard deviation of the measurements (Y. Hihara et al., *The Plant Cell*, 13, 793-806, 2001).

The results of the Student's t-test on the gene expression rations of each gene separately are shown in Table 3. At a significance level of $\alpha=0.001$, 167 genes were found to be significantly affected by HL condition. Note that we would expect about three type-1 errors among these 167 genes. In comparison, 164 ORFs were found to be affected by the HL condition in the original analysis (Y. Hihara et al., *The Plant Cell*, 13, 793-806, 2001).

By considering the fold-change for the psbD2 gene (slr0927), it was concluded that it was not significantly induced by HL (Y. Hihara et al., *The Plant Cell*, 13, 793-806, 2001). This was remarkable, since this gene had been reported to be inducible by HL in the cyanobacterium *Synechococcus* sp. PCC 7942 (S. A. Bustos, et al. *Mol. Gen. Genet.*, 232, 221-230, 1992; S. Anandan et al., *J. Bacteriology* 179, 6865-6870, 1997). However, performing Student's t-test on the gene expression data for the psbD2 gene at t=6 hours yields p $3.3 \times 10^{-5}$, suggesting that this gene was indeed affected by HL.

Analysis Using Linear Spline Functions

Figure 23:
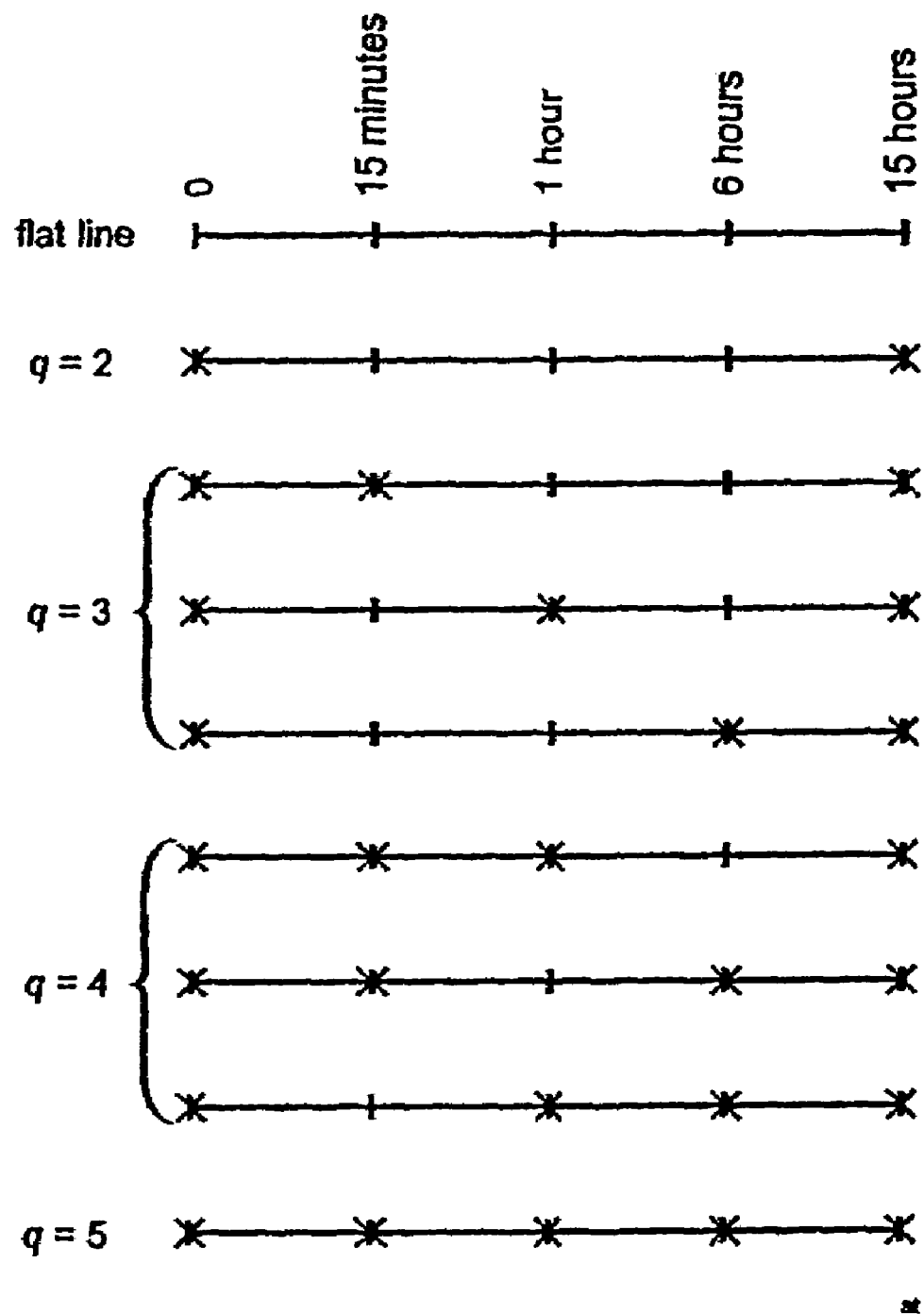
FIG. 23 possible placement of knots for a time ordered set of measurements at five time points.

Next we fit linear spline functions to the measured gene expression ratios. The number of knots q were between one and five, with a fixed knot equal to unity at time zero. For q=3 and q=4, three possibilities exist for the placement of the knots between the linear segments of the linear spline. These are indicated in FIG. 23, together with the cases q=1, q=2, and q=5. Notice that the number of possible knot placements increases exponentially with the maximum number of knots $q_{max}$.

In the fold-change analysis, temporal gene expression patterns were classified into six categories (Y. Hihara et al., *The Plant Cell*, 13, 793-806, 2001), listed in Table 4. Fitting a linear spline function to the measured gene expression data provided a more flexible way to describe the data than categorizing. In addition, a numerical description of the gene expression response pattern is an important step in deriving a gene regulatory network.

Analyzing Expression Data Using Linear Splines

Figure 24:
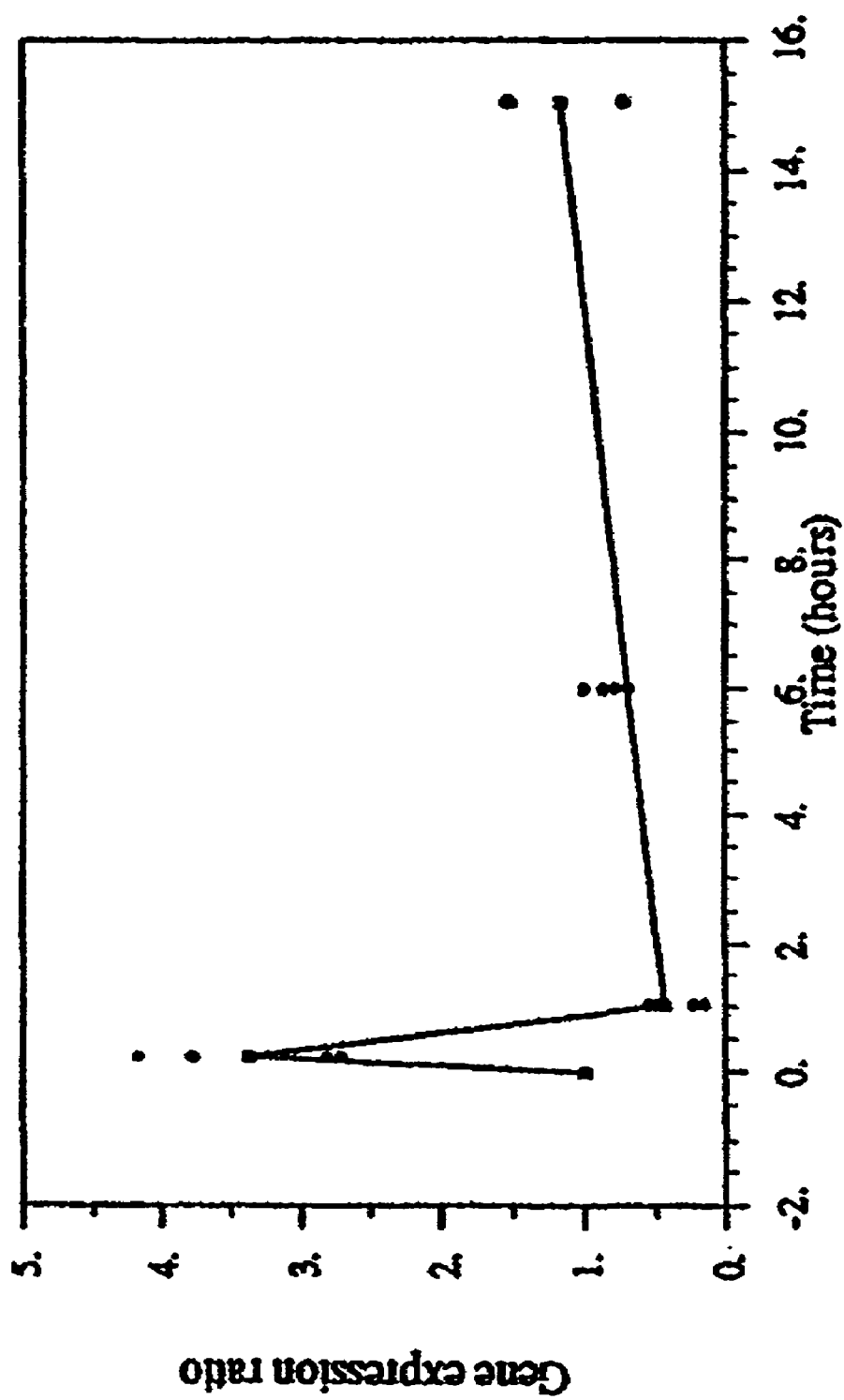
FIG. 24 the measured gene expression levels for the threonine synthase gene thrC (slll688), together with the fitted linear spline.

We next illustrate the usage of the AIC with an example. In the fold-change analysis, the threonine synthase gene thrC (sll1688) was found to be repressed at the approximately one hour. The calculated values of the AIC for the different sets of knots are listed in Table 5. The minimum AIC was achieved for knots at 0, 15 minutes, 1 hour, and 15 hours. FIG. 24 shows the measured gene expression levels, together with the linear spline that was fitted to the data.

Performing this procedure for all the gene expression measures let us classify different genes based on their time-dependent response to HL. Several choices can be made as to which genes to include in this analysis. In the original analysis, genes were removed from the calculation if their expression levels were among the 2000 lowest out of 3079 ORFs (Y. Hihara et al., *The Plant Cell*, 13, 793-806, 2001). Alternatively, we can eliminate genes if Student's t-test showed that they were not significantly affected by HL. Table 6 shows the number of genes whose measured expression levels correspond to each pattern for these different cases. For Student's t-test, a significance level q=0.001 was used.

We compared the 167 genes which were identified by Student's t-test as significantly affected by HL with the results from the fold-change analysis (Y. Hihara et al., *The Plant Cell*, 13, 793-806, 2001), in which 164 ORFs were identified. First, we removed those genes from our analysis for which an outlier was present in the data. We define an outlier as a data point that deviates more than two standard deviations from the mean of the data at a given time point. Only one gene was found for which the measured expression data contained an outlier; the linear spline function fitted to its expression data was a flat line. None of the other gene expression levels was described by a flat line, which is consistent with the results from Student's t-test.

Next, we removed those genes whose expression level was among the lowest 2000 in order to avoid using data that are dominated by noise. The same procedure had been used for the fold-change analysis (Y. Hihara et al., *The Plant Cell*, 13, 793-806, 2001). After removal of these genes, 107 genes remained that were significantly affected by HL.

Figure 25:
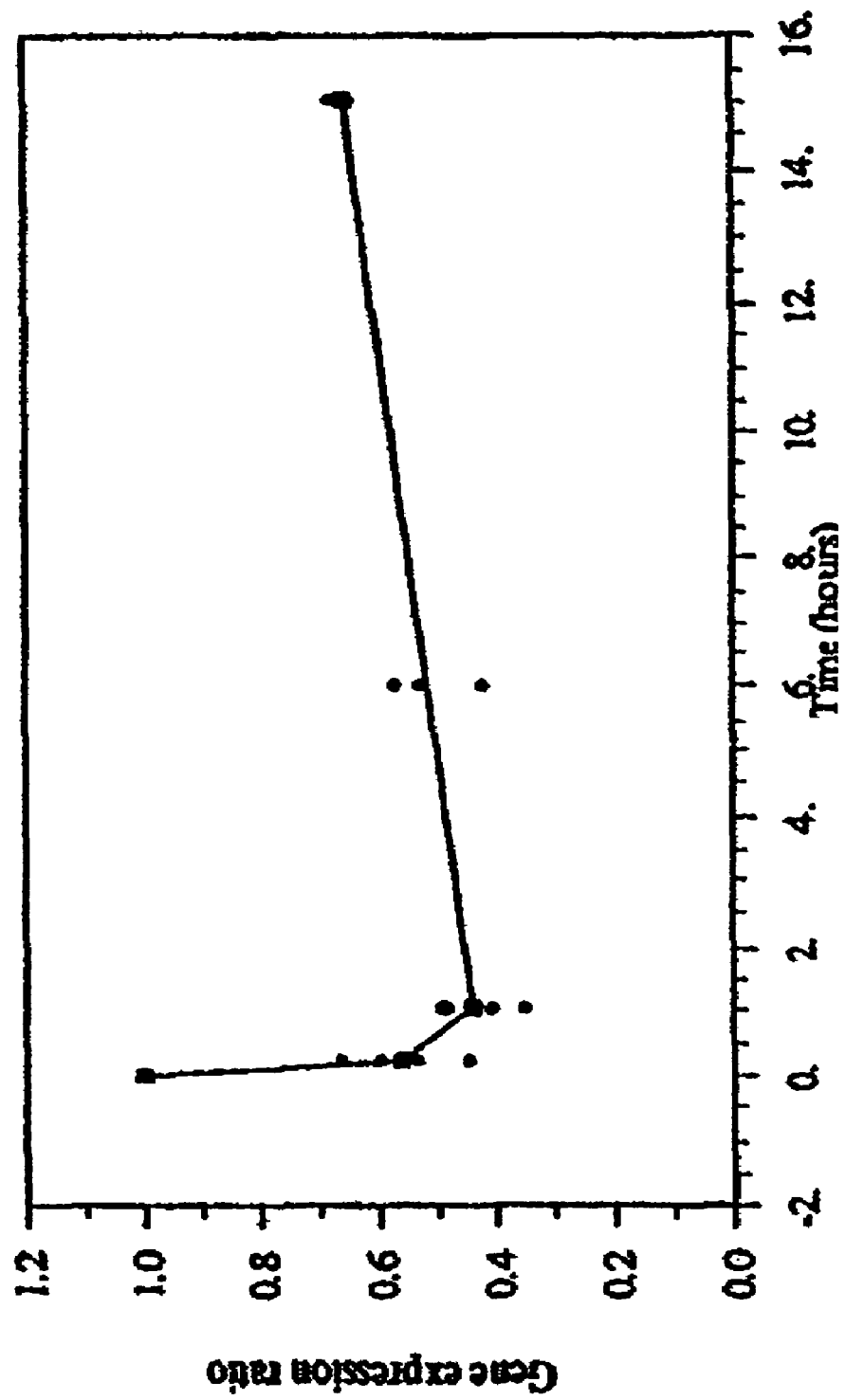
FIG. 25 the measured gene expression levels for the gene xylR (slr0329), together with the fitted linear spline. This gene was considered to be unaffected by HL in the fold-change analysis (Y. Hihara et al., *The Plant Cell*, 13, 793-806, 2001).

Of the 107 genes, 42 had not been identified in the fold-change analysis (Y. Hihara et al., *The Plant Cell*, 13, 793-806, 2001). These genes are listed in Table 7, together with the location of the knots that we found for each gene. For each linear spline function the percentage variance explained was calculated as a measure of the goodness of fit. As an example, FIG. 25 shows the measured gene expression ration as well as the fitted linear spline function of the gene sylR (slr0329), having four knots at zero, fifteen minutes, one hour, and fifteen hours. Of the 42 genes, the gene xyIR (slr0329) had the largest percentage variance explained (98.7%). Of the 164 ORFs that were identified in the fold-change analysis, 39 were not significantly affected by HL according to Student's t-test at a significance level q=0.001. These ORFs are listed in Table 8.

Finally, we established whether the number of measurements at each time point was sufficient to reliably determine the placements of knots for the linear spline function. To do so, we repeated the estimation of the linear spline function. To do so, we repeated the estimation of the linear spline function using subsets of the measured data. We then counted for how many genes the estimated knot positions changed if a subset of the data was used instead of the complete set of data. The average and standard deviation of this number for four, three, and two data points at each time point is shown in Table 9.

Even if only two data points (at the one hour time point) are removed, and four data points are used at each time point in 15% of the cases the estimated knot positions changed. Thus, in certain embodiments, four or more data points are needed for each time point to reliably deduce information from gene expression measurements.

Discussion

We have described a strategy based on maximum likelihood methods to analyze a set of time-ordered measurements.

By applying Student's t-test to the measured gene expression data, we first established which of the measured genes are significantly affected by the experimental manipulation. The expression responses of those genes were then described by fitting a linear spline function. The number of knots to be used for the linear spline function was determined using Akake's Information Criterion (AIC).

Using linear spline functions permits more flexibility in describing the measured gene expression than using a nominal classification. Also, to set up a gene regulatory network, it can be desirable that the gene response as determined from gene expression measurements is available in a numerical form. Finally, positions of the knots specify those time points at which the expression of a gene changes markedly, which can be desirable in identifying its biological function. Classification of gene expression responses based on the position of the knots can be refined by creating subcategories that take the magnitude of the linear spline function at the knots into account. For instance, for linear spline functions with three knots, we may consider creating six subcategories in which changes in the gene expression level are described by (flat, increasing), (flat decreasing), (increasing, flat), (decreasing, flat), (increasing, decreasing), or (decreasing, increasing).

Applying the technique of linear spline functions to measured gene expression data, we can identify the temporal expression response pattern of genes that were significantly affected by the experimental manipulations. The response of 42 of those genes was not noticed in earlier fold-change analyses of expression data. Furthermore, it was shown that the expression response levels found in a fold-change analysis were not found to be significant by Student's t-test for 33 out of 164 genes some genes. In some embodiments, gene expression data may be nosy and are plagued by outliers. Whereas Student's t-test and maximum likelihood methods described here take the statistical significance of noisy data into account, the issue of outliers needs to be addressed separately. As a simple procedure to remove outliers, we calculated the mean and standard deviation of the data for each point in time, and removed those data that deviate more than two standard deviations or so from the mean.

Finally, the number of expression measurements needed at each time point to reliably fit a linear spline function was determined by removing some data points and fitting a linear spline function anew. It was found that if four data points per time point were used, in about 15% of the cases the knot positions will not be estimated reliably. It is therefore advisable to make more than four measurements per time point.

VI. Use of Gene Networks for Identifying and Validating Drug Targets

We describe new methods for identifying and validating drug targets by using gene networks, which are estimated from cDNA microarray gene expression data. We created novel gene disruption and drug response microarray gene expression data libraries for the purpose of drug target elucidation. We used two types of microarray gene expression data for estimating gene networks and then identifying drug targets. Estimated gene networks can be useful in understanding drug response data and this information is unattainable from clustering analysis methods, which are the standard for gene expression analysis. In the construction of gene networks in certain embodiments, we used both Boolean and Bayesian network models for different steps in analysis and capitalize on their relative strengths. We used an actual example from analysis of the *Saccharomyces cerevisiae* gene expression and drug response data to validate our strategy for the application of gene network information to drug discovery.

1. Introduction

Cluster methods have become a standard tool for analyzing microarray gene expression data. However, they cannot offer information sufficient for identifying drug targets in either a theoretical or practical sense. We provide methods to determine how estimated gene networks can be used for identifying and validating target genes for the understanding and development of new therapeutics. Gene regulation pathway information is desirable for our purpose, and we used both Boolean and Bayesian network modeling methods for inferring gene networks from gene expression profiles. The procedure for identifying drug targets can be separated into two parts. At first, identify the drug-affected genes. Second, we search for the "target" genes, which are usually upstream of the drug-affected genes in the gene network. A Boolean network model is useful for identifying the drug affected genes by using "virtual gene" gene technique, described herein and a Bayesian network model can be used for exploring the druggable gene targets related to the elucidated affected genes. We applied our methods to novel *Saccharomyces cerevisiae* gene expression data, comprised of expression experiments from 120 gene disruptions and several dose and time responses to a drug.

2. Gene Networks for Identifying Drug Targets

A. Clustering Methods

Clustering methods such as the hierarchical clustering and the self-organizing maps are commonly used as a standard tool for gene expression data analysis in the field of Bioinformatics. Eisen focuses on the hierarchical clustering and provides software, Cluster/TreeView, for clustering analysis of gene expression data. De Hoon et al. (M. J. L. de Hoon, et al., Bioinformatics, submitted) improved this software especially in the k-means clustering algorithm.

Clustering methods only provide the information on gene groups via the similarity of the expression patterns. However, it can be desirable to have additional hierarchical pathway information, not only cluster information to detect drug targets that are affected by an agent. We show the limitations of clustering techniques for drug targeting purposes through real data analysis.

We use two new methods for estimating gene networks from gene expression data. In this subsection, we give the brief introductions of both methods. For detailed discussions of the algorithms, please refer the papers in the references section.

B. Boolean Network

To estimate a boolean network model, we can discretize the gene expression values into two levels, 0 (not-expressed) and 1 (expressed). Suppose that $u_1, \ldots u_k$ are input nodes of a node v. The state of v is determined by a Boolean functions $f_v(\psi(u_1), \ldots, \psi(u_k))$, where $\psi(u_1)$ is the state or the expression pattern of $u_1$. If we have time series gene expression data, the state depends on the time t and the state of the node at time t depends on the states of inputs at time t−1. On the other hand, suppose that we have gene expression data obtained by gene disruptions. Akutsu et al. proposed the theory and methodology for estimating a Boolean network model without time delay. Maki et al. provides a system, named AIGNET, for estimating a gene network based on the Boolean network and an S-system. We use the AIGNET system for estimating Boolean network models.

Advantages of the use of the Boolean network model includes:

a) This model is simple and can be easily understood. A Boolean network model can detect the parent-child relations correctly, when the data has sufficient accuracy and information and b) the estimated Boolean network model can be directly applied to the Genome Object Net, a software tool for biopathway simulation. A disadvantage of Boolean methods is that data must be discretized into two levels, and the quantization loses information. Moreover, the threshold for discretizing is a parameter and should be chosen by a suitable criterion.

C. Bayesian Networks

A Bayesian network is a graphic representation of complex relationships of a large number of random variables. We consider the directed acyclic graph with Markov relations of nodes in the context of Bayesian network. We can thus describe complex phenomena through conditional probabilities instead of the joint probability of the random variables. Further description can be found in Example 5 herein.

Friedman et al. (N. Friedman et al., *J Comput Biol.*, 7, 601-620, 2000) proposed an approach for estimating a gene network from gene expression profiles. They discretized the expression values into three values and used the multinomial distributions as the conditional distributions of the Bayesian network. However, this did not solve the problem of choosing threshold values for discretizing.

We developed a nonparametric regression model that offers a solution that does not require quantization together with new criterion, named BNRC, for selecting an optimal graph. The BNRC is defined as the approximation of the posterior probability of the graph by using the Laplace approximation for integrals. We applied the proposed method to *Saccharomyces cerevisiae* gene expression data and estimated a gene network. The advantages of this method are as follows: a) one can analyze the Microarray data as a continuous data set, b) this model can detect not only linear structures but also nonlinear dependencies between genes and c) the proposed criterion can optimize the parameters in the model and the structure of the network automatically.

A Bayesian network has some advantageous based on the mathematics of inference, and we use the method for constructing Bayesian networks. We can construct cyclic regulations and multilevel directional models of regulatory effects from data created from logical joins of expression data from disruptants and drug response experiments by combining the Bayesian and Boolean networks in analysis. Hence, the Boolean and Bayesian networks used together can cover the shortcomings one another and we can obtain more reliable information.

3. Applications to Microarray Data

We created two libraries of microarray data from *Saccharomyces cerevisiae* gene expression profiles. One was obtained by disrupting 120 genes, and the other was comprised of the response to an oral antifungal agent. (four concentrations and five time points). We selected 735 genes from the yeast genome for identifying drug targets. In YPD, 314 genes were defined as "Transcription factors", and 98 of these have already been studied for their control mechanism. The expression profile data for 735 genes chosen for analysis included the genes controlled by these 98 "Transcription factors" from 5871 gene species measured in addition to nuclear receptor genes which have a role in gene expression regulation and are popular drug targets. We constructed network models from the data set of 735 genes over 120 gene disruption conditions. The details of the disruption data are also described in Imoto et al.

As for drug response microarray gene expression data, we incubated yeast cultures in dosages of 10, 25, 50, 100 mg of an antifungal medication in culture and took aliquots of the culture at 5 time points (0, 15, 30, 45 and 60 minutes) after addition of the agent. Here time 0 means the start point of this observation and just after exposure to the drug. We then extracted the total RNA from these experiments, labeled the RNA with cy5, hybridized them with cy3 labeled RNA from non-treated cells and applied them to full genome cDNA microarrays thus creating a data set of 20 microarrays for drug response data. In this paper, we use these 140 microarrays to elucidate drug targets using gene networks.

4. Results

A. Clustering Analysis

In the identification of the drug targets, a popular but problematic prior art strategy has been to use clustering analysis often even with a library of base perturbation control data to compare to (( )). We have two types of microarray data, gene disruption and drug response, allowing us to compare drug response patterns to gene expression patterns caused by disruption. In the clustering analysis, if there is significant and strong similarity between the expression patterns of a single disruptant or group of disruptants and a given drug response microarray, we may conclude that an agent probably plays the same role as the disrupted gene(s). Moreover, if this disrupted gene has known functional role, we may obtain more information about the response to a drug.

Figure 26:
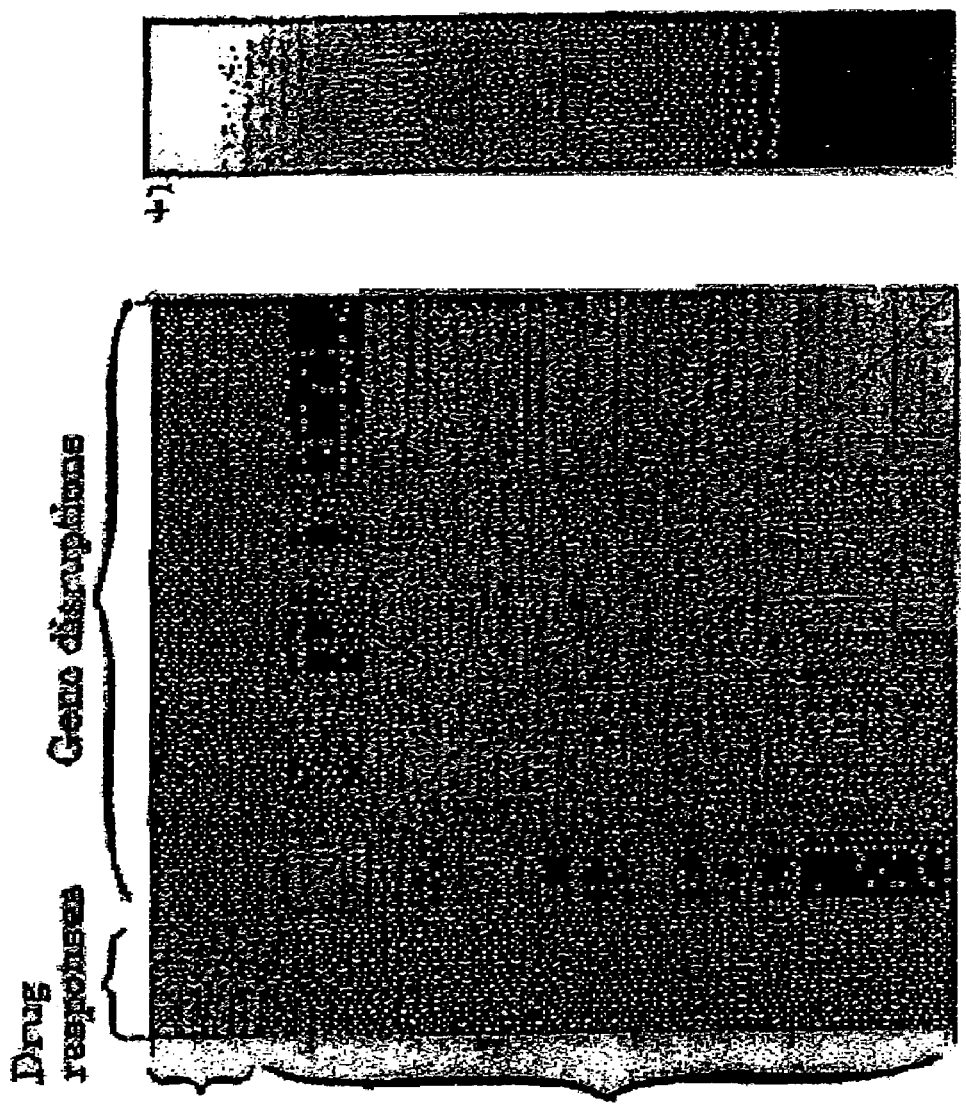
FIG. 26 the image of the correlation matrix R of combined gene expression data.

Unfortunately, as if often the case with such experiments we cannot gain such a straightforward result from clustering our data. FIG. 26 shows the image representation of the correlation matrix of our microarray data. We combine the two types of data and make the matrix Z=(X:Y), where X and Y are the drug response and the gene disruption microarray data matrix, respectively. Here, each column denotes an expression pattern obtained by one microarray, and each column is standardized with a mean of 0 and variance of 1. Therefore, FIG. 26 depicts the information of the correlation matrix $R=Z^T z/p$, where p is the number of genes. To illustrate our methods, we focus on 735 genes for estimating gene networks and identifying drug targets.

In FIG. 26, the light and dark colors denote the positive and negative high correlations, respectively. Drug response microarrays have high correlation amongst each other and a low correlation with any of the gene disruption microarrays. Under such a situation, it may be difficult to identify interactions between gene disruptions and drug responses from the clustering analysis that would be meaningful in the context of drug response. We further implemented hierarchical clustering of the drug response microarrays, but this produced one cluster and we could not extract any more information on the actual drug targets from this analysis. This result was essentially unchanged when we use other distance measurements or clustering techniques. Hence, it is difficult to obtain information for identifying meaningful drug targets from the clustering methods.

B. Boolean Network Analysis

To overcome shortcomings of prior art clustering methods, we estimated gene network by using the microarray data, Z, which was created by combining gene disruption and drug response microarrays. We consider the conditions of the drug responses data as "virtual genes", e.g., the condition 100 mg/ml and 30 min is given an assignment as the gene YEXP100mg30min. By using a Boolean network model, we found child genes of these virtual genes, with the drug affecting these child genes in progeny generational order. We focus on genes which five or more virtual genes as the parent genes, as the putative drug-affected genes, that is, genes which are under direct influence of the virtual genes (drug affect). However, a gene which has only one virtual gene as its parent gene may be the primary drug-affected gene, depending on the mode of action for a given agent. The virtual gene technique highlights the use of Boolean network models compared with the Bayesian network model in the initial screening for genes under drug-induced expression influence.

In addition, fold-change analysis can provide similar information to the proposed virtual gene technique. We identified the affected genes under certain experimental conditions by fold-change analysis. However, our virtual gene technique can improve the result of the fold-change analysis. Suppose that we find gene A and B are affected by the drug from fold-change analysis. The fold-change analysis cannot take into account the baseline interactions between geneA and geneB. That is, if there is a regulation pathway between geneA and geneB that geneA→geneB, the geneB may not be affected by the drug directly. Rather, an effect of the drug on geneA may result in an indirect effect on geneB. The virtual gene technique can take into account such interaction by using the information of the gene disruption data and thus reduce the search set to more probable target genes given available interaction data.

There is not guarantee that genes that are most affected by an agent are the genes that were "drugged" by the agent, nor is there any guarantee that the drugged target represents the most biologically available and advantageous molecular target for intervention with new drugs. Thus, even after identifying probable molecular modes of action, it is desirable to find the most druggable target genes upstream of the drug-affected genes in a regulatory network and to then screen low molecular weight compounds for drug activity on those targets. In the estimated Boolean network, virtual genes can be placed on the top of the network. Therefore, it can be difficult or sometimes impossible to find upstream information for drug-affected genes in this estimated Boolean network. In such circumstances, we use a Bayesian network model for exploring the upstream region of the drug-affected genes in an effective manner.

C. Bayesian Network Analysis

We found that a gene network can be estimated by a Bayesian network and nonparametric regression method together with BNRC optimization strategy. We use the *Saccharomyces cerevisiae* microarray gene expression data as described herein obtained by disrupting 120 genes. From Boolean network analysis, we found the candidate set of the drug-affected genes effectively. Druggable genes are drug targets related to these drug-affected genes, which we want to identify for the development of novel leads. We explored the druggable genes on the upstream region of the drug-affected genes in the estimated gene network by a Bayesian network method. Using a Bayesian model of network regulatory data available to us from our knockout expression library, we searched upstream of drug affected target genes, which have a known regulatory control relationship over drug affected target expression. For example, we focus on nuclear receptor genes as the druggable genes because: a) nuclear receptor proteins are known to be useful drug targets and together represent over 20% of the targets for medications presently in the market, b) nuclear receptors are involved in the transcription regulatory affects that are directly measured in cDNA microarray experiments.

Figure 27:
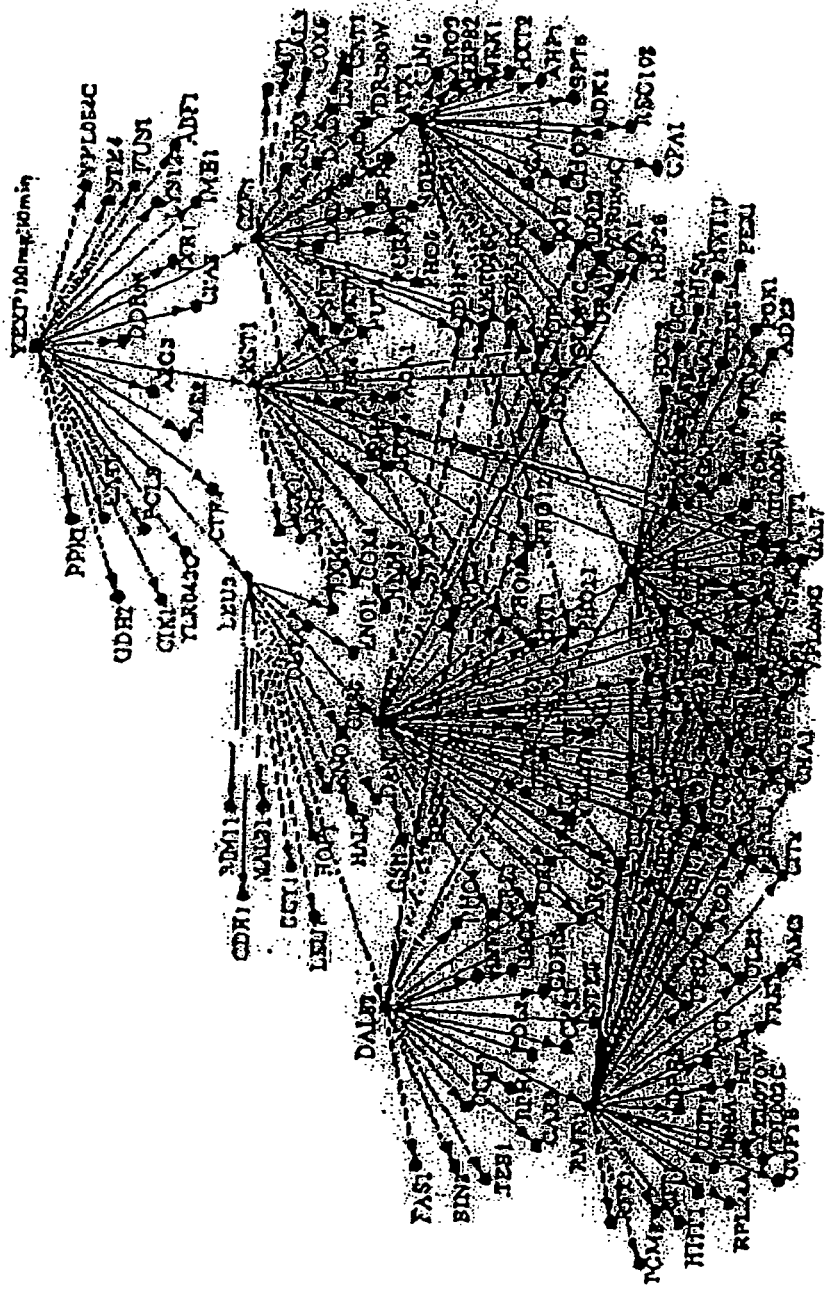
FIG. 27 the downstream pathway of the virtual gene YEXP100mg30min.
Figure 28:
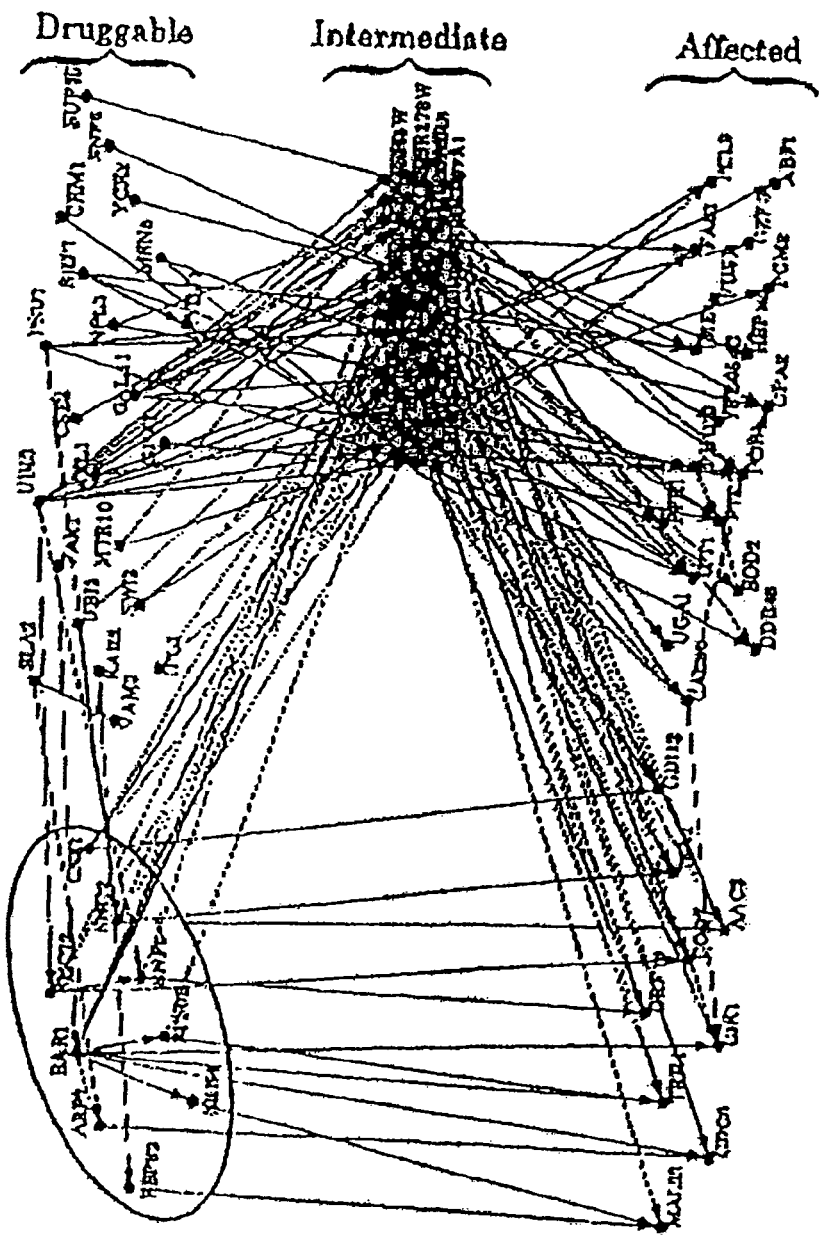
FIG. 28 a partial network among the druggable (Top), drug-affected (Bottom) and intermediary genes (Middle).

FIG. 27 depicts the downstream pathway of the virtual gene YEXP100mg30min. FIG. 28 shows a partial network, which includes the drug-affected genes (Bottom), the druggable genes (Top) and the intermediary genes (Middle). Of course, we can find more pathways from the druggable genes to the drug-affected genes if we admit more intermediary genes. Due to the use of the Bayesian network model, we can find the intensities of the edges and can select more reliable pathway. This is an advantage of Bayesian network models in searching for suitable druggable targets. In FIG. 28, druggable genes in the circle connect directly to the drug-affected genes and the other druggable genes have one intermediary gene per one druggable gene. From FIG. 28, we identified druggable genes for each drug-affected gene, e.g., we found the druggable genes for MAL33 and CDC6 shown in Table 10.

5. Discussion

We describe new strategies for identifying and validating drug targets using computational models of gene networks. Boolean and Bayesian networks can be useful for estimating gene networks from microarray gene expression data. Using both methods we can obtain more reliable information than by using either method above. A Boolean network is suitable for identifying drug-affected genes by using the virtual gene technique set forth herein. Bayesian network models can provide information for upstream regions of the drug-affected genes and we can thus attain a set of candidate druggable genes. Our novel strategies are established based on the sophisticated use of a combination of two network methods. The strength of each network method can be clearly seen in this strategy and the integrated method can provide a methodological foundation for the practical application of bioinformatics techniques for gene network inference in the identification and validation of drug targets.

VII. Drug Target Discovery and Validation with Gene Regulatory Networks

Gene regulatory networks developed with full genome expression libraries from gene perturbation variant cell lines can be used to quickly and efficiently to identify the molecular mechanism of action of drugs or lead compound molecules. We developed an extensive yeast gene expression library consisting of full-genome cDNA array data for over 500 yeast strains each with a single gene disruption. Using this data, combined with dose and time course expression experiments with the oral antifungal agent Griseofulvin, we used Boolean and Bayesian network discovery techniques to determine the genes whose expression was most profoundly affected by this drug. Griseofulvin, whose exact molecular target was previously unknown, interferes with mitotic spindle formation in yeast. Our system was used to directly discover CIK1 as the primarily affected target gene in the presence of Griseofulvin. Deletion of CIK1, the primary affected target determined by gene network discovery produces similar morphological effects on mitotic spindle formation to those of the drug. Using the base hierarchical data from the expression library and nonparametric Bayesian network modeling we were able to identify alternative ligand dependant transcription factors and other proteins upstream of CIK1 that can serve as potential alternative molecular targets to induce the same molecular response as Griseofulvin. This process for network based drug discovery can significantly decrease the time and resources necessary to make rational drug targeting decisions.

1. Introduction

Rational drug design methodologies have previously been concentrated on optimizing small molecules against a predetermined molecular target. The randomized lead to target to phenotype screening for target selection that is currently the prevailing paradigm in drug discovery has failed to offer a more efficient and accurate target selection process even with the advent of wide scale availability of genomic information and high throughput screening processes (A. Smith, *Nature*, 418, 453-459, 2002; G. W. Aherne et al., *Breast Cancer Res.* 4, 148-154, 2002; D. A. Willins et al., *Curr Pharm Des.* 8, 1137-1154, 2002). The availability of genomic sequences, full genome microarrays and recent advances in gene network inference computational techniques allows for a new rational paradigm for drug target selection that takes into account global networked regulatory interactions among molecules in the genome. Accurate models of gene regulatory network data can be produced from disruptant based expression data (T. R. Hughes, et al., *Cell*, 102, 109-126, 2000; G. Glaever et al., *Nature*, 418, 387-391, 2002) by using various computational inference techniques (N. Friedman et al., *J Comput Biol.*, 7, 601-620, 2000; R. Somogyi et al. *Complexity*, 1, 45-63, 1996). Here we show how this gene regulatory information can be used to quickly determine the molecular networks and gene targets affected by a given compound. The same information allows for the identification and selection of alternative druggable molecular targets upstream or downstream of a drug targeted molecule in the gene expression regulatory cascade.

We have developed a gene regulatory network-driven iterative drug target discovery process. In this methodology, first large numbers of gene expression experiments are performed on single gene disruptant cell lines. This information is used to create computationally inferred maps of hierarchical gene expression control. The hierarchical regulatory information is used as a basis for evaluation of drug response experiments and for generation of hypotheses of molecular action mechanisms. Information from the literature and further biological experimentation on the elucidated regulatory subnetworks is used to understand and validate results before selecting a candidate molecule for drug targeting.

Most effective drugs in clinical use including aspirin and other popular medications have not been rationally designed to interact with a specific molecular target. Thus, even when the desired clinical effect or phenotype is achieved with these drugs, the underlying molecular mechanisms of action and thus the mechanisms of the drug's side effects remain unknown. Full genome gene expression experiments have been shown to be useful in determining alternative genes and pathways affected by a drug (M. J. Marton et al., *Nature Medicine*, 4, 1293-1301, 1998; M. J. Heller, *Annu Rev Biomed Eng.*, 4, 129-153, 2002; M. A. Reynolds, *J Ind Microbiol Biotechnol.*, 28, 180-185, 2002), but determination of the primary molecular target for many drugs which affect hundreds of genes with standard gene expression analysis methods such as clustering is impractical without a priori information on potential targets for the drug. Here we demonstrate the use of hierarchical gene expression regulation networks from full genome expression libraries and gene network modeling techniques together with drug response expression experiments to determine the previously underlying molecular targets for the popular generic antifungal agent, Griseofulvin.

Griseofulvin is a widely prescribed oral antifungal agent that is indicated primarily for severe fungal infections of the hair and nails. While Griseofulvin's molecular action is unknown, the drug disrupts mitotic spindle structure in fungi to lead to metaphase arrest.

2. Methods

Microarray Experiments

The yeast strain used in this study is BY4741. To monitor the gene expression profile, cells were pre-grown at 30° C. in YPD (2% polypeptone, 1% yeast extract and 2% glucose) to mid-exponential phase and were exposed with Griseofulvin by adding it to the medium to the concentrations at 0, 10, 25, 50, and 100 mg/ml. The exposed cells were harvested at 0, 15, 30, 45 and 60 min after addition by Griseofulvin and used for RNA extraction. Total RNAs were extracted by the hot-phenol method.

Boolean Network Inference Algorithms

In addition to the Boolean methods for gene disruption experiments reported elsewhere (T. Akutsu et al., *J. Comp.*

*Biol*, 7, 331-343, 2000), we created a gene expression matrix E from a set of the drug treatment experiments combined with disruptant expression data. In the case of drug generated perturbation, we created a "virtual" gene to represent the drug affect analogous to a gene disruption. We then were able to use standard disruption matrix algorithms designed for disruption based data.

Bayesian Network Inference Algorithms

We performed non-parametric regulation and Bayesian networks to define regulatory subnetworks upstream of CIK1 using algorithms and methods reported elsewhere herein.

Data Normalization

We measured the quantities of 5871 mRNA species from 20 drug treated strains by cDNA microarray assay. A difference in fluorescent strength between Cy3, Cy5 causes bias of the expression quantity ratio. We normalized the expression quantity ratios of each expression profile. The ratio bias had a fixed trend in each spotted block, thus we calculated a linear regression to normalize the mean value ratio of each block to 1.0. The logarithm value of the ratio was used to indicate the standard expression level, therefore we found the logarithm value of ratio and calculated the average and standard deviation of these log values (see Table 1). The Standard Deviation (SD) of expression levels of all spotted genes from the UME6 (YDR207C) disruptant expression array for which UME6 is defined as a "Global Regulator" in YPD disruptant was 0.4931, therefore we recognized that there are an unacceptable number of errors in array data whose overall SD was larger than 0.5 and eliminated such experiments from analysis.

Selection of Genes for Modeling

In YPD, 314 genes were defined as "transcription factors", and 98 of these have previously been studied for control mechanism. The expression profile data of 552 genes including the genes that are controlled by these 98 "transcription factors" were selected from 5871 profiles. Thus we constructed the gene regulatory network from the expression profile data set based on the values of these 552 genes in 120 gene disruption experiments and 20 drug treatment experiments.

3. Results

We incubated yeast cultures in dosages of 10, 50 and 100 mg in 10 ml of DMF and took aliquots of the culture at 5 time points (0, 15, 30, 45 and 60 minutes) after addition of Griseofulvin. We then extracted the total RNA from these experiments, labeled the RNA with cy5, hybridized them with cy3 labeled RNA from non-treated cells and applied them to full genome cDNA microarrays. 183 genes were downregulated by over a 2 sigma threshold among 552 genes which differed in expression between drug treated and normal yeast (FIG. 7a). Standard hierarchical clustering methodologies (FIG. 7b) applied to the combined expression libraries from drug response and gene disruption experiments, clustered genes into two major groups; first, genes affected by Griseofulvin and second, genes affected by disruption. Within the Griseofulvin clusters, genes were further grouped by dosage or time course. However, clustering did not discover any gene expression patterns that significantly indicated correlated regulation by a given gene and the drug Griseofulvin. This result would be expected except in cases where the antifungal agent affects the expression of only one discrete gene and minimal (FIG. 7b).

However, the use of gene regulatory network models, combined with the drug perturbation data allows for a hierarchical gene regulatory view of the drug's interaction with genes in the transcriptome. To generate this gene network drug perturbation data, we first created a full genome expression library of 542 single-gene disruption mutants. The 120 array data selected from the library was logically joined with the array matrices generated from the Griseofulvin experiments. A Boolean methodology designed for gene network elucidation (T. Akutsu et al., *J. Comp. Biol.*, 7, 331-343, 2000; T. Akutsu et al., *Bioinformatics*, 16, 727-734, 2000) was then applied to the joint expression matrices for each time course and hierarchical regulatory maps for each experiment were generated for each dose and time point. We produced joint Boolean regulatory subnetworks for each dosage and time point experiment. The Boolean algorithm was selected for its suitability for handling joint matrices, its ability to handle looped regulatory processes and the ease creation of hierarchical directed graphs with several orders of regulatory separation. From this data we were able to identify the first order drug affects as opposed to secondary cascades initiated by those initial perturbation regulatory events.

By evaluating the Boolean data from each time and dose differential experiments we were able to identify 8 genes that were consistently and significantly suppressed as first effects at each time and drug concentration. Of these genes, CIK1 exhibited the strongest suppression effects across the experiments. CIK1 codes for a protein described in the yeast proteome database (YPD) as a coiled-coil protein of the spindle pole body involved in spindle formation and the congression (nuclear migration) step of karyogamy (M.D. Rose, *Ann. Rev. Cell. Dev. Biol.*, 12, 663-695, 1996). Since the action of Griseofulvin is known to affect mitotic spindle formation, which is in agreement with the function of CIK1 (F. R. Cottingham et al., Mitotic Spindle Motors, *The Rockefeller University Press*, 147, 335-349 (1999), we performed a pathological examination of a yeast strain with a disrupted CIK1 gene and yeast affected by Griseofulvin. While neither the treatment with Griseofulvin at normal physiological dosage nor the disruption of CIK1 are lethal, both cultures show similar morphological differences and growth characteristics Furthermore, microscopic examination of the mitotic spindle structure in Griseofulvin treated yeast and CIK1 deleted yeast show very similar changes of the spindle body and surrounding organizational structures D. B. Manning et al., Differential Regulation of the Kar3p Kinesin-related Protein by Two Associated Proteins, Cik1p and Vik1p, *The Rockefeller University Press*, 144, 1219-1233 (1999).

The methodologies described here clearly demonstrate the utility of a combined expression array and computational approach using gene network techniques to rapidly ascertain and validate the molecular mechanisms of action of a given compound on a cell.

Use of such techniques will help to rationalize the target selection process of pharmaceutical development in the post-genomic era and could contribute to efficiency of discovery and a reduction in development risk for the pharmaceutical industry. The same techniques can further be applied to other biological discovery and agrochemical targeting. Our laboratories are currently replicating this discovery model in human and other biological systems. Additional descriptions can be found in U.S. Provisional Patent Application Ser. No. 60/395,756, filed Jul. 12, 2002 incorporated herein fully by reference.

VII. Systems for Discovering Network Relationships and Uses Thereof

In other embodiments, methods for elucidating genetic networks are provided that include Example 6 described herein. Accordingly, a desirable system can include those in which:

(1) one can collect experimental data for enabling the network to be elucidated when the genome structure is elucidated;
(2) data of all the related genes can be measured;
(3) many tools for enabling many experiments to be used, such as gene chips;
(4) an output is measured after applying a disturbance to obtain many standardized data; and
(5) analysis of the genetic relationships can be determined.

Figure 29:
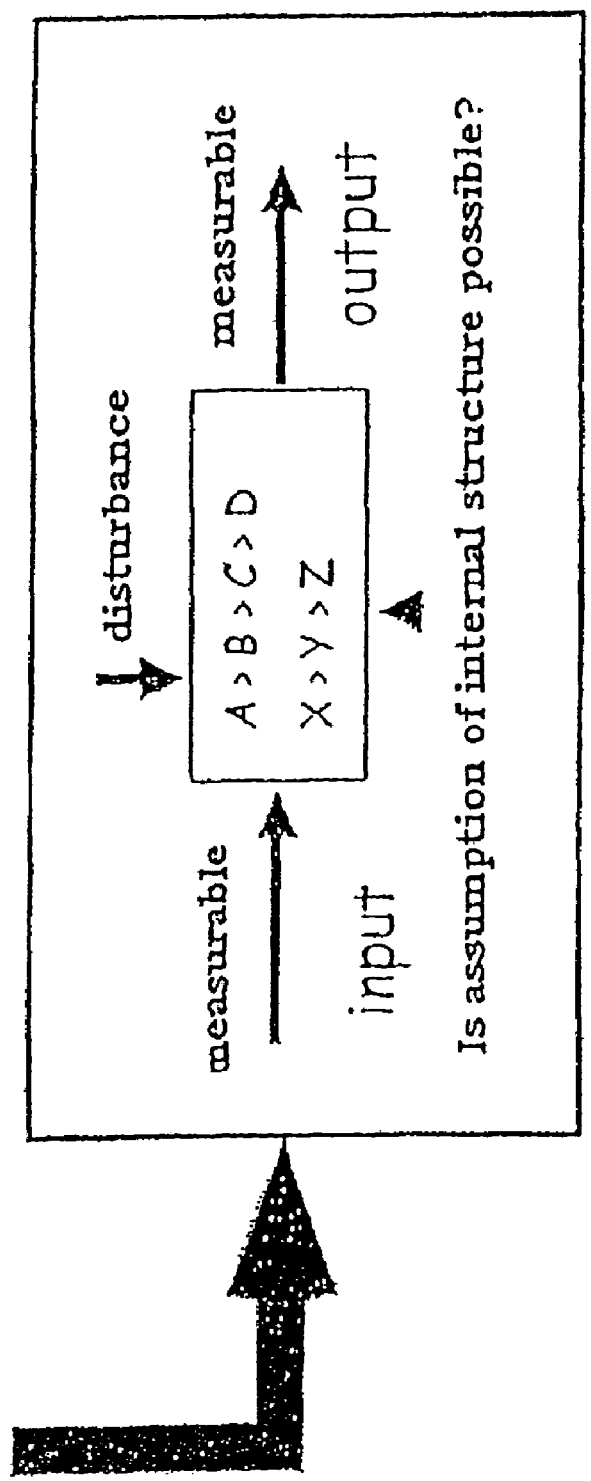
FIG. 29 molecular network.
Figure 30:
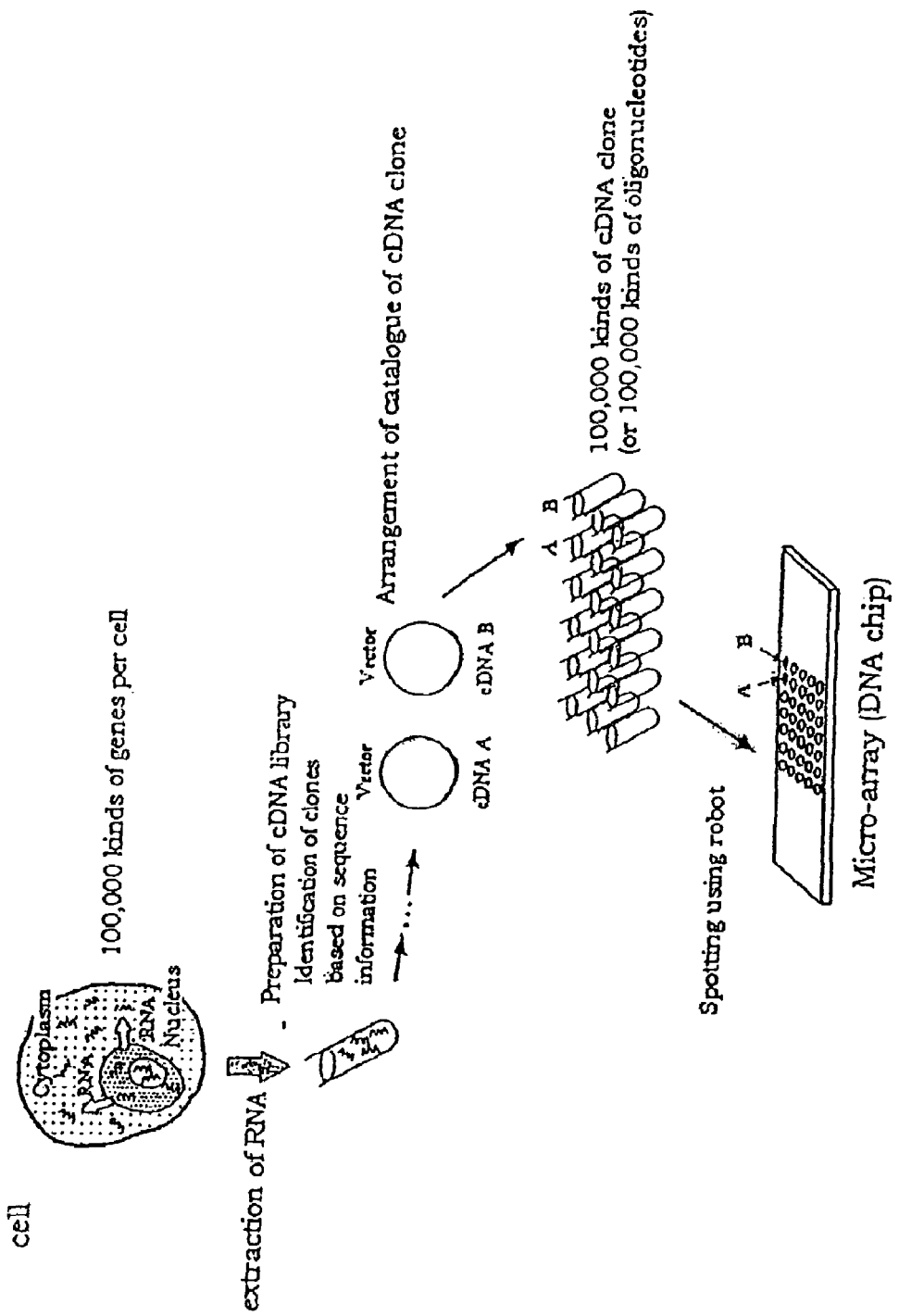
FIG. 30 outline for preparing a micro-array.
Figure 31:
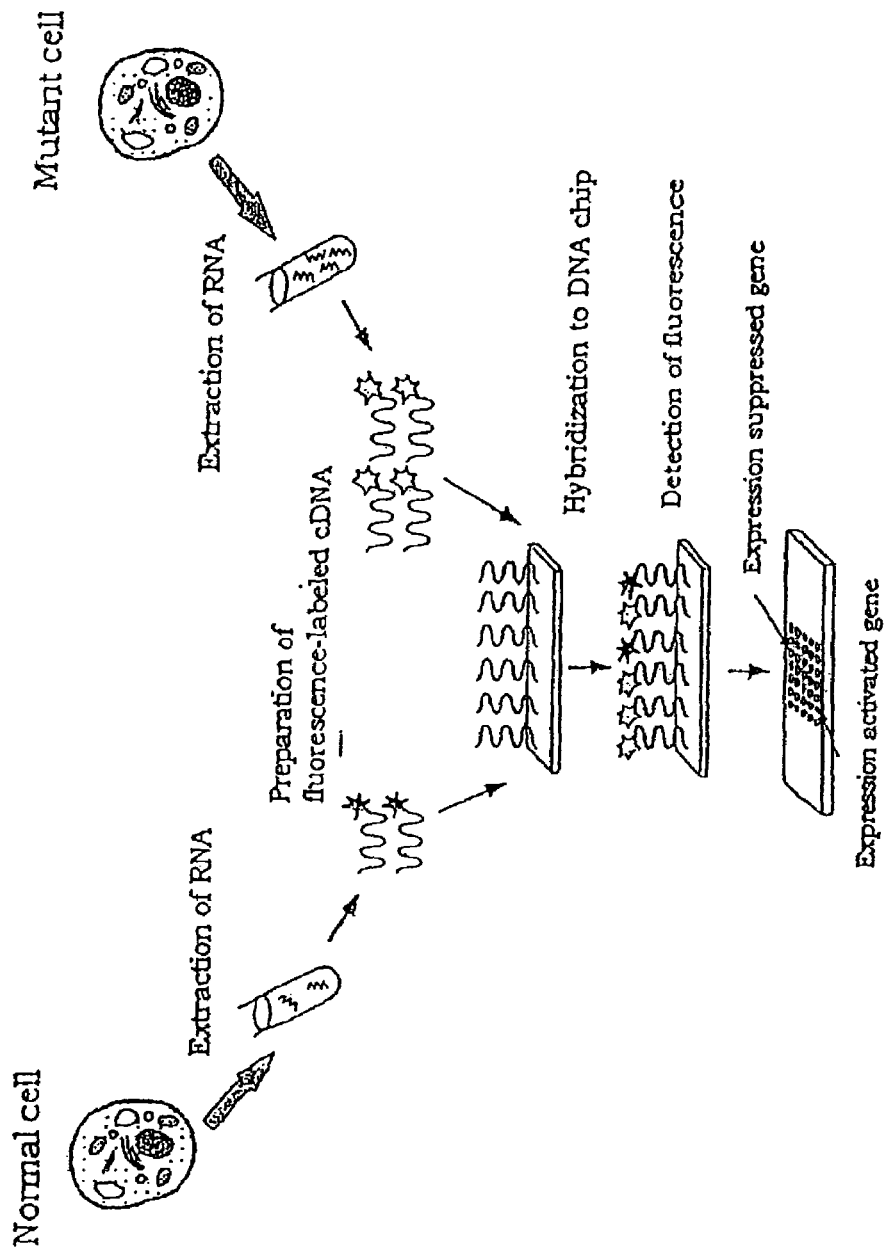
FIG. 31 measurement of expression profile using microarray.

An example of such a system is presented in FIG. 29. FIG. 30 depicts schematically, a method for obtaining microarray data on expressed genes from an organism. FIG. 31 depicts schematically a method for assessing and quantifying the expression of a gene by comparing the amounts of gene products (e.g., RNA) from mutated cells (disruptants) in which a particular gene is disrupted with the amounts of gene products from normal (wild-type) cells.

Analysis of a large scale network can be accomplished, in some embodiments, using the guideline provided as FIG. 32. Time course studies can be carried out and the expression of each gene under study can be evaluated. A Boolean network model can be provided and a dynamic model of the network can be made. Positive and negative interactions can be mapped, thereby producing a gene network. A multilevel diagraph approach can be taken to relate effects of disrupting (or altering expression) each gene with respect to other genes under study.

INCORPORATION BY REFERENCE

All patents, patent applications and references cited in this application are incorporated herein fully by reference.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

EXAMPLES

The following Examples are provided to illustrate embodiments of this invention. Other specific applications of the teachings in this patent application can be used without departing from the spirit of this invention. Other modifications of the methods can be used, and are considered to be within the scope of this invention.

Example 1

Estimation of Genetic Networks and Functional Structures Between Genes By Using Bayesian Networks and Nonparametric Regression We propose a new method for constructing genetic network from gene expression data by using Bayesian networks. We use nonparametric regression for capturing nonlinear relationships between genes and derive a new criterion for choosing the network in general situations. In a theoretical sense, our proposed theory and methodology include previous methods based on Bayes approach. We applied proposed method to the *S. cerevisiae* cell cycle data (Friedman et al., *J. Comp. Biol.*, 7, 601 (2000); P. Spellman, et al., *Mol. Biol. Cell*, 9, 3273 (1998)) and showed the effectiveness of our methods compared with previous methods.

1. Introduction

The improvement of the genetic engineering provide us enormous amount of valuable data such as microarray gene expression data. The analysis of the relationship among genes has drawn remarkable attention in the field of molecular biology and Bioinformatics. However, due to the cause of dimensionality and complexity of the data, it will be no easy task to find structures, which are buried in noise. To extract the effective information from biological data, thus, theory and methodology are expected to be developed from a statistical point of view. Our purpose is to establish a new method for understanding the relationship among genes clearer.

In the analysis of the microarray gene expression data, Bayesian networks are adopted for constructing genetic networks (T. Akutsu, et al., *Pacific Symposium on Biocomputing*, 17, (1999); T. Akutsu, et al., *Bioinformatics*, 16, 727 (2000); T. Akutsu, et al., *J. Comp. Biol.*, 7, 331 (2000); N. Friedman et al. in M. I. Jordan ed., *Learning in Graphical Models*, Kluwer Academic Publisher, 421 (1998)) from a graph-theoretic approach. Friedman and Goldszmidt (N. Friedman et al., in M. I. Jordan, ed., *Learning in Graphical Models*, Kluwer Academic Publisher 421 (1998) proposed an interesting method for constructing genetic links by using Bayesian networks. They discretized the expression value and considered to fit the models based on multinomial distributions. However, a problem still remains to be done in choosing the threshold value for discretizing by not only the experiments. The threshold value assuredly gives essential changes of the results and unsuitable threshold value leads to wrong results. On the other hand, recently, Friedman et al. (Friedman et al., *J. Comp. Biol.*, 7, 601 (2000)) pointed out that discretizing was probably loosing the information. To use the expression data as continuous values, thus, they considered the use of Gaussian models based on linear regression. However this model can only detect linear dependencies and we cannot obtain sufficient results.

In this paper we propose a new method for constructing genetic networks by using Bayesian networks. To capture not only linear dependencies but also nonlinear structures between genes, we use nonparametric regression models with Gaussian noise (R. L. Eubank, *Spline Smoothing and Nonparametric Regression*, Marcel Dekker, New York (1988); T. Hastie and R. Tibshirani, *Generalized Additive Models*, Chapman & Hall, London (1990); B. W. Silverman, *J. R. Stat. Soc. Series* B, 47, 1 (1985); J. S. Simonoff, *Smoothing Methods in Statistics*, Springer, New York (1996)). Nonparametric regression has been developed in order to explore the complex nonlinear form of the expected responses without the knowledge about the functional relationship in advance. Due to the new structure of the Bayesian networks, a suitable criterion is needed for evaluating models. We derive a new criterion from Bayesian statistics. By using proposed method, we will overcome the defects of previous methods and attain more effective information. In addition, our method includes the previous methods as special cases. We demonstrate our proposed method through the analysis of the *S. cerevisiae* cell cycle data.

2. Bayesian Network and Nonparametric Regression

Let $X=(X_1, X_2, \ldots, X_p)^T$ be a p-dimensional random vector and let G be a directed acyclic graph. Under the Bayesian network framework, we look upon a gene as a random variable and decompose the joint probability into the product of conditional probabilities, that is $$P(X_1, X_2, \ldots, X_p) = P(X_1|P_1)P(X_2|P_2) \times \ldots \times P(X_p|P_p), \quad (1)$$

where $P_j=(P_1^{(j)}, P_2^{(j)}, \ldots, P_{q_j}^{(j)})^T$ is a $q_j$-dimensional vector of parent variables of $X_j$ in the graph G.

Suppose that we have n observations $x_1, \ldots, x_n$ of the random vector X and the observations of $P_j$ are denoted by $p_{1j}, \ldots, p_{nj}$, where $p_{ij}$ is a $q_j$-dimensional vector with k-th element $P_{ik}^{(j)}$ for $k=1, \ldots, q_j$. For example, let $X_n$ be an n×p matrix, where $X_n=(x_1, \ldots, x_n)^T=(x_{(1)}, \ldots, x_{(p)})=(x_{ij})i=1, \ldots, n; j=1, \ldots p, x_i=(x_{i1}, \ldots, x_{ip})^T, x_{(j)}=(x_{1j}, \ldots, x_{nj})^T$ and $x_i^T$ is the transpose of the vector $x_i$. If $X_1$ have a parent vector $P_1=(X_2, X_3)^T$, we have $p_{11}(x_{12}, x_{13})^T, \ldots p_{n1}=(x_{n2}, x_{n3})^T$.

It is immediately found that the equation is held when we replace the probability measure P in (1) by densities $$f(x_{i1}, x_{i2}, \ldots, x_{ip}) = f_1(x_{i1}|p_{i1})f_2(x_{i2}|p_{i2}) \times \ldots \times f_p(x_{ip}|p_{ip}).$$

Then all we need to do is to consider how to construct the conditional densities $$f_j(x_{ij}|p_{ij})(j=1, \ldots, p).$$

In this paper, we use nonparametric regression models for capturing the relationship between $x_{ij}$ and $p_{ij}=(p_{i1}^{(j)}, \ldots, p_{iq_j}^{(j)})^T$ in the form $$x_{ij}=m_1(p_{i1}^{(j)})+m_2(p_{i2}^{(j)})+\ldots+m_{q_j}(p_{iq_j}^{(j)})+\epsilon_{ij}, i=1, \ldots, n; j=1, \ldots, p,$$

where $m_k(k=1, \ldots, q_j)$ are smooth functions from R to R and $\epsilon_{ij}(i=1, \ldots, n)$ depend independently and normally on mean 0 and variance $\sigma_j^2$. For the function $m_k$, it is assumed that $$m_k(p_{ik}^{(j)}) = \sum_{m=1}^{M_{jk}} \gamma_{mk}^{(j)} b_{mk}^{(j)}(p_{ik}^{(j)}), \quad i = 1, \ldots, n; k = 1, \ldots, q_j, \text{where} \{b_{1k}^{(j)}, \ldots b_{M_{jk}k}^{(j)}\} \quad (2)$$

is a prescribed set of basis functions (such as Fourier series, polynomial bases, regression spline bases, B-spline bases, wavelet bases and so on), the coefficients $\gamma_{1k}^{(j)}, \ldots, \gamma_{M_{jk}k}^{(j)}$ are unknown parameters and $M_{jk}$ is the number of basis functions.

Then a nonparametric regression model can be written as a probability density function in the form $$j(x_{ij} | p_{ij}; \gamma_j, \sigma_j^2) = \frac{1}{\sqrt{2\pi\sigma_j^2}} \exp\left[-\frac{\left\{x_{ij} - \sum_{k=1}^{q_j}\sum_{m=1}^{M_{jk}} \gamma_{mk}^{(j)} b_{mk}^{(j)}(p_{ik}^{(j)})\right\}^2}{2\sigma_j^2}\right], \quad (3)$$

where $\gamma_j=(\gamma_{j1}^T, \ldots, \gamma_{jq_j}^T)^T$ is a parameter vector with $\gamma_{jk}=(\gamma_{1k}^{(j)}, \ldots, \gamma_{M_{jk}k}^{(j)})^T$. If a variable $X_j$ has not parent variables, we consider the model based on the normal distributions with mean $\mu_j$ and variance $\sigma_j^2$.

Finally we have a Bayesian network model based on the nonparametric regression model with Gaussian noise $$f(x_i; \theta_G) = \prod_{j=1}^{p} f_j(x_{ij} \mid p_{ij}; \theta_j), 1, \ldots, n,$$

where $\theta_G = (\theta_1^T, \ldots, \theta_p^T)^T$ is a parameter vector included in the graph G and $\theta_j$ is a parameter vector in the model $f_j$, i.e., $\theta_j = (\gamma_j^T, \theta_j^2)^T$ or $\theta_j = (\mu_j, \sigma_j^2)^T$.

3. Proposed Criterion for Choosing Graph

Let $\pi(\theta_G|\lambda)$ be the prior distribution on the unknown parameter vector $\theta_G$ with hyper parameter vector $\lambda$ and let log $\pi(\theta_G|\lambda) = O(n)$. The marginal probability of the data $X_n$ is obtained by integrating over the parameter space, and we choose a graph G with the largest posterior probability $$\pi_G \int \prod_{i=1}^{N} F(x_i; \theta_G)\pi(\theta_G \mid \lambda)d\theta_G, \qquad (4)$$

where $\pi_G$ is a prior probability of G. Friedman and Goldszmidt (N. Friedman et al., in M. I. Jordan ed., *Learning in Graphical Models*, Kluwer Academic Publisher. 421 (1998)) considered the multinomial distribution as the Bayesian network model $f(x_i, \theta_G)$, and also supposed the Dirichlet prior on the parameter $\theta_G$. In this case, the Dirichlet prior is the conjugate prior and the posterior distribution belongs to the same class of distribution. Then a closed form solution of the integration in (4) is obtained, and they called it BDe score for choosing graph (G. F. Cooper et al., *Machine Learning*, 9, 309 (1992); D. Heckerman et al., *Machine Learning*, 20, 274 (1995)). Recall that the BDe score is confined to the multinomial model, and we propose a criterion for choosing graph in more general and various situations.

The essential problem of constructing criterion based on (4) is how compute the integration. Some methods can be considered for computing the integration such as Markov chain Monte Carlo, we use the Laplace approximation for integrals (A. C. Davison, *Biometrika*, 73, 323 (1986); D. Heckerman, A tutorial on learning with Bayesian networks, in M. I. Jordan ed., *Learning in Graphical Models* 301, Kluwer Academic Publisher (1998); L. Tinerey et al., *J. Amer. Statist. Assoc.*, 81, 82 (1986)). The Laplace approximation to the marginal probability of $X_n$ is $$\int \prod_{i=1}^{n} f(x_i; \theta_G)\pi(\theta_G \mid \lambda)d\theta_G \int \exp\{nl_\lambda(\theta_G \mid X_n)\}d\theta_G =$$

$$\frac{(2\pi/n)^{r/2}}{|J_\lambda(\hat{\theta}_G)|^{1/2}} \exp\{nl_\lambda(\hat{\theta}_G \mid X_n)\}\{1 + O_p(n^{-1})\},$$

where $r$ is the dimension of $\theta_G$, $$l_\lambda(\theta_G \mid X_n) = \frac{1}{n}\sum_{i=1}^{n} \log f(x_i; \theta_G) + \frac{1}{n}\log \pi(\theta_G \mid \lambda),$$

$$J_\lambda(\theta_G) = -\partial^2 \{l_\lambda(\theta_G \mid X_n)\}/\partial\theta_G\partial\theta_G^T$$

and $\hat{\theta}_G$ is the mode of $l_\lambda(\theta_G|X_n)$. Then we have a criterion, BNRC, for selecting graph $$BNRC(G) = -2\log\left\{\pi_G \int \prod_{i=1}^{n} f(x_i; \theta_G)\pi(\theta_G \mid \lambda)d\theta_G\right\} \qquad (5)$$

$$= -2\log\pi_G - r\log(2\pi/n) + \log|J_\lambda(\hat{\theta}_G)| - 2nl_\lambda(\hat{\theta}_G \mid X_n).$$

The optimal graph is chosen such that the criterion BNRC (5) is minimal.

This criterion is derived under log $\pi(\theta_G|\lambda) = O(n)$. If log $\pi(\theta_G|\lambda) = O(1)$, the mode $\hat{\theta}_G$ is equivalent to the maximum likelihood estimate, MLE, and the criterion is resulted in Bayesian information criterion, known as BIC (G. Schwarz, *Ann. Stat.*, 6, 461 (1978)) by removing the higher order terms $O(n^{-j})$ ($j \geq 0$). Konishi (S. Konishi (in Japanese), Sugaku, 52, 128, (2000)) provided a general framework for constructing model selection criteria based on the Kullback-Leibler information and Bayes approach.

It is assumed that the prior density $\pi(\theta_G|\lambda)$ is decomposed into the product of the prior densities on $\theta_j$, $\pi_G(\theta_G|\lambda) = \pi_1(\theta_1|\lambda_1) \times \ldots \times \pi_p(\theta_p|\lambda_p)$. Hence $l_{\lambda(\hat{\theta}_G)}|X_n)$ and log $|J_\lambda(\theta_G)|$ in (5) are, respectively, $$\sum_{j=1}^{p} l_\lambda^{(j)}(\hat{\theta}_j \mid X_n) \text{ and } \sum_{j=1}^{p} \log\left|-\frac{\partial^2 l_\lambda^{(j)}(\theta_j \mid X_n)}{\partial\theta_j\partial\theta_j^T}\right|, \qquad (6)$$

where $l_\lambda^{(j)}(\theta_j \mid X_n) = \frac{1}{n}\sum_{i=1}^{n} \log f_j(x_{ij} \mid p_{ij}; \theta_j) + \frac{1}{n}\log \pi_j(\theta_j \mid \lambda_j)$.

Thus the BNRC (5) can be obtained by the local scores of graph as follows: We define the local BNRC score, $BNRC_j$, for the j-th variable $X_j$ by $$BNRC_j = -2\log\left\{\pi_{L_j} \int \prod_{i=1}^{n} f_j(x_{ij} \mid p_{ij}; \theta_j)\pi_j(\theta_j \mid \lambda_j)d\theta_j\right\}, \qquad (7)$$

where $\pi_{L_j}$ is a prior probability of the local structure associated with $X_j$. We also apply Laplace's method to the $BNRC_j$ and the BNRC is obtained by $$BNRC = -2\log\pi_G + \sum_{j=1}^{p} \{BNRC_j + 2\log\pi_{L_j}\}.$$

Notice that the final graph is selected as a minimizer of the BNRC and not have to be minimize each local score $BNRC_j$, because the graph is constructed as acyclic.

4. Estimating Graph and Related Structures by Using BNRC

In this Section we express our method in more concrete terms. Essential points of our proposed method are the use of the nonparametric regression and the new criterion for choosing graph from Bayesian statistics.

As for nonparametric regression in section 2, we use the B-splines (C. de Boor, *A Practical Guide to Splines*. Springer, Berlin. (1978)) as the basis functions in (2). FIG. 8 is an example of B-splines of degree 3 with equidistance knots $t_1, \ldots, t_{10}$. We place the knots dividing the domain $[\min_i(p^{(j)}_{ik}), \max_i(p^{(j)}_{ik})]$ into $M_{jk}$−3 equidistance interval (P. H. C. Eilers and B. Marx, *Statistical Science*, 11, 89 (1996)) and set $M_{jk}$ B-splines of degree 3.

FIG. 8: example of 6 β-splines of degree 3. $t_1, \ldots, t_{10}$ are called knots. These knots are equally spaced.

We assume that the prior distribution on the parameter vector $\theta_j$ is $$\pi_j(\theta_j \mid \lambda_j) = \prod_{k=1}^{q_j} \pi_{jk}(\gamma_{jk} \mid \lambda_{jk}).$$

Each prior distribution $\pi_{jk}(\gamma_{jk}|\lambda_{jk})$ is a singular $M_{jk}$ variate normal distribution given by $$\pi_{jk}(\gamma_{jk} \mid \lambda_{jk}) = \left(\frac{2\pi}{n\lambda_{jk}}\right)^{-(M_{jk}-2)/2} |K_{jk}|_+^{1/2} \exp\left(-\frac{n\lambda_{jk}}{2}\gamma_{jk}^T K_{jk}\gamma_{jk}\right),$$

where $\lambda_{jk}$ is a hyper parameter, $K_{jk}$ is an $M_{jk} \times M_{jk}$ matrix, $\gamma_{jk}^T K_{jk}\gamma_{jk} = \Sigma_{l=3}^{M_{jk}}(\gamma_{lk}^{(j)} - 2\gamma_{l-1,k}^{(j)} + \gamma_{l-2,k}^{(j)})^2$ and $|K_{jk}|_+$ is the product of $M_{jk}-2$ nonzero eigenvalues of $K_{jk}$. The score $BNRC_j$ (7) can be obtained as $$BNRC_j = -2\log\pi_{L_j} - 2\sum_{i=1}^{n} \log f(x_{ij} \mid p_{ij}; \hat{\theta}_j) - 2\sum_{k=1}^{q_j} \log\pi_k(\hat{\gamma}_{jk} \mid \lambda_{jk}) + \log\left|-\frac{\partial^2 l_\lambda^{(j)}(\hat{\theta}_j \mid X_n)}{\partial \theta_j \partial \theta_j^T}\right| - \left(\sum_{k=1}^{q_j} M_{jk} + 1\right)\log(2\pi n^{-1}), \quad (9)$$

where $\hat{\theta}_j = (\hat{\gamma}^T, \hat{\sigma}_j^2)^T$ is a mode of $l_\lambda^{(j)}(\theta_j|X_n)$ defined in (6) for fixed $\lambda_{jk}$.

For computational aspect, we approximate the logarithm of the determinant of the Hessian matrix in (9) by $$\sum_{k=1}^{q_j} \{\log|B_{jk}^T B_{jk} + n\hat{\sigma}_j^2 \lambda_{jk} K_{jk}| - M_{jk}\log(n\hat{\sigma}_j^2)\} - \log(2\hat{\sigma}_j^4),$$

where $B_{jk}$ is an $n \times M_{jk}$ matrix defined by $B_{jk} = (b_{jk}(p_{1k}^{(j)}), \ldots, b_{jk}(p_{nk}^{(j)}))^T$ with $b_{jk}(p_{ik}^{(j)}) = (b_{1k}^{(j)}(p_{ik}^{(j)}), \ldots, b_{M_{jk}k}^{(j)}(p_{ik}^{(j)}))^T$. Hence combining (3), (8) and (9), $BNRC_j$ is resulted in $$BNRC_j = C_j + (n - 2q_j - 2)\log\hat{\sigma}_j^2 + \sum_{k=1}^{q_j} \left\{\frac{n\beta_{jk}}{\hat{\sigma}_j^2}\hat{\gamma}_{jk}^T K_{jk}\hat{\gamma}_{jk} + \log|\Lambda_{jk}| - (M_{jk} - 2)\log\beta_{jk}\right\},$$

where $\beta_{jk} = \sigma_j^2 \lambda_{jk}$ is a hyper parameter, $$C_j = -2\log\pi_{L_j} + (n + \overline{M}_{j^*} - 2q_j)\log(2\pi) + n - \log 2 - 2(\overline{M}_{j^*} - q_j)\log n - \sum_{k=1}^{q_j} \log|K_{jk}|_+,$$

$$\Lambda_{jk} = B_{jk}^T B_{jk} + n\beta_{jk}K_{jk}, \overline{M}_{j^*} = \sum_{k=1}^{q_j} M_{jk}.$$

By using the backfitting algorithm (T. Hastie and R. Tibshirani, *Generalized Additive Models*, Chapman & Hall, London (1990)) the modes $\hat{\gamma}_{jk}(k=1, \ldots, q_j)$ can be obtained when the values of $\beta_{jk}$ are given. The backfitting algorithm can be expressed as follows:

Step 1 Initialize: $\gamma_{jk}=0, k=1, \ldots, q_j$.

Step 2 Cycle: $k=1, \ldots, q_j, 1, \ldots, q_j, 1, \ldots$ $$\gamma_{jk} = (B_{jk}^T B_{jk} + n\beta_{jk}K_{jk})^{-1}B_{jk}^T\left(x_{(j)} - \sum_{k' \neq k} B_{jk'}\gamma_{jk'}\right).$$

Step 3 Continue Step 2 until a suitable convergence criterion is satisfied.

The mode $\hat{\sigma}_j^2$ is given by $\hat{\sigma}_j^2 = \|x_{(j)} - \Sigma_{k=1}^{q_j} B_{jk}\gamma_{jk}\|^2/n$ In attention, the modes $\hat{\gamma}_{jk}$ and $\hat{\sigma}_j^2$ are depend on the hyper parameters $\beta_{jk}$ and we have to choose the optimal values of $\beta_{jk}$. In the context of our method, it is a natural way that the optimal values of $\beta_{jk}$ are chosen as the minimizers of $BNRC_j$.

Recall that the B-splines coefficients vectors $\gamma_{jk}$ are estimated by maximizing (6). The modes of (6) are the same as the penalized likelihood estimates (B. W. Silverman, *J. R. Stat. Soc. Series* B, 47, 1 (1985); G. Wahba, *J. R. Stat. Soc. Series* B, 40, 364 (1978)) and we can look upon the hyper parameters $\lambda_{jk}$ or $\beta_{jk}$ as the smoothing parameters in penalized likelihood. Hence, the hyper parameters play an important role for fitting the curve to the data.

Figure 9A:
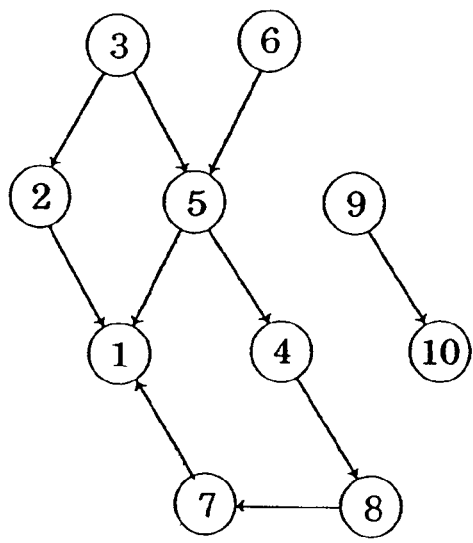
FIG. 9 Monte Carlo Simulation (9a) true, (9b) estimate.
Figure 9B:
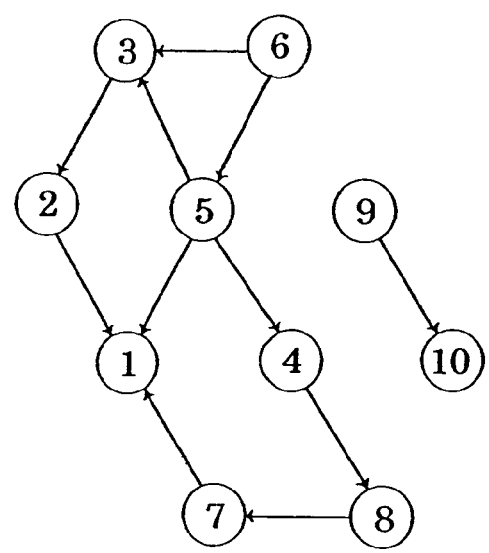

FIG. 9: Monte Carlo simulations: (9a) true, (9b) estimate.

$$X_1 = X_2^2 + 2\sin(X_5) - 2X_7 + \varepsilon_1$$

$$X_2 = \{1 + \exp(-4X_3)\}^{-1} + \varepsilon_2$$

$$X_3 = \varepsilon_3; X_6 = \varepsilon_6; X_9 = \varepsilon_9$$

$$X_4 = X_5^2/3 + \varepsilon_4, X_5 = X_3 - X_6^2 + \varepsilon_5$$

$$X_7 = \begin{cases} -1 + \varepsilon_7, & X_8 \leq -0.5 \\ X_8 + \varepsilon_7, & -0.5 < X_8 \leq 0.5 \\ 1 + \varepsilon_7, & 0.5 < X_8 \end{cases}$$

$$X_8 = \exp(-X_4 - 1)/2 + \varepsilon_8$$

$$X_{10} = \cos(X_9) + \varepsilon_{10}$$

5. Computational Experiments

Before analyzing the real data, we used Monte Carlo simulations to examine the properties of our method. The data were generated from artificial graph and structures between variables (FIG. 9) and then the results can be summarized as follows:

Proposed criterion BNRC can detect linear and nonlinear structure of the data very well. But BNRC score have a tendency toward overgrow of graph. In the analysis of the real data, then, we consider the use of Akaike's information criterion known as AIC (Akaike, in B. N. Petrov et al., eds., *2nd Inter. Symp. on Information Theory*, Akademiai Kiado, Budapest, 267 (1973); H. Akaike, *IEEE Trans. Autom. Contr.*, AC-19, 716 (1974)) and use both methods. AIC was originally introduced as a criterion for evaluating models estimated by maximum likelihood method. But the estimates by our method is the same as the maximum penalized likelihood estimates and is not MLE. In this case, the modified version of AIC (P. H. C. Eilers et al., *Statistical Science*, 11, 89 (1996)) is given by $$AIC = -2\sum_{i=1}^{n} \log f(x_{ij} | p_{ij}; \hat{\gamma}_j, \hat{\sigma}_j^2) + 2\left(\sum_{k=1}^{q_j} trS_{jk}\right),$$

where $S_{jk}=B_{jk}(B_{jk}^T B_{jk}+n\hat{\beta}_{jk}K_{jk})^{-1}B_{jk}^T$. The trace of $S_{jk}$ shows the degree of freedom of the fitted curve and is a great help. That is to say, if $trS_{jk}$ is nearly 2, the dependency is looked upon linear. We use both BNRC and AIC for decision whether we add up to a parent variable. By using this method, the estimated graph and structures are close to true model.

We analyze the *S. cerevisiae* cellcycle data discussed by Spellman et al. P. Spellman et al., *Mol. Biol. Cell*, 9, 3273 (1998) and Friedman et al. (N. Friedman et al., *J. Comp. Biol.*, 7, 601.(2000)). The data were collected from 800 genes with 77 experiments.

We set the prior probability $\pi_G$ is constant, because we have no reason why the large graph is unacceptable and no information about the size of the true graph. The nonparametric regressors are constructed 20 B-splines. In fact, the number of B-splines is also a parameter. However we use somewhat large number of B-splines, the hyper parameters control the smoothness of fitted curve and we cannot visually find differences among fitted curves corresponding with various number of B-splines.

The results of the analysis can be summarized as follows: FIGS. 10*a*, 10*b* and 10*c* shows BNRC scores when we predict CLN2 (FIG. 10*a*), CDC5 (FIG. 10*b*) and SVS1 (FIG. 10*c*) by one gene. The genes which give smaller BNRC scores give a better expression the target gene. We can observe that which gene is associated with target gene and we find the gene set which strongly depend on. In fact, we can construct a brief network by using these information. We can look upon the optimal graph as a revised version of the brief network by taking account of the effect of interactions. We note that if there is a linear dependency between genes, the score BNRC is also good when the parent-child relationship is reversed. Therefore, the directions of the causal associations in the graph are not strict especially when the dependencies are almost linear. Our result basically advocates the result of Friedman et al., (N. Friedman et al., *J. Comp. Biol.*, 7, 601 (2000), but, of cause, there are different points in parts. There are some genes that mediate Friedman et al.'s result, such as MCD1, CSI2, YOX1 and so on. Most of these genes had been reported to play an important role. A large number of the relationships between genes are nearly linear. But we could find some nonlinear dependencies which linear models hardly find. FIG. 12 shows the estimated graph associated with genes which were classified their processes into cell cycle and their neighborhood. Here, we omit some branches in FIG. 12, but important information are almost shown. As for the networks given by us and Friedman et al (N. Friedman, et al., *J. Comp. Biol.*, 7, 601 (2000)), we confirmed parent-children relationships and observed that both two networks are similar to each other. Especially, our network includes typical relationships which were reported by Friedman et al. As for the differences between both networks, we attention the parents of SVS1. Friedman et al. employed CLN2 and CDC5 as the parent genes of SVS1. On one hand, our result gives CSI2 and YKR090W for SVS1. We check up on the difference of these two results. After all, in the sense of BNRC and AIC, our candidate parent genes are more appropriate than Friedman et al's. The reason might be the effect of discretizing, because our model suitably fits to both cases in FIG. 11. Especially we conclude that CDC5 gives just weak effects to SVS1 compared with other genes only in the case in which Spellman's (P. Spellman, et al., *Mol. Biol. Cell*, 9, 3273 (1998)) data (see also FIG. 10). In fact, as the parent gene of SVS1, the order of BNRC score of CDC5 is 247th. Considering the circumstances mentioned above, our method can provide us valuable information in understandable and useful form.

FIG. 11: Cell cycle data and smoothed estimates. FIGS. 11(*a*) and 11(*b*) Friedman et al. (N. Friedman et al., *J. Comp. Biol.*, 7, 601 (2000), BNRC=57.71, AIC=167.96; (c) and (d) Proposed method, BNRC=32.53, AIC=140.16.

6. Discussion

We proposed the new method for estimating genetic networks from microarray gene expression data by using Bayesian network and nonparametric regression. We derived a new criterion for choosing graph theoretically, and represented its effectiveness though the analysis of cell cycle data. The advantages of our method are mainly as follow: We can use the expression data as continuous values. Not only linear dependencies, we can also detect nonlinear structures and can visualize their functional structures being easily understandable. Fully automatic search can accomplish the creation of optimal graph.

We also pointed out that Friedman et al.'s (N. Friedman, et al., *J. Comp. Biol.*, 7, 601 (2000)) method remained the unknown parameters such as threshold value for discretizing and hyper parameters in the Dirichlet priors which selected by trial and error and were not optimized in a narrow sense. On the other hand, our proposed method can automatically and appropriately estimate any parameters based on proposed criterion which has a sounder theoretical basis. Besides, our method includes Friedman et al's as a special case.

We consider the following problems for our future works: (1) We used the statistical models based on Gaussian distribution. However we derive the criterion BNRC in more general situations. In fact, we can construct the graph selection criterion based on other statistical models. (2) It is a possible case that the outliers cause strange results. Thus, the development of the robust methods and the technique for detecting the outliers are important problems. (3) The intensities of the unions are probably measured by using bootstrap method (B. Efron, *Ann. Stat.*, 7, 1 (1979)). We would like to investigate these problems in a future paper.

FIG. 12 depicts cell cycle result.

Example 2

Nonlinear Modeling of Genetic Network by Bayesian Network and Nonparametric Regression with Heterogeneous Error Variances and Interactions We propose a new statistical method for constructing genetic networks from microarray gene expression data based on Bayesian networks. In the context of Bayesian network, an essential point of network construction is in the estimation of the conditional distribution of each random variable. We consider fitting the nonparametric regression models with heterogeneous error variances and interactions for capturing the nonlinear structures between genes. Once we set a graph by using Bayesian network and nonparametric regression, a problem still remains to be solved in selecting an optimal graph, which gives a best representation of the system among genes. We theoretically derive a new criterion for choosing graph from Bayes approach in general situations.

The proposed method contains the previous methods for estimating genetic networks by using Bayesian networks. We demonstrate the effectiveness of proposed method through the analysis of *Saccharomyces cerevisiae* gene expression data newly obtained by disrupting 100 genes.

Key words: microarray gene expression data; Bayesian network; nonparametric regression; heteroscedasticity; interaction; posterior probability

1. INTRODUCTION

Under the development of the microarray technology, we can observe the gene expression data of thousands now simultaneously. In the analysis of gene expression data, constructing genetic network receives a large amount of attention in the field of molecular biology and bioinformatics (see T. Akutsu, et al., *Proc. Pacific Symposium on Biocomputing* 1999, 17 (1999); T. Akutsu, et al., *Bioinformatics*, 16, 727 (2000); T. Akutsu, et al., *J. Comp. Biol.*, 7, 331 (2000); N. Friedman et al., Learning Bayesian Networks with Local Structure, in M. I. Jordan ed., Kluwer Academic Publisher. 421 (1998); N. Friedman et al., *J. Comp. Biol.* 7, 601 (2000); S. Imoto et al., *Proc. Pacific Symposium on Biocomputing* 2002, (2002) in Press; and D. Pe'er, et al., *Bioinformatics*, 17, Suppl.1, 215 (ISMB 2001)). However, the causes of dimensionality and complexity of the data disturb the progress of the microarray gene expression data analysis. That is to say, the information that we want is buried with a huge amount of the data with noise. In this paper, we propose a new statistical method for constructing a genetic network that can capture even the nonlinear relationships between genes clearer.

Bayesian networks (F. V. Jensen, *An introduction to Bayesian Networks*. University College London Press (1996)) is an effective method in modeling the phenomena through the joint distribution of a large number of random variables. In recent years, some interesting works have been established in constructing genetic networks from the microarray gene expression data by using Bayesian networks. Friedman and Goldszmidt (N. Friedman et al., Learning Bayesian Networks with Local Structure, in M. I. Jordan ed., Kluwer Academic Publisher, 421 (1998)) discretized the expression values and assumed the multinomial distributions as candidate statistical models. Pe'er et al. (D. Pe'er et al., *Bioinformatics*, 17, Suppl.1, 215 (ISMB 2001) investigated the threshold value for discretizing. On the other hand, Friedman et al. (N. Friedman et al., *J. Comp. Biol.* 7, 601 (2000)) pointed out that the discretizing probably looses the information of the data and considered to fit the linear regression models, which analyze the data in the continuous. However, the assumption that the parent genes depend linearly on the objective gene is not always guaranteed. Imoto et al. (S. Imoto, et al., Proc. Pacific Symposium on Biocomputing 2002 (2002) in Press) proposed the use of nonparametric additive regression models (see also T. Hastie and R. Tibshirani, *Generalized Additive Models*, Chapman & Hall (1990)) for capturing not only linear dependencies but also nonlinear structures between genes. In this paper, we propose the method for constructing the genetic network by using Bayesian networks and the nonparametric heteroscedastic regression model, which is more resistant to the effect of outliers and can also capture the effects of the interactions of parent genes.

Once we set the graph, we have to evaluate its goodness or closeness to the true graph, which is completely unknown. Hence, the construction of a suitable criterion becomes the center of attention of statistical genetic network modeling. Friedman and Goldszmidt (N. Friedman et al., Learning Bayesian Networks with Local Structure, in M. I. Jordan ed., Kluwer Academic Publisher, 421 (1998)) derived the criterion, BDe, for choosing graph based on the multinomial models and Dirichlet priors. However, they remained the unknown hyper parameters in Dirichlet priors and we only set up the values experientially. We investigate the graph selection problem as the statistical model selection or evaluation problem and theoretically derive a new criterion for choosing graph from Bayes approach (J. O. Berger, *Statistical Decision Theory and Bayesian Analysis*. Springer-Verlag New York (1985)). The proposed criterion automatically optimizes the all parameters in the model and gives the optimal graph. In addition, our proposed method includes the previous methods for constructing genetic network by Bayesian network. To show the effectiveness of the proposed method, we analyze gene expression data of *Saccharomyces cerevisiae* by disrupting 100 genes.

2. BAYESIAN NETWORK AND NON-PARAMETRIC HETEROSCEDASTIC REGRESSION MODEL WITH INTERACTIONS

2.1 Nonlinear Model in Bayesian Network

Suppose that we have n sets of data $\{x_1, \ldots, x_n\}$ of the p-dimensional random variable vector $X=(X_1, \ldots, X_p)^T$, where $x_i=(x_{i1}, \ldots, x_{ip})^T$ and $x^T$ denotes the transpose of x. In microarray gene expression data, n and p correspond to the numbers of arrays and genes. Under the Bayesian network framework, we consider a directed acyclic graph G and Markov assumption between nodes. The joint density function is then decomposed into the conditional density (see also R. Cowell, et al., *Probabilistic Networks and Expert Systems*. Springer-Verlag New York (1999)) of each variable, that is, $$f(x_{i1}, \ldots, x_{ip}) = f_1(x_{i1}|p_{i1}) \times \ldots \times f_p(x_{ip}|p_{ip}), \quad (1)$$

where $p_{ij}=(p_{i1}^{(j)}, \ldots, p_{iq_j}^{(j)})^T$ T are $q_j$-dimensional parent observation vectors of $x_{ij}$ in the graph G. When $P_1=(X_2,X_3)^T$ is the parent variable vector of $X_1$, we see $p_{i1}=(x_{i2},x_{i3})^T$, (i= 1, . . . , n). Through the formula (1), the focus of interest in statistical modeling by Bayesian networks is how we can construct the conditional densities, $f_j$. We assume that the conditional densities, $f_j$, are parameterized by the parameter vectors $\theta_j$, and the effective information is extracted from these probabilistic models.

Imoto et al. (S. Imoto et al., Proc. Pacific Symposium on Biocomputing 2002, (2002) in Press) proposed the use of nonparametric regression strategy for capturing the nonlinear relationships between $x_{ij}$ and $p_{ij}$. In many cases, this method can capture the objective relationships very well. When the data, however, contain outliers especially near the boundary on the domain $\{p_{ij}\}$, nonparametric regression models sometimes lead to unsuitable smoothed estimates, i.e., the estimated curve exhibits some spurious waviness due to the effects of the outliers. Since what is estimated is the system of a being, the too much complicated relationship is unsuitable. In fact, this inappropriate case sometimes occurs in the real data analysis. To avoid this problem, we consider fitting the nonparametric regression model with heterogeneous error variances $$x_{ij}=m_j(p_{ij})+\epsilon_{ij}, \epsilon_{ij} \sim N(0,\sigma_{ij}^2), \quad (2)$$

where $m_j(\cdot)$ is a smooth function from $R^{q_j}$ to R and $N(\mu,\sigma^2)$ denotes Gaussian distribution with mean $\mu$ and variance $\sigma^2$. Here R denotes a set of real numbers. This model includes Imoto et al. (S. Imoto et al., Proc. Pacific Symposium on Biocomputing 2002, (2002) in Press) model and, clearly, the linear regression model as special cases.

One possible approach to the construction of the systematic component, $m_j(p_{ij})$, is the nonparametric additive regressor (S. Imoto et al., Proc. Pacific Symposium on Biocomputing 2002, (2002) in Press)

$$m_j(p_{ij}) = m_{j1}(p_{i1}^{(j)}) + \ldots + m_{jq_j}(p_{iq_j}^{(j)}) \quad (3)$$

which is a straightforward extension of the multiple linear regression. In general, each smooth function $m_{jk}(\cdot)$ is characterized by the n values $m_{jk}(p_{1k}^{(j)}), \ldots, m_{jk}(p_{nk}^{(j)})$ and the system (3) contains $n \times q_j$ parameters. Then the number of the parameters in the model is much larger than the number of observations and it has a tendency toward unstable parameter estimates. In this paper, we construct the smooth function $m_{jk}(\cdot)$ by basis functions approach $$m_{jk}(p_{ik}^{(j)}) = \sum_{m=1}^{M_{jk}} \gamma_{mk}^{(j)} b_{mk}^{(j)}(p_{ik}^{(j)}), k = 1, \ldots, q_j,$$

where $\gamma_{1k}^{(j)}, \ldots, \gamma_{M_{jk}}^{(j)}$ are unknown coefficient parameters and $b_{1k}^{(j)}(\cdot), \ldots, b_{M_{jk}}^{(j)}(\cdot)$ are basis functions. From this representation, the n parameters $m_{jk}(p_{ik}^{(j)}), \ldots, m_{jk}(p_{nk}^{(j)})$ are reparameterized by the $M_{jk}$ coefficient parameters $\gamma_{1k}^{(j)}, \ldots, \gamma_{M_{jk}}^{(j)}$. On the other hand, our interest is in the effects of interactions, we can construct the interaction model $$m_j(p_{ij}) = \sum_{l=1}^{s_j} \psi_{jl}(p_{il}^{(j)}), \quad (4)$$

where $p_{il}^{(j)}$ is the subvector of $p_{ij}$, that is, if we interest in the interaction of $p_{i1}^{(j)}$ and $p_{i2}^{(j)}$, we then obtain $p_{il}^{(j)} = (p_{i1}^{(j)}, p_{i2}^{(j)})^T$. We can also construct the function $\psi_{jl}(\cdot)$ by $$\psi_{jl}(p_{il}^{(j)}) = \sum_{k=1}^{L_{jl}} \xi_{lk}^{(j)} c_{lk}^{(j)}(p_{il}^{(j)}), l = 1, \ldots, s_j,$$

where $c_{lk}^{(j)}(p_{il}^{(j)})$ are basis functions and $\xi_{lk}^{(j)}$ like are parameters. Combining (3) and (4), the nonparametric regressor with interactions is generally given by $$m_j(p_{ij}) = \sum_{k=1}^{q_j} \sum_{m=1}^{M_{jk}} \gamma_{mk}^{(j)} b_{mk}^{(j)}(p_{ik}^{(j)}) + \sum_{l=1}^{s_j} \sum_{t=1}^{L_{jl}} \xi_{tl}^{(j)} c_{tl}^{(j)}(p_{il}^{(j)}). \quad (5)$$

In the error variances, $\sigma_{ij}^2$, we assume the following structures:

$$\sigma_{ij}^2 = w_{ij}^{-1} \sigma_j^2, i=1,\ldots,n; j=1,\ldots,p, \quad (6)$$

where $w_{1j}, \ldots, w_{nj}$ are constants and $\sigma_j^2$ is an unknown parameter. By setting up the constants $w_{1j}, \ldots, w_{nj}$ in reflecting the feature of the error variances, we can represent the heteroscedasticity of the data. Combining (2), (5) and (6), we obtain a nonparametric regression model with heterogeneous error variances and interactions $$f_j(x_{ij} \mid p_{ij}; \gamma_j, \xi_j, \sigma_j^2) = \quad (7)$$

$$\left(\frac{w_{ij}}{2\pi\sigma_j^2}\right)^{1/2} \exp\left[-\frac{w_{ij}}{2\sigma_j^2}\left\{x_{ij} - \sum_{k=1}^{q_j} \gamma_{jk}^T b_{jk}(p_{ik}^{(j)}) - \sum_{l=1}^{s_j} \xi_{jl}^T c_{jl}(p_{il}^{(j)})\right\}^2\right],$$

where $\gamma_{jk}$ and $b_{jk}(p_{ik}^{(j)})$ are $M_{jk}$-dimensional vectors given by, respectively, $$\gamma_{jk} = (\gamma_{1k}^{(j)}, \ldots, \gamma_{M_{jk}}^{(j)})^T,$$

$$b_{jk}(p_{ik}^{(j)}) = (b_{1k}^{(j)}(p_{ik}^{(j)}), \ldots, b_{M_{jk}}^{(j)}(p_{ik}^{(j)}))^T,$$

and $\xi_{jl}$ and $c_{jl}(p_{il}^{(j)})$ are $L_{jl}$-dimensional vectors given by, respectively, $$\xi_j = (\xi_{1l}^{(j)}, \ldots, \xi_{L_{jl}l}^{(j)})^T,$$

$$c_{jl}(p_{il}^{(j)}) = (c_{1l}^{(j)}(p_{il}^{(j)}), \ldots, c_{L_{jl}l}^{(j)}(p_{il}^{(j)}))^T.$$

Thus the parameters in the model (7) are $\gamma_j = (\gamma_{j1}^T, \ldots, \gamma_{jq_j}^T)^T$, $\xi_j = (\xi_{j1}^T, \ldots, \xi_{js_j}^T)^T$ and $\sigma_j^2$. If the variable $X_j$ has no parent variables in the graph, we specify the model based on the normal distribution with mean $\mu_j$ and variance $\sigma_j^2$. Hence the Bayesian network model is given by $$f(x_i; \theta_G) = \prod_{j=1}^{p} f_j(x_{ij} \mid p_{ij}; \theta_j), \quad (8)$$

where $\theta_G = (\theta_1^T, \ldots, \theta_p^T)^T$ is the parameter vector included in the graph G and $\theta_j$ is the parameter vector in the conditional density $f_j$, that is, we see $$\theta_j = (\gamma_j^T, \xi_j^T, \sigma_j^2)^T \text{ or } \theta_j = (\mu_j, \sigma_j^2)^T.$$

2.2 Criterion for Choosing Graph

Once we set a graph, the statistical model (8) based on the Bayesian network and nonparametric regression can be constructed and be estimated by a suitable method. However, the problem that still remains to be solved is how we can choose the optimal graph, which gives a best approximation of the system underlying the data Notice that we can not use the likelihood function as a model selection criterion, because the value of likelihood becomes large in a more complicated model. Hence, it needs to consider the statistical approach based on the generalized or predictive error, Kullback-Leibler information, Bayes approach and so on (S. Konishi, Statistical model evaluation and information criteria, in S. Ghosh ed., Marcel Dekker, New York (1999)). In this section, we construct a criterion for evaluating graph based on our model (8) from Bayes approach.

When we set a graph, the criterion for evaluating the goodness of the graph can be constructed from Bayesian theoretic approach as follows: The posterior probability of the graph is obtained by the product of the prior probability of the graph, $\pi_G$, and the marginal probability of the data By removing the standardized constant, the posterior probability of the graph is proportional to $$\pi(G \mid X_n) = \pi_G \int \prod_{i=1}^{n} f(x_i; \theta_G) \pi(\theta_G \mid \lambda) d\theta_G, \quad (9)$$

where $X_n = (x_1, \ldots, x_n)^T$ is an $n \times p$ gene profile matrix, $\pi(\theta_G \mid \lambda)$ is the prior distribution on the parameter $\theta_G$ satisfying log $\pi(\theta_G \mid \lambda) = O(n)$ and $\lambda$ is the hyper parameter vector. Under Bayes approach, we can choose the optimal graph such that $\pi(G \mid X_n)$ is maximum. A crucial problem for constructing a criterion based on the posterior probability of the graph is the computation of the high dimensional integral (9). Friedman and Goldszmidt (N. Friedman et al., Learning Bayesian Networks with Local Structure, in M. I. Jordan ed., Kluwer Academic Publisher. 421 (1998)) used the conjugate priors for solving the integral and gave a closed-form solution. To compute this high dimensional integral, we use Laplace's approximation (A. C. Davison, *Biometrika,* 73, 323 (1986); D. Heckerman, A tutorial on learning with Bayesian networks, in M. I. Jordan ed., Kluwer Academic Publisher. (1998); and L. Tinerey et al., *J. Amer. Statist. Assoc.,* 81, 82 (1986)) for integrals:

$$\int \prod_{i=1}^{n} f(x_i; \theta_G) \pi(\theta_G | \lambda) d\theta_G = \frac{(2\pi/n)^{r/2}}{|J_\lambda(\hat{\theta}_G)|^{1/2}} \exp\{nl_\lambda(\hat{\theta}_G | X_n)\}\{1 + O_p(n^{-1})\},$$

where $r$ is the dimension of $\theta_G$, $$l_\lambda(\theta_G | X_n) = \frac{1}{n}\sum_{i=1}^{n} \log f(x_i; \theta_G) + \frac{1}{n}\log \pi(\theta_G | \lambda), \quad J_\lambda(\theta_G) = -\frac{\partial^2 \{l_\lambda(\theta_G | X_n)\}}{\partial \theta_G \partial \theta_G^T}$$

and $\hat{\theta}_G$ is the mode of $l_\lambda(\theta_G | X_n)$. Then we have a criterion, BNRC, for selecting a graph $$BNRC(G) = -2\log\left\{\pi_G \int \prod_{i=1}^{n} f(x_i; \theta_G)\pi(\hat{\theta}_G | \lambda) d\theta_G\right\} \approx \quad (10)$$

$$-2\log \pi_G - r\log(2\pi/n) + \log|J_\lambda(\hat{\theta}_G)| - 2nl_\lambda(\hat{\theta}_G | X_n).$$

The optimal graph is chosen such that the criterion $BNRC_{hetero}$ (10) is minimal. The merit of the use of the Laplace method is that it is not necessary to consider the use of the conjugate prior distribution. Hence the modeling in the larger classes of distributions of the model and prior is attained.

Suppose that the parameter vectors $\theta_j$ are independent one another, the prior distribution then can be decomposed into $$\pi(\theta_G | \lambda) = \prod_{j=1}^{p} \pi_j(\theta_j | \lambda_j).$$

Therefore, $\log |J_\lambda(\theta_G | X_n)|$ and $nl_\lambda(\theta_G | X_n)$ in (10) are, respectively, $$\log|J_\lambda(\theta_G | X_n)| = \sum_{j=1}^{p}\log\left|-\frac{\partial^2 l_{\lambda_j}(\theta_j | X_n)}{\partial \theta_j \theta_j^T}\right|, \quad nl_\lambda(\theta_G | X_n) = \sum_{j=1}^{p} nl_{\lambda_j}(\theta_G | X_n),$$

where $$l_{\lambda_j}(\theta_j | X_n) = \frac{1}{n}\log f_j(x_{ij} | p_{ij}; \theta_j)) + \frac{1}{n}\log \pi_j(\theta_j | \lambda_j).$$

Here $\lambda_j$ is the hyper parameter vector. Hence by defining $$BNRC_{hetero}^{(j)} = -2\log\left\{\int \pi_{L_j}\prod_{i=1}^{n} f_j(x_{ij} | p_{ij}; \theta_j)\pi_j(\theta_j | \lambda_j) d\theta_j\right\}$$

where $\pi_{L_j}$ are prior probabilities satisfying $\Sigma_{j=1}^{P} \log \pi_{L_j} = \log \pi_G$, the $BNRC_{hetero}$ score is given by the sum of the local BNRC scores $$BNRC_{hetero} = \sum_{j=1}^{p} BNRC_{hetero}^{(j)}. \quad (11)$$

The smoothed estimates based on nonparametric regression are obtained by replacing the parameters $\gamma_j$ and $\xi_j$ by $\hat{\gamma}_j$ and $\hat{\xi}_j$, respectively. Noticed that we derive the criterion, BNRC, under the assumption $\log \pi(\theta_G|\lambda) = O(n)$. If we use the prior density satisfying $\log \pi(\theta_G|\lambda) = 0(1)$, the BNRC criterion is resulted in Schwarz's (G. Schwarz, *Ann. Statist.,* 6, 461, 1978) criterion known as BIC or SIC. In such case, the mode $\hat{\theta}_G$ is equivalent to the maximum likelihood estimate.

3. ESTIMATING GENETIC NETWORK

3.1 Nonparametric Regression

In this section we practically present the method for constructing genetic network based on proposed method described in Section 2. First we would like to mention the nonparametric regression model. The nonparametric regressor (5) has the two components: the main effects represented by the additive model of each parent gene and the interactions. In the additive model, we construct each smooth function $m_{jk}(\bullet)$ by B-splines (C. de Boor, *A Practical Guide to Splines,* Springer-Verlag, Berlin (1978) and S. Imoto et al., *Proc. Pacific Symposium on Biocomputing* 2002, (2002) in Press.)

In the interaction terms, we use Gaussian radial basis function $$c_{il}^{(j)}(p_{il}^{(j)}) = \exp\left(-\frac{\|p_{il}^{(j)} - z_{jl}\|^2}{2\xi_{jl}s_{jl}^2}\right),$$

where $z_{jl}$ is a center vector, $s_{jl}^2$ is a width parameter and $\zeta_{jl}$ is a hyper parameter. In the context of the regression modeling based on the radial basis functions, there are two methods for estimating the centers $z_{jl}$ and the widths $s_{jl}^2$. First, $z_{jl}$ and $s_{jl}^2$ are estimated by minimizing or maximizing a suitable object function like the squared loss and likelihood. This method is called fully supervised learning. On one hand, an alternative method determines $z_{jl}$ and $s_{jl}^2$ by using only the parent observation data $p_{jl}^{(j)}$ in advance. In this paper, we employ the latter method and use the k-means clustering algorithm for constructing the basis functions. The details of the radial basis functions are shown in (T. Andou et al., Submitted; J. Moody et al., *Neur. Comp.* 1, 281 (1989); and B. D. Ripley, Pattern recognition and neural networks, Cambridge University Press (1996)). The hyper parameters $\zeta_{jl}$ control the amount of overlapping among basis functions.

In the error variances, we consider the heteroscedastic regression model and assume the structure (6). The design of the constants $w_{1j}, \ldots, w_{nj}$ is an important problem for capturing the heteroscedasticity of the data. We set the weights as $$w_{ij} = g(p_{ij}; \rho) = \exp\{-\rho \|p_{ij} - \bar{p}_j\|^2 / 2s_j^2\}, \quad (12)$$

where $\rho$ is a hyper parameter, $\bar{p}_j = \Sigma_{i=1}^{n} p_{ij}/n$ and $s_j^2 = \Sigma_{i=1}^{n}\|p_{ij} - \bar{p}_j\|^2/nq_j$. If we set $\rho = 0$, the weights are $w_{1j} = \ldots = w_{nj} = 1$ and the model has homogeneous error variances. If we use the large value of $\rho$, the error variances of the data, which exist near the boundary on the domain of the parent variables, are large. Hence, if there are the outliers near the boundary, we can reduce their effects and gain the suitable smoothed estimates by using the appropriate value of $\rho$.

3.2 Priors

Suppose that the prior distribution $\pi_j(\theta_j|\lambda_j)$ is factorized into $$\pi_j(\theta_j | \lambda_j) = \prod_{k=1}^{q_j} \pi_{jk}(\gamma_{jk} | \lambda_{jk}) \prod_{l=1}^{s_j} \pi_{jl}(\xi_{jl} | \nu_{jl}),$$

where $\lambda_{jk}$ and $v_{jl}$ are hyper parameters. We use a singular $M_{jk}$ variate normal distribution as the prior distribution on $\gamma_{jk}$, $$\pi_{jk}(\gamma_{jk} \mid \lambda_{jk}) = \left(\frac{2\pi}{n\lambda_{jk}}\right)^{-(M_{jk}-2)/2} |K_{jk}|_+^{1/2} \exp\left(-\frac{n\lambda_{jk}}{2}\gamma_{jk}^T K_{jk}\gamma_{jk}\right), \quad (13)$$

where $K_{jk}$ is an $M_{jk} \times M_{jk}$ symmetric positive semidefinite matrix satisfying $$\gamma_{jk}^T K_{jk}\gamma_{jk} = \sum_{\alpha=3}^{M_{jk}}(\gamma_{\alpha,k}^{(j)} - 2\gamma_{\alpha-1,k}^{(j)} + \gamma_{\alpha-2,k}^{(j)})^2.$$

The prior distributions on $\xi_{jl}$ are $$\pi_{jl}(\xi_{jl} \mid v_{jl}) = \left(\frac{2\pi}{nv_{jl}}\right)^{-v_{jl}/2} \exp\left(-\frac{nv_{jl}}{2}\|\xi_{jl}\|^2\right),$$

where $v_{jl}$ is the dimension of $\xi_{jl}$.

Next we consider the prior probability of the graph $\pi_G$. Friedman and Goldszmidt (N. Friedman et al., Learning Bayesian Networks with Local Structure, in M. I. Jordan ed., Kluwer Academic Publisher, 1998) employed the prior based on the MDL encoding of the graph. In our context, the marginal probability of the data is seemed to be the type II likelihood adjusted by the hyper parameters. Thus we set the prior probability of the graph, $\pi_G$, $$\pi_G = \exp\{-(\text{No. of hyper parameters})\} = \prod_{j=1}^{p}\exp\{-(q_j + 2s_j + 1)\}\prod_{j=1}^{p}\pi L_j$$

The justification of this prior is based on Akaike's (H. Akaike, Likelihood and the Bayes procedure, in J. M. Bernardo, M. H. DeGroot, D. V. Lindley & A. F. M. Smith, eds., Univ. Press, Valencia (1980) Bayesian information criterion, known as ABIC, and Akaike's (H. Akaike, Information theory and an extension of the maximum likelihood principle, in B. N. Petrov & F. Csaki, eds., Akademiai Kiado, Budapest, 267 (1973)) information criterion, AIC.

3.3 Criterion

In Section 2.2, we derived the criterion, BNRC, for choosing the graph in general framework. By using the equation (11), the BNRC score of the graph can be obtained by the sum of the local scores, $BNRC_j$. The result is summarized in the following theorem. Theorem 1. Let $f(x_i;\theta_G)$ be a Bayesian network and nonparametric regression model given by (8), and let $\pi(\gamma_{jk}|\lambda_{jk})$ and $\pi(\xi_{j1}|v_{j1})$ be the prior densities on the parameters $\gamma_{jk}$ and $\xi_{j1}$ defined by (13) and (14) respectively. Then a criterion for evaluating graph is given by $$BNRC = \sum_{j=1}^{p} BNRC_j, \text{ where}$$

$$BNRC_j = 2(q_j + 2s_j + 1) - \left(\sum_{k=1}^{q_j} M_{jk} + \sum_{l=1}^{s_j} L_{jl} + 1\right)\log(2\pi/n) -$$

$$\sum_{i=1}^{n}\log w_{ij} + n\log(2\pi\hat{\sigma}_j^2) + n + \sum_{k=1}^{q_j}\{\log|\Lambda_{jk}| - M_{jk}\log(n\hat{\sigma}_j^2)\} -$$

-continued $$\log(2\hat{\sigma}_j^2) + \sum_{l=1}^{s_j}\{\log|\Gamma_{jl}| - L_{jl}\log(n\hat{\sigma}_j^2)\} +$$

$$\sum_{k=1}^{q_j}\left\{(M_{jk} - 2)\log\left(\frac{2\pi\hat{\sigma}_j^2}{n\beta_{jk}}\right) - \log|K_{jk}| + \frac{n\beta_{jk}}{\hat{\sigma}_j^2}\hat{\gamma}_{jk}^T K_{jk}\hat{\gamma}_{jk}\right\} +$$

$$\sum_{l=1}^{s_j}\left\{v_{jl}\log\left(\frac{2\pi\hat{\sigma}_j^2}{n\tau_{jl}}\right) + \frac{n\tau_{jl}}{\hat{\sigma}_j^2}\|\hat{\xi}_{jl}\|^2\right\}$$

with $$\Lambda_{jk} = B_{jk}^T W_j B_{jk} + n\beta_{jk} K_{jk}; (M_{jk} \times M_{jk}),$$

$$\Gamma_{jl} = C_{jl}^T W_j C_{jl} + n\tau_{jl} I_{jl}; (L_{jl} \times L_{jl}),$$

$$I_{ij} = diag[1, \ldots, 1]; (L_{jl} \times L_{jl}),$$

$$B_{jk} = \left(b_{1k}^{(j)}(p_{1k}^{(j)}), \ldots, b_{M_{jk}k}^{(j)}(p_{nk}^{(j)})\right)^T; (n \times M_{jk}),$$

$$C_{jl} = \left(c_{1l}^{(j)}(p_{1l}^{(j)}), \ldots, c_{L_{jl}l}^{(j)}(p_{nl}^{(j)})\right)^T; (n \times L_{jl}),$$

$$W_j = diag(w_{1j}, \ldots, w_{nj}); (n \times n)$$

$$\hat{\sigma}_j^2 = \sum_{i=1}^{n} w_{ij}\left\{x_{ij} - \sum_{k=1}^{q_j}\hat{\gamma}_{jk}^T b_{jk}(p_{ik}^{(j)}) - \sum_{l=1}^{s_j}\hat{\xi}_{jl}^T c_{jl}(p_{il}^{(j)})\right\}^2/n.$$

Here we approximate the Hessian matrix by $$\log\left|-\frac{\partial^2 l_{\lambda_j}(\theta_j \mid X_n)}{\partial\theta_j\partial\theta_j^T}\right| \approx \sum_{k=1}^{q_j}\log\left|-\frac{\partial^2 l_{\lambda_j}(\theta_j \mid X_n)}{\partial\gamma_{jk}\partial\gamma_{jk}^T}\right| +$$

$$\sum_{l=1}^{s_j}\log\left|-\frac{\partial^2 l_{\lambda_j}(\theta_j \mid X_n)}{\partial\xi_{jl}\partial\xi_{jl}^T}\right| + \log\left|-\frac{\partial^2 l_{\lambda_j}(\theta_j \mid X_n)}{\partial(\sigma_j^2)^2}\right|$$

3.4 Penalized Likelihood

Consider the nonparametric regression model defined in (7). When the estimation method is the maximum likelihood method which maximizes the log-likelihood function $l(\gamma_j, \xi_j, \sigma_j^2) = \sum_{i=1}^{n}\log f_j(x_{ij}|p_{ij}; \gamma_j, \xi_j, \sigma_j^2)$, then the parameter estimates yield unstable and lead to overfitting due to the flexibility of the model. In our method, the estimate $\hat{\theta}_j = (\hat{\gamma}_j^T, \hat{\xi}_j^T, \hat{\sigma}_j^2)^T$ is obtained as a mode of $l_{\lambda_j}(\theta_j|X_n)$ and the estimation method is equivalent to the maximum penalized likelihood (P. J. Green et al., Nonparametric regression and generalized linear models, Chapman & Hall (1994) and I. J. Good et al., Nonparametric roughness penalties for probability densities. *Biometrika*, 58, 255 (1971)), which includes the maximum likelihood method as a special case.

The mode $\hat{\theta}_j$ depends on the hyper parameters. In fact, the hyper parameter plays an essential role for estimating the smoothed curve. We use the distributions (13) and (14) as the prior distributions on $\gamma_{jk}$ and $\xi_{jl}$, respectively. Then $l_{\lambda_j}(\theta_j|X_n)$ is resulted in $$l_{\lambda_j}(\theta_j \mid X_n) \propto \sum_{i=1}^{n}\log f_j(x_{ij} \mid p_{ij}; \theta_j) - \sum_{k=1}^{q_j}\frac{n\lambda_{jk}}{2}\gamma_{jk}^T K_{jk}\gamma_{jk} - \sum_{l=1}^{s_j}\frac{nv_{jl}}{2}\|\xi_{jl}\|^2.$$

The first term in the right hand side is the log-likelihood function and the second and third terms are called roughness penalties. The hyper parameters $\lambda_{jk}$ and $v_{ji}$ are called smoothing parameters which control the smoothness of the fitted curves.

FIGS. 13a and 13b depict: smoothed estimates by the various values of the hyperparameter.

That is, if the smoothing parameter is small, the estimated curve close to the data, what is called overfitting. On the other hand, the large value of the smoothing parameter is used, the estimate is nearly linear fit. Hence, the choice of the hyper parameter plays an essential role for capturing the relationship between genes. The performances of the hyper parameters are shown in the next section.

4. REAL DATA ANALYSIS

In this section we show the effectiveness of the proposed method through the analysis of *S. cerevisiae* gene expression data. Our research group has installed a systematic experimental method, which observes the changes of expression level of genes on a microarray by gene disruption. By using this method, we have launched a project whose purpose is to reveal the gene regulatory networks between the 5871 genes of *Saccharomyces cerevisiae* while many laboratories have also reported similar projects. We have already collected a large number of expression profiles from gene disruption experiments to evaluate genetic regulatory networks. Over 400 mutants are stocked and gene expression profiles are accumulating.

FIGS. 14a and 14b depict the effect of the weight constraints.

We monitored the transcriptional revel of 5871 genes spotted on a microarray by a scanner. The expression profiles of over 400 disruptants were piled up in our database. The standard deviation (SD) of all genes on a microarray were evaluated and the value of SD represented roughly the error of a experiment. In our data, we estimated the value of 0.5 as the critical point of the accuracy of experiments. We have evaluated the accuracy of those profiles on the basis of the standard deviation of the expression ratio of all genes. 107 disruptants including 68 mutants where the transcription factors were disrupted could be selected from 400 profiles.

FIG. 15: The estimated surface by the nonparametric regression with interaction.

We used 100 microarrays and constructed the genetic network of 521 genes from the above data. Because, the 94 transcription factors whose regulating genes are clearly identified were found, and the profiles of the 521 genes in control by 94 factors were selected from 5871 profiles.

FIG. 16: the resulted partial network of *Saccharomyces cerevisiae* genes. In our model, we construct the nonparametric regression model by 20 B-splines and 20 radial basis functions. We confirmed that the differences of the smoothed estimates against the various number of the basis functions can not visually found, because when we use the somewhat large number of the basis functions, the hyper parameters control the smoothness of the fitted curves. We applied the two genes effect to the interaction components. Hence, the effects of the interactions are obtained as the fitted surfaces and can be visually understandable.

Before we mention the result of this analysis, we show the roles of the hyper parameters in the prior distributions and weight constants. FIG. 13a shows the scatter plot of YGL237C and YEL071W with smoothed estimates by 3 different values of the hyper parameters. Clearly, the smoothed estimate strongly depends on the values of the hyper parameters. FIG. 13b is the behavior of the BNRC criterion of the two genes in FIG. 13a. We can choose the optimal value of the hyper parameter as the minimizers of the BNRC and the optimal smoothed estimate (solid curve) can capture the structure between these genes well. The dashed and dotted curves are near the maximum likelihood estimate and the parametric linear fit, respectively. The effect of the weight constants $w_{1j}, \ldots, w_{nj}$ is shown in FIG. 14a. If we use the homoscedastic regression model, we obtained the dashed curve, which exhibits some spurious waviness due to the effect of the data in the upper-left corner. By adjusting the hyper parameter $\rho$ in (12), the estimated curve is resulted in the solid curve. The optimal value of $\rho$ is also chosen by minimizing the BNRC criterion (see FIG. 14b). Of course, when the smoothed estimate is properly obtained, the optimal value of $\rho$ tends to zero.

We employ a two step strategy for fitting the nonparametric regression model with interactions. First, we estimate the main effects represented by the additive B-spline regressors. Next, we fit the interaction components to the residuals. FIG. 15 is an example of the fitted surface to the relationship between YIL094C and its parent genes, YKL152C and YER055C. It is clearly shown that the interaction of the two parent genes leads more overexpress when both parent genes increase.

The results of the analysis and their evaluations are as follows: In *Saccharomyces cerevisiae* the GCN4 gene encodes the transcriptional activator of the "general control" system of amino acid biosynthesis, a network of at least 12 different biosynthetic pathways (G. Albrecht et al., *J. Biol. Chem.*, 273, 12696 (1998)). Experiments showed that the consequences of the general control response upon the signal "amino acid starvation" induced by the histidine analogue 3-aminotriazole with respect to Gcn4p levels. GCN4 activates transcription of more than 30 genes involved in the biosynthesis of 11 amino acids in response to amino acid starvation or impaired activity of tRNA synthetases (see R. J. Rolfes et al., *Mol. Cell Biol.*, 13, 5099, 1993). Purine biosynthetic genes ADE1, ADE4, ADE5,7, and ADE8 display GCN4-dependent expression in response to amino acid starvation (R. J. Rolfes et al., *Mol Cell Biol.*, 13, 5099, 1993). GCN4 activates transcription of biosynthetic genes for amino acids and purines in response to either amino acid or purine starvation (R. J. Rolfes et al., *Mol. Cell Biol.*, 13, 5099, 1993). Those results of experiments shows that there are the strong relations between purine metabolism and amino acid metabolism by a GCN4. Our map of relation realized well the many relations among purine and amino acid metabolism.

5. CONCLUSION

In this example we proposed a new statistical method for estimating genetic network from microarray gene expression data by using Bayesian network and nonparametric regression. The key idea of our method is the use of the nonparametric heteroscedastic regression models for capturing nonlinear relationships between genes and heteroscedasticity of the expression data. An essential problem for network construction is in the evaluation of the graph. We investigated this problem as a statistical model selection or evaluation problem and derived the new criterion for selecting graph from Bayes approach. Our method covers the previous methods for constructing genetic networks by using Bayesian networks and improves them in the theoretical and methodological sense. We showed the effectiveness of our method through the analysis of Saccharomyces cerevisiae gene expression data and evaluated the resulted network by comparing with the knowledge of biology. We construct the genetic network without the biological information. Nevertheless, the resulted network includes the many important connections, which agree with the biological knowledge. Hence, we expect that our method can demonstrate its power against the analysis of completely unknown system like the human genome.

Example 3

Bayesian Network and Nonparametric Heteroscedastic Regression for Nonlinear Modeling of Genetic Network Summary We propose a new statistical method for constructing a genetic network from microarray gene expression data by using a Bayesian network. An essential point of Bayesian network construction is in the estimation of the conditional distribution of each random variable. We consider fitting nonparametric regression models with heterogeneous error variances to the microarray gene expression data to capture the nonlinear structures between genes. A problem still remains to be solved in selecting an optimal graph, which gives the best representation of the system among genes. We theoretically derive a new graph selection criterion from Bayes approach in general situations. The proposed method includes previous methods based on Bayesian networks. We demonstrate the effectiveness of the proposed method through the analysis of *Saccharomyces cerevisiae* gene expression data newly obtained by disrupting 100 genes.

1. Introduction

Due to the development of the microarray technology, constructing genetic network receives a large amount of attention in the fields of molecular biology and bioinformatics (T. Akutsu et al., *Proc. Pacific Symposium on Biocomputing*, 4, 17-28, 1999; T. Akutsu et al., Inferring qualitative relations in genetic networks and metabolic pathways. *Bioinformatics*, 16, 727-734, 2000; T. Akutsu et al., *J. Comp. Biol.*, 7, 331-344, 2000; N. Friedman et al., in M. I. Jordan ed., Kluwer Academic Publisher, 1998; N. Friedman, et al., *J. Comp. Biol.*, 7, 601-620, 2000; A. J. Hartemink et al., *Proc. Pacific Symposium on Biocomputing*, 7, 437-449, (2002); S. Imoto et al., *Proc. Pacific Symposium on Biocomputing*, 7, 175-186, 2002; and D. Pe'er et al., *Bioinformatics*, 17, Suppl. 1, 215-224, 2001). However, the dimensionality and complexity of the data disturb the progress of the microarray gene expression data analysis. That is to say, the information that we want is buried in a huge amount of the data with noise. In this paper, we propose a new statistical method for constructing a genetic network that can capture even the nonlinear relationships between genes clearer.

A Bayesian network (R. Cowell, et al., Probabilistic Networks and Expert Systems, Springer-Verlag N.Y., 1999; F. V. Jensen. An introduction to Bayesian Networks, University College London Press, 1996) is an effective method in modeling phenomena through the joint distribution of a large number of random variables. In recent years, some interesting works have been established in constructing genetic networks from microarray gene expression data by using Bayesian networks. Friedman and Goldszmidt (N. Friedman et al., *Proc. 13'th International Conference on Machine Learning*, 157-165, 1996; N. Friedman et al., *Proc. Twelfth Conf. on Uncertainty in Artificial Intelligence*, 252-262, 1996; and N. Friedman et al., Learning Bayesian Networks with Local Structure, in M. I. Jordan ed., Kluwer Academic Publisher, 1998) discretized the expression values and assumed multinomial distributions as the candidate statistical models. Pe'er et al. D. Pe'er et al., *Bioinformatics*, 17, Suppl. 1, 215-224, 2001) investigated the threshold value for discretizing. On the other hand, Friedman et al. (N. Friedman, et al., *J. Comp. Biol.*, 7, 601-620, 2000) pointed out that the discretizing probably loses information of the data. In fact, the number of discretizing values and the thresholds are unknown parameters, which have to be estimated from the data. The resulted network strongly depends on their values.

Then Friedman et al. (N. Friedman, et al., *J. Comp. Biol.*, 7, 601-620, 2000) considered fitting linear regression models, which analyze the data in the continuous (see also D. Heckerman et al., *Proc. Eleventh Conf. on Uncertainty in Artificial Intelligence*, 274-284, 1995). However, the assumption that the parent genes depend linearly on the objective gene is not always guaranteed. Imoto et al. (S. Imoto et al., *Proc. Pacific Symposium on Biocomputing*, 7, 175-186, 2002) proposed the use of nonparametric additive regression models (see also P. J. Green et al., Nonparametric Regression and Generalized Linear Models, Chapman & Hall, 1994; and Hastie and R. Tibshirani, Generalized Additive Models, Chapman & Hall, 1990) for capturing not only linear dependencies but also nonlinear structures between genes. In this paper, we propose a method for constructing the genetic network by using Bayesian networks and the nonparametric heteroscedastic regression, which is more resistant to the effect of outliers.

Once we set the graph, we have to evaluate its goodness or closeness to the true graph, which is completely unknown. Hence, the construction of a suitable criterion becomes the center of attention of statistical genetic network modeling. Friedman and Goldszmidt (N. Friedman et al., Learning Bayesian Networks with Local Structure, in M. I. Jordan ed., Kluwer Academic Publisher, 1998) used the BDe criterion, which was originally derived by (D. Heckerman, et al., *Machine Learning*, 20, 197-243, 1995) for choosing a graph. The BDe criterion only evaluates the Bayesian network model based on the multinomial distributions and Dirichlet priors. However, Friedman and Goldszmidt (N. Friedman et al., *Proc. Twelfth Conf. On Uncertainty in Artificial Intelligence*, 252-262, 1996) kept the unknown hyper parameters in Dirichlet priors and we only set up the values experimentally. We investigate the graph selection problem as a statistical model selection or evaluation problem and theoretically derive a new criterion for choosing a graph using the Bayes approach (see J. O. Berger, Statistical Decision Theory and Bayesian Analysis, Springer-Verlag New York, 1985). The proposed criterion automatically optimizes all parameters in the model and gives the optimal graph. In addition, our proposed method includes the previous methods for constructing genetic network based on Bayesian network. To show the effectiveness of the proposed method, we use the Monte Carlo simulation method. We also analyze gene expression data of *Saccharomyces cerevisiae* newly obtained by disrupting 100 genes.

2. Bayesian Network and Nonparametric Heteroscedastic Regression Model 2.1. Nonlinear Bayesian Network Model Suppose that we have n sets of array data $\{x_1, \ldots, x_n\}$ of p genes, where $x_i = (x_{i1}, \ldots x_{ip})^T$ and $x^T$ denotes the transpose of x. In the Bayesian network framework, we consider a directed acyclic graph G and Markov assumption between nodes. The joint density function is then decomposed into the conditional density of each variable, that is, $$f(x_{i1}, \ldots, x_{ip}) = \prod_{j=1}^{p} f_j(x_{ij} | p_{ij}), \quad (1)$$

where $p_{ij} = (p_{i1}^{(j)}, \ldots, p_{iq_j}^{(j)})^T$ are $q_j$-dimensional parent observation vectors of $x_{ij}$ in the graph G. When gene$_2$ and gene$_3$ are parent genes of gene$_1$, we see $p_{i1} = (x_{i2}, x_{i3})^T$, (i=1, ..., n). Through formula (1), the focus of interest in statistical modeling by Bayesian networks is how we can construct the conditional densities, $f_j$. We assume that the conditional densities, $f_j$, are parameterized by the parameter vectors $\theta_j$, and the information is extracted from these probabilistic models.

Imoto et al. (S. Imoto et al., *Proc. Pacific Symposium on Biocomputing*, 7, 175-186, 2002) proposed the use of nonparametric regression strategy for capturing the nonlinear relationships between $x_{ij}$ and $p_{ij}$ and suggested that there are many nonlinear relationships between genes and the linear model hardly achieves a sufficient result. In many cases, this method can capture the objective relationships very well. When the data, however, contain outliers especially near the boundary of the domain $\{p_{ij}\}$, nonparametric regression models sometimes lead to unsuitable smoothed estimates, i.e., the estimated curve exhibits some spurious waviness due to the effects of the outliers. Since what is estimated is the system of a living nature, a too complicated relationship is unsuitable. In fact, this inappropriate case unfortunately sometimes occurs in the analysis of real data. To avoid this problem, we consider fitting a nonparametric regression model with heterogeneous error variances $$x_{ij} = m_{j1}(p_{i1}^{(j)}) + \ldots + m_{jq_j}(p_{iq_j}^{(j)}) + \varepsilon_{ij}, \qquad (2)$$

where $\varepsilon_{ij}$ depends independently and normally on mean 0 and variance $\sigma_{ij}^2$ and $m_{jk}(\bullet)$ is a smooth function from R to R. Here R denotes a set of real numbers. This model includes Imoto et al's (S. Imoto et al., *Proc. Pacific Symposium on Biocomputing*, 7, 175-186, 2002) model and, clearly, the linear regression model as special cases. In general, each smooth function $m_{jk}(\bullet)$ is characterized by the n values $m_{jk}(p_{1\ k}^{(j)}), \ldots, m_{jk}(p_{n\ k}^{(j)})$ and the system (2) contains $(n \times q_j+n)$ parameters. Then the number of the parameters in the model is much larger than the number of observations and it has a tendency toward unstable parameter estimates. In this paper, we construct the smooth function $m_{jk}(\bullet)$ by the basis functions approach $$m_{jk}(p_{ik}^{(j)}) = \sum_{m=1}^{M_{jk}} \gamma_{mk}^{(j)} b_{mk}^{(j)}(p_{ik}^{(j)}), k = 1, \ldots, q_j,$$

where $\gamma_{1k}^{(j)}, \ldots, \gamma_{M_{jk}}^{(j)}$ are unknown coefficient parameters and $b_{1k}^{(j)}(\bullet), \ldots, b_{M_{jk}}^{(j)}(\bullet)$ are basis functions. From this representation, the n parameters $m_{jk}(p_{i1\ k}^{(j)}), \ldots, m_{jk}(p_{n\ k}^{(j)})$ are reparameterized by the $M_{jk}$ coefficient parameters $\gamma_{1k}^{(j)}, \ldots, \gamma_{M_{jk}}^{(j)}$.

We strongly recommend the use of nonparametric regression instead of linear regression, because linear regression cannot decide the direction of the Bayes causality or leads to the wrong direction in many cases. We show the advantage of the proposed model compared with linear regression through a simple example. Suppose that we have data of $gene_1$ and $gene_2$ in FIG. 17a. We consider the two models $gene_1 \to gene_2$ and $gene_2 \to gene_1$, and obtain the smoothed estimates shown in FIGS. 17b and 17c, respectively. We decide that the model (b: $gene_1 \to gene_2$) is better that (c: $gene_2 \to gene_1$) by the proposed criterion, which is derived in a later section (the scores of the models are (b) 120.6 (c) 134.8). Since we generated this data from the true graph $gene_1 \to gene_2$, our method yields the correct result. However, if we fit the linear regression model to this data, the model (c) is chosen (the scores are (b) 156.0 (c) 135.8). The method, which is based on linear regression, yields an incorrect result in this case.

Consider the case that the relationship is almost linear. Our method and linear regression can fit the data appropriately. However, it is clearly difficult to decide the direction of Bayes causality. In such a case, the direction is not strict.

FIGS. 17a-17c: Simulated data: The true causality is $gene_1 \to gene_2$. FIG. 17a: Scatter plot of the simulated data. FIG. 17b: Smoothed curve of the graph $gene_1 \to gene_2$. FIG. 17c: Smoothed curve of the graph $gene_2 \to gene_1$. These curves are obtained by the proposed method.

In the error variances, $\sigma_{ij}^2$, we assume the structures, $$\sigma_{ij}^2 = w_{ij}^{-1} \sigma_j^2, i=1, \ldots, n; j=1, \ldots, p, \qquad (3)$$

where $w_{1j}, \ldots, w_{nj}$ are constants and $\sigma_j^2$ is an unknown parameter. By setting up the constants $w_{1j}, \ldots, w_{nj}$ in reflecting the feature of the error variances, we can represent the heteroscedasticity of the data. Combining (2) and (3), we obtain a nonparametric regression model with heterogeneous error variances $$f_j(x_{ij} \mid p_{ij}; \gamma_j, \sigma_j^2) = \left(\frac{w_{ij}}{2\pi\sigma_j^2}\right)^{1/2} \exp\left[-\frac{w_{ij}}{2\sigma_j^2}\left\{x_{ij} - \sum_{k=1}^{q_j} \gamma_{jk}^T b_{jk}(p_{ik}^{(j)})\right\}^2\right], \qquad (4)$$

where $\gamma_{jk}$ and $b_{jk}(p_{ik}^{(j)})$ are $M_{jk}$-dimensional vectors given by, respectively, $\gamma_{jk}=(\gamma_{1k}^{(j)}, \ldots, \gamma_{M_{jk}}^{(j)})^T$ and $b_{jk}(p_{ik}^{(j)})=(b_{1k}^{(j)}(p_{ik}^{(j)}), \ldots, b_{M_{jk}}^{(j)}(p_{ik}^{(j)}))^T$. If the j-th gene has no parent genes in the graph, we specify the model based on the normal distribution with mean $\mu_j$ and variance $\sigma_j^2$. Hence, we define the nonlinear Bayesian network model $$f(x_i; \theta_G) = \prod_{j=1}^{p} f_j(x_{ij} \mid p_{ij}; \theta_j), \qquad (5)$$

where $\theta_G=(\theta_1^T, \ldots, \theta_p^T)^T$ is the parameter vector included in the graph G and $\theta_j$ is the parameter vector in the conditional density $f_j$, that is, we see $\theta_j=(\gamma_j^T, \sigma_j^2)^T$ or $\theta_j=(\mu_j, \sigma_j^2)^T$.

2.2 Criterion for Choosing Graph

Once we set a graph, the statistical model (5) based on the Bayesian network and nonparametric regression can be constructed and be estimated by a suitable procedure. However, the problem that still remains to be solved is how we can choose the optimal graph, which gives a best approximation of the system underlying the data. Notice that we cannot use the likelihood function as a model selection criterion, because the value of likelihood becomes large in a more complicated model. Hence, we need to consider the statistical approach based on the generalized or predictive error, Kullback-Leibler information, Bayes approach and so on (see e.g., H. Akaike, Information theory and an extension of the maximum likelihood principle. in B. N. Petrov, & F. Csaki, eds., Akademiai Kiado, Budapest, 267-281, 1973; S. Konishi, Statistical model evaluation and information criteria. in S. Ghosh ed., Marcel Dekker, New York, 1999; S. Konishi et al., Generalised information criteria in model selection, *Biometrika*, 83, 875-890, 1996) for the statistical model selection problem). In this section, we construct a criterion for evaluating a graph based on our model (5) from Bayes approach.

The posterior probability of the graph is obtained by the product of the prior probability of the graph, $\pi_G$, and the marginal probability of the data. By removing the standardizing constant, the posterior probability of the graph is proportional to $$\pi(G \mid X_n) = \pi_G \int \prod_{i=1}^{n} f(x_i; \theta_G)\pi(\theta_G \mid \lambda) d\theta_G, \quad (6)$$

where $X_n=(x_1, \ldots, x_n)^T$ is an n×p gene profile matrix, $\pi(\theta_G|\lambda)$ is the prior distribution on the parameter $\theta_G$ satisfying log $\pi(\theta_G|\lambda)$=O(n) and $\lambda$ is the hyper parameter vector. Under Bayes approach, we can choose the optimal graph such that $\pi(G|X_n)$ is maximum. A crucial problem for constructing a criterion based on the posterior probability of the graph is the computation of the high dimensional integration (6). Heckerman and Geiger (D. Heckerman and D. Geiger *Proc. Eleventh Conf. on Uncertainty in Artificial Intelligence*, 274-284, 1995) used the conjugate priors for solving the integral and gave a closed-form solution. To compute this high dimensional integration, we use Laplace's approximation (A. C. Davison, *Biometrika*, 73, 323-332, 1986; D. Heckerman. A tutorial on learning with Bayesian networks. in M. I. Jordan ed., Kluwer Academic Publisher, 1998; L. Tinerey and J. B. Kadane. Accurate approximations for posterior moments and marginal densities. J. Amer. Statist. Assoc., 81, 82-86, 1986) for integrals $$\int \prod_{i=1}^{n} f(x_i; \theta_G)\pi(\theta_G \mid \lambda) d\theta_G = \frac{(2\pi/n)^{r/2}}{|J_\lambda(\hat{\theta}_G)|^{1/2}} \exp\{nl_\lambda(\hat{\theta}_G \mid X_n)\}\{1 + O_p(n^{-1})\},$$

where $r$ is the dimension of $\theta_G$, $$l_\lambda(\theta_G \mid X_n) = \sum_{i=1}^{n} \log f(x_i; \theta_G)/n + \log\pi(\theta_G \mid \lambda)/n,$$

$$J_\lambda(\theta_G) = -\frac{\partial^2\{l_\lambda(\theta_G \mid X_n)\}}{\partial \theta_G \partial \theta_G^T} \text{ and } \hat{\theta}_G$$

is the mode of $l_\lambda(\theta_G|X_n)$. Then we define the Bayesian network and nonparametric heteroscedastic regression criterion, named BNRC$_{hetero}$, for selecting a graph $$BNRC_{hetero}(G) = -2\log\left\{\pi_G \int \prod_{i=1}^{n} f(x_i; \theta_G)\pi(\theta_G \mid \lambda) d\theta_G\right\} \quad (7)$$

$$\approx -2\log \pi_G - r\log(2\pi/n) + \log|J_\lambda(\hat{\theta}_G)| - 2nl_\lambda(\hat{\theta}_G \mid X_n).$$

The optimal graph is chosen such that the criterion BNRC$_{hetero}$ (7) is minimal. The merit of the use of the Laplace method is that it is not necessary to consider the use of the conjugate prior distribution. Hence the modeling in the larger classes of distributions of the model and prior is attained.

Suppose that the parameter vectors $\theta_j$ are independent one another, the prior distribution can be decomposed into $\pi(\theta_G|\lambda)=\pi_{j=1}^{P}\pi_j(\theta_j|\lambda_j)$. Therefore, log $|J_\lambda(\theta_G|X_n)|$ and $nl_\lambda(\theta_G|X_n)$ in (7) result in, respectively, $$\log|J_\lambda(\theta_G \mid X_n)| = \sum_{j=1}^{P} \log\left|-\frac{\partial^2 l_{\lambda_j}(\theta_j \mid X_n)}{\partial \theta_j \partial \theta_j^T}\right|, l_\lambda(\theta_G \mid X_n) = \sum_{j=1}^{P} l_{\lambda_j}(\theta_j \mid X_n),$$

where $l_{\lambda_j}(\theta_j|X_n)$=log $f_j(x_{ij}|p_{ij};\theta_j)$/n+log $\pi_j(\theta_j|\lambda_j)$/n. Here $\lambda_j$ is the hyper parameter vector. Hence by defining $$BNRC_{hetero}^{(j)} = -2\log\left\{\int \pi_{L_j} \prod_{i=1}^{n} f_j(x_{ij} \mid p_{ij}; \theta_j)\pi_j(\theta_j \mid \lambda_j) d\theta_j\right\}$$

$\pi_{L_j}$ are prior probabilities satisfying $\Sigma_{j=1}^{P}$ log $\pi_{L_j}$=log $\pi_G$, the BNRC$_{hetero}$ score is given by the sum of the local scores where $$BNRC_{hetero} = \sum_{j=1}^{P} BNRC_{hetero}^{(j)}. \quad (8)$$

Figure 18:
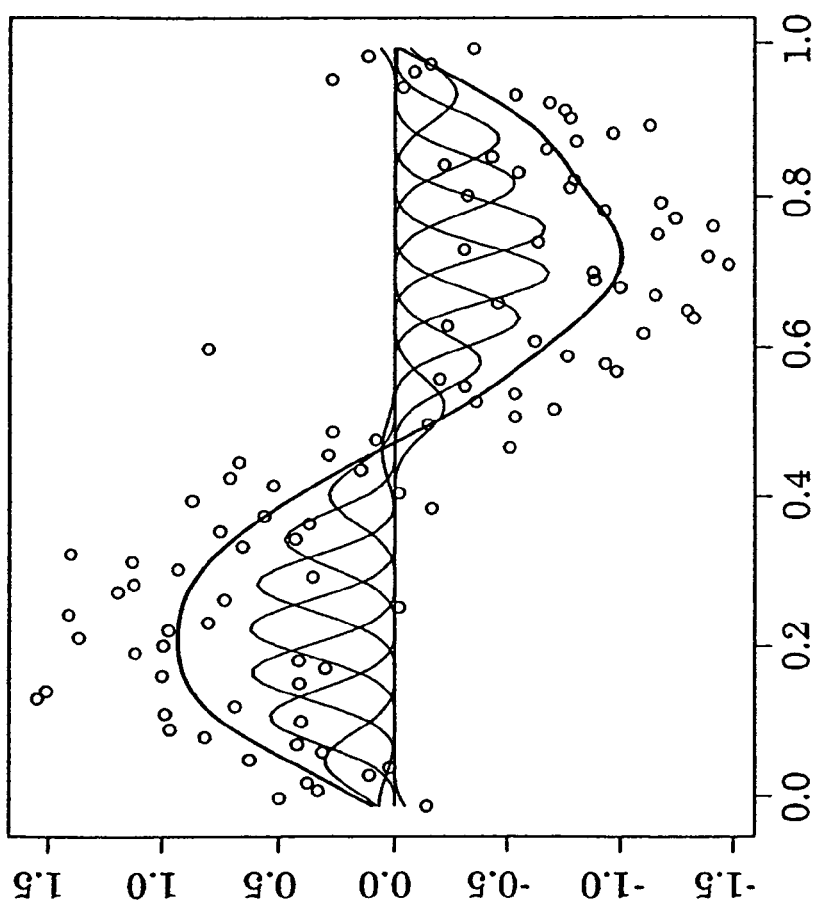
FIG. 18 the fitted curve to simulated data: The thin curves are B-splines that are weighted by coefficients and the thick curve is the smoothed estimate that is obtained by the linear combination of weighted B-splines.

FIG. 18. The fitted curve to simulated data: The thin curves are B-splines that are weighted by coefficients and the thick curve is the smoothed estimate that is obtained by the linear combination of weighted B-splines.

The smoothed estimates based on nonparametric heteroscedastic regression are obtained by replacing the parameters $\gamma_j$ by $\hat{\gamma}_j$. Noticed that we derive the criterion, BNRC$_{hetero}$, under the assumption log $\pi(\theta_G|\lambda)$=O(n). If we use the prior density satisfying log $\pi(\theta_G|\lambda)$=O(1), the BNRC$_{hetero}$ score results in Schwarz's criterion known as BIC or SIC (G. Schwarz, *Ann. Statist.*, 6, 461-464, 1978). In such case, the mode $\hat{\theta}_G$ is equivalent to the maximum likelihood estimate.

3. Estimating Genetic Network 3.1. Nonparametric Regression

In this section we present the method for constructing genetic network in practice based on the proposed method described above. First we would like to mention the nonparametric regression model. In the additive model, we construct each smooth function $m_{jk}(\cdot)$ by B-splines (C. De Boor, A Practical Guide to Splines, Springer-Verlag, Berlin, 1978; S. Imoto et al., *Proc. Pacific Symposium on Biocomputing*, 7, 175-186, 2002.) FIG. 18 is an example of B-splines smoothed curve. The thin curves are B-splines that are weighted by coefficients and thick line is a smoothed curve that is obtained by the linear combination of weighted B-splines.

In the error variances, we consider the heteroscedastic regression model and assume the structure (3). Choosing constants $w_{1j}, \ldots, w_{nj}$ is an important problem for capturing the heteroscedasticity of the data. In this paper, we set the weights $$w_{ij} = g(p_{ij}; \rho_j) = \exp\left\{\frac{-\rho_j\|p_{ij} - \bar{p}_j\|^2}{2s_j^2}\right\}, \text{ where } \rho_j \text{ is a hyper parameter,}$$

$$\bar{p}_j = \sum_{i=1}^{n} p_{ij}/n \text{ and } s_j^2 = \sum_{i=1}^{n} \frac{\|p_{ij} - \bar{p}_j\|^2}{nq_j}.$$

If we set $\rho_j$=0, the weights are $w_{1j}$= ... =$w_{nj}$=1 and the model has homogeneous error variances. If we use a large value of $\rho_j$, the error variances of the data, which exist near the boundary on the domain of the parent variables, are large. Hence, if there are outliers near the boundary, we can reduce their effect and gain the suitable smoothed estimates by using the appropriate value of $\rho_j$.

3.2. Priors

Suppose that the prior distribution $\pi_j(\theta_j|\lambda_j)$ is factorized as $\pi_j(\theta_j|\lambda_j)=\pi_{k=1}^{q_j}\pi_{jk}(\gamma_{jk}|\lambda_{jk})$, where $\lambda_{jk}$ are hyper parameters. We use a singular $M_{jk}$ variate normal distribution as the prior distribution on $\gamma_{jk}$, $$\pi_{jk}(\gamma_{jk} \mid \lambda_{jk}) = \left(\frac{2\pi}{n\lambda_{jk}}\right)^{-(M_{jk}-2)/2} |K_{jk}|_+^{1/2} \times \exp\left(-\frac{n\lambda_{jk}}{2}\gamma_{jk}^T K_{jk}\gamma_{jk}\right), \quad (10)$$

where $K_{jk}$ is an $M_{jk} \times M_{jk}$ symmetric positive semidefinite matrix satisfying $$\gamma_{jk}^T K_{jk} = \sum_{\alpha=3}^{M_{jk}} \left(\gamma_{\alpha k}^{(j)} - 2\gamma_{\alpha-1,k}^{(j)} + \gamma_{\alpha-2,k}^{(j)}\right)^2.$$

Next we consider the prior probability of the graph $\pi_G$. Friedman and Goldszmidt (N. Friedman and M. Goldszmidt, Learning Bayesian Networks with Local Structure. in M. I. Jordan ed., Kluwer Academic Publisher, 1998) employed the prior based on the MDL encoding of the graph. In our context, the marginal probability of the data is equivalent to the type II likelihood adjusted by the hyper parameters. Thus we set the prior probability of the graph, $\pi_G$, $$\pi_G = \exp\{-(\text{No. of hyper parameters})\} = \prod_{j=1}^{p} \exp\{-(q_j+1)\} = \prod_{j=1}^{p} \pi_{Lj}$$

The justification of this prior is based on Akaike's Bayesian information criterion, known as ABIC (H. Akaike. Likelihood and the Bayes procedure. in J. M. Bernardo, M. H. DeGroot, D. V. Lindley and A. F. M. Smith, eds., Univ. Press, Valencia, 41-166, 1980), and Akaike's information criterion, AIC (H. Akaike, Information theory and an extension of the maximum likelihood principle. in B. N. Petrov, & F. Csaki, eds., Akademiai Kiado, Budapest, 267-281, 1973).

3.3. Criterion

We derived the criterion, $BNRC_{hetero}$, for choosing the graph in a general framework. By using the equation (8), the $BNRC_{hetero}$ score of the graph can be obtained by the sum of the local scores, $BNRC_{hetero}^{(j)}$. The result is summarized in the following theorem.

Theorem 1. Let $f(x_i; \theta_G)$ be a Bayesian network and nonparametric heteroscedastic regression model given by (5), and let $\pi(\gamma_{jk}|\lambda_{jk})$ be the prior densities on the parameters $\gamma_{jk}$ defined by (10). Then a criterion for evaluating graph is given by $$BNRC_{hetero} = \sum_{j=1}^{p} BNRC_{hetero}^{(j)}, \text{ where}$$

-continued $$BNRC_{hetero}^{(j)} = 2(q_j+1) - \left(\sum_{k=1}^{q_j} M_{jk} + 1\right)\log(2\pi/n) - \sum_{i=1}^{n}\log w_{ij} +$$

$$n\log(2\pi\hat{\sigma}_j^2) + n + \sum_{k=1}^{q_j}\{\log|\Lambda_{jk}| - M_{jk}\log(n\hat{\sigma}_j^2)\} -$$

$$\log(2\hat{\sigma}_j^2) + \sum_{k=1}^{q_j}\{(M_{jk}-2)\log(2\pi\hat{\sigma}_j^2/n\beta_{jk}) -$$

$$\log|K_{jk}| + n\beta_{jk}\hat{\gamma}_{jk}^T K_{jk}\hat{\gamma}_{jk}/\hat{\sigma}_j^2\},$$

with $$\Lambda_{jk} = B_{jk}^T W_j B_{jk} + n\beta_{jk} K_{jk}; (M_{jk} \times M_{jk}),$$

$$B_{jk} = \left(b_{1k}^{(j)}(p_{1k}^{(j)}), \ldots, b_{M_{jk}k}^{(j)}(p_{nk}^{(j)})\right)^T; (n \times M_{jk}),$$

$$W_j = diag(w_{1j}, \ldots, w_{nj}); (n \times n)$$

$$\hat{\sigma}_j^2 = \sum_{i=1}^{n} w_{ij}\left\{x_{ij} - \sum_{k=1}^{q_j}\hat{\gamma}_{jk}^T b_{jk}(p_{ik}^{(j)})\right\}^2 / n.$$

Here we approximate the Hessian matrix by $$\log\left|-\frac{\partial^2 l_{\lambda_j}(\theta_j \mid X_n)}{\partial \theta_j \partial \theta_j^T}\right| \approx \sum_{k=1}^{q_j} \log\left|-\frac{\partial^2 l_{\lambda_j}(\theta_j \mid X_n)}{\partial \gamma_{jk} \partial \gamma_{jk}^T}\right| + \log\left|-\frac{\partial^2 l_{\lambda_j}(\theta_j \mid X_n)}{\partial (\sigma_j^2)^2}\right|.$$

3.4 Learning Network

In the Bayesian network literature, it is shown that determining the optimal network is an NP-hard problem. In this paper, we use the greedy hill-climbing algorithm for learning network as follows:

Step 1: Make the score matrix whose (i,j)-th element is the $BNRC_{hetero}^{(j)}$ score of the graph $gene_i \rightarrow gene_j$.

Step 2: For each gene, implement one of three procedures for an edge: "add", "remove", "reverse", which gives the smallest $BNRC_{hetero}$.

Step 3: Repeat Step 2 until the $BNRC_{hetero}$ does not reduce.

Generally, the greedy hill-climbing algorithm has many local minima and the result depends on the computational order of variables. To avoid this problem, we permute the computational order of genes and make many candidate learning orders in Step 3. Another problem of the learning network is that the search space of the parent genes is enormously wide, when the number of genes is large. Then we restrict the set of the candidate parent genes based on the score matrix, which is given by Step 1.

Figure 13:
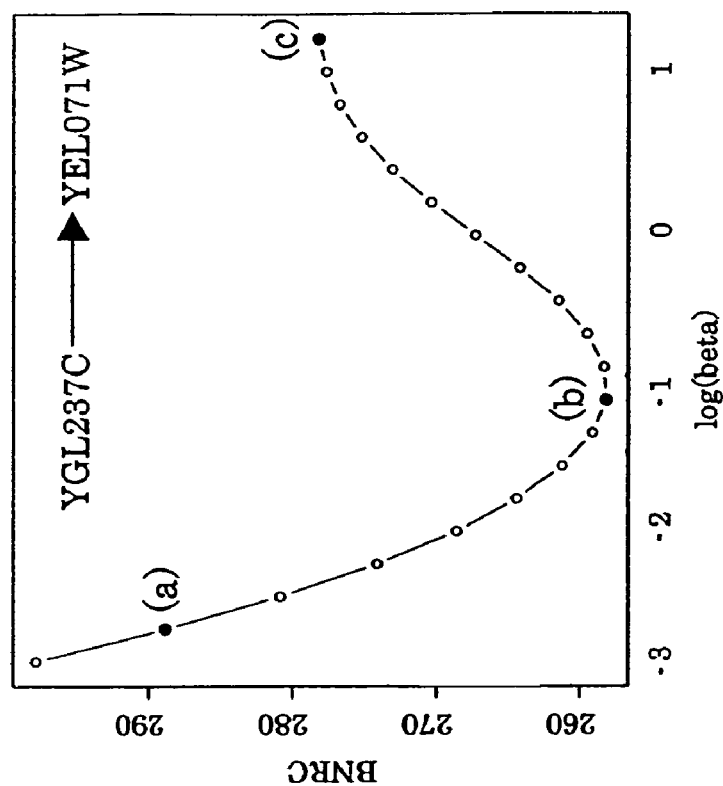
FIGS. 13a and 13b the smoothed estimates by the various values of the hyper parameter. 13(a) the effect of hyperparameter $\beta_{jk}$ in the prior distribution of the coefficients of B-splines. This parameter can control the smoothness of the fitted curve.
Figure 13:
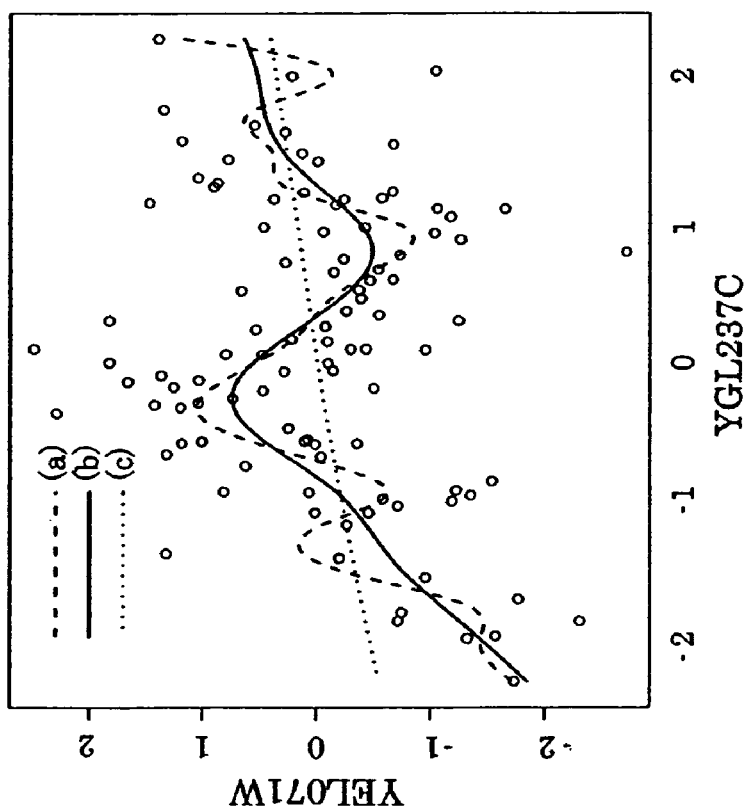
Figure 14:
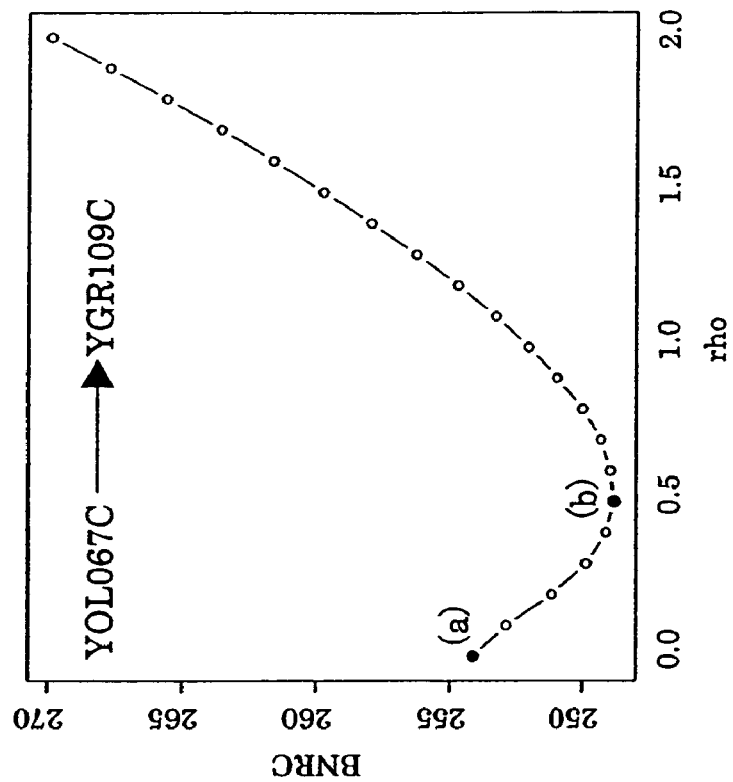
FIGS. 14a and 14b the smoothed estimates by the various values of the hyper parameter; the effect of the weight constants. 14(a) the effect of hyperparameter pj in the parameter of the error variances. This parameter can capture the heteroscedastisity of the data and can reduce the effects of outliers.
Figure 14:
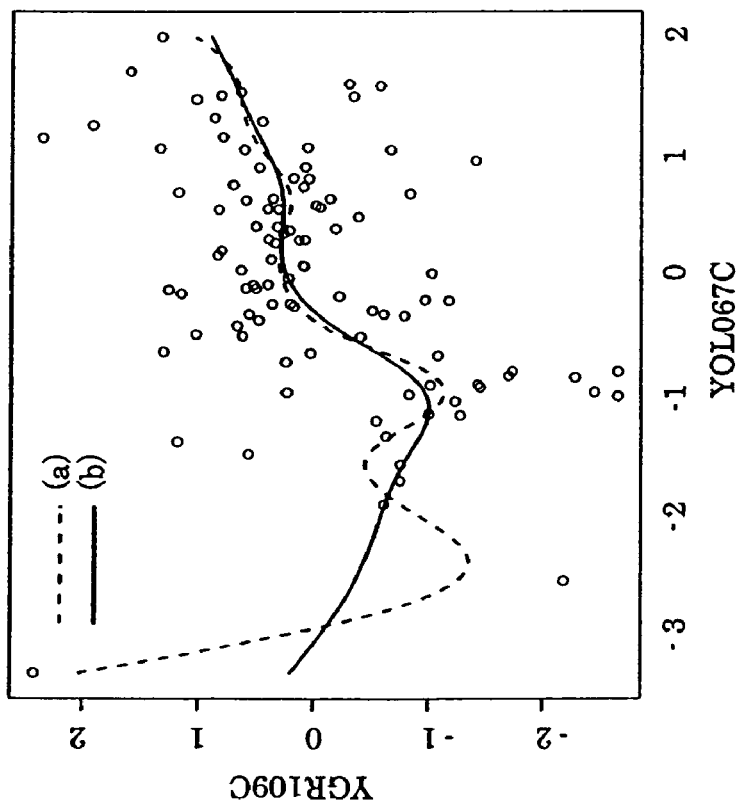
Figure 19:
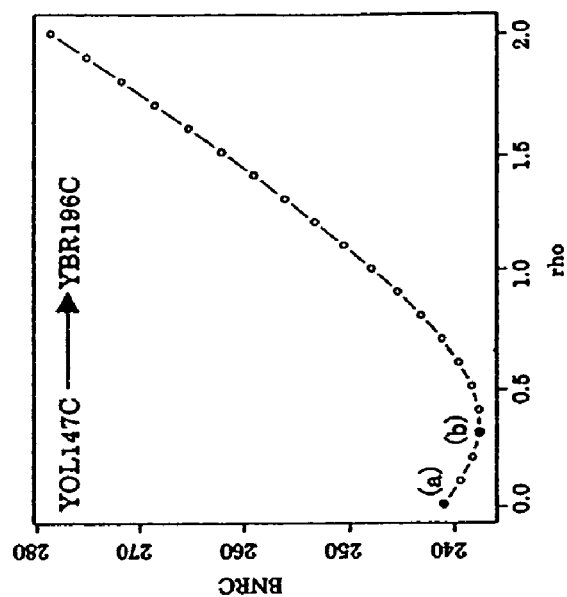
FIGS. 19a and 19b the smoothed estimates by the various values of the hyper parameters. The effect of hyperparameter $\rho_j$ in the parameter of the error variances. This parameter can capture the heteroscedasticity of the data and can reduce the effects of outliers.
Figure 19:
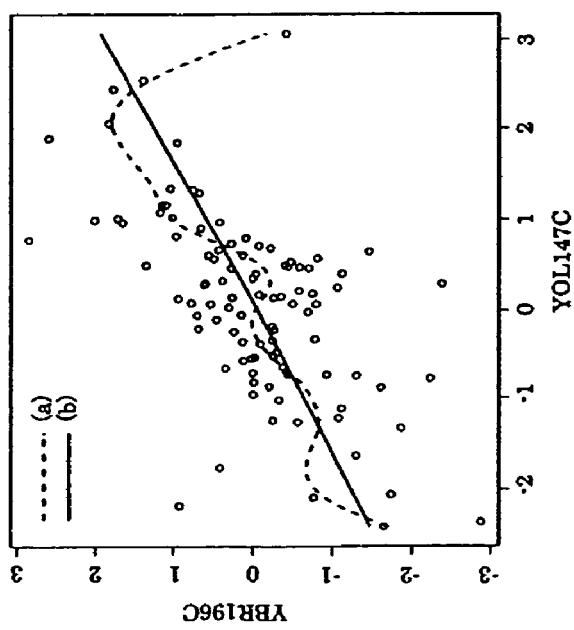

FIGS. 13, 14, and 19. The smoothed estimates by the various values of the hyper parameters. 13a: The effect of hyperparameter $\beta_{jk}$ in the prior distribution of the coefficients of B-splines. This parameter can control the smoothness of the fitted curve. 14a and 19a: The effect of hyperparameter $\rho_j$ in the parameter of the error variances. This parameter can capture the heteroscedasticity of the data and can reduce the effect of outliers.

3.5 Hyperparameters

Consider the nonparametric regression model defined in (4). The estimate $\hat{\theta}_j$ is a mode of $l_{\lambda_j}(\theta_j|X_n)$ and depends on the hyper parameters. In fact, the hyper parameter plays an essential role for estimating the smoothed curve.

In our model, we construct the nonparametric regression model by 20 B-splines. We confirmed that the differences of the smoothed estimates against the various number of the basis functions cannot be found visually. Because when we use a somewhat large number of the basis functions, the hyper parameters control the smoothness of the fitted curves. FIG. 13a shows the scatter plot of YGL237C and YEL071W with smoothed estimates for 3 different values of the hyper parameters. The details of the data are shown in later section. Clearly, the smoothed estimate strongly depends on the values of the hyper parameters. FIG. 13b is the behavior of the $BNRC_{hetero}$ criterion of the two genes in FIG. 13a. We can choose the optimal value of the hyper parameter as the minimizer of the $BNRC_{hetero}$ and the optimal smoothed estimate (solid curve in FIG. 13a can capture the structure between these genes well. The dashed and dotted curves are near the maximum likelihood estimate and the parametric linear fit, respectively.

The effect of the weight constants $w_{1j}, \ldots, w_{nj}$ is shown in FIGS. 14a and 19a. If we use the nonparametric homoscedastic regression model (S. Imoto et al., *Proc. Pacific Symposium on Biocomputing*, 7, 175-186, 2002), we obtain the dashed curve, which exhibits some spurious waviness due to the effect of the data in the upper-left corner of FIG. 14a. By adjusting the hyper parameter $\rho_j$ in (9), the estimated curve results in the solid curve. The optimal value of $\rho_j$ is also chosen by minimizing the $BNRC_{hetero}$ criterion (see FIG. 14b and FIG. 19b). Of course, when the smoothed estimate is properly obtained, the optimal value of $\rho_j$ tends to zero.

Finally, we show the algorithm for estimating the smoothed curve and optimizing the hyper parameters.

Step 1: Fix the hyper parameter $\rho_j$.

Step 2: Initialize: $\gamma_{jk}=0$, $k=1, \ldots, q_j$.

Step 3: Find the optimal $\beta_{jk}$ by repeating Step 3-1 and Step 3-2

Step 3-1: Compute: $\gamma_{jk} =$ $$(B_{jk}^T W_{jk} B_{jk} + n\beta_{jk} K_{jk})^{-1} B_{jk}^T W_{jk} \times \left(x_{(j)} - \sum_{k' \neq k} B_{jk'} \gamma_{jk'}\right),$$

for fixed $\beta_{jk}$.

Step 3-2: Evaluate: Repeat Step 3-1 against the candidate value of $\beta_{jk}$, and choose the optimal value of $\beta_{jk}$, which minimizes the $BNRC_{hetero}^{(j)}$.

Step 4: Convergence: Repeat Step 3 for $k=1, \ldots, q_j, 1, \ldots, q_j, 1, \ldots$ until a suitable convergence criterion is satisfied.

Step 5: Repeat Step 1 to Step 4 against the candidate value of $\rho_j$, and choose the optimal value of $\rho_j$, which minimizes the $BNRC_{hetero}^{(j)}$.

4. Computational Experiments 4.1. Monte Carlo Simulation

We use the Monte Carlo simulation method to show the effectiveness of our method. The data ware generated from the artificial network of FIG. 20(a) with the functional structures between nodes as follows:

$$X_1 = X_2^2 + 2\sin(X_5) - 2X_7 + \varepsilon_1, \ \varepsilon_1 \sim N(0, (4s)^2),$$

$$X_2 = \{1 + \exp(-4X_3)\}^{-1} + \varepsilon_2, \ \varepsilon_2 \sim N(0, s)^2,$$

$$X_3 = \varepsilon_3, \ , \ \varepsilon_3 \sim N(0, 1),$$

$$X_4 = X_5^2/3 + \varepsilon_4, \ \varepsilon_4 \sim N(0, (4s)^2),$$

$$X_5 = X_3 - X_6^2 + \varepsilon_5, \ \varepsilon_5 \sim N(0, (4s)^2),$$

$$X_6 = \varepsilon_6, \ \varepsilon_6 \sim N(0, 1),$$

$$X_7 = \begin{cases} -1 + \varepsilon_7, \ (X_8 \leq -0.5), \\ X_8 + \varepsilon_7, \ (-0.5 < X_8 \leq -0.5), \\ 1 + \varepsilon_7, \ (0.5 < X_8), \varepsilon_7 \sim N(0, (2s)^2), \end{cases}$$

$$X_8 = \exp(-X_4 - 1)/2 + \varepsilon_8, \ \varepsilon_8 \sim N(0, (2s)^2),$$

$$X_9 = e_9, \ \varepsilon_9 \sim N(0, 1),$$

$$X_{10} = \chi o \sigma(\Xi_9) + \varepsilon_{10}, \ e_{10} \sim N(0, (4\sigma)^2),$$

where s is a constant. After transforming the observations of the parent variables to mean 0 and variance 1, then the observations of the child variable are generated.

We generate 100 observations from this artificial network and our aim is to rebuild the network in FIG. 20a from the simulated data. We use two different settings of the noise variance, one is s=0.2 and another is s=0.1. The observations from the setting of the noise s=0.2 are experientially similar to the real microarray data. The Monte Carlo simulation was repeated 1000 times and we focused on the number of correct estimations. FIGS. 20b and 20c are the results of the Monte Carlo simulations for s=0.2 and s=0.1, respectively.

TABLE 1

The False Positives of the Monte Carlo Simulations.

| | | s = 0.2 | | |
|---|---|---|---|---|
| X1 | - | X4 | 15 | 87% |
| | | X6 | 73 | 99% |
| | | X9 | 72 | 99% |
| | | X10 | 10 | 70% |
| X2 | - | X4 | 20 | 65% |
| | | X6 | 71 | 87% |
| | | X8 | 65 | 78% |
| | | X9 | 120 | 92% |
| | | X10 | 27 | 59% |
| X3 | - | X1 | 31 | 55% |
| | | X4 | 20 | 90% |
| | | X8 | 66 | 52% |
| | | X9 | 149 | 70% |
| X4 | - | X6 | 35 | 51% |
| | | X9 | 137 | 95% |
| X5 | - | X2 | 9 | 100% |
| | | X8 | 28 | 97% |
| | | X9 | 108 | 100% |
| | | X10 | 6 | 100% |
| X6 | - | X3 | 325 | 81% |
| | | X9 | 190 | 53% |
| X7 | - | X2 | 12 | 58% |
| | | X3 | 32 | 97% |
| | | X4 | 24 | 71% |
| | | X5 | 27 | 85% |
| | | X6 | 12 | 98% |
| | | X9 | 68 | 96% |
| | | X10 | 3 | 67% |
| X8 | - | X1 | 1 | 100% |
| | | X6 | 139 | 87% |
| | | X9 | 146 | 65% |

TABLE 1-continued

The False Positives of the Monte Carlo Simulations.

| | | | | |
|---|---|---|---|---|
| X10 | - | X3 | 71 | 87% |
| | | X4 | 8 | 75% |
| | | X6 | 139 | 95% |
| | | X8 | 83 | 94% |
| s = 0.1 | | | | |
| X1 | - | X4 | 16 | 100% |
| | | X6 | 53 | 83% |
| | | X9 | 68 | 100% |
| | | X10 | 1 | 100% |
| X2 | - | X4 | 4 | 100% |
| | | X6 | 57 | 91% |
| | | X8 | 31 | 97% |
| | | X9 | 89 | 96% |
| | | X10 | 10 | 80% |
| X3 | - | X1 | 23 | 57% |
| | | X4 | 5 | 80% |
| | | X8 | 58 | 52% |
| | | X9 | 157 | 69% |
| X4 | - | X9 | 172 | 99% |
| X5 | - | X2 | 8 | 75% |
| | | X8 | 27 | 100% |
| | | X9 | 106 | 100% |
| | | X10 | 6 | 100% |
| X6 | - | X3 | 308 | 74% |
| | | X4 | 4 | 50% |
| X7 | - | X2 | 1 | 100% |
| | | X3 | 28 | 100% |
| | | X4 | 20 | 95% |
| | | X5 | 18 | 89% |
| | | X6 | 93 | 99% |
| | | X9 | 43 | 98% |
| X8 | - | X1 | 1 | 100% |
| | | X6 | 154 | 81% |
| | | X9 | 123 | 77% |
| X9 | - | X6 | 169 | 51% |
| X10 | - | X3 | 81 | 88% |
| | | X4 | 9 | 67% |
| | | X6 | 156 | 100% |
| | | X7 | 1 | 100% |
| | | X8 | 77 | 96% |

The number attached after node name is the number of estimated connection without direction information and the percentage is the direction information. For example, in s=0.2, the proposed method estimated the relationship "X1→X4" or "X1←X4" 15 times from 1000 Monte Carlo simulations and 87% of 15 times represents the direction from left to right ("X1→X4").

The results of the Monte Carlo simulations can be summarized as follows: In the setting of noise variance s=0.2, our model can rebuild the target network very well. Table 1 shows the false positives of the Monte Carlo simulations and we can see the percentages of the false positives are almost less than 10%. Since the simulated data is similar to the real microarray data in the setting s=0.2, we can expect that our network estimation method can work effectively in the real data analysis. From FIGS. 20b and 20c and Table 1, the number of true negatives is much less than the number of false positives. We believe that this tendency is preferred in the exploratory data analysis. In the setting s=0.1, our model can rebuild the target network more precisely, and the number of false positives decrease compared with the result of s=0.2.

FIGS. 20a-20c. The results of the Monte Carlo simulations. FIG. 20a True network. FIG. 20b Result for s=0.2. FIG. 20c Result for s=0.1. The number next to edge represents the number of estimated connections from 1000 Monte Carlo experiments. The percentage includes the information of the edge direction. For example, in s=0.2, the connection between X5 and X1 appeared 958 times from 1000 Monte Carlo experiments and those 97% is the correct direction (from X5 to X1).

4.2 Real Data Analysis

In this section we show the effectiveness of our proposed method through the analysis of Saccharomyces cerevisiae gene expression data, which is newly obtained by disrupting 100 genes. Our research group has installed a systematic experimental method, which observes changes in the expression levels of genes on a microarray by gene disruption. By using this method, we have launched a project whose purpose is to reveal the gene regulatory networks between the 5871 genes of Saccharomyces cerevisiae. Many laboratories have also reported similar projects. We have already collected a large number of expression profiles from gene disruption experiments to evaluate genetic regulatory networks. Over 400 mutants are stocked and gene expression profiles are accumulating.

We monitored the transcriptional level of 5871 genes spotted on a microarray by a scanner. The expression profiles of over 400 disruptants were stored in our database. The standard deviation (SD) of the levels of all genes on a microarray was evaluated. The value of SD represents roughly the experimental error. In our data, we estimated the value of 0.5 as the critical point of the accuracy of experiments. We have evaluated the accuracy of those profiles on the base of the standard deviation of the expression ratio of all genes. 107 disruptants including 68 mutants where the transcription factors were disrupted could be selected from 400 profiles.

We used 100 microarrays and constructed a genetic network of 521 genes from the above data. The 94 transcription factors whose regulating genes have been clearly identified were found. The profiles of the 521 genes in control by those 94 factors were selected from 5871 profiles.

Bas1p and Bas2p also activate expression of three genes in the histidine biosynthesis pathway. In a gcn4 background, mutations that abolish the BAS1 or BAS2 function lead to a histidine auxotrophy. Previous investigation indicated that Bas1p and Bas2p are DNA binding proteins required for transcription of HIS4 and these ADE genes like GCN4 (B. Daignan-Fornier et al., Proc. Natl. Acad. Sci. USA, 89, 6746-6750, 1992; V. Denis, et al., Mol. Microbiol., 30, 556-566, 1998; R. J. Rolfes et al., Mol. Cell Biol., 13, 5099-5111, 1993). In this paper, we made clear that both genetic relation. FIGS. 20a-20c indicates that those ADE genes and histidine biosynethesis genes are related with BAS1 more directly than GCN4. The ribose component of purine ribonucleotides is derived from ribose 5-P, an intermediate of the pentose phosphate cycle. The atoms of the base moiety are contributed by many compounds. They are added step wise to the preformed ribose. There exist striking interrelationships with the pathway for histidine synthesis.

Studies on the regulation of the purine biosynthesis pathway in Saccharomyces cerevisiae revealed that all the genes encoding enzymes required for AMP de novo biosynthesis are repressed at transcriptional level by the presence of extracellular purines. ADE genes are transcriptionally activated as well as some histidine biosynthesis genes. Especially the fact that expression of HIS4 is related with ADE genes were known. In our regulated network, HIS4 were related with some ADE genes closely, and some HIS genes are related with ADE genes like HIS4. The biosynthesis of the essential amino acid histidine shows in Saccharomyces cerevisiae shows close connection to purine metabolism, and our result satisfied this fact.

Figure 21:
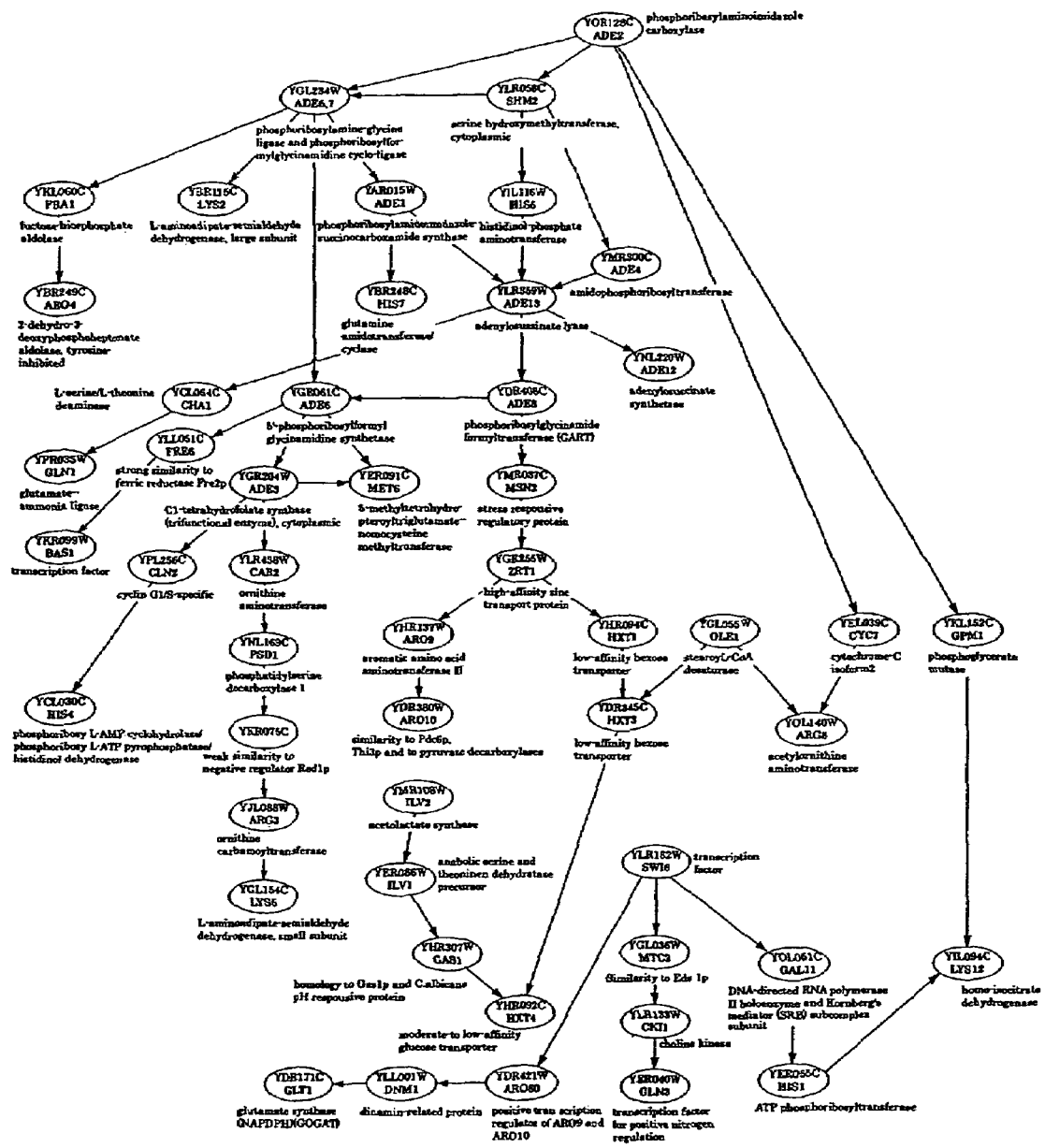
FIG. 21 the resulting partial network of the analysis of 521 Saccharomyces cerevisiae genes.

FIG. 21. The resulting partial network of the analysis of 521 Saccharomyces cerevisiae genes.

CONCLUSION

In this paper we proposed a new statistical method for estimating a genetic network from microarray gene expression data by using a Bayesian network and nonparametric regression. The key idea of our method is the use of nonparametric heteroscedastic regression models for capturing nonlinear relationships between genes and heteroscedasticity of the expression data. If we have a network that represents the causal relationship among genes, we can simulate the genetic system on the computer, e.g., Genomic Object Net (H. Matsuno et al., *Proc. Pacific Symposium on Biocomputing*, 5, 338-349, 2000; H. Matsuno et al., *Genome Informatics*, 12 54-62, 2001). In this stage, it is required that the relationships between genes are suitably estimated. In this sense, the proposed heteroscedastic model can give an essential improvement, because the previous models sometimes lead to unsuitable estimates of the systems. We consider the simulation of biological system as a future work.

An essential problem for network construction is the evaluation of the graph. We investigated this problem as a statistical model selection or evaluation problem and derived the new criterion for selecting graph from Bayes approach. Our method covers the previous methods for constructing genetic networks by using Bayesian networks and improves them in the theoretical and methodological senses. The proposed method successfully extracts the effective information and we can find these information in the resulting genetic network visually. We use the simple greedy algorithm for learning network. However, this algorithm needs much time for determining the optimal graph. Hence, the development of a better algorithm is one of the important problems and we would like to discuss it in a future paper.

We showed the effectiveness of our method through the Monte Carlo simulations and the analysis of *Saccharomyces cerevisiae* gene expression data and evaluated the resulting network by comparing with biological knowledge. We construct the genetic network without using biological information. Nevertheless, the resulting network includes many important connections, which agree with the biological knowledge. Hence, we expect that our method can demonstrate its power in the analysis of a completely unknown system, like the human genome.

Example 4

Statistical Analysis of a Small Set of Time-Ordered Gene Expression Data Using Linear Splines Summary Motivation: Recently, the temporal response of genes to changes in their environment has been investigated using cDNA microarray technology by measuring the gene expression levels at a small number of time points. Conventional techniques for time series analysis are not suitable for such a short series of time-ordered data. The analysis of gene expression data has therefore usually been limited to a fold-change analysis, instead of a systematic statistical approach.

Methods: We use the maximum likelihood method together with Akaike's Information Criterion to fit linear splines to a small set of time-ordered gene expression data in order to infer statistically meaningful information from the measurements. The significance of measured gene expression data is assessed using Student's t-test.

Results: Previous gene expression measurements of the cyanobacterium Synechocystis sp. PCC6803 were reanalysed using linear splines. The temporal response was identified of many genes that had been missed by a fold-change analysis. Based on our statistical analysis, we found that about four gene expression measurements or more are needed at each time point.

Contact: Michiel deHoon at the University of Tokyo

1. Introduction

In recent years, many cDNA microarray experiments have been performed measuring gene expression levels under different conditions. Measured gene expression data have become widely available in publicly accessible databases, such as the KEGG database (M. Nakao et al. *Genome Informatics*, 10, 94-103, 1999).

In some of these experiments, the steady-state gene expression levels are measured under several environmental conditions. For instance, the expression levels of the cyanobacterium *Synechocystis sp.* PCC6803 and a mutant have been measured at different temperatures, leading to the identification of the gene Hik33 as a potential cold sensor in this cyanobacterium (I. Suzuki et al., *Synechocystis. Mol. Microbiol.*, 40, 235-244, 2001).

In other experiments, the temporal pattern of gene expression is considered by measuring expression levels at a limited number of points in time. Gene expression levels that vary periodically have for instance been measured during the cell cycle of the yeast *Saccharomyces cerevisiae* (P. Spellman et al., *Mol. Biol. Cell*, 9, 3273-3297, 1998). The gene expression levels of the same yeast species were measured during the metabolic shift from fermentation to respiration (J. L. DeRisi et al., *Science*, 278, 680-686, 1997). In this experiment, the environmental conditions were changing slowly over time. Conversely, the gene response to an abruptly changing environment can be measured. As an example, the gene expression levels of the cyanobacterium *Synechocystis* sp. PCC 6803 were measured at several points in time after a sudden shift from low light to high light (Y. Hihara et al., *The Plant Cell*, 13, 793-806, 2001).

In cDNA microarray experiments, gene expression levels are typically measured at a small number of time points. Conventional techniques of time series analysis, such as Fourier analysis or autoregressive or moving-average modelling, are not suitable for such a small number of data points. Instead, the gene expression data are often analysed by clustering techniques or by considering the relative change in the gene expression level only. Such a fold-change analysis may miss significant changes in gene expression levels, while it may inadvertently attribute significance to measurements dominated by noise. In addition, a simple fold-change analysis may not be able to identify important features in the temporal gene expression response.

Several techniques to analyse gene expression data, such as deriving Boolean or Bayesian networks, have been proposed in the past (S. Liang et al. *Proc. Pac. Symp. on Biocomputing*, 3, 18-29, 1998; T. Akutsu et al., *Bioinformatics*, 16, 727-734, 2001; N. Friedman et al., *J. Comp. Biol.*, 7, 601-620, 2000; and S. Imoto et al., *Proc. Pac. Symp. On Biocomputing*, 2002, In Press). Whereas describing gene interactions in terms of a regulatory network is very important, deriving a network model requires gene expression data at a large number of time points, which is currently often not yet available. It should be noted that the number of genes is on the order of several thousands, while the gene expression levels are usually measured at only five or ten points in time.

So far, a systematic method has been lacking to statistically analyse gene expression measurements from a small number of time-ordered data. In this paper, we will outline a strategy based on fitting linear spline functions to time-ordered data using the maximum likelihood method and Akaike's Information Criterion (H. Akaike, Information theory and an extension of the maximum likelihood principle, Research Memorandum No. 46, Institute of Statistical Mathematics, Tokyo, In Petrov, B. N., Csaki, F. (eds.), *2nd Int. Symp. on Inf. Theory*, Akadémiai Kiadó, Budapest (1973), pp. 267-281, 1971). The significance of the gene expression measurements is assessed by applying Student's t-test. This allows us to infer information from gene expression measurements while taking the statistical significance of the data into consideration. This kind of analysis should be viewed as a first step toward building gene regulatory networks. As an example, we reanalysed the gene expression measurements of the cyanobacterium *Synechocystis* sp. PCC 6803 (Y. Hihara et al., *The Plant Cell*, 13, 793-806, 2001). It is shown that information can be inferred from the measured data that is missed when considering the fold-change only. By repeating our analysis with a subset of the available data, we were able to determine how many measurements are needed at each time point in order to estimate the linear spline function reliably.

2. Methods 2.1 Student's t-Test

First, we would first like to assess if the measured gene expression ratios are significantly different from unity. If for a specific gene we can conclude that for all time points the measured expression ratios are not significantly different from unity, we can eliminate that gene from further analyses. The significance level can be established by applying Student's t-test for each time point separately. Since multiple comparisons are being made for each gene, the value of the significance level a should be chosen carefully.

We define $H_0^{(i)}$ as the hypothesis that for a given gene the expression ratio is equal to unity at a given time point $t_i$, and $H_0$ as the hypothesis that for a given gene the expression ratios at all time points are equal to unity. If we denote $\alpha$ as the significance level for rejection of hypothesis $H_0$, and $\alpha'$ as the significance level for rejection of hypothesis $H_0^{(i)}$, then $\alpha'$ and $\alpha$ are related via $$1-\alpha=(1-\alpha')^a, \qquad (1)$$

in which a is the number of time points at which the gene expression ratio was measured. Note that by expanding the right hand side in a first order Taylor series, this equation reduces to Bonferoni's method for adjusting significance levels (see also T. W. Anderson and J. D. Finn, *The New Statistical Analysis of Data*, Springer-Verlag, New York, 1996).

By performing Student's t-test at every time point for each gene, using $\alpha'$ as the significance level, we will find whether $H_0^{(i)}$ and therefore $H_0$ should be rejected. If $H_0$ is not rejected, we can conclude that that gene is not significantly affected by the experimental manipulations, and should therefore not be included in further analyses. If for a given gene the null hypothesis $H_0$ is rejected, we conclude that that gene was significantly affected by the experimental manipulations.

2.2 Analysing Time-Ordered Data Using Lenear Splines

Next, we analyse the temporal gene expression response for genes that were found to be significantly affected. The measured gene expression ratios form a small set of time-ordered data, to which we can fit a linear spline function. A linear spline function is a continuous function consisting of piecewise linear functions, which are connected to each other at knots (J. H. Friedman et al. *Technometrics*, 31, 3-39, 1989; T. Higuchi (in Japanese), *Proceedings of the Institute of Statistical Mathematics*, 47, 291-306, 1999). Whereas cubic splines are used more commonly, for the small number of data points we are dealing with linear spline functions are more suitable. A conceptual example of a linear spline function with knots $t_1^*, t_2^*, t_3^*, t_4^*$ is shown in FIG. 22.

Consider a set of data points $(t_j, x_j)$, $j \in \{1, \ldots, n\}$. We wish to fit a nonparametric regression model of the form $$x_j = g(t_j) + \epsilon_j \qquad (2)$$

to these data, in which g is a linear spline function and $\epsilon_j$ is an independent random variable with a normal distribution with zero mean and variance $\sigma^2$.

We estimate the linear spline function g using the maximum likelihood method. The probability distribution of one data point $x_j$, given $t_j$, is $$f(x_j \mid t_j; g, \sigma^2) = \frac{1}{\sqrt{2\pi\sigma^2}} \exp\left\{-\frac{(x_j - g(t_j))^2}{2\sigma^2}\right\}. \qquad (3)$$

The log-likelihood function for the n data points is then given by $$L(g, \sigma^2) = -\frac{n}{2}\ln[2\pi\sigma^2] - \frac{1}{2\sigma^2}\sum_{j=1}^{n}(x_j - g(t_j))^2. \qquad (4)$$

The maximum likelihood estimate of the variance $\sigma^2$ can be found by maximising the log-likelihood function with respect to $\sigma^2$. This yields $$\hat{\sigma}^2 = \frac{1}{n}\sum_{j=1}^{n}(x_j - g(t_j))^2. \qquad (5)$$

The log-likelihood function can then be written in the form $$L(g, \sigma^2 = \hat{\sigma}^2) = -\frac{n}{2}\ln[2\pi\hat{\sigma}^2] - \frac{n}{2}. \qquad (6)$$

The maximum likelihood estimate $\hat{g}$ of the linear spline function g can now be found by minimising $\hat{\sigma}^2$. It can be shown that the minimum value of $\hat{\sigma}^2$ will be achieved if the linear spline function is chosen such that $$\underline{\underline{A}}\hat{g} = \underline{b}, \qquad (7)$$

in which $\hat{g}$ is a vector containing the q values of the linear spline function at the knots $t_i^*$, $\underline{\underline{A}}$ is a tridiagonal symmetric matrix given by $$A_{1,1} = \sum_{j: t_1^* \leq t_j < t_2^*} \left(\frac{t_2^* - t_j}{t_2^* - t_1^*}\right)^2; \qquad (8)$$

$$A_{i,i} = \sum_{j: t_{i-1}^* < t_j \leq t_i^*} \left(\frac{t_j - t_{i-1}^*}{t_i^* - t_{i-1}^*}\right)^2 + \sum_{j: t_i^* < t_j < t_{i+1}^*} \left(\frac{t_{i+1}^* - t_j}{t_{i+1}^* - t_i^*}\right)^2 \text{ for } 1 < i < q; \qquad (9)$$

-continued $$A_{q,q} = \sum_{j: t^*_{q-1} < t_j \le t^*_q} \left(\frac{t_j - t^*_{q-1}}{t^*_q - t^*_{q-1}}\right)^2; \quad (10)$$

$$A_{i+1,i} = A_{i,i+1} = \sum_{j: t^*_i < t_j < t^*_{i+1}} \frac{(t^*_{i+1} - t_j)(t_j - t^*_i)}{(t^*_{i+1} - t^*_i)^2} \text{ for } 1 \le i < q; \quad (11)$$

and $\underline{b}$ is a vector given by $$b_1 = \sum_{j: t^*_1 \le t_j \le t^*_2} \frac{t^*_2 - t_j}{t^*_2 - t^*_1} x_j; \quad (12)$$

$$b_i = \sum_{j: t^*_{i-1} < t_j \le t^*_i} \frac{t_j - t^*_{i-1}}{t^*_i - t^*_{i-1}} x_j + \sum_{j: t^*_i < t_j < t^*_{i+1}} \frac{t^*_{i+1} - t_j}{t^*_{i+1} - t^*_i} x_j \text{ for } 1 < i < q; \quad (13)$$

$$b_q = \sum_{j: t^*_{q-1} < t_j \le t^*_q} \frac{t_j - t^*_{q-1}}{t^*_q - t^*_{q-1}} x_j. \quad (14)$$

The fitted model depends on the number of knots q. The number of knots can be chosen using Akaike's Information Criterion, known as the AIC (H. Akaike, Information theory and an extension of the maximum likelihood principle, Research Memorandum No. 46, Institute of Statistical Mathematics, Tokyo, In Petrov, B. N., Csaki, F. (eds.), *2nd Int. Symp. on Inf. Theory*, Akadêmiai Kiadô, Budapest (1973), pp. 267-281, 1971; see also M. B. Priestley, *Spectral Analysis and Time Series*, Academic Press, London, 1994)

$$\text{AIC} = 2L(\hat{g}, \hat{\sigma}^2) + 2(q+1), \quad (15)$$

where $q+1$ is the number of estimated parameters $\hat{c}^2$ and the q entries in the estimated vector $\hat{g}$). Substituting the estimated log-likelihood function from equation (6), we find $$\text{AIC} = n \ln[2\pi\hat{\sigma}^2] + n + 2q + 2, \quad (16)$$

in which $\hat{c}^2$ is given by equation (5) after substitution of the maximum likelihood estimate $\hat{g}$ for the linear spline function g.

For each value of q, we will calculate the value of the AIC after fitting the linear spline function as described above, and select the value of q that yields the minimum value of the AIC. The case q=2 corresponds to linear regression. For the special case q=1, we are effectively fitting a flat line to the data. If we find that for a particular gene, the minimum AIC is achieved for the constant function (q=1), then we can conclude that the expression level of that gene was unaffected by the experimental manipulations.

Gene expression data are typically given in term of expression ratios. At time zero, the expression ratio is equal to unity by definition. This fixed point can be incorporated easily in our methodology by modifying equation (7). It can be shown that the minimum value of $\hat{c}^2$ will now be achieved by choosing the linear spline function such that $$\begin{pmatrix} A_{22} & A_{23} & 0 & 0 & 0 \\ A_{32} & A_{33} & A_{34} & 0 & 0 \\ 0 & A_{43} & A_{44} & 0 & 0 \\ 0 & 0 & 0 & A_{q-1,q-1} & A_{q-1,q} \\ 0 & 0 & 0 & A_{q,q-1} & A_{q,q} \end{pmatrix} \begin{pmatrix} \hat{g}_2 \\ \hat{g}_3 \\ \hat{g}_4 \\ \vdots \\ \hat{g}_{q-1} \\ \hat{g}_q \end{pmatrix} = \begin{pmatrix} b'_2 \\ b_3 \\ b_4 \\ \vdots \\ b_{q-1} \\ b_q \end{pmatrix}, \quad (17)$$

in which $b'_2 \equiv b_2 - A_{21}$, and $\hat{g}_1 = 1$

3. Results 3.1 Student's t-Test

We will illustrate using Student's t-test and fitting linear spline functions by reanalysing the measured gene expression profile of the cyanobacterium sp. PCC 6803 after a sudden exposure to high light (HL) (Y. Hihara et al., *The Plant Cell*, 13, 793-806, 2001). The expression levels of 3079 ORFs were measured at zero, fifteen minutes, one hour, six hours, and fifteen hours both for cyanobacteria exposed to HL and cyanobacteria that remained in the low light (LL) condition. Table 2 shows the number of measurements at each time point. Data from the cDNA expression measurements were obtained from the KEGG database (M. Nakao, et al., *Genome Informatics*, 10, 94-103, 1999).

TABLE 2

The gene expression measurements as a time-ordered set of data.

| Time point | Number of measurements |
|---|---|
| t = 15 minutes | 4(*) |
| t = 1 hour | 6 |
| t = 6 hours | 4 |
| t = 15 hours | 4 |

(*)Two sets of measurements are missing from the KEGG database at the t = 15 minutes time point.

TABLE 3

Student's t-test of gene expression measurements (3079 ORFs total).

| Significance level | Number of ORFs |
|---|---|
| p < 0.0003 | 98 |
| 0.0003 < p < 0.001 | 69 |
| 0.001 < p < 0.01 | 320 |
| 0.01 < p < 0.05 | 517 |
| p > 0.05 | 2075 |

It should be mentioned that the data used for the original analysis (Y. Hihara et al., *The Plant Cell*, 13, 793-806, 2001) may not be identical to the raw data submitted to KEGG (Y. Hihara, personal communication). In addition, two measurement sets out of six at the t=15 minutes time point are missing in the KEGG database. Recalculating the gene expression ratios from the raw data gives numbers very close to the previously published results though.

After subtracting the background signal intensities from the HL and LL raw data, global normalisation was applied and the ratio of the HL to the LL signal intensities was calculated to find the relative change in gene expression level with respect to the control (LL) condition. In the fold-change analysis, a gene was regarded as being affected by HL if its expression level changed by a factor of two or more. The statistical significance of such changes was assessed heuristically by considering the size of the standard deviation of the measurements (Y. Hihara et al., *The Plant Cell*, 13, 793-806, 2001).

The results of Student's t-test on the gene expression ratios of each gene separately are shown in Table 3. At a significance level of α=0.001, 167 genes were found to be significantly affected by HL condition. Note that we would expect about three type-1 errors among these 167 genes. In comparison, 164 ORFs were found to be affected by HL condition in the original analysis (Y. Hihara et al., *The Plant Cell*, 13, 793-806, 2001).

By considering the fold-change for the psbD2 gene (slr0927), it was concluded that it was not significantly induced by HL (Y. Hihara et al., *The Plant Cell*, 13, 793-806, 2001). This was remarkable, since this gene had been reported to be inducible by HL in the cyanobacterium *Synechococcus* sp. PCC 7942 (S. A. Bustos, et al., *Mol. Gen. Genet.*, 232, 221-230, 1992; S. Anandan et al., *J. Bacteriology* 179, 6865-6870, 1997). However, performing Student's t-test on the gene expression data for the psbD2 gene at t=6 hours yields $p=3.3 \times 10^{-5}$, suggesting that this gene was indeed affected by HL.

3.2 Analysis Using Linear Spline Functions

Next, we fit linear spline functions to the measured gene expression ratios. The number of knots q will be between one and five, with a fixed knot equal to unity at time zero. For q=3 and q=4, three possibilities exist for the placement of the knots between the linear segments of the linear spline. These are indicated in FIG. 23, together with the cases q=1, q=2, and q=5. Notice that the number of the possible knot placements increases exponentially with the maximum number of knots as $1+q_{max}2^{q_{max}-2}$.

In the fold-change analysis, the temporal gene expression patterns were classified into six categories (Y. Hihara et al., *The Plant Cell*, 13, 793-806, 2001), listed in Table 4. Fitting a linear spline function to the measured gene expression data provides a more flexible way to describe the data than categorising. In addition, a numerical description of the gene expression response pattern is an important initial step in deriving a gene regulatory network.

FIG. 23. Possible placement of knots for a time-ordered set of measurements at five time points.

TABLE 4

Six categories were used in the fold-change analysis to classify the temporal pattern of gene expression (Y. Hihara et al., The Plant Cell, 13, 793-806, 2001).

| | |
|---|---|
| Type 1 | Induced within 15 minutes, then decreased |
| Type 2 | Induced continuously at high levels |
| Type 3 | Induced at approximately one hour |
| Type 4 | Repressed within 15 minutes, then increased |
| Type 5 | Repressed continuously at low levels |
| Type 6 | Repressed at approximately one hour |

We will illustrate the usage of AIC with an example. In the fold-change analysis, the threonine synthase gene thr (sll1688) was found to be repressed at approximately one hour. The calculated values of the AIC for the different sets of knots are listed in Table 5. The minimum AIC was achieved for knots at 0, 15 minutes, 1 hour, and 15 hours.

Performing this procedure for all the gene expression measurements lets us classify the different genes based on their time-dependent response to HL. Several choices can be made as to which genes to include in this analysis. In the original analysis, genes were removed from the calculation if their expression levels were among the 2000 lowest out of 3079 ORFs (Y. Hihara et al., *The Plant Cell*, 13, 793-806, 2001). Alternatively, we can eliminate genes if Student's t-test showed that they were not significantly affected by HL. Table 6 shows the number of genes whose measured expression levels correspond to each response pattern for these different cases. For Student's t-test, a significance level $\alpha=0.001$ was used.

TABLE 5

The calculated AIC for the different sets of knots for the threonine synthase gene thrC (sll1688).

| Placement of Knots | AIC |
|---|---|
| Flat line | 62.55 |
| (0, 15 hours) | 64.54 |
| (0, 15 minutes, 15 hours) | 64.54 |
| (0, 1 hour, 15 hours) | 66.24 |
| (0, 6 hours, 15 hours) | 66.38 |
| (0, 15 minutes, 1 hour, 15 hours) | 25.24 |
| (0, 15 minutes, 6 hours, 15 hours) | 64.69 |
| (0, 1 hour, 6 hours, 15 hours) | 68.23 |
| (0, 15 minutes, 1 hour, 6 hours, 15 hours) | 26.45 |

FIG. 24. The measured gene expression levels for the threonine synthase gene (sll1688), together with the fitted linear spline.

TABLE 6

The number of genes for each response pattern.

| | Number of genes | | |
|---|---|---|---|
| Placement of knots | Keeping All Genes | Removing lowest 2000 | Using t-test to remove genes |
| Flat line | 927 | 249 | 1 (*) |
| (0, 15 hours) | 280 | 69 | 3 |
| (0, 15 minutes, 15 hours) | 663 | 217 | 61 |
| (0, 1 hour, 15 hours) | 386 | 178 | 7 |
| (0, 6 hours, 15 hours) | 160 | 64 | 3 |
| (0, 15 minutes, 1 hour, 15 hours) | 296 | 119 | 27 |
| (0, 15 minutes, 6 hours, 15 hours) | 178 | 83 | 39 |
| (0, 1 hour, 6 hours, 15 hours) | 103 | 49 | 12 |
| (0, 15 minutes, 1 hour, 6 hours, 15 hours) | 86 | 51 | 14 |

We can compare the 167 genes which were identified by Student's t-test as significantly affected by HL with the results from the fold-change analysis (Y. Hihara et al., *The Plant Cell*, 13, 793-806, 2001; S. Anandan et al., *J. Bacteriology*, 179, 6865-6870, 1997), in which 164 ORFs were identified. First, we remove those genes from our analysis for which an outlier was present in the data. We define an outlier as a data point that deviates more than two standard deviations from the mean of the data at a given time point. Only one gene was found for which the measured expression data contained an outlier; the linear spline function fitted to its expression data was a flat line. None of the other gene expression levels was described by a flat line, which is consistent with the results from Student's t-test.

Next, we remove those genes whose expression level was among the lowest 2000 in order to avoid using data that are predominantly determined by noise. The same procedure had been used for the fold-change analysis (Y. Hihara et al. *The Plant Cell*, 13, 793-806, 2001). After removal of these genes, 107 genes remained that were significantly affected by HL.

Of the 107 genes, 42 had not been identified in the fold-change analysis (Y. Hihara et al., *The Plant Cell*, 13, 793-806, 2001). These genes are listed in Table 7, together with the location of the knots that was found for each gene. For each linear spline function the percentage variance explained was calculated as a measure of the goodness of fit. As an example, FIG. 25 shows the measured gene expression ration as well as the fitted linear spline function of the gene xylR (slr0329), having four knots at zero, fifteen minutes, one hour, and fifteen hours. Of the 42 genes, the gene xylR (slr0329) had the largest percentage variance explained (98.7%).

Of the 164 ORFs that were identified in the fold-change analysis, 39 were not significantly affected by HL according to Student's t-test at a significance level of $\alpha=0.001$. These ORFs are listed in Table 8.

TABLE 7

ORFs that were significantly affected by HL, but had not been identified in the fold-change analysis (Y. Hihara et al., The Plant Cell, 13, 793-806, 2001).

| ORF | Gene | Placement of Knots | % variance Explained |
|---|---|---|---|
| sll1300 | | (0, 15 min., 15 hours) | 91.8 |
| sll1797 | ycf2I | (0, 15 min., 15 hours) | 61.4 |
| slr0121 | | (0, 15 min., 15 hours) | 78.7 |
| slr0343 | petD | (0, 15 min., 15 hours) | 93.5 |
| slr0442 | | (0, 15 min., 15 hours) | 81.1 |
| slr0769 | | (0, 15 min., 15 hours) | 64.7 |
| slr0906 | psbB | (0, 15 min., 15 hours) | 94.6 |
| slr1128 | | (0, 15 min., 15 hours) | 63.7 |
| slr1152 | | (0, 15 min., 15 hours) | 60.7 |
| slr1277 | gspD | (0, 15 min., 15 hours) | 40.5 |
| slr1610 | | (0, 15 min., 15 hours) | 70.02 |
| slr1813 | | (0, 15 min., 15 hours) | 84.3 |
| slr2052 | | (0, 15 min., 15 hours) | 87.1 |
| sll0144 | pyrH or smbA | (0, 1 hour, 15 hours) | 88.5 |
| sll1327 | atpC | (0, 1 hour, 15 hours) | 70.3 |
| sll1496 | | (0, 1 hour, 15 hours) | 77.4 |
| slr1367 | glgP or glgY | (0, 1 hour, 15 hours) | 88.2 |
| slr1793 | talB | (0, 1 hour, 15 hours) | 87.0 |
| sll1878 | | (0, 6 hours, 15 hours) | 65.8 |
| slr1600 | | (0, 6 hours, 15 hours) | 46.6 |
| sll0851 | psbC | (0, 15 min., 1 hour, 15 hours) | 91.9 |
| sll1471 | cpcG | (0, 15 min., 1 hour, 15 hours) | 96.6 |
| sll1812 | rps5 | (0, 15 min., 1 hour, 15 hours) | 60.3 |
| slr0076 | | (0, 15 min., 1 hour, 15 hours) | 85.8 |
| slr0329 | xylR | (0, 15 min., 1 hour, 15 hours) | 98.7 |
| slr0927 | psbD2 | (0, 15 min., 1 hour, 15 hours) | 48.9 |
| slr1513 | | (0, 15 min., 1 hour, 15 hours) | 84.8 |
| sll0547 | | (0, 15 min., 6 hours, 15 hours) | 79.3 |
| sll1528 | | (0, 15 min., 6 hours, 15 hours) | 90.9 |
| slr0056 | G4 | (0, 15 min., 6 hours, 15 hours) | 76.6 |
| slr0161 | pilT | (0, 15 min., 6 hours, 15 hours) | 96.2 |
| slr1239 | pntA | (0, 15 min., 6 hours, 15 hours) | 96.7 |
| slr1545 | | (0, 15 min., 6 hours, 15 hours) | 96.7 |
| slr1799 | | (0, 15 min, 6 hours, 15 hours) | 95.5 |
| sll0617 | im30 | (0, 1 hour, 6 hours, 15 hours) | 84.9 |
| sll0921 | | (0, 1 hour, 6 hours, 15 hours) | 46.9 |
| sll0985 | | (0, 1 hour, 6 hours, 15 hours) | 89.2 |
| slr1237 | codA | (0, 1 hour, 6 hours, 15 hours) | 80.7 |
| sll0108 | amtl | (0, 15 min, 1 hour, 6 hours, 15 hours) | 84.4 |
| sll0185 | | (0, 15 min., 1 hour, 6 hours, 15 hours) | 94.9 |
| sll1873 | | (0, 15 min., 1 hour, 6 hours, 15 hours) | 92.0 |
| slr0116 | hemD | (0, 15 min, 1 hour, 6 hours, 15 hours) | 89.2 |

FIG. 25. The measured gene expression levels for the gene xylR (slr0329), together with the fitted linear spline. This gene was considered to be unaffected by HL in the fold-change analysis (Y. Hihara et al., *The Plant Cell*, 13, 793-806, 2001).

TABLE 8

ORFs that were identified to be affected by HL in the fold-change analysis (Hihara, 2001), but found not significant by Student's t-test.

| | | |
|---|---|---|
| slr1311 | sll1867 | sll1732 |
| sll1733 | sll1734 | slr1280 |
| sll0170 | sll0430 | sll1514 |
| slr1641 | slr1350 | slr1516 |
| slr0228 | slr1604 | slr1675 |
| ssl3044 | sll1483 | sll1541 |

TABLE 8-continued

ORFs that were identified to be affected by HL in the fold-change analysis (Hihara, 2001), but found not significant by Student's t-test.

| | | |
|---|---|---|
| sll2012 | slr0394 | slr0426 |
| slr1351 | slr1594 | sll0217 |
| sll0218 | sll0219 | sll0528 |
| sll0668 | sll0814 | sll0846 |
| sll1884 | slr0007 | slr0476 |
| slr0740 | slr0959 | slr1544 |
| slr1674 | slr1686 | slr1963 |

TABLE 9

Reliability of the linear spline fitting procedure as a function of number of data used. Only those genes were considered which were significantly affected by HL according to Student's t-test, and whose data did not contain any outliers.

| | |
|---|---|
| Using four data points at 15 min., 6 hours, and 15 hours, and six data points at 1 hour | linear spline functions are estimated for 166 genes |
| Using four data points at each time point | 25 ± 8 estimated differently |
| Using three data points at each time point | 55 ± 10 estimated differently |
| Using two data points at each time point | 79 ± 17 estimated differently |

Finally, we would like to establish whether the number of measurements at each time point was sufficient to reliably determine the placements of knots for the linear spline function. To do so, we repeated the estimation of the linear spline function using subsets of the measured data. We then counted for how many genes the estimated knot positions changed if a subset of the data was used instead of the complete set of data. The average and standard deviation of this number for four, three, and two data points at each time point is shown in Table 9.

Even if only two data points (at the one hour time point) are removed, and four data points are used at each time point, in 15% of the cases the estimated knot positions change. This suggests that four or more data points are needed for each time point to reliably deduce information from gene expression measurements.

4. Discussion

We have described a strategy based on the maximum likelihood methods to analyse a set of time-ordered measurements. By applying Student's t-test to the measured gene expression data, we first establish which of the measured genes are significantly affected by the experimental manipulation. The expression responses of those genes are then described by fitting a linear spline function. The number of knots to be used for the linear spline function is determined using Akaike's Information Criterion (AIC).

Using linear spline functions allows us more flexibility in describing the measured gene expression than using a nominal classification. Also, in order to set up a gene regulatory network, it is important that the gene response as determined from gene expression measurements is available in a numerical form. Finally, the positions of the knots specify those time points at which the expression of a gene changes markedly, which is important in identifying its biological function. As a next step, the classification of gene expression responses based on the position of the knots can be refined by creating subcategories that take the magnitude of the linear spline function at the knots into account. For instance, for linear spline functions with three knots we may consider creating six subcategories in which changes in the gene expression level are described by (flat, increasing), (flat, decreasing), (increasing, flat), (decreasing, flat) (increasing, decreasing), or (decreasing, increasing).

Applying the technique of linear spline functions to measured gene expression data, we were able to identify the temporal expression response pattern of genes that were significantly affected by the experimental manipulations. The response of 42 of those genes was not noticed in earlier fold-change analyses of expression data. Furthermore, it was shown that the expression response levels found in a fold-change analysis were not found to be significant by Student's t-test for 33 out of 164 genes some genes.

Gene expression data tends to be noisy and are often plagued by outliers. Whereas Student's t-test and maximum likelihood methods described here take the statistical significance of noisy data into account, the issue of outliers needs to be addressed separately. As a simple procedure to remove outliers, we calculated the mean and standard deviation of the data for each point in time, and removed those data that deviated more than two standard deviations or so from the mean.

Finally, the number of expression measurements needed at each time point to reliably fit a linear spline function was determined by removing some data points and fitting a linear spline function anew. It was found that if four data points per time point are used, in about 15% of the cases the knot positions will not be estimated reliably. It is therefore advisable to make more than four measurements per time point.

Key Words: Gene Expression Data, Linear Splines, AIC, Time-Ordered Data, Maximum Likelihood Method.

Example 5

Use of Gene Networks for Identifying and Validating Drug Targets

We propose a new methodology for identifying and validating drug targets by using gene networks, which are estimated from cDNA microarray gene expression data. We created novel gene disruption and drug response microarray gene expression data libraries for the purpose of drug target elucidation. We use two types of microarray gene expression data for estimating gene networks and then identifying drug targets. The estimated gene networks play an essential role in understanding drug response data and this information is unattainable from clustering analysis methods, which are the standard for gene expression analysis. In the construction of gene networks, we use both Boolean and Bayesian network models for different steps in analysis and capitalize on their relative strengths. We use an actual example from analysis of the Saccharomyces cerevisiae gene expression and drug response data to suggest a concrete strategy for the application of gene network information to drug discovery.

1. Introduction

In recent years, the development of microarray technology has produced a largevolume of gene expression data under the various experimental conditions. Constructing gene network from gene expression data has received considerable attention and several methodologies for gene network inference have been proposed in the fields of computer science and statistics, e.g., see T. Akutsu, et al.; *Genome Informatics*, 9, 151, 1998; T. Akutsu, et al., *Proc. Pacific Symposium on Biocomputing*, 4, 17, 1999; T. Akutsu, et al., *Bioinformatics*, 16, 727, 2000; T. Akutsu, et al., *J. Comp. Biol.*, 7, 331, 2000; N. Friedman, et al., *J. Comp. Biol.*, 7, 601, 2000; A. J. Hartemink, et al., *Proc. Pacific Symposium on Biocomputing*, 7, 437, 2002; S. Imoto, S. Imoto et al., *Proc. Pacific Symposium on Biocomputing*, 7, 175, 2002; S. Imoto et al., *Proc. IEEE Computer Society Bioinformatics Conference*, 2002, in press; Y. Maki, et al., *Proc. Pacific Symposium on Biocomputing*, 6, 446, 2001; D. Pe'er, et al., *Bioinformatics*, 17 Suppl. 1, 215, ISMB 2001; I. Shmulevich, et al., *Bioinformatics*, 18, 261, 2002. The development of new methods for constructing a gene network is import and should progress. On the other hand, real world application of estimated gene networks to solve medical or biological problems has recently become the center of interest. In this paper, we introduce a methodology for identifying and validating drug targets based on gene expression data.

Clustering methods (M. J. L. de Hoon, et al., *Bioinformatics*, submitted; M. B. Eisen, et al., *Proc. Natl. Acad. Sci. USA*, 95, 14863, 1998; P. Tamayo, et al., *Proc. Natl. Acad. Sci. USA*, 96, 2907, 1999) have become a standard tool for analyzing microarray gene expression data. However, they cannot offer information sufficient for identifying drug targets in either a theoretical or practical sense. In this paper, we show how estimated gene networks can be used as a key for identifying and validating target genes for the understanding and development of new therapeutics. Gene regulation pathway information is essential for our purpose, and we used both Boolean and Bayesian networks as the methods for inferring gene networks from gene expression profiles. The procedure for identifying drug targets can be separated into two parts. At first, we should identify the drug-affected genes. Second, we search for the druggable genes, which are usually upstream of the drug-affected genes in the gene network. The Boolean network model shows its most useful for identifying the drug affected genes by using "virtual gene" gene technique, proposed herein, and the Bayesian network model can work effectively for exploring the druggable gene targets related to the elucidated affected genes. We apply the proposed method to novel *Saccharomyces cerevisiae* gene expression data, comprised of expression experiments from 120 gene disruptions and several dose and time responses to a drug. We demonstrate a concrete strategy for identifying genes for drug targeting through this application study.

2. Gene Networks for Identifying Drug Targets 2.1 Clustering Methods

Clustering methods such as the hierarchical clustering (M. B. Eisen, et al., *Proc. Natl. Acad. Sci. USA*, 95, 14863, 1998) and the self-organizing maps (P. Tamayo, et al., *Proc. Natl. Acad. Sci. USA*, 96, 2907, 1999) are commonly used as a standard tool for gene expression data analysis in the field of Bioinformatics. Eisen (M. B. Eisen, http://rana.lbl.gov/EisenSoftwareSource.htm, 2000) focuses on the hierarchical clustering and provides software, Cluster/TreeView, for clustering analysis of gene expression data. De Hoon et al. (M. J. L. de Hoon, The C clustering library manual, 2002; M. J. L. de Hoon et al., *Bioinformatics*, submitted) improves this software especially in the k-means clustering algorithm. These clustering algorithms can work effectively in the early stage of analysis. In the clustering analysis of gene expression data, we assume that the genes, which have similar expression patterns, play the same functional role in cell. Therefore, we often use the clustering methods for predicting gene functions.

We agree with the usefulness of the clustering methods, however, they cannot provide sufficient information for our purpose. Clustering methods only provide the information on gene groups via the similarity of the expression patterns. In fact, we need additional hierarchical pathway information, not only cluster information, in order to detect drug targets that are affected by an agent. In Section 3, we show the limitations of clustering techniques for drug targeting purposes through real data analysis.

2.2 Network Methods

We use two methods for estimating gene networks from gene expression data. In this subsection, we give the brief introductions of both methods. For detailed discussions of the algorithms, please refer to T. Akutsu, et al., *Genome Informatics*, 9, 151, 1998; T. Akutsu, et al., *Proc. Pacific Symposium on Biocomputing* 1999, 17 1999; T. Akutsu, et al., *Bioinformatics*, 16, 727 2000; T. Akutsu, et al., *J. Comp. Biol.*, 7, 331, 2000; N. Friedman et al., *J. Comp. Biol.* 7, 601, 2000; A. J. Hartemink et al., *Proc. Pacific Symposium on Biocomputing*, 7, 437-449, (2002); S. Imoto, S. Imoto et al., *Proc. Pacific Symposium on Biocomputing*, 7, 175, 2002; S. Imoto et al., *Proc. IEEE Computer Society Bioinformatics Conference*, 2002, in press; Y. Maki, et al., *Proc. Pacific Symposium on Biocomputing*, 6, 446, 2001; D. Pe'er, et al., *Bioinformatics*, 17, Suppl.1, 215 ISMB 2001; and I. Shmulevich, et al., *Bioinformatics*, 18, 261, 2002.

2.2.1 Boolean Network

A number of groups (T. Akutsu, et al., *Genome Informatics*, 9, 151, 1998; T. Akutsu, et al., *Proc. Pacific Symposium on Biocomputing* 1999, 17 1999; T. Akutsu, et al., *Bioinformatics*, 16, 727 2000; T. Akutsu, et al., *J. Comp. Biol.*, 7, 331, 2000; N. Friedman et al., *J. Comp. Biol.* 7, 601, 2000; Y. Maki, et al., *Proc. Pacific Symposium on Biocomputing*, 6, 446, 2001; and I. Shmulevich, et al., *Bioinformatics*, 18, 261, 2002) have proposed Boolean network models as a gene network construction method. To estimate a Boolean network model, we must discretize the gene expression values into two levels, 0 (not-expressed) and 1 (expressed). Suppose that $u_1, \ldots u_k$ are input nodes of a node v. The state of v is determined by a Boolean functions $f_v(\psi(u_1), \ldots, \psi(u_k))$, where $\psi(u_j)$ is the state or the expression pattern of $u_j$. If we have time series gene expression data, the state depends on the time t and the state of the node at time t depends on the states of inputs at time t−1. On the other hand, suppose that we have gene expression data obtained by gene disruptions. Akutsu et al. (T. Akutsu, et al., *Genome Informatics*, 9, 151, 1998) proposed the theory and methodology for estimating a Boolean network model without time delay. Maki et al. (Y. Maki, et al., *Proc. Pacific Symposium on Biocomputing*, 6, 446, 2001) provides a system, named AIGNET, for estimating a gene network based on the Boolean network and an S-system. (M. A. Savageau, *Biochemical Systems analysis: a study of function and design in molecular biology*, Addison-Wesley, Reading, 1976). In this paper, we use the AIGNET system for estimating Boolean network models.

The advantages of the use of the Boolean network model are as follows:

a) This model is very simple and can be easily understood, b) the Boolean network model can detect the parent-child relations correctly, when the data has sufficient accuracy and information and c) the estimated Boolean network model can be directly applied to the Genome Object Net (Genomic Object Net, genomicobject.net/public/index, 2002; H. Matsuno, et al., *Proc. Pacific Symposium on Biocomputing* 6, 338-349, 2000; H. Matsuno, et al., *Genome Informatics*, 12, 54-62, 2001), a software tool for biopathway simulation. The negative side of the Boolean method is that we must discretize the expression values into two levels, and the quantization probably causes information loss. Moreover, the threshold for discretizing is a parameter and should be chosen by a suitable criterion.

2.2.2 Bayesian Networks

The Bayesian network (F. V. Jensen, *An introduction to Bayesian Networks*, University College London Press, London, 1996) is a graph representation of the complex relations of a large number of random variables. We consider the directed acyclic graph with Markov relations of nodes in the context of Bayesian network. We can thus describe complex phenomena through conditional probabilities instead of the joint probability of the random variables. That is, suppose that we have a gene expression data $x_{ij}$ of the i-th array and j-th gene for i=1, ..., n and j=1, ..., p, we have $f(x_{i1}, \ldots, x_{ip}) = f_1(x_{i1}|p_{i1}) \times \ldots \times f_p(x_{ip}|p_{ip})$, where $p_{ij} = (p_{i1}^{(j)}, \ldots, p_{iq_j}^{(j)})^T$ is a $q_j$-dimensional parent observation vector of $x_{ij}$.

Friedman et al. (N. Friedman et al., *J. Comp. Biol.*, 7, 601, 2000) proposed an interesting approach for estimating a gene network from gene expression profiles. They discretized the expression values into three values and used the multinomial distributions as the conditional distributions of the Bayesian network. However, this did not solve the problem of choosing threshold values for discretizing. Imoto, et al. (S. Imoto, et al., *Proc. Pacific Symposium on Biocomputing*, 7, 175, 2002; S. Imoto, et al., *Proc. IEEE Computer Society Bioinformatics Conference*, 2002, in Press) recently used the nonparametric regression model that offers a solution that does not require quantization $x_{ij} m_{j1}(p_{i1}^{(j)}) + \ldots + m_{iq_j}(p_{iq_j}^{(j)}) + \epsilon_{ij}$ where $\epsilon_{ij}$ depends independently and normally on mean 0 and variance $\sigma_j^2$ and $m_{jk}(\bullet)$ is a smooth function constructed by B-splines of the form $m_{jk}(p_{ik}^{(j)}) = \sum_{m=1}^{M_{jk}} \gamma_{mk}^{(j)} b_{mk}^{(j)}(p_{ik}^{(j)})$ for k=1, ... $q_j$. Here $\gamma_{1k}^{(j)}, \ldots, \gamma_{M_{jk}}^{(j)}$ are unknown coefficients and $b_{ik}^{(j)}(\bullet), \ldots, b_{M_{jk}}^{(j)}(\bullet)$ are B-splines. Imoto, et al. (S. Imoto, et al., *Proc. Pacific Symposium on Biocomputing*, 7, 175, 2002; S. Imoto, et al., *Proc. IEEE Computer Society Bioinformatics Conference*, 2002, in Press) proposed the nonlinear Bayesian network model of the form $$f(xi;\theta) = \prod_{j=1}^{p} \exp\left[-\left\{x_{ij} - \sum_{k=1}^{qi}\sum_{m=1}^{M_{jk}} \gamma_{mk}^{(j)} b_{mk}^{(j)}(p_{ik}^{(j)})\right\}^2 \Big/ 2\sigma_j^2\right] \Big/ \sqrt{2\pi\sigma_{ij}^2}$$

together with new criterion, named BNRC, for selecting an optimal graph. The BNRC is defined as the approximation of the posterior probability of the graph by using the Laplace approximation for integrals. Imoto et al. (S. Imoto, et al., *Proc. Pacific Symposium on Biocomputing*, 7, 175, 2002; S. Imoto, et al., *Proc. IEEE Computer Society Bioinformatics Conference*, 2002, in Press) applied the proposed method to the *Saccharomyces cerevisiae* gene expression data and estimated a gene network. The advantages of this method are as follows: a) We can analyze the microarray data as a continuous data set, b) this model can detect not only linear structures but also nonlinear dependencies between genes and c) the proposed criterion can optimize the parameters in the model and the structure of the network automatically.

The Bayesian network has theoretical advantageous base on the mathematics of inference and in this paper we use the method proposed by Imoto et al. (S. Imoto, et al., *Proc. Pacific Symposium on Biocomputing*, 7, 175, 2002; S. Imoto, et al., *Proc. IEEE Computer Society Bioinformatics Conference*, 2002, in Press) for constructing Bayesian networks. Unfortunately, the Bayesian network cannot construct cyclic regulations and are not useful for creating multilevel directional models of regulatory effects from data created from logical joins of expression data from disruptants and drug response experiments. However, we can get around this problem by combining the Bayesian and Boolean networks in analysis. Hence, the Boolean and Bayesian networks used together can cover the shortcomings one another and we can obtain more reliable information by using both network methods.

3. Application 3.1 Microarray Data

We created two libraries of microarray data from the *Saccharomyces cerevisiae* gene expression profiles. One was obtained by disrupting 120 genes, and another was comprised of the responses to an oral antifungal agent (four concentrations and five time points). We selected 735 genes from the yeast genome for identifying drug targets. In YPD, 314 genes were defined as "Transcription factors", and 98 of these have already been studied for their control mechanisms. The expression profile data for 735 genes chosen for analysis included the genes controlled by these 98 "Transcription factors" from 5871 gene species measured in addition to nuclear receptor genes which have a pivotal role in gene expression regulation and are popular drug targets. We constructed the gene network models from the data set of 735 genes over 120 gene disruption conditions. The details of the disruption data are also described in Imoto et al. (S. Imoto, et al., *Proc. IEEE Computer Society Bioinformatics Conference*, 2002, in Press.)

As for the drug response microarray gene expression data, we incubated yeast cultures in dosages of 10, 25, 50 and 100 mg of an antifungal medication in culture and took aliquots of the culture at 5 time points (0, 15, 30, 45 and 60 minutes) after addition of the agent. Here time 0 means the start point of this observation and just after exposure to the drug. We then extracted the total RNA from these experiments, labeled the RNA with cy5, hybridized them with cy3 labeled RNA from non-treated cells and applied them to full genome cDNA microarrays thus creating a data set of 20 microarrays for drug response data. In this paper, we use these 140 microarrays to elucidate drug targets using gene networks.

3.2 Result

Clustering Result

In the identification of the drug targets, a popular but problematic strategy is the use of clustering analysis (T. R. Hughes et al., *Cell* 102, 109, 2000; M. J. Marton et al., *Nat. Med.*, 4, 1293, 1998) often even with a library of base perturbation control data to compare to drug response data based on the correlations. We have two types of microarray data, gene disruption and drug response, allowing us to compare drug response patterns to gene expression patterns caused by disruption. In the clustering analysis, if there is significant and strong similarity between the expression patterns of a single disruptant or group of disruptants and a given drug response microarray, we may conclude that an agent probably plays the same role as the disrupted gene(s). Moreover, if this disrupted gene has known functional role, we may obtain more information about the response to a drug.

FIG. 26: The image of the correlation matrix R of combined gene expression data.

Unfortunately, as if often the case with such experiments we cannot gain such a straightforward result from clustering our data. FIG. 26 shows the image representation of the correlation matrix of our microarray data. We combine the two types of data and make the matrix $Z=(X:Y)$, where X and Y are the drug response and the gene disruption microarray data matrix, respectively. Here, each column denotes an expression pattern obtained by one microarray, and each column is standardized with a mean of 0 and variance of 1. Therefore, FIG. 26 is the information of the correlation matrix R of combined gene expression data, where $R=Z^T Z/p$, where p is the number of genes and is 735.

In FIG. 26, the light and dark colors denote the positive and negative high correlations, respectively. It is clear that the drug response microarrays have high correlation amongst each other and a low correlation with any of the gene disruption microarrays. Under such a situation, we cannot find any interactions between gene disruptions and drug responses from the clustering analysis that would be useful to identify the strongly affected genes that are meaningful in the context of drug response. We further implemented hierarchical clustering of the gene disruption and drug response microarrays, but the drug response microarrays produce one cluster and we cannot extract any more information on what the actual drug targets from this analysis. This result is essentially unchanged when we use other distance measurements or clustering techniques. Hence, we cannot obtain the information for identifying the meaningful drug targets from the clustering methods with our data.

Boolean Network Result

We estimated gene network by using the microarray data, Z, which was created by the combining gene disruption and drug response microarrays. We introduce a method called virtual gene technique. We consider the conditions of the drug responses data as "virtual genes", e.g., the condition 100 mg/ml and 30 min is given an assignment as the gene YEXP100mg30min. By using the Boolean network model, we can find the child genes of these virtual genes, with the drug affecting these child genes in progeny generational order. We focus on genes which have five or more virtual genes as the parent genes, as the putative drug-affected gene, that is, genes which are under direct influence of the virtual genes (drug affect). However, a gene which has only one virtual gene as its parent gene, may be the primary drug-affected gene, depending on the mode of action for a given agent and this must be analyzed on a case by case basis. The virtual gene technique highlights the advantages of Boolean network models compared with the Bayesian network model in the initial screening for genes under drug-induced expression influence.

In addition, fold-change analysis can provide similar information to the proposed virtual gene technique. In fact, we can obtain the affected genes under certain experimental conditions by fold-change analysis. However, our virtual gene technique can improve the result of the fold-change analysis. Suppose that we find gene A and B are affected by the drug from fold-change analysis. The fold-change analysis cannot take into account the baseline interactions between geneA and geneB. That is, if there is a regulation pathway between geneA and geneB that geneA→geneB, the geneB is probably not affected by the drug directly. The virtual gene technique can take into account such interaction by using the information of the gene disruption data and thus reduce the search set to more probable target genes given available interaction data.

There is no guarantee that genes that are most affected by an agent are the genes that were "drugged" by the agent, nor is there any guarantee that the drugged target represents the most biologically available and advantageous molecular target for intervention with new drugs. Thus, even after identifying probable molecular modes of action, we should find the most druggable genes upstream of the drug-affected genes in a regulatory network and to then screen low molecular weight compounds for drug activity on those targets. In the estimated Boolean network, virtual genes should be placed on the top of the network. Therefore, it is difficult or sometimes impossible to find upstream information for drug-affected genes in this estimated Boolean network. At this stage, we can use the Bayesian network model for exploring the upstream region of the drug-affected genes in an effective manner.

FIG. 27: The downstream pathway of the virtual gene YEXP100mg30min.

Bayesian Network Result

The gene network is estimated by the Bayesian network and nonparametric regression method together with BNRC optimization strategy. (S. Imoto, et al., *Proc. Pacific Symposium on Biocomputing*, 7, 175, 2002; S. Imoto, et al., *Proc. IEEE Computer Society Bioinformatics Conference*, 2002, in Press). We use the *Saccharomyces cerevisiae* microarray gene expression data obtained by disrupting 120 genes. From the Boolean network analysis, we found the candidate set of the drug-affected genes effectively. The druggable genes are the drug targets related to these drug-affected targets, which we want to identify for the development of novel leads. We can explore the druggable genes on the upstream region of the drug-affected genes in the estimated gene network by Bayesian network method. Using the Bayesian models of network regulatory data available to us from our knockout expression library we are able to search upstream of drug affected for genes, which have a know regulatory control relationship over drug affected target expression. Here we focus on the nuclear receptor genes as the druggable genes because a) Nuclear receptor proteins are known to be useful drug targets and together represent over 20% of the targets for medications presently in the market. b) Nuclear receptors are involved in the transcription regulatory affects that are directly measured in cDNA microarray experiments.

FIG. 28 shows a partial network, which includes the drug-affected genes (Bottom), the druggable genes (Top) and the intermediary genes (Middle). Of course, we can find more pathways from the druggable genes to the drug-affected genes if we admit more intermediary genes. Due to the use of the Bayesian network model, we can find the intensities of the edges and can select more reliable pathway. This is an advantage of the Bayesian network model in searching for ideal druggable targets. In FIG. 28, the druggable genes in the circle connect directly to the drug-affected genes and the other druggable genes have one intermediary gene per one druggable gene. From FIG. 28, we can find the druggable genes for each drug-affected gene, e.g., we can find the druggable genes for MAL33 and CDC6 shown in Table 10.

TABLE 10

The druggable genes of MAL33 and CDC6. "Parents" means these genes connected directly to the drug-affected gene. "Grandparents" means there is one intermediary gene between these genes and the drug-affected gene.

| Drug-affected | MAL33 (YBR297W): Maltose fermentation regulatory protein | |
|---|---|---|
| Druggable | Parents | |
| | HSP82 (YPL240C): | Heat shock protein |
| | SRB4 (YER022W): | DNA-directed RNA polymerase II holoenzyme and Kornberg's mediator (SRB) subcomplex unit |
| | Grandparents | |
| | BAR1 (YIL015W): | Barrierpepsin precursor |
| | GPA1 (YHR005C): | GTP-binding protein alpha subunit of the pheromone pathway |
| | KAR2 (YJL034W): | nuclear fusion protein |
| Drug-affected | CDC5 (YJL194W): Cell division control protein | |
| Druggable | Parents | |
| | ARP7 (YPR034W): | Component of SW1-SNF global transcription activator complex and RSC chromatin remodeling complex |
| | BAR1 (YIL015W): | Barrierpepsin precursor |
| | Grandparents | |
| | GAL11 (YOL051W): | DNA-directed RNA polymerase II holoenzyme and Kornberg's mediator (SRB) subcomplex subunit |
| | FAR1 (YJL157C): | Cyclin-dependent kinase inhibitor (CKI) |
| | SLA2 (YNL243W): | Cytoskeleton assembly control protein |

Discussion

In this paper, we propose a new strategy for identifying and validating drug targets using computational models of gene networks. We showed that the clustering methods cannot provide the sufficient information and we that there is a need for the kind of hierarchical interaction data provided by network methods. We focus on the Boolean and Bayesian networks for estimating gene networks from microarray gene expression data. These two methods were originally proposed from the different points of view, however, both methods have relative strengths and weaknesses and we can obtain more reliable information from employing both methods in our analysis. The Boolean network is ideally used for identifying the drug-affected genes by using the virtual gene technique set forth above. We also described the theoretical advantages of the virtual gene technique over results obtained from simple fold-change analysis. This is a positive point for using the simpler Boolean networks for certain purposes. However, we show that the Boolean network cannot give the valuable information when we explore the druggable genes upstream of the drug-affected genes in the estimated network. We solve this difficulty by applying the Bayesian network model to this problem. The Bayesian network model can provide the information of the upstream region of the drug-affected genes effectively and we can thus attain a set of candidate druggable genes for each drug-affected gene. The strategy proposed by this paper is established based on the sophisticated use of a combination of two network methods. The strength of each network method can be clearly seen in this strategy and the proposed integrated method can be clearly seen in this strategy and the proposed integrated method can provide a methodological foundation for the practical application of bioinformatics techniques for gene network inference in the identification and validation of drug targets.

Example 6

System for Discovering Network Relationships, and Uses Thereof

1. Objects

Determining network relationships is highly desirable in numerous disciplines, including drug discovery, genomics, proteomics, computational networks, human networks, and other systems in which elements interact with each other in complex fashions.

One of the most important points in drug development is to explore action sites of lead compounds. Screening of the drug involves the processes of 1) synthesis of the lead compounds and screening thereof, 2) retrieval of the action sites and direct approach to diseases, 3) improvement to more effective drugs and 4) improvement to the drugs having less side effects. The important technology not available today in the process of the drug development is an assay assist system taking advantage of genomes. It is currently very difficult to construct an assist system using human genomes, although the human genome has been already elucidated. Underlying difficulties are based on the fact that construction of models using knock-in/knock-out genes is very difficult, and the models should be established for respective organs since each organ has its own specific expression.

Under these situations, it is considered to be an effective system for most effectively developing drugs having less side effects to determine the target site of the drug using yeast as an eukaryotic microorganism that may be easily modeled and for which abundant data have been accumulated, and to construct a system for extracting features of the network concerning the target site. Practically, differences of expression among the genes are accumulated using the knock-in/knock-out effect of each gene, and an expression control network is constructed from the data. Then, a lead compound is added to the culture medium of yeast utilizing this network, and any action sites of the lead compound are estimated by comparing the difference of gene expression with accumulated data. GNI has developed a genome assay assist system to provide an analysis environment and services for assisting pharmaceutical companies with more accurate and efficient development of drugs.

2. Technologies for Constructing Network

As an achievement of the genome project that is considered to be one of the greatest molecular biology projects in the 20th century, genome structures of many model animals have been elucidated, and analysis of the structure of even human genomes are now under way. Elucidation of genome functions are made possible by this rapid progress of the genome structure analysis that have been impossible by conventional biochemical and genetic methods. The most advanced results comprises transcriptome for investigating expression of total genes, and proteome for investigating expression of total proteins. In addition to these results, it has been practically available to elucidate the overall cell functions through investigation of the expression network of all genes constituting an organism by analyzing these data. Based on these facts, the next project for determining the genome structure is to elucidate genome functions involved in each organism. Studies for controlling overall functions of an organism have started by classifying and systematizing each genome depending on its nature. Consequently, a new era is now beginning when the observed data should be finally combined and connected to elucidation of the genome functions. Under these situations, it is almost impossible to collect and analyze multiple lines of information using conventional methods by which a single gene is analyzed.

A novel analysis method is required for attaining the object as hitherto described. In contrast to the conventional model constructed by experimentally confirming respective relations, it should be considered to totally construct a model from these large scale data. For example, a gene expression control network can be constructed by analyzing expression profiles and time course of total genes of an organism under various culture conditions, or by analyzing expression profiles in a mutant whose genes are destroyed. A study as shown in FIG. 29 is possible from a systematic point of view, and studies for assuming internal structure of the system from the data on input and output, and disturbance has became possible. When disturbance is considered to be destruction of a gene (no expression of the gene), it is a problem from the systematic point of view whether the gene expression system can be conjectured assuming that the input means expression of normal total genes and the output means expression of total genes when a part of the gene is destroyed.

Identification of System from Systematic Point of View

It is possible to collect experimental data for enabling the network to be assumed when the genome structure is elucidated.

Data of all the related genes can be measured.

Many tools for enabling many experiments to be performed—such as chips have been developed.

When an output is measured by applying a disturbance to obtain many standardized data, then:

FIG. 29 Molecular Network

The first step that enabled this expression profile to be analyzed is emergence of micro-arrays (M. Schena, et al., Science, 270, 467-470, 1995; J. L. DeRisi, Science 278, 680-686, 1997) that enables variation of many kinds of DNA or RNA (expression profile) to be simultaneously measured, or GeneChip method (D. J. Lockhart, et al., Nature Biotechnol., 14, 1675-1680, 1996). "Nature Genetics, January, 1999" have issued a special edition (The chipping forecast, Supplement to Nature Genetics, 21(1), 1999) on the gene chips. This method is now beginning to be widely used in the biological and medical fields, and many venture enterprises have been established worldwide to start sales of total system involving the chips and trays (see, for example, incyte.com and affymetrix.com). DNA Chip Laboratories Co., Takara Brewery Co. and Hokkaido System Science Co. have also joined in manufacture of the chip in Japan. Since a vast amount of experimental results are expected to be obtained from these methods, novel hypotheses and analysis methods will be required. Such methods would enable to replace conventional models that have been constructed by experimentally confirming individual relations with novel models that may be constructed from large scale data at one stroke.

For example, it is possible to construct a control network of gene expression by analyzing the expression profile of entire genes under a variety of environments. Search with comprehensive methods enables cause genes of diseases to be explored and to construct a disease model.

Analyzing Gene Expression Networks

1. Basic Array Technology

The same principle as the conventional Southern blot method is basically used in the array experiments. Technical developments that have brought about a rapid advance in the array technology include development of measuring instruments by which quantitative ratio between the sample and control is precisely measured by binding DNAs in high density on a slide glass having good optical characteristics. Recently, 10,000 or more of cDNAs were successfully spotted on a slide glass using an instrument (an arrayer or a spotter) developed by Dr. P. O. Brown et al.) (M. Schena, et al., Science, 270, 467-470, 1995) of Stanford University in USA. Expression of the gene could be measured by hybridizing sample and reference DNAs labeled with two kinds or more of fluorescent substances with the cDNAs on the slide. In a different method, a GeneChip has been manufactured using a more industrially available photolithographic method by which oligonucleotides are directly synthesized in high density on the surface of the glass. This method is now being practically used (D. J. Lockhart, et al., Nature Biotechnol., 14, 1675-1680, 1996). Otherwise, a method using an ink-jet mechanism is under development, and this method is expected to have a possibility that can form the array in higher speed with a higher density.

2. Practice of Micro-Array

An example of practical experiments will be described hereinafter. In our laboratory, direct and indirect influences of genes are comprehensively collected by allowing some genes in budding yeast to be destroyed or to be excessively expressed to investigate expression profiles of the total genes. The experimental procedure of the micro-array will be described herein with reference to FIGS. 30 and 31.

(I) Total genes of the microorganism to be studied are prepared at first. Usually, a set of PCR (polymerase chain reaction) primers (with a length of 20 bases) against the total genes are prepared, and PCR reactions are applied against the genomes or clones to obtained amplified fragments of the total genes.

(II) DNA of each amplified gene is spotted on a slide glass using a robot called a spotter or arrayer, and the genes are fixed. Each spot has a diameter of 150 μ, and 2,500 genes are spotted per 1 square cm.

(III) Subsequently, the sample is prepared. In the case of the budding yeast, a selected strain after the genome analysis and a mutant strain in which a specified gene has been destroyed are cultured under the same condition. mRNAs are extracted from both strains. cDNAs are prepared from these mRNAs, and are simultaneously labeled with two kinds of fluorescent substances (having different excitation wavelength and fluorescence wavelength with each other). An equal amount of cDNAs prepared from respective strains are mixed. The mixture is placed on the micro-array, and cDNAs are bound with the probes fixed on the glass surface by complementary bonds. The slide is washed to remove non-specifically bound cDNAs, thereby obtaining the expression profile of about 6,000 total genes in one experiment.

(IV) The micro-array binding the sample is quantified with a two-wavelength fluorometer to calculate the sample to reference ratio. The fluorometer is required to have a high sensitivity since the spot size is very small.

FIG. 30 Outline for preparing a microarray.

FIG. 31 Measurement of expression profile using microarray.

The mutant cells in the drawing mean the cells treated with a chemical. The gene expression profiles are prepared for comparison among the profiles, followed by identification of the location of the profile in the network.

3. Analysis of Gene Expression Network by Information Technology

1. Kinds of Data

Data is acquired at one selected time, or the cells are sampled with a given time interval during cultivation to acquire the expression profile data at that time as a time course. Otherwise, the experiment is carried out at one point on the time axis under different experimental conditions in order to collect as many expression profile changes as possible. Table 11 shows a part of Gene Expression Matrix in which the data of the gene destroy experiments are compiled. The results of gene destroy experiments with respect to 6,000 genes are shown in the columns of the table as ratios to wild type strains, in which the data of respective destroyed strains are accumulated.

The columns denote the destroyed gene names, and the rows denote the gene names. The figures are represented as relative amounts of expression by taking the normal level as unity.

2. Analysis Model

Determination of Network From Array Data

According to the prediction that the functional expression of microorganisms is defined by gene expression information based on the central dogma of the molecular biology, a line of information for elucidating the functions of organisms whose expression network has been investigated are expected to be obtained by analysis of the large scale gene expression data. Generally speaking, the methods used involve elucidation of gene groups having the same gene expressing pattern from the gene expression profiles issued from the project using clustering method. P. Tamayo, et al., Proc. Natl. Acad. Sci. USA, 96, 2907-2912, 1999; P. Toronen, et al., FEBS left. 451, 142-146, 1999; A. Arkin, et al., Science, 277, 1257-1279, 1997). Apart from these methods, studies for presuming the gene expression control network have started worldwide. The basic object thereof is to develop calculation methods for forming a construction diagram of the gene expression control network as shown in FIG. 32 from the gene expression matrix or time course data.

FIG. 32 Conceptual diagram of identification of gene network.

Network analysis using such model is largely divided into two groups. A boolean model is used in one group, wherein the relation among the genes is represented by a binary state in which one gene is controlled by the other gene or not (S. Liang, et al., Pac. Symp. On Biocomputing, 18-29, 1998; T. Akutsu, et al., Pac. Symp. on Biocomputing, 17-28, 1999). Different models deal with actual number of expression, wherein most of the models are based on differential equations related to dynamics of continuous values (R. Somogyi, et al., In The Second World Congress of Nonlinear Analysis (WCNA), 1996; D. Weaver, et. al., Pac. Symp. on Biocomputing, 112-123, 1999). However, the model based on the differential equation requires some devices since the reaction constants involved in the model should be optimized in the expression control network analysis carried out against the total genome.

岡本正宏, S-system による遺伝子の相互作用推定, ゲノム情報生物学, 165-188 (2000)

An analysis method using a Bayes network have been introduced in addition to these method (N. Friedman, et. al., Using Bayesian Networks to Analyze Expression Data, RECOMB 2000, 127-135, 2000).

TABLE 11

| Gene Expression MATRIX | | | | | | | | | | | |
|---|---|---|---|---|---|---|---|---|---|---|---|
| Gene | YLR228C | YLR266C | YML081W | YNR063W | YOL055C | YER088C | YER130C | YFL052W | YJR147C | YNL204C | YOL028C |
| Normal | 1.00 | 1.00 | 1.00 | 1.00 | 1.00 | 1.00 | 1.00 | 1.00 | 1.00 | 1.00 | 1.00 |
| YLR228C | — | 0.33 | 2.00 | 3.17 | 5.79 | 2.37 | 3.62 | 2.43 | 2.07 | 3.99 | 1.37 |
| YLR266C | 2.60 | — | 3.33 | 3.68 | 3.46 | 3.17 | 2.49 | 2.72 | 2.83 | 3.54 | 3.78 |
| YML081W | 1.57 | 2.33 | — | 0.42 | 2.23 | 1.68 | 1.71 | 2.10 | 2.49 | 1.76 | 2.69 |
| YNR063W | 2.32 | 2.71 | 2.55 | — | 1.65 | 2.25 | 1.80 | 3.20 | 2.51 | 2.07 | 2.45 |
| YOL055C | 1.84 | 3.61 | 1.94 | 1.78 | — | 0.91 | 1.12 | 1.54 | 1.81 | 1.76 | 6.33 |
| YER088C | 2.97 | 3.01 | 4.07 | 4.23 | 3.47 | | 4.34 | 4.93 | 4.22 | 2.45 | 3.44 |
| YER130C | 3.19 | 2.71 | 3.14 | 3.68 | 4.20 | 2.66 | — | 4.22 | 18.21 | 2.44 | 0.00 |
| YFL052W | 3.78 | 3.66 | 3.72 | 3.36 | 4.23 | 2.65 | 5.33 | — | 3.14 | 2.97 | 3.03 |
| YJR147W | 7.20 | 3.96 | 4.94 | 4.42 | 5.16 | 2.91 | 4.96 | 5.16 | — | 2.58 | 3.55 |
| YNL204C | 22.65 | 9.82 | 8.21 | 22.30 | 12.57 | 11.95 | 79.26 | 45.74 | 19.50 | — | 5.59 |
| YOL028C | ERR | 11.83 | 8.64 | 10.54 | 22.37 | 12.94 | 73.04 | 17.78 | 19.40 | 12.59 | — |

2. Our Trial

1. Expression Profile Construction Program

Since genome level studies have became possible today in the environment that allows multi-dimensional data to be readily measured, it is considered to be necessary to collect many expression profiles of gene destroyed or gene excess expression strains for the purpose of elucidation of the gene expression control network. We have also constructed many gene destroyed mutants for genes mainly comprising the genes related to transcription, genes related to signal transfer and genes related to cell cycles as shown in Table 12, and are trying to collect their expression profiles. One hundred and seventy three mutants mainly involving transfer factors have been constructed today, and their expression profiles are under construction with a program for disclosing the expression profile data this year.

TABLE 12

Construction program of gene-destroyed strains

| Category | Total | Fatal Gene | Goal |
|---|---|---|---|
| Transfer System | 741 | 239 | 502 |
| Transfer Factor | 538 | 142 | 396 |
| Signal Transfer System | 126 | 21 | 105 |
| Cell Proliferation, Budding and DNA Synthesis | 784 | 190 | 594 |

2. Trial for Identifying the Network

The multi-level digraph method we are trying will be introduced below. While the network is determined by the method shown in FIG. 33, it involves the following steps. (1) A gene expression matrix GE is constructed from the gene expression profile data collected; (2) The effect of one gene on any of the other genes, if any, is inquired by an operation to assign 1 for the gene in which its expression ratio has been remarkably changed, and 0 for the others, thereby forming a binary matrix. (3) The parts in which this matrix forms a cycle is searched, and the parts are collected and defines as a new gene group B'. Since handling of the looped control structure is complex, the parts are collected together to define as a new gene group again. (4) The columns and lows of the matrix are replaced to align related genes at an upper right portion of the matrix. This makes most of network topologies of the genes that are controlled with each other to be clear. (5) Finally, the gene expression network may be further defined by removing the indirectly connected parts. The network determined by this method from the expression profile of 70 gene destroyed strains we have constructed is shown in FIG. 34.

FIG. 33 Outline of multi-level digraph method.

Figure 34:
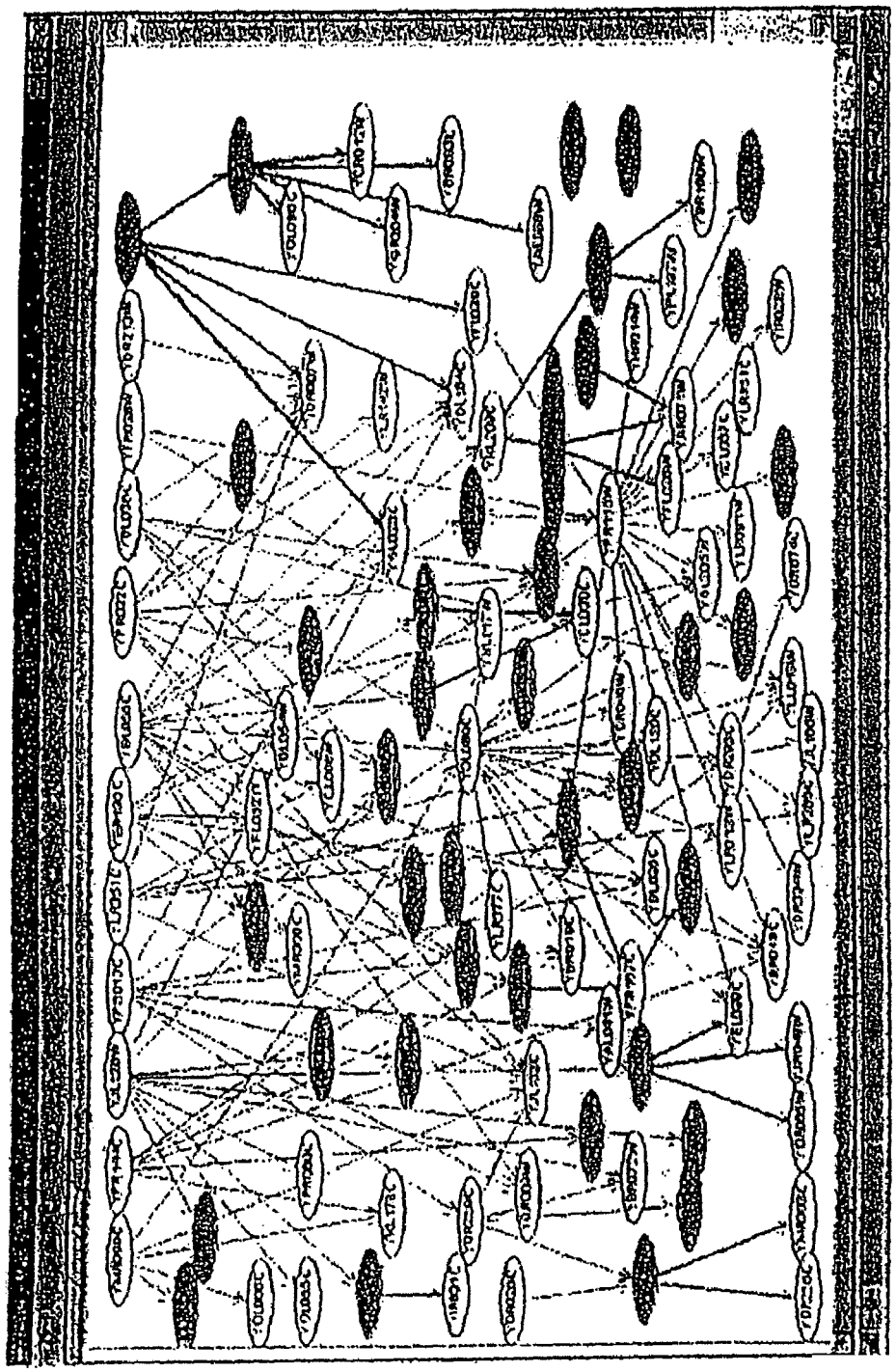
FIG. 34 a part of network determined from 70 destroyed strains.

FIG. 34 A part of network determined from 70 destroyed strains

4. Problems in the Future

The largest problem is errors involved in the data. Since the currently available experimental technologies may give rise to about errors in the order of from 30% to 40%, developments of informatex technologies is necessary based on such errors. However, the method for dealing with such large errors is not currently sufficient. Therefore, methodologies capable of experimentally reducing the errors, or methodology for estimating the errors to a certain extent are expected to be introduced.

Developments of display methods of the results are important for treating a vast number of genes. Since the network among 6,000 genes should be displayed for transcription factors were selected for analysis. We constructed an initial 552 gene-member model of regulatory control relationships and then constructed a sub-network model composed of the 98 known transcription factors. In creating these models we employed a Boolean computational algorithm as reported in L. Shoudan, *Pac. Sym. Bio.*, 3, 18-29, 1998. An outline of our method is shown in FIG. 35.

Figure 35:
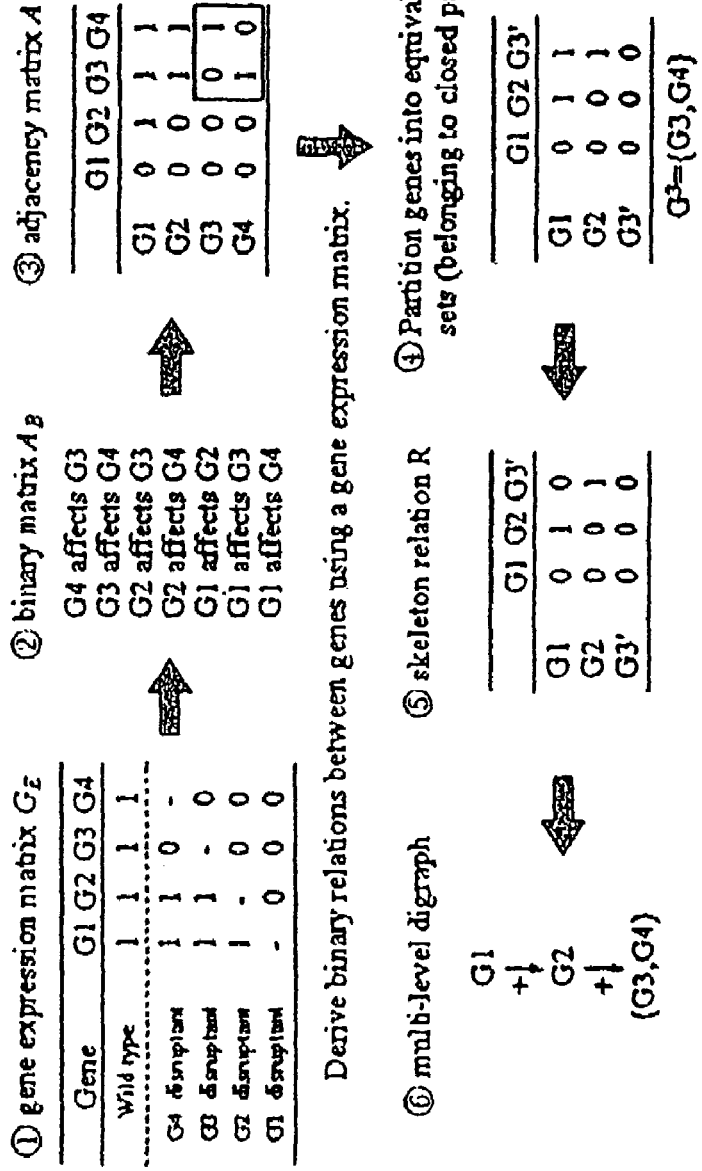
FIG. 35 construction of a gene regulatory subnetwork model with the Boolean method.

FIG. 35. Construction of a gene regulatory subnetwork model with the Boolean method. First, a gene expression matrix is created from a set of gene disruption experiments. Each element of the matrix indicates the ratio of gene expression and the binary relation matrix shows that if gene 'a' is deleted and intensity of gene 'b' is largely changed, gene 'a' affects gene 'b'. If gene a and gene 'b' affect each other mutually, they form a loop (strongly connected component). An equivalence set is introduced which treats a loop logically as a gene. An equivalence set is a group of genes that affect each other or only one gene. Next genes are partitioned into equivalence sets. These semi-ordered accessibility matrices among equivalence sets are describe influence as an equivalence set group even when individual genes with the set do not directly influence each other. Connections that are also included in lower rows are then removed to build the hierarchical connections in the network and generating the network topology of the gene in control relationships.

The network model constructed by Boolean models of the expression experiments resulted in a well-defined regulatory transcription factor sub-network involved in mitosis and meiosis pathway. FIG. 4 shows this transcription factor sub-network in detail. As can be seen in this figure, the sub-network describes specific regulatory relationships among transcription factors involved in mating, meiosis and DNA structure and repair mechanisms. For example HAP2, which is a gene whose function has yet to be reported shows indirect regulatory influence on Alpha2, a known mating response gene via an intermediary product, THI2 whose specific function is likewise unknown. Furthermore, various elements related to chromosome structure and DNA repair thought to be unconnected to known meiosis pathways are influenced by MET28 and CIN5. Both of these results make sense biologically; the dependence on error-free DNA replication for successful sexual reproduction and the relationship between meiosis and mating are obvious.

To understand the generalized regulatory relationships among various functional groups of transcription factors, we classified transcription factors in the network model with their "cellular roles". A "cellular role" here is defined as the major biological process involving the protein in YPD. We defined 10 groups for categorization in our transcription factor network. FIG. 4 displays graphically the interrelationships of classified transcription factors in our network, and FIG. 36 shows the numerical relationships among the groups.

As seen in FIG. 4, the cell cycle transcription factors were influenced by only a two of the 10 categories of transcription factors and only three genes in total. The three elements that independently influenced cell cycle transcription factors were related to meiosis, mating response, and cell stress, processes that for functional reasons would necessitate limited interaction with the cell cycle process. It is known that eukaryotic organisms use discreet and highly conserved cell-cycle checkpoints to ensure that nuclear division is restrained while DNA is undergoing replication or repair.

Likewise, it is apparent that the lipid fatty-acid metabolism transcription factors were affected by the carbohydrate metabolism transcription factors. Our data demonstrates, for example, that expression of INO4, a UDFHGDHG, is influenced by RTG1, a JJHGDGGH. Also, PDR1, a BIG HORSE is influenced by the expression of CAT8, a SMALL DOG. Other such interactions between proteins involved in phospholipid synthesis pathway with genes of the glucose response pathway, the lipid signaling pathway and other lipid synthesis pathways have been well described previously in the literatures. It is well known that the genes encoding many enzymes of phospholipid biosynthesis all contain variants of UASINO in their promoters and these are regulated in response to growth phase and nutrient starvation (G. M. Carman (1991)). Especially, Snf1p/Snf4p and Ire1p are reported that the key molecules that bind to UASINO sequence, which are associated with the glucose response, are required for derepression of $UAS_{INO}$-containing genes.

To confirm validity of our models on a genome-wide basis, we searched for the existence of previously described regulatory relationships from the literature within our 552 gene-member regulatory model. Of 98 known transcription factors, the regulatory networks upstream and downstream of 26 of these can be elucidated from the interactions reported in the literature. We examined how many of these pathways for well-known genes were reconstructed in our model. As a result, we found that approximately 27% of these relations were apparent from our expression data.

Our gene regulatory network construction using gene disruptant based expression profile data along with Boolean computational models has elucidated a number of gene regulatory relationships that make specific predictions relevant to pathway biology. Further tuning of these models from new biological insights and correlation of data with other expression data such as protein expression experiments will allow for increased resolution of specific pathway interactions. In addition, we are currently investigating other computational methodologies for examination of stochastic relationships contained in expression profile data such as Bayesian Modeling. Use of this and similar strategies for the elucidation of dynamic regulatory pathways from static expression data will allow for a new era of cost-effective, high throughput research into novel biological pathways and mechanisms.

FIGS. 4 and 36. Gene regulatory networks by cellular function. FIG. 4. A regulatory subnetwork of 98 transcription factors grouped by cellular function according to information provided in the YPD database. Genes inside the circles are those grouped into a given cellular functional category. Lines of hierarchical relationship in regulatory control are depicted with colored lines with the lines the same color as the category of genes from which the control relationship emanate toward the genes on which they exert regulatory influence. The bold red lines indicate regulatory control of transcription factors related to cell cycle originating from genes in the meiosis/mating response group. The dark blue lines indicate control relationships eminating from the carbohydrate metabolism group exerting influence over genes in the lipid fatty-acid metabolism group. This result is supported by the literature and also common sense. This well-conserved gene regulatory relationship insures that you will get fat if you eat too many sweets.

FIG. 36: Frequency of control relationships among functional categories of transcription factors. Row headings indicate gene control responses initiating from the category and column headings represent the categories of genes controlled. Numbers indicate the number of discreet control relationships initiated from a gene in one category and exerting control over a gene in the other category. The bold red numbers highlight the relatively sparse control relationships exerting influence over the cell cycle transcription factors. Bold blue numbers highlight the relatively sparse control relationships exerting control over lipid fatty acid metabolism, both of which emanate from the carbohydrate metabolism category.

FIG. 5: A detailed view of a gene regulatory subnetwork of transcription factors reconstructed from Boolean analysis of gene expression experiments on disruptant mutant yeast strains. Black lines indicate a regulatory relationship, with the arrows showing the hierarchical direction of the expression influence. The colors and shapes of the nodes denote the general categories of cellular function of the gene product according to their descriptions in the YPD database. Genes related to cell division mechanisms are indicated with triangular nodes and genes related to DNA repair and chromosome structure are depicted with squares. The elucidated network shows novel topological control relationships among genes related to meiosis, the mating response and DNA structure and repair mechanisms. Genes related to meiosis and mating response genes are downstream of a cascade regulated by INO2 and a further sub-grouping of genes related to DNA repair and structure appears hierarchically downstream of UME6.

Figure 37:
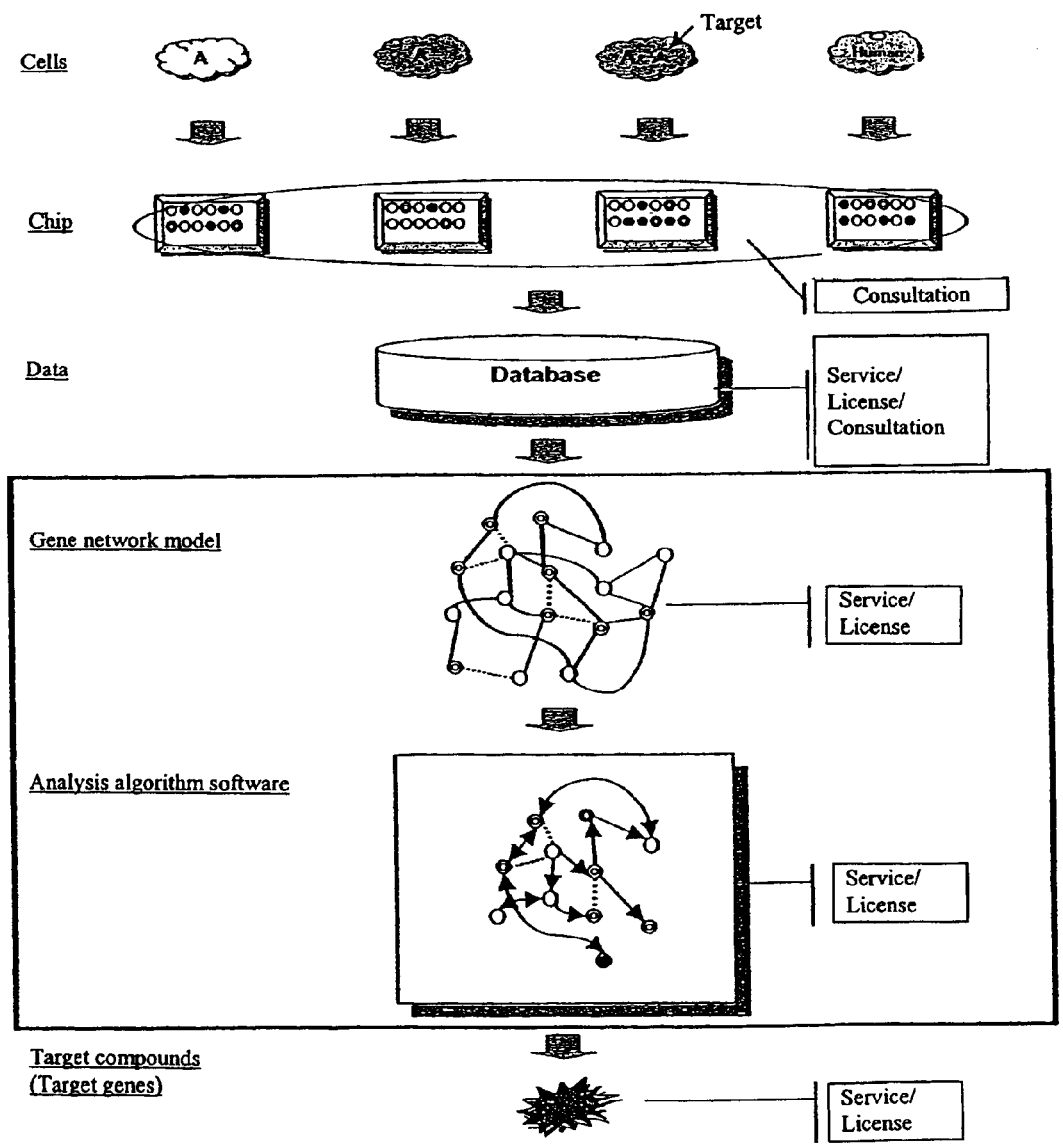
FIG. 37 GNI business model.

FIG. 37 depicts a schematic diagram of a system for discovering networks of this invention. Cells (top line: "A") are grown and treated with and without interventions to produce mRNA reflecting the treatments of lack thereof. Messenger RNA is reverse transcribed into cDNA and spotted onto arrays (second line from top). Information regarding the levels of expression is collected and stored in the Database. Information from the Database is analyzed according to the network modeling of this invention to produce a network of relationships between the different genes (in box). The output from the system is then displayed on a monitor or other visualization tool.

The above approach in determining networks can be applied to a variety of linear and non-linear analysis methods, including, but not limited to Boolean analysis, Bayesian analysis, graphical modeling, clustering analysis, maximum likelihood estimation, maximum penalized likelihood estimation and other types of analytical methods.

INDUSTRIAL APPLICABILITY

Methods for determining network relationships between genes is useful in the development of lead compounds in the pharmaceutical, health care and other industries in which relationships between genes is desired. Inferential methods of this invention find application in any area of statistical analysis in which complex relationships between groups of data are desired. Such areas include engineering, economics and biology.

REFERENCES

Higuchi, T. and Ohtani, S. (2000) Automatic identification of a large-scale field-aligned current structures. J. Geophys. Res., 105, 25305-25315. 田代康介, 牟田 滋原 哲, DNA マイクロアレイを用いた酵母の遺伝子発現解析, 細胞工学, 18. 1050-1056 (1999)

We claim:

1. A method for constructing a gene network and a graph of network relationships associated with said gene network, comprising the steps of:
   (a) providing a quantitative disruptant data library for a set of genes of an organism, said library including expression results based on disruption of each gene in said set of genes, quantifying an average effect and a measure of variability of each disruption on each other of said genes;
   (b) creating a gene expression matrix from said library, said gene expression matrix represents expression of each of said genes by each of said other genes in the library;
   (c) constructing said graph of network relationships between said genes in said expression matrix, said constructing said graph carried out by a computerized visualization and simulation method comprising minimizing a BNRC criterion; wherein said step of minimizing a BNRC criterion comprises computing maximum likelihood estimation; and
   (d) outputting said graph to a user.

2. The method of claim 1, wherein said step of minimizing a BNRC criterion comprises using a non-linear curve fitting method selected from the group consisting of polynomial bases, Fourier series, wavelet bases, regression spline bases and B-splines.

3. The method of claim 2, wherein said non-linear curve fitting method is a non-parametric method.

4. The method of claim 1, wherein said data library is created using a drug to alter gene expression.

5. The method of claim 1, wherein said step to minimize said BNRC criterion further comprises selecting a Bayesian model and solving a backfitting algorithm, as follows:
   (1) Initialize $\gamma_{jk}=0$, k=1, ..., $q_j$, Set $k = 1, \ldots, q_j, 1, \ldots, q_j, 1, \ldots$ and calculate  (2)

$$\gamma_{jk} = (B_{jk}^T B_{jk} + n\beta_{jk} K_{jk})^{-1} B_{jk}^T \left( x_{(j)} - \sum_{k' \neq k} B_{jk'} \gamma_{jk'} \right)$$

(3) Repeat step 2 until a suitable convergence criterion is satisfied.

6. The method of claim 1, wherein said step of minimizing a BNRC criterion further comprises computing Akaike's information criterion.

7. The method of claim 1, wherein said genes are associated with a cell cycle.

8. The method of claim 1, wherein said measure of variability is variance.

9. The method of claim 1, wherein said method for minimizing a BNRC criterion includes using heterogeneous error variances and said instructions minimize $$-2\log\pi_G + \sum_{j=1}^{p} \{BNRC_j + 2\log\pi_{L_j}\};$$

where $BNRC_j$ is given by:

$$-2\log\left\{\pi_{L_j} \int \prod_{i=1}^{n} f_j(x_{ij} \mid p_{ij;}; \theta_j)\pi_j(\theta_j \mid \lambda_j)d\theta_j\right\}$$

and based on Laplace approximation $$\int \prod_{i=1}^{n} f_j(x_{ij} \mid p_{ij;}; \theta_j)\pi_j(\theta_j \mid \lambda_j)d\theta_j =$$

$$\int \exp\{nl_\lambda(\theta_G \mid X_n)\}d\theta_G = \frac{\left(\frac{2\pi}{n}\right)^{\frac{r}{2}}}{|J_\lambda(\hat\theta_G)|^{\frac{1}{2}}} \exp\{nl_\lambda(\theta_G \mid X_n)\}\{1 + O_p(n^{-1})\}$$

where r is the dimension of $\theta_G$ $$l_\lambda(\theta_G \mid X_n) = \frac{1}{n}\sum \log f(x_i; \theta_G) + \frac{1}{n}\log\pi(\theta_G \mid \lambda), \quad J_\lambda(\theta_G) = \frac{-\partial^2 \{l_\lambda(\theta_G \mid X_n)\}}{\partial\theta_G\partial\theta_G^T}$$

and $\hat\theta_G$ is the mode of $l_\lambda(\theta_G \mid X_n)$, $\pi(\theta_G \mid \lambda)$ is the prior distribution on the unknown parameter $\theta_G$ with hyper parameter vecor $\lambda$, and $\log \pi(\theta_G \mid \pi)=O(n)$.

10. The method of claim 9, wherein step (c) construction of the graph of network relationships comprises:
   (1) fixing hyper parameters $p_j$;
   (2) initializing $\gamma_{jk}=0$, k-1, ..., $q_j$;
   (3) finding the optimal $\beta_{jk}$ by repeating steps 3-1 and 3-2;

(3-1) computing: $\gamma_{jk} = (B_{jk}^T W_{jk} B_{jk} + n\beta_{jk} K_{jk})^{-1} B_{jk}^T W_{jk} \times \left( x_{(j)} - \sum_{k' \neq k} \beta_{jk'} \gamma_{jk'} \right)$, for fixed $\beta_{jk}$;

(3-2) repeating step 3-1 against a candidate value of $\beta_{jk}$ and choosing the optimal value of $\beta_{jk}$, which minimizes $BNRC_{hetero}$;

(4) repeating step 3 for k=1, ..., qj, 1, ..., qj, 1, ... until a suitable convergence criterion is satisfied; and (5) repeating steps 1 to Step 4 against a candidate value of pj, and choosing the optimal value of pj, which minimizes the $BNRC_{hetero}$.

11. The method of claim 1, wherein said step to minimize a BNRC criterion further comprises the steps of minimizing $BNRC^j_{hetero}$ according to the following algorithm:

$$BNRC_{hetero}^{(j)} = -2\log \left\{ \int \pi_{L_j} \prod_{i=1}^{n} f_j(x_{ij} \mid p_{ij}; \theta_j) \pi_j(\theta_j \mid \lambda_j) d\theta_j \right\}$$

where
$\pi_{L_j}$ are prior probabilities satisfying $\Sigma_{j=1}^P \log \pi_{L_j} = \log \pi_G$ and the $BNRC_{hetero}$ score is given by the sum of the local scores where $$BNRC_{hetero} = \sum_{j=1}^{p} BNRC_{hetero}^{(j)},$$

and wherein the algorithm is implemented using the steps:

(1) making a score matrix whose (i, j)$^{th}$ element is the $BNRC^{hetero,j}$ score of the graph gene$_i \rightarrow$ gene$_j$;

(2) for each gene implementing for an edge one or more of add, remove and reverse which provides the smallest $BNRC_{hetero}$; and (3) repeating step 2 until the $BNRC_{hetero}$ does not reduce further.

12. The method of claim 11, wherein an intensity of the edge is determined using a bootstrap method, wherein said bootstrap method comprises the steps:

(1) providing a bootstrap gene expression matrix by randomly sampling a number of times, with replacement, from the original gene library expression data;

(2) estimating the genetic network for gene$_i$ and gene$_j$;

(3) repeating steps (1) and (2) T times, thereby producing T genetic networks; and (4) calculating the bootstrap edge intensity between gene$_i$ and gene$_j$ as $(t_1+t_2)/T$.

13. The method of claim 1, wherein step (b) includes grouping said genes into one or more equivalence sets based on the level of expression of said genes as determined in step (a).

* * * * *

SEQUENCE LISTING

<160> NUMBER OF SEQ ID NOS: 2

<210> SEQ ID NO 1
<211> LENGTH: 9
<212> TYPE: DNA
<213> ORGANISM: Saccharomyces cerevisiae

<400> SEQUENCE: 1 tagccgcca                                                                 9

<210> SEQ ID NO 2
<211> LENGTH: 10
<212> TYPE: DNA
<213> ORGANISM: Saccharomyces cerevisiae

<400> SEQUENCE: 2
tgggcggcta                                                               10